(12) United States Patent
Woo et al.

(10) Patent No.: US 8,022,224 B2
(45) Date of Patent: *Sep. 20, 2011

(54) 1,2,4-TRIAZOL-1-YL BISPHENYL DERIVATIVES FOR USE IN THE TREATMENT OF ENDOCRINE-DEPENDENT TUMORS

(75) Inventors: Lok Wai Lawrence Woo, Slough (GB); Toby Jackson, Slough (GB); Atul Purohit, Slough (GB); Michael John Reed, Slough (GB); Barry Victor Lloyd Potter, Slough (GB)

(73) Assignee: *Sterix Limited*, Slough, Berkshire (GB)

( * ) Notice: Subject to any disclaimer, the term of this patent is extended or adjusted under 35 U.S.C. 154(b) by 184 days.

This patent is subject to a terminal disclaimer.

(21) Appl. No.: 12/139,237

(22) Filed: Jun. 13, 2008

(65) Prior Publication Data
US 2008/0319037 A1 Dec. 25, 2008

Related U.S. Application Data

(63) Continuation-in-part of application No. PCT/GB2006/004630, filed on Dec. 12, 2006.

(30) Foreign Application Priority Data

Dec. 13, 2005 (GB) .................................. 0525323.2

(51) Int. Cl.
*C07D 249/00* (2006.01)
(52) U.S. Cl. ...................................... 548/255; 548/262.2
(58) Field of Classification Search .................. 548/255, 548/262.2
See application file for complete search history.

(56) References Cited

U.S. PATENT DOCUMENTS

| 3,941,800 | A | 3/1976 | Draber et al. | |
|---|---|---|---|---|
| 4,118,487 | A | 10/1978 | Regel et al. | |
| 2007/0117855 | A1* | 5/2007 | Lawrence Woo et al. | 514/383 |
| 2010/0173963 | A1* | 7/2010 | Woo et al. | 514/383 |

FOREIGN PATENT DOCUMENTS

| GB | 1 580 389 | 12/1980 |
|---|---|---|
| WO | WO 94/27989 | 12/1994 |
| WO | WO 2004/067703 | 8/2004 |
| WO | WO 2005/118560 | 12/2005 |

OTHER PUBLICATIONS

Peter Nussbaumer, et al., Steroid Sulfatase Inhibitors, Expert Opinion Ther. Patents (2003) 13(5): 605-625.

* cited by examiner

*Primary Examiner* — Susannah Chung
(74) *Attorney, Agent, or Firm* — Frommer Lawrence & Haug LLP

(57) ABSTRACT

There is provided a compound of Formula I

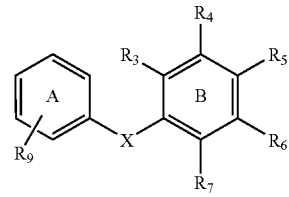

Figure 1:
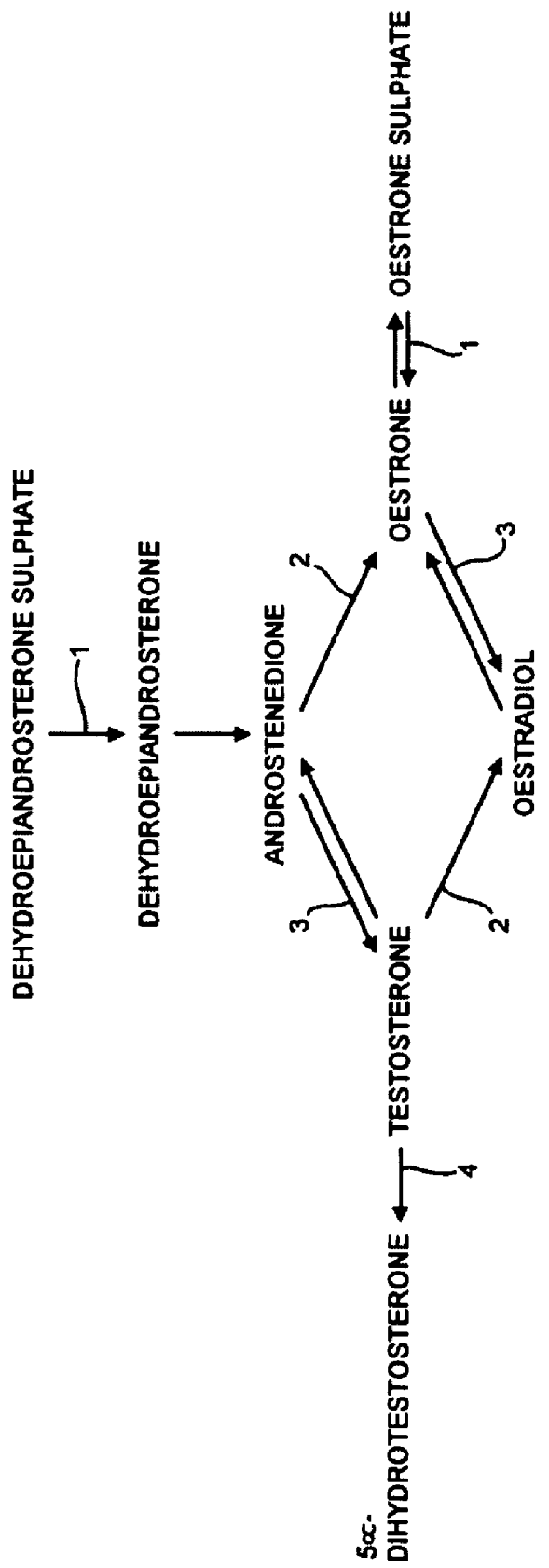

Formula I wherein $R_3$, $R_4$, $R_5$, $R_6$ and $R_7$ are independently selected from H and —Y—$R_8$; wherein each $R_8$ is independently selected from —OH, hydrocarbyl groups, oxyhydrocarbyl groups, cyano (—CN), nitro (—$NO_2$), H-bond acceptors, and halogens; wherein at least one of $R_3$, $R_4$, $R_5$, $R_6$ and $R_7$ is —Y—$R_8$ wherein $R_8$ is selected from substituted and unsubstituted heterocyclic rings and amino substituted phenyl groups, wherein X is a bond or a linker group; wherein Y is an optional linker group; and wherein ring A is optionally further substituted; wherein $R_9$ is selected from H, —OH and —$OSO_2NR_1R_2$; wherein $R_1$ and $R_2$ are independently selected from H and hydrocarbyl; wherein (a) X is a bond and at least one of $R_3$, $R_4$, $R_5$, $R_6$ and $R_7$ is —Y—$R_8$; OR (b) $R_9$ is —$OSO_2NR_1R_2$ or —OH and four of $R_3$, $R_4$, $R_5$, $R_6$ and $R_7$ are H and one of $R_3$, $R_4$, $R_5$, $R_6$ and $R_7$ is —Y—$R_8$. These compounds inhibit steroid sulphatase and aromatase activity and are useful in the treatment of endocrine-dependent tumors.

16 Claims, 2 Drawing Sheets

ORIGIN OF OESTROGENIC STEROIDS IN POSTMENOPAUSAL WOMEN

ER=OESTROGEN RECEPTOR, DHA / -S=DEHYDROEPIANDROSTERONE / -SULPHATE, ADIOL=ANDROSTENEDIOL, E1-STS=OESTRONE SULPHATASE, DHA -STS= DHA-SULPHATASE, ADIOL-STS=ADIOL SULPHATASE, 17B-HSD=OESTRADIOL 17B-HYDROXYSTEROID DEHYDROGENASE

1,2,4-TRIAZOL-1-YL BISPHENYL DERIVATIVES FOR USE IN THE TREATMENT OF ENDOCRINE-DEPENDENT TUMORS

INCORPORATION BY REFERENCE

This application is a continuation-in-part of International Patent Application PCT/GB2006/004630 filed Dec. 12, 2006 and published as WO 2007/068905 on Jun. 21, 2007, which claims priority from GB Application No. 0525323.2 filed Dec. 13, 2005.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

These and other embodiments are disclosed or are obvious from and encompassed by, the following Detailed Description.

FIELD OF INVENTION

The present invention relates to a compound. In particular the present invention relates to a compound and to a pharmaceutical composition comprising the compound. The present invention also relates to the use of the compound or composition in therapy applications.

BACKGROUND OF THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), and aromatase (i.e. conversion of androstenedione to oestrone) account for the production of oestrogens in breast tumours.

Figure 2:
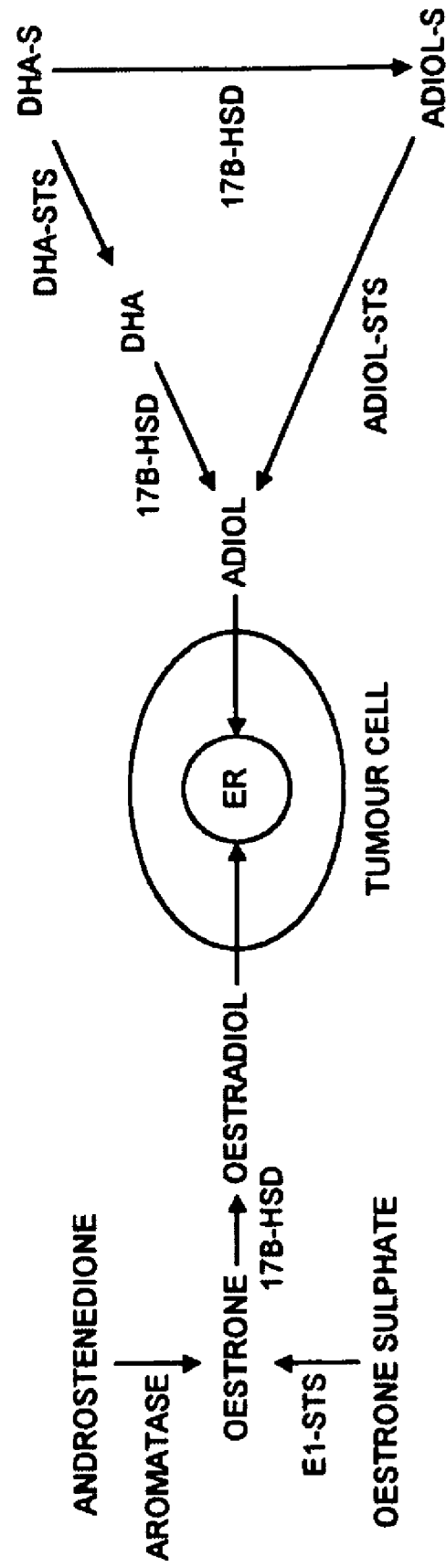

FIGS. 1 and 2 are schematic diagrams showing some of the enzymes involved in the in situ synthesis of oestrone from oestrone sulphate, oestradiol and androstenedione.

In FIG. 2, which schematically shows the origin of oestrogenic steroids in postmenopausal women, "ER" denotes Oestrogen Receptor, "DHEA-S" denotes Dehydroepiandrosterone-Sulphate, "Adiol" denotes Androstenediol, "E1-STS" denotes Oestrone Sulphatase, "DHEA-STS" denotes DHEA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral synthesis of oestrogens are the aromatase enzyme and the enzyme oestrone sulphatase.

In short, the aromatase enzyme converts androstenedione, which is secreted in large amounts by the adrenal cortex, to oestrone. Recent reports have suggested that some flavones could inhibit aromatase activity.

Much of the oestrone so formed, however, is converted to oestrone sulphate (E1S) and there is now a considerable body of evidence showing that E1S in plasma and tissue acts as a reservoir for the formation of oestrone by the action of oestrone sulphatase.

In this regard, it is now believed that the oestrone sulphatase (E1-STS) pathway—i.e. the hydrolysis of oestrone sulphate to oestrone (E1S to E1) is a major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10-12 h) compared with the unconjugated oestrogens (20 min) and high levels of steroid sulphatase activity in liver and, normal and malignant breast tissues, also lend support to this theory.

Thus, oestrogen formation in malignant breast and endometrial tissues via the sulphatase pathway makes a major contribution to the high concentration of oestrogens which are present in these tumours. However, inhibition of both the aromatase and sulphatase pathways could offer considerable therapeutic benefit.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE"). EMATE has the following structure:

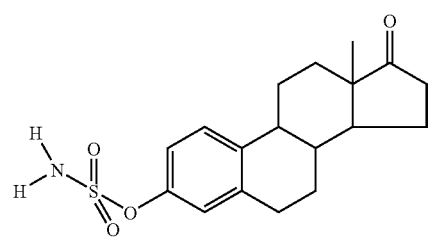

It is known that EMATE is a potent E1-STS inhibitor as it displays more than 99% inhibition of E1-STS activity in intact MCF-7 cells at 0.1 nM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHEA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHEA-STS (99%) activities resulted when it is administered either orally or subcutaneously. In addition, EMATE has been shown to have a memory enhancing effect in rats. Studies in mice have suggested an association between DHEA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

In addition to oestrone, the other major steroid with oestrogenic properties which is produced by postmenopausal women is androstenediol (see FIG. 2).

Androstenediol, although an androgen, can bind to the oestrogen receptor (ER) and can stimulate the growth of ER positive breast cancer cells and the growth of carcinogen-induced mammary tumours in the rat. Importantly, in postmenopausal women 90% of the androstenediol produced originates from the androgen dehydroepiandrosterone sulphate (DHEA-S) which is secreted in large amounts by the adrenal cortex. DHEA-S is converted to DHEA by DHEA sulphatase, which may be the same as, or different from, the enzyme, oestrone sulphatase, which is responsible for the hydrolysis of E1S.

During the last 10-15 years considerable research has also been carried out to develop potent aromatase inhibitors, some of which are now marketed. However, in three recent reports of postmenopausal women with breast cancer who received aromatase inhibitor therapy, plasma E1S concentrations remained between 400-1000 pg/ml.

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

Our earlier application WO03/045925 teaches compounds which may act as inhibitors of both aromatase and sulphatase. Many of the compounds of the disclosure are found to be extremely potent inhibitors of both of these enzymes. However, there is a desire to provide alternative compounds or improved compounds.

The present invention seeks to provide novel compounds suitable for the inhibition of steroid sulphatase activity and aromatase activity.

Citation or identification of any document in this application is not an admission that such document is available as prior art to the present invention.

SUMMARY OF THE INVENTION

The present invention is based on the surprising finding that certain polycyclic compounds could be used as effective steroid sulphatase inhibitors and/or aromatase inhibitors and/or as agents that can influence cell cycling and/or as agents that can influence apoptosis.

DETAILED DESCRIPTION

According to one aspect of the present invention, there is provided a compound of Formula I

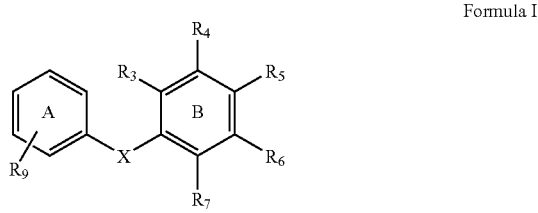

Formula I wherein $R_3$, $R_4$, $R_5$, $R_6$ and $R_7$ are independently selected from H and —Y—$R_8$
wherein each $R_8$ is independently selected from —OH, hydrocarbyl groups, oxyhydrocarbyl groups, cyano (—CN), nitro (—NO$_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein X is a bond or a linker group
wherein Y is an optional linker group; and
wherein ring A is optionally further substituted
wherein $R_9$ is selected from H, —OH and —OSO$_2$NR$_1$R$_2$
wherein $R_1$ and $R_2$ are independently selected from H and hydrocarbyl
wherein
  (a) X is a bond and at least one of $R_3$, $R_4$, $R_5$, $R_6$ and $R_7$ is —Y—$R_8$; OR
  (b) $R_9$ is —OSO$_2$NR$_1$R$_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

According to one aspect of the present invention, there is provided a method comprising (a) performing a steroid sulphatase (STS) assay and/or aromatase assay with one or more candidate compounds defined herein; (b) determining whether one or more of said candidate compounds is/are capable of modulating STS activity and/or aromatase activity and/or cell cycling and/or cell growth and/or apoptosis; and (c) selecting one or more of said candidate compounds that is/are capable of modulating STS activity and/or aromatase activity and/or cell cycling and/or cell growth and/or apoptosis.

According to one aspect of the present invention, there is provided a method comprising (a) performing a steroid sulphatase assay and/or aromatase assay with one or more candidate compounds as defined herein; (b) determining whether one or more of said candidate compounds is/are capable of inhibiting STS and/or aromatase activity; and (c) selecting one or more of said candidate compounds that is/are capable of inhibiting STS activity and/or aromatase activity and/or cell cycling and/or cell growth and/or apoptosis. In any one of the methods of the present invention, one or more additional steps may be present. For example, the method may also include the step of modifying the identified candidate compound (such as by chemical and/or enzymatic techniques) and the optional additional step of testing that modified compound for STS inhibition effects (which may be to see if the effect is greater or different) and/or aromatase inhibition effects (which may be to see if the effect is greater or different). By way of further example, the method may also include the step of determining the structure (such as by use of crystallographic techniques) of the identified candidate compound and then performing computer modelling studies—such as to further increase its STS and/or aromatase inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as enzyme and/or protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS and/or aromatase and/or cell cycling and/or apoptosis and/or cell growth.

According to one aspect of the present invention, there is provided the use of a compound according to the present invention in the manufacture of a medicament for use in the therapy of a condition or disease associated with adverse STS levels and/or adverse aromatase levels and/or cell cycling and/or apoptosis and/or cell growth.

According to one aspect of the present invention, there is provided the use of a compound according to the present invention in the manufacture of a medicament for inhibiting STS activity and/or inhibiting aromatase activity.

According to one aspect of the present invention, there is provided the use of a compound according to the present invention in the manufacture of a medicament for inhibiting STS activity and inhibiting aromatase activity.

The present invention also encompasses the novel compounds of the present invention (such as those presented herein), as well as processes for making same (such as the processes presented herein) as well as novel intermediates (such as those presented herein) for use in those processes.

The compounds of the present invention may comprise other substituents. These other substituents may, for example, further increase the activity of the compounds of the present invention and/or increase stability (ex vivo and/or in vivo).

For ease of reference, these and further aspects of the present invention are now discussed under appropriate section headings. However, the teachings under each section are not necessarily limited to each particular section.

One key advantage of the present invention is that the compounds of the present invention can act as aromatase inhibitors.

One key advantage of the present invention is that the compounds of the present invention can act as STS inhibitors.

One key advantage of the present invention is that the compounds of the present invention can act as STS inhibitors and aromatase inhibitors.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity. Here, by the term "non-oestrogenic" means exhibiting no or substantially no systemic oestrogenic activity, such as that determined by Protocol 4.

Another advantage is that some of the compounds may not be capable of being metabolised to compounds which display or induce hormonal activity.

Some of the compounds of the present invention are also advantageous in that they may be orally active.

Some of the compounds of the present invention may useful for the prevention and/or treatment of cancer, such as breast cancer, as well as (or in the alternative) non-malignant conditions, such as the prevention and/or treatment of inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. acne, psoriasis and contact dermatitis; graft versus host disease; eczema; asthma and organ rejection following transplantation. The compounds of the present invention are useful particularly when pharmaceuticals may need to be administered from an early age.

Thus, some of the compounds of the present invention are also believed to have therapeutic uses other than for the treatment of endocrine-dependent cancers, such as the treatment of autoimmune diseases.

The compounds of the present invention may also be useful as an inducer of apoptosis.

The compounds of the present invention may also be useful as a cell growth inhibitors.

Hydrocarbyl Group

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

The hydrocarbyl/hydrocarbon/alkyl may be straight chain or branched and/or may be saturated or unsaturated.

In one preferred aspect the hydrocarbyl/hydrocarbon/alkyl may be selected from straight or branched hydrocarbon groups containing at least one hetero atom in the group.

In one preferred aspect the hydrocarbyl/hydrocarbon/alkyl may be a hydrocarbyl group comprising at least two carbons or wherein the total number of carbons and hetero atoms is at least two.

In one preferred aspect the hydrocarbyl/hydrocarbon/alkyl may be selected from hydrocarbyl groups containing at least one hetero atom in the group. Preferably the hetero atom is selected from sulphur, nitrogen and oxygen.

In one preferred aspect the hydrocarbyl/hydrocarbon/alkyl may be selected from straight or branched hydrocarbon groups containing at least one hetero atom in the group. Preferably the hetero atom is selected from sulphur, nitrogen and oxygen.

In one preferred aspect the hydrocarbyl/hydrocarbon/alkyl may be selected from straight or branched alkyl groups, preferably $C_{1-10}$ alkyl, more preferably $C_{1-5}$ alkyl, containing at least one hetero atom in the group. Preferably the hetero atom is selected from sulphur, nitrogen and oxygen.

In one preferred aspect the hydrocarbyl/hydrocarbon/alkyl may be selected from straight chain alkyl groups, preferably $C_{1-10}$ alkyl, more preferably $C_{1-5}$ alkyl, containing at least one hetero atom in the group. Preferably the hetero atom is selected from sulphur, nitrogen and oxygen.

The hydrocarbyl/hydrocarbon/alkyl may be selected from
$C_1$-$C_{10}$ hydrocarbyl,
$C_1$-$C_5$ hydrocarbyl
$C_1$-$C_3$ hydrocarbyl.
hydrocarbon groups
$C_1$-$C_{10}$ hydrocarbon
$C_1$-$C_5$ hydrocarbon
$C_1$-$C_3$ hydrocarbon.
alkyl groups
$C_1$-$C_{10}$ alkyl
$C_1$-$C_5$ alkyl
$C_1$-$C_3$ alkyl.

The hydrocarbyl/hydrocarbon/alkyl may be straight chain or branched and/or may be saturated or unsaturated.

The hydrocarbyl/hydrocarbon/alkyl may be straight or branched hydrocarbon groups containing at least one hetero atom in the group.

Oxyhydrocarbyl Group

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Each of the above teachings in respect of hydrocarbyl groups equally applies to the analogous oxyhydrocarbyl groups, that is the corresponding oxyhydrocarbyl group which comprises an oxygen in addition to the hydrocarbyl.

Typically, the oxyhydrocarbyl group is of the formula $C_{1-6}O$ (such as a $C_{1-3}O$).

Compound

According to one aspect of the present invention, there is provided a compound of Formula I

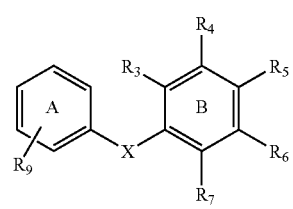

Formula I wherein $R_3$, $R_4$, $R_5$, $R_6$ and $R_7$ are independently selected from H and —Y—$R_8$ wherein each $R_8$ is independently selected from —OH, hydrocarbyl groups, oxyhydrocarbyl groups, cyano (—CN), nitro (—$NO_2$), H-bond acceptors, and halogens;

wherein at least one of $R_3$, $R_4$, $R_5$, $R_6$ and $R_7$ is —Y—$R_8$ wherein $R_8$ is selected from substituted and unsubstituted heterocyclic rings and amino substituted phenyl groups, wherein X is a bond or a linker group wherein Y is an optional linker group; and wherein ring A is optionally further substituted wherein $R_9$ is selected from H, —OH and —$OSO_2NR_1R_2$ wherein $R_1$ and $R_2$ are independently selected from H and hydrocarbyl wherein (a) X is a bond and at least one of $R_3$, $R_4$, $R_5$, $R_6$ and $R_7$ is —Y—$R_8$; OR (b) $R_9$ is —$OSO_2NR_1R_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

In a further aspect the present invention provides a compound of Formula II

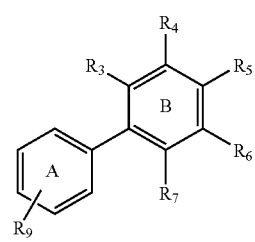

Formula II wherein $R_9$ is selected from H, —OH and —$OSO_2NR_1R_2$ (in one aspect $R_9$ is —$OSO_2NR_1R_2$), and wherein at least one of $R_3$, $R_4$, $R_5$, $R_6$ and $R_7$ is —Y—$R_8$ and at least one of $R_3$, $R_4$, $R_5$, $R_6$ and $R_7$ is or comprises a groups selected from cyano (—CN), nitro (—$NO_2$), H-bond acceptors, and halogens.

In a further aspect the present invention provides a compound of Formula II

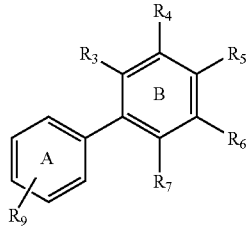

Formula II wherein $R_3$, $R_4$, $R_5$, $R_6$ and $R_7$ are independently selected from H and —Y—$R_8$
wherein each $R_8$ is independently selected from —OH, hydrocarbyl groups, oxyhydrocarbyl groups, cyano (—CN), nitro (—$NO_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein Y is an optional linker group; and
wherein ring A is optionally further substituted
wherein $R_9$ is selected from H, —OH and —$OSO_2NR_1R_2$ (in one aspect $R_9$ is —$OSO_2NR_1R_2$)
wherein $R_1$ and $R_2$ are independently selected from H and hydrocarbyl
wherein four of $R_3$, $R_4$, $R_5$, $R_6$ and $R_7$ are H and one of $R_3$, $R_4$, $R_5$, $R_6$ and $R_7$ is —Y—$R_8$.

In a further aspect the present invention provides a compound of Formula III

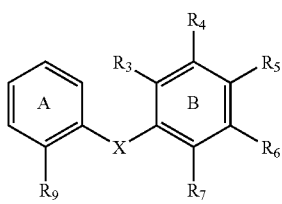

Formula III wherein $R_3$, $R_4$, $R_5$, $R_6$ and $R_7$ are independently selected from H and —Y—$R_8$
wherein each $R_8$ is independently selected from —OH, hydrocarbyl groups, oxyhydrocarbyl groups, cyano (—CN), nitro (—$NO_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein X is a bond or a linker group
wherein Y is an optional linker group; and
wherein ring A is optionally further substituted
wherein $R_9$ is selected from H, —OH and —$OSO_2NR_1R_2$ (in one aspect $R_9$ is —$OSO_2NR_1R_2$)
wherein $R_1$ and $R_2$ are independently selected from H and hydrocarbyl
wherein
(a) X is a bond and at least one of $R_3$, $R_4$, $R_5$, $R_6$ and $R_7$ is —Y—$R_8$; OR
(b) $R_9$ is —$OSO_2NR_1R_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

In this aspect $R_3$ is —Y—$R_8$ and/or $R_4$ is —Y—$R_8$ and/or $R_5$ is —Y—$R_8$ and/or $R_6$ is —Y—$R_8$ and/or $R_7$ is —Y—$R_8$.

In a further aspect the present invention provides a compound of Formula IIa

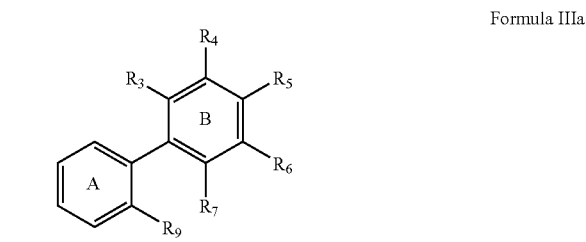

Formula IIIa wherein $R_3$, $R_4$, $R_5$, $R_6$ and $R_7$ are independently selected from H and —Y—$R_8$
wherein each $R_8$ is independently selected from —OH, hydrocarbyl groups, oxyhydrocarbyl groups, cyano (—CN), nitro (—$NO_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein Y is an optional linker group; and
wherein ring A is optionally further substituted
wherein $R_9$ is selected from H, —OH and —$OSO_2NR_1R_2$ (in one aspect $R_9$ is —$OSO_2NR_1R_2$)
wherein $R_1$ and $R_2$ are independently selected from H and hydrocarbyl
wherein
(a) X is a bond and at least one of $R_3$, $R_4$, $R_5$, $R_6$ and $R_7$ is —Y—$R_8$; OR
(b) $R_9$ is —$OSO_2NR_1R_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

In this aspect $R_3$ is —Y—$R_8$ and/or $R_4$ is —Y—$R_8$ and/or $R_5$ is —Y—$R_8$ and/or $R_6$ is —Y—$R_8$ and/or $R_7$ is —Y—$R_8$.

In a further aspect the present invention provides a compound of Formula IV

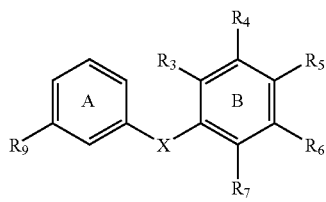

Formula IV wherein $R_3$, $R_4$, $R_5$, $R_6$ and $R_7$ are independently selected from H and —Y—$R_8$
wherein each $R_5$ is independently selected from —OH, hydrocarbyl groups, oxyhydrocarbyl groups, cyano (—CN), nitro (—$NO_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein X is a bond or a linker group
wherein Y is an optional linker group; and
wherein ring A is optionally further substituted
wherein $R_9$ is selected from H, —OH and —$OSO_2NR_1R_2$ (in one aspect $R_9$ is —$OSO_2NR_1R_2$)
wherein $R_1$ and $R_2$ are independently selected from H and hydrocarbyl wherein
(a) X is a bond and at least one of $R_3$, $R_4$, $R_5$, $R_6$ and $R_7$ is —Y—$R_8$; OR
(b) $R_9$ is —$OSO_2NR_1R_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

In this aspect $R_3$ is —Y—$R_8$ and/or $R_4$ is —Y—$R_8$ and/or $R_5$ is —Y—$R_8$ and/or $R_6$ is —Y—$R_8$ and/or $R_7$ is —Y—$R_8$.

In a further aspect the present invention provides a compound of Formula IVa

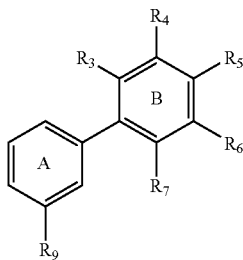

Formula IVa wherein $R_3$, $R_4$, $R_5$, $R_6$ and $R_7$ are independently selected from H and —Y—$R_8$
wherein each $R_5$ is independently selected from —OH, hydrocarbyl groups, oxyhydrocarbyl groups, cyano (—CN), nitro (—$NO_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein Y is an optional linker group; and
wherein ring A is optionally further substituted
wherein $R_9$ is selected from H, —OH and —$OSO_2NR_1R_2$ (in one aspect $R_9$ is —$OSO_2NR_1R_2$)
wherein $R_1$ and $R_2$ are independently selected from H and hydrocarbyl
wherein
(a) X is a bond and at least one of $R_3$, $R_4$, $R_5$, $R_6$ and $R_7$ is —Y—$R_8$; OR
(b) $R_9$ is —$OSO_2NR_1R_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

In this aspect $R_3$ is —Y—$R_8$ and/or $R_4$ is —Y—$R_8$ and/or $R_5$ is —Y—$R_8$ and/or $R_6$ is —Y—$R_8$ and/or $R_7$ is —Y—$R_8$.

In a further aspect the present invention provides a compound of Formula V

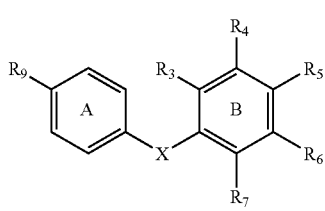

Formula V wherein $R_3$, $R_4$, $R_5$, $R_6$ and $R_7$ are independently selected from H and —Y—$R_8$
wherein each $R_5$ is independently selected from —OH, hydrocarbyl groups, oxyhydrocarbyl groups, cyano (—CN), nitro (—$NO_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein Y is an optional linker group; and
wherein ring A is optionally further substituted
wherein $R_9$ is selected from H, —OH and —$OSO_2NR_1R_2$ (in one aspect $R_9$ is —$OSO_2NR_1R_2$)
wherein $R_1$ and $R_2$ are independently selected from H and hydrocarbyl
wherein
(a) X is a bond and at least one of $R_3$, $R_4$, $R_5$, $R_6$ and $R_7$ is —Y—$R_8$; OR
(b) $R_9$ is —$OSO_2NR_1R_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

In this aspect $R_3$ is —Y—$R_8$ and/or $R_4$ is —Y—$R_8$ and/or $R_5$ is —Y—$R_8$ and/or $R_6$ is —Y—$R_8$ and/or $R_7$ is —Y—$R_8$.

In a further aspect the present invention provides a compound of Formula Va

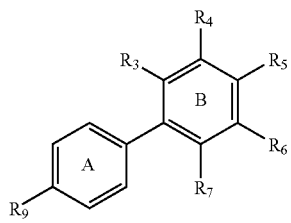

Formula Va wherein $R_3$, $R_4$, $R_5$, $R_6$ and $R_7$ are independently selected from H and —Y—$R_8$
wherein each $R_8$ is independently selected from —OH, hydrocarbyl groups, oxyhydrocarbyl groups, cyano (—CN), nitro (—$NO_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein Y is an optional linker group; and
wherein ring A is optionally further substituted
wherein $R_9$ is selected from H, —OH and —$OSO_2NR_1R_2$ (in one aspect $R_9$ is —$OSO_2NR_1R_2$)
wherein $R_1$ and $R_2$ are independently selected from H and hydrocarbyl
wherein
(a) X is a bond and at least one of $R_3$, $R_4$, $R_5$, $R_6$ and $R_7$ is —Y—$R_8$; OR
(b) $R_9$ is —$OSO_2NR_1R_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

In this aspect $R_3$ is —Y—$R_8$ and/or $R_4$ is —Y—$R_8$ and/or $R_5$ is —Y—$R_8$ and/or $R_6$ is —Y—$R_8$ and/or $R_7$ is —Y—$R_8$.

In a further aspect the present invention provides a compound of Formula VI

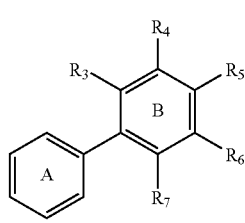

Formula VI wherein $R_3$, $R_4$, $R_5$, $R_6$ and $R_7$ are independently selected from H and —Y—$R_8$ wherein each $R_5$ is independently selected from —OH, hydrocarbyl groups, oxyhydrocarbyl groups, cyano (—CN), nitro (—NO$_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein Y is an optional linker group; and
wherein ring A is optionally substituted
wherein $R_1$ and $R_2$ are independently selected from H and hydrocarbyl
wherein
  (a) X is a bond and at least one of $R_3$, $R_4$, $R_5$, $R_6$ and $R_7$ is —Y—$R_8$; OR
  (b) $R_9$ is —OSO$_2$NR$_1$R$_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

In this aspect $R_3$ is —Y—$R_8$ and/or $R_4$ is —Y—$R_8$ and/or $R_5$ is —Y—$R_8$ and/or $R_6$ is —Y—$R_8$ and/or $R_7$ is —Y—$R_8$.

X

As discussed herein linker X is a linker group or is a bond. In one aspect X is a linker group. In one aspect X is a bond. It will be appreciated by one skilled in the art that when X is a bond the present invention provides a compound of the formula

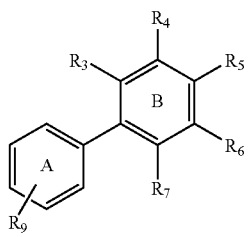

wherein $R_3$, $R_4$, $R_5$, $R_6$ and $R_7$ are independently selected from H and —Y—$R_8$
wherein each $R_5$ is independently selected from —OH, hydrocarbyl groups, oxyhydrocarbyl groups, cyano (—CN), nitro (—NO$_2$), H-bond acceptors, and halogens;
wherein at least one of $R_3$, $R_4$, $R_5$, $R_6$ and $R_7$ is —Y—$R_8$
wherein $R_8$ is selected from substituted and unsubstituted heterocyclic rings and amino substituted phenyl groups,
wherein Y is an optional linker group; and
wherein ring A is optionally further substituted
wherein $R_9$ is selected from H, —OH and —OSO$_2$NR$_1$R$_2$
wherein $R_1$ and $R_2$ are independently selected from H and hydrocarbyl
wherein
  (a) X is a bond and at least one of $R_3$, $R_4$, $R_5$, $R_6$ and $R_7$ is —Y—$R_8$; OR
  (b) $R_9$ is —OSO$_2$NR$_1$R$_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

The aspect wherein X is a bond is applicable to each of the preferred aspects described herein for example the aspect shown in preferred Formulae II to VI.

Preferably X is selected from, or when X is a linker it is selected from, a bond, hydrocarbyl, oxyhydrocarbyl, thiohydrocarbyl, COO, CO, S, O, SO, SO$_2$, NR, and SO$_2$NR, wherein R is selected from H and hydrocarbyl groups.

Preferably X is selected from hydrocarbyl, oxyhydrocarbyl, thiohydrocarbyl, COO, CO, S, O, SO, SO$_2$, NR, and SO$_2$NR, wherein R is selected from H and hydrocarbyl groups.

Preferably X is selected from —CH$_2$—S—, —C≡C—, —CH$_2$—O—, —O—, and —CH$_2$CH$_2$—.

The term "thiohydrocarbyl group" as used herein means a group comprising at least S, C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the thiohydrocarbyl group may contain hetero atoms. Suitable hetero atoms will be apparent to those skilled in the art and include, for instance, nitrogen and oxygen.

When X is a hydrocarbyl group or in the option that X may be a hydrocarbyl group, preferably the hydrocarbyl group is a straight of branched alkyl group.

When X is a hydrocarbyl group or in the option that X may be a hydrocarbyl group, preferably the hydrocarbyl group is a straight chain alkyl group.

When X is a oxyhydrocarbyl group or in the option that X may be a oxyhydrocarbyl group, preferably the oxyhydrocarbyl group is —O-alkyl-, wherein alkyl is a straight of branched alkyl group.

When X is a oxyhydrocarbyl group or in the option that X may be a oxyhydrocarbyl group, preferably the oxyhydrocarbyl group is —O-alkyl-, wherein alkyl is a straight chain alkyl group In one preferred aspect X is selected from groups selected from —O—, —C≡C—, (CH$_2$)$_n$, CH=CH (preferably trans configuration), O(CH$_2$)$_n$, (CH$_2$)$_n$O, S(CH$_2$)$_n$, (CH$_2$)$_n$S, CO(CH$_2$)$_n$, (CH$_2$)$_n$CO, CONH(CH$_2$)$_n$, (CH$_2$)$_n$CONH, COO(CH$_2$)$_n$, (CH$_2$)$_n$COO, SO(CH$_2$)$_n$, (CH$_2$)$_n$SO, SO$_2$(CH$_2$)$_n$, (CH$_2$)$_n$SO$_2$, SO$_2$NC$_{1-6}$alkyl(CH$_2$)$_n$ (such as SO$_2$NMe(CH$_2$)n), (CH$_2$)$_n$SO$_2$NC$_{1-6}$alkyl (such as (CH$_2$)$_n$SO$_2$NMe); SO$_2$NH(CH$_2$)$_n$, and (CH$_2$)$_n$SO$_2$NH; wherein n is independently an integer from 0 to 6. Preferably n is independently an integer from 1 to 6, more preferably from 1 to 3, such as 1, 2 or 3.

In one preferred aspect X is selected from groups selected from —O—, —C≡C—, (CH$_2$)$_n$, O(CH$_2$)$_n$, (CH$_2$)$_n$O, S(CH$_2$)$_n$, (CH$_2$)$_n$S, CO(CH$_2$)$_n$, (CH$_2$)$_n$CO, CONH(CH$_2$)$_n$, (CH$_2$)$_n$CONH, COO(CH$_2$)$_n$, (CH$_2$)$_n$COO, SO(CH$_2$)$_n$, (CH$_2$)$_n$ SO, SO$_2$(CH$_2$)$_n$, (CH$_2$)$_n$SO$_2$, SO$_2$NH(CH$_2$)$_n$, and (CH$_2$)$_n$ SO$_2$NH; wherein n is independently an integer from 0 to 6. Preferably n is independently an integer from 1 to 6, more preferably from 1 to 3, such as 1, 2 or 3.

In one preferred aspect X is selected from groups selected from —O—, —C≡C—, OCH$_2$, and SCH$_2$.

Y

In one preferred aspect Y is selected from hydrocarbyl, oxyhydrocarbyl, COO, CO, S, O, SO, SO$_2$, NR, and SO$_2$NR, wherein R is selected from H and hydrocarbyl groups.

In one preferred aspect Y is selected from hydrocarbyl, CO, and SO$_2$.

When Y is a hydrocarbyl group or in the option that Y may be a hydrocarbyl group, preferably the hydrocarbyl group is a straight of branched alkyl group.

When Y is a hydrocarbyl group or in the option that Y may be a hydrocarbyl group, preferably the hydrocarbyl group is a straight chain alkyl group.

In one preferred aspect Y is selected from groups selected from C$_m$H$_{2m}$ such as (CH$_2$)$_m$, CO(CH$_2$)$_m$, (CH$_2$)$_m$CO, SO$_2$(CH$_2$)$_m$ and wherein m is independently an integer from 0 to 6. Preferably m is independently an integer from 1 to 6, more preferably from 1 to 3, such as 1, 2 or 3.

In another preferred aspect Y is $C_mH_{2m}$ such as $(CH_2)_m$, wherein m is an integer from 0 to 6, preferably an integer from 1 to 6, more preferably from 1 to 3, such as 1, 2 or 3. In another preferred aspect Y is —$CH_2$— or —$C(CH_3)_2$—.

R8

$R_8$ may be selected from any suitable substituents. For example $R_8$ may be selected from hydrocarbyl, oxyhydrocarbyl, thiohydrocarbyl, halogens, —CN, COO, CO, S, O, SO, $SO_2$, NR, and $SO_2NR$, wherein R is selected from H and hydrocarbyl groups. However at least one $R_8$ is selected from substituted and unsubstituted heterocyclic rings and amino substituted phenyl groups.

Preferably at least one $R_8$ is selected from or each $R_8$ is selected from hydrocarbyl, oxyhydrocarbyl, halogens, and —CN.

In respect of $R_8$, preferred hydrocarbyl and oxyhydrocarbyl are cyclic groups.

$R_8$ need not be a cyclic structure. In this regard, $R_8$ may be a linear structure that may have the ability to conform to a ring like structure when in in vivo. However in preferred aspects $R_8$ is a cyclic structure.

$R_8$ may be a heterocyclic group (a heterocycle) or a non-heterocyclic group. Suitable hetero atoms of a heterocyclic group include N, S and O. Preferably R is a heterocyclic group wherein the ring comprises carbon and nitrogen.

When hetero atoms are present in a ring system to provide a heterocyclic group, the hetero atoms may be present in any amount. In one preferred aspect $R_8$ is a ring system comprising carbon and one or more hetero atoms selected from N, S and O.

$R_8$ may be is a saturated ring structure or an unsaturated ring structure (such as an aryl group).

Preferably, $R_8$ is an aryl ring.

In one aspect of the invention at least one $R_8$ is selected from or each $R_8$ is selected from substituted or unsubstituted aromatic rings.

In one aspect at least one $R_8$ is selected from or each $R_8$ is selected from polycyclic groups, which need not be a fused polycycle. The term "polycyclic" includes fused and non-fused ring structures including combinations thereof. If the ring system of $R_8$ is polycyclic some or all of the ring components of the ring system may be fused together or joined via one or more suitable spacer groups.

The ring size of $R_8$ may be chosen by one skilled in the art to achieve compounds having desired activity. Typically $R_8$ is a ring system comprising from 3 to 10 members, such as ring systems comprising from 5, 6 or 7 members.

Heterocyclic ring systems for use in the present invention include imidazole, tetrazole, pyrazole, triazole, such as 1H-1,2,3-triazole, 1H-1,2,4-triazole, 4H-1,2,4-triazole; optionally substituted 5- or 6-membered heterocyclic group containing 1 to 3 hetero atoms each selected from N, O and S, optionally substituted aryl (monocyclic or polycyclic aromatic), pyridazine, pyrimidine, pyridine, triazine such as 1,3,5 triazine, and optionally substituted bicyclic condensed heterocyclic group consisting of the above heterocyclic group condensed with benzene.

In one preferred aspect at least one $R_8$ is selected from or each $R_8$ is selected from ring systems described herein, halogens, and —CN.

In one preferred aspect at least one $R_8$ is selected from or each $R_8$ is selected from —CN, halogens and ring systems comprising carbon and one, two or three hetero atoms.

In one preferred aspect at least one $R_8$ is selected from or each $R_8$ is selected from —CN, halogens and ring systems comprising carbon and one or more hetero atoms selected from Nitrogen, Sulphur and Oxygen.

In one preferred aspect at least one $R_8$ is selected from or each $R_8$ is selected from —CN, halogens and heterocyclic ring systems, wherein the ring comprises carbon and nitrogen.

In one preferred aspect at least one $R_8$ is selected from or each $R_8$ is selected from cyano (—CN), halogens and 4H-1,2,4-triazole, 1H-1,2,4-triazole and 1H-1,2,3-triazole.

In one preferred aspect at least one $R_8$ is selected from or each $R_8$ is selected from 4H-1,2,4-triazole, 1H-1,2,4-triazole and 1H-1,2,3-triazole.

In one preferred aspect at least one $R_8$ is or each $R_8$ is 1H-1,2,4-triazole.

In another preferred aspect at least one $R_8$ is or each $R_8$ is

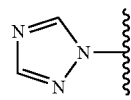

In one preferred aspect at least one of $R_3$, $R_4$, $R_5$, $R_6$ and $R_7$ is —Y—$R_8$ wherein $R_8$ is selected from substituted and unsubstituted heterocyclic rings.

In one preferred aspect at least one of $R_3$, $R_4$, $R_5$, $R_6$ and $R_7$ is —Y—$R_8$ wherein $R_8$ is selected from substituted and unsubstituted ring systems comprising carbon and one, two or three hetero atoms.

In one preferred aspect at least one of $R_3$, $R_4$, $R_5$, $R_6$ and $R_7$ is —Y—$R_8$ wherein $R_8$ is selected from substituted and unsubstituted ring systems comprising carbon and one or more hetero atoms selected from Nitrogen, Sulphur and Oxygen.

In one preferred aspect at least one of $R_3$, $R_4$, $R_5$, $R_6$ and $R_7$ is —Y—$R_8$ wherein $R_8$ is selected from substituted and unsubstituted heterocyclic ring systems, wherein the ring comprises carbon and nitrogen.

In one preferred aspect at least one of $R_3$, $R_4$, $R_5$, $R_6$ and $R_7$ is —Y—$R_8$ wherein $R_8$ is selected from substituted and unsubstituted heterocyclic ring systems comprising from 3 to 10 members.

In one preferred aspect at least one of $R_3$, $R_4$, $R_5$, $R_6$ and $R_7$ is —Y—$R_8$ wherein $R_8$ is selected from substituted and unsubstituted heterocyclic ring systems comprising from 5, 6 or 7 members.

In one preferred aspect at least one of $R_3$, $R_4$, $R_5$, $R_6$ and $R_7$ is —Y—$R_8$ wherein $R_8$ is selected from 4H-1,2,4-triazole, 1H-1,2,4-triazole and 1H-1,2,3-triazole.

In one preferred aspect at least one of $R_3$, $R_4$, $R_5$, $R_6$ and $R_7$ is —Y—$R_8$ wherein $R_8$ is 1H-1,2,4-triazole.

In one preferred aspect at least one of $R_3$, $R_4$, $R_5$, $R_6$ and $R_7$ is —Y—$R_8$ wherein —Y—$R_8$ is —$CH_2$-1H-1,2,4-triazole.

Thus according to one preferred aspect of the present invention, there is provided a compound of Formula I

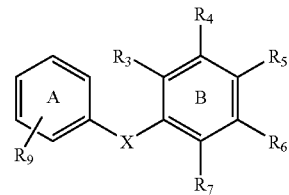

Formula I wherein $R_3$, $R_4$, $R_5$, $R_6$ and $R_7$ are independently selected from H and —Y—$R_8$ wherein each $R_8$ is independently selected from —OH, hydrocarbyl groups, oxyhydrocarbyl groups, cyano (—CN), nitro (—NO$_2$), H-bond acceptors, and halogens;

wherein at least one of $R_3$, $R_4$, $R_5$, $R_6$ and $R_7$ is —Y—R$_8$ wherein $R_8$ 1H-1,2,4-triazole;

wherein X is a bond or a linker group wherein Y is an optional linker group; and wherein ring A is optionally further substituted wherein $R_9$ is selected from H, —OH and —OSO$_2$NR$_1$R$_2$ wherein $R_1$ and $R_2$ are independently selected from H and hydrocarbyl wherein (a) X is a bond and at least one of $R_3$, $R_4$, $R_5$, $R_6$ and $R_7$ is —Y—R$_8$; OR (b) $R_9$ is —OSO$_2$NR$_1$R$_2$ or —OH, and four of $R_3$, $R_4$, $R_5$, $R_6$ and $R_7$ are H and one of $R_3$, $R_4$, $R_5$, $R_6$ and $R_7$ is —Y—R$_8$.

In one aspect $R_8$ may an amino substituted phenyl group. It will be understood by one skilled in the art that a typical amino substituted phenyl group is of the formula

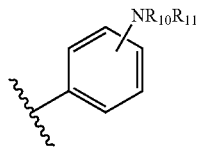

wherein $R_{10}$ and $R_{11}$ are independently selected from H and hydrocarbyl.

A preferred amino substituted phenyl group is of the formula

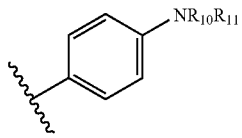

wherein $R_{10}$ and $R_{11}$ are independently selected from H and hydrocarbyl.

In one preferred aspect $R_{10}$ and $R_{11}$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups. When substituted, the amino phenyl groups may contain one or two N-alkyl, N-alkenyl, N-cycloalkyl or N-aryl substituents, preferably containing or each containing a maximum of 10 carbon atoms.

When $R_{10}$ and/or $R_{11}$ is hydrocarbyl, the preferred values are those where $R_1$ and $R_2$ are each independently selected $C_1$-$C_{10}$ hydrocarbyl, $C_1$-$C_5$ hydrocarbyl, $C_1$-$C_3$ hydrocarbyl, $C_1$-$C_{10}$ hydrocarbon, $C_1$-$C_5$ hydrocarbon, $C_1$-$C_3$ hydrocarbon, $C_1$-$C_{10}$ alkyl, $C_1$-$C_5$ alkyl and $C_1$-$C_3$ alkyl.

When $R_{10}$ and/or $R_{11}$ is alkyl, the preferred values are those where $R_{10}$ and $R_{11}$ are each independently selected from lower alkyl groups containing from 1 to 6 carbon atoms, that is to say methyl, ethyl, propyl etc. $R_{10}$ and $R_{11}$ may both be methyl.

When $R_{10}$ and/or $R_{11}$ is aryl, typical values are phenyl and tolyl (PhCH$_3$).

Where $R_{10}$ and/or $R_{11}$ represent cycloalkyl, typical values are cyclopropyl, cyclopentyl, cyclohexyl etc.

When joined together $R_{10}$ and $R_{11}$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

In some preferred embodiments, at least one of $R_{10}$ and $R_{11}$ is H.

In some further preferred embodiments, each of $R_{10}$ and $R_{11}$ is H.

$R_8$ may be substituted by one or more substituents. Typical substituents include hydrocarbyl, oxyhydrocarbyl, halo and cyano (—C≡N) groups. $R_8$ may also be substituted by one or more substituents selected from phosphonate groups, thiophosphonate groups, sulphonate groups and sulphonamide groups.

In one preferred aspect $R_8$ is unsubstituted.

—Y—R8

In one preferred aspect at least one or each —Y—R$_8$ is selected —CH$_2$-1H-1,2,4-triazole, —CN, —C(CH$_3$)$_2$—CN, and —F.

In another preferred aspect at least one or each —Y—R$_8$, Y is —CH$_2$— and $R_8$ is

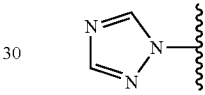

Thus in this aspect for at least one or each —Y—R$_8$, —Y—R$_8$ together are the group

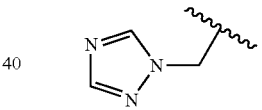

In another preferred aspect for at least one or each —Y—R$_8$, Y is not present and $R_8$ is —CN. Thus in this aspect for at least one or each —Y—R$_8$, —Y—R$_8$ together are the group —CN.

In another preferred aspect for at least one or each —Y—R$_8$, Y is —C(CH$_3$)$_2$— and $R_8$ is —CN. Thus in this aspect —Y—R$_8$ together are the group —C(CH$_3$)$_2$—CN.

In another preferred aspect for at least one or each —Y—R$_8$, Y is not present and $R_8$ is —F. Thus in this aspect for at least one or each —Y—R$_8$, —Y—R$_8$ together are the group —F.

In another preferred aspect at least one of $R_3$, $R_4$, $R_5$, $R_6$ and $R_7$ is —Y—R$_8$ wherein Y is —CH$_2$— and $R_8$ is

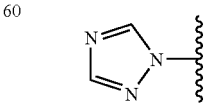

Thus in this aspect at least one of $R_3$, $R_4$, $R_5$, $R_6$ and $R_7$ is the group

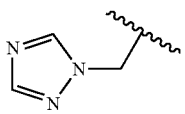

R9

As discussed herein $R_9$ is selected from H, —OH and —$OSO_2NR_1R_2$.

In a preferred aspect $R_9$ is selected from —OH and —$OSO_2NR_1R_2$.

In one aspect $R_9$ is H.

In a preferred aspect $R_9$ is —OH. We have found that the presence of the —OH may enhance the aromatase inhibitory activity of compounds of the present invention. In this respect the presence of this group is advantageous.

In a preferred aspect $R_9$ is —$OSO_2NR_1R_2$. We have found that the presence of the —$OSO_2NR_1R_2$ group provide steroid sulphatase inhibitory activity. In this respect the presence of this group is advantageous.

R1 & R2

In one preferred aspect $R_1$ and $R_2$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

In one preferred aspect at least one of $R_1$ and $R_2$ is H.

In one preferred aspect $R_1$ is H and $R_2$ is H.

Ring A

As noted herein the compounds of the present invention may comprise other substituents. These other substituents may, for example, further increase the activity of the compounds of the present invention and/or increase stability (ex vivo and/or in vivo). For example the ring denoted A and B in the general formulae may comprise other substituents. However in one preferred aspect rings A and B are independently not further substituted.

In one aspect ring A is further substituted.

If ring A is further substituted, the further substitution may be by groups selected from
- —OH, hydrocarbyl groups, oxyhydrocarbyl groups, cyano (—CN), nitro (—$NO_2$), H-bond acceptors, and halogens.
- C1-6 alkyl groups, C1-6 alkoxy groups, cyano (—CN), nitro (—$NO_2$) and halogens.
- —$CH_3$, —$CH_2CH_3$, —$OCH_3$, cyano (—CN), nitro (—$NO_2$) and halogens.

If ring A is further substituted the substituent may be attached to ring A at more than one point such that ring A and the substituent provide fused rings which form a polycyclic structure. For example ring A together with the optional further substituents may form a substituted or unsubstituted naphthalene ring or may form a substituted or unsubstituted dibenzofuranyl ring. Preferred substituents of the fused systems and in particular the naphthalene ring are —O-alkyl such as —OMe and —OH If ring A is further substituted, the further substitution is preferably a halogen and in particular, Cl, Br and/or F.

If ring A is further substituted, preferably ring A is substitution by only one further substituent, that is preferably a halogen and in particular, Cl, Br and/or F.

If ring A is substituted, preferably ring A is substituted by only one or two groups.

In a preferred aspect ring is A is optionally further substituted by groups selected —Cl, —OH, fused phenyl, phenyl, —OMe, —$OCH_2Ph$, —CN, —C(O)-Ph, —F, —O-Ph, —C(O)-Me, fused phenyl optional substituted with one of —OMe or —OH, and a fused heterocyclic group such that ring A forms a dibenzofuranyl.

In a preferred aspect ring A together with any optional substituents is selected from:

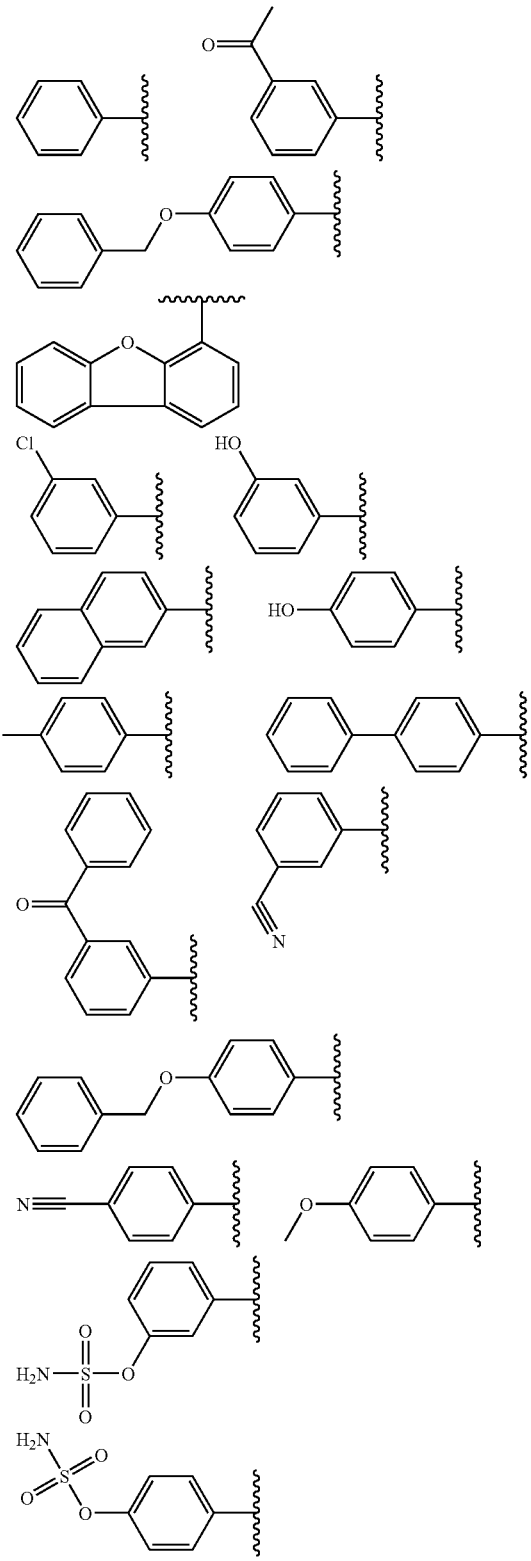

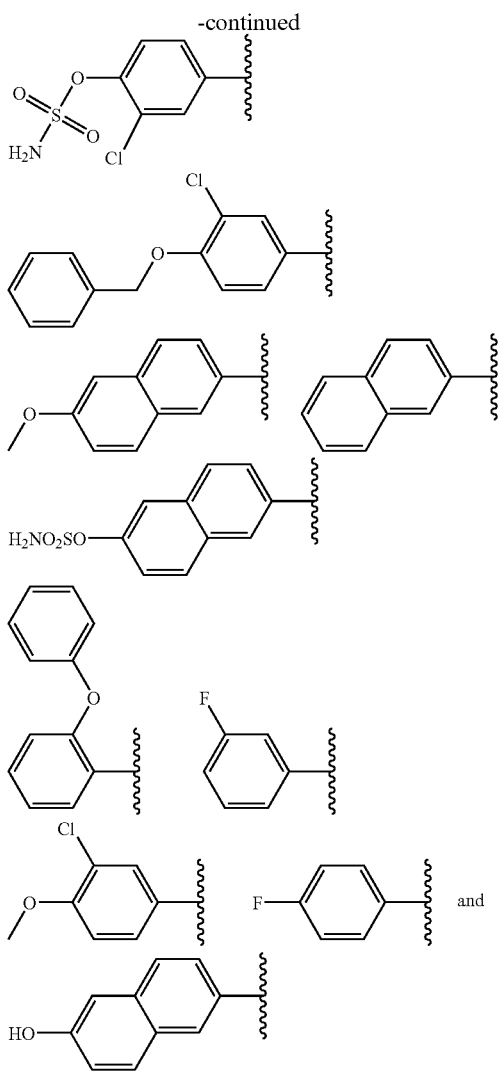

If R₉ is a sulphamate group and ring A is further substituted, preferably the further substituent is at a position on the ring ortho to the sulphamate group.

R3 to R7

As discussed herein $R_3$, $R_4$, $R_5$, $R_6$ and $R_7$ are independently selected from H and —Y—R₈, wherein each $R_5$ is independently selected from —OH, hydrocarbyl groups, oxyhydrocarbyl groups, cyano (—CN), nitro (—NO₂), H-bond acceptors, and halogens; with the proviso that (a) X is a bond and at least one of $R_3$, $R_4$, $R_5$, $R_6$ and $R_7$ is —Y—R₈ wherein R₈ is selected from substituted and unsubstituted heterocyclic rings and amino substituted phenyl groups; OR (b) R₉ is —OSO₂NR₁R₂ or —OH and four of $R_3$, $R_4$, $R_5$, $R_6$ and $R_7$ are H and one of $R_3$, $R_4$, $R_5$, $R_6$ and $R_7$ is —Y—R₈ wherein R₈ is selected from substituted and unsubstituted heterocyclic rings and amino substituted phenyl groups.

In one aspect X is a bond and at least $R_3$, $R_4$, $R_5$, $R_6$ and $R_7$ is —Y—R₈ (wherein R₈ is selected from substituted and unsubstituted heterocyclic rings and amino substituted phenyl groups).

In this aspect preferably at least one of $R_3$, $R_4$, $R_5$, $R_6$ and $R_7$ is —Y—R₈ wherein R₈ is selected from substituted and unsubstituted heterocyclic rings and amino substituted phenyl groups, and at least one of $R_3$, $R_4$, $R_5$, $R_6$ and $R_7$ is a —CN group.

In one aspect R₉ is —OSO₂NR₁R₂ and four of $R_3$, $R_4$, $R_5$, $R_6$ and $R_7$ are H and one of $R_3$, $R_4$, $R_5$, $R_6$ and $R_7$ is —Y—R₈. In this aspect it is possible that $R_3$, $R_4$, $R_6$ and $R_7$ are H and $R_5$ is —Y—R₈ (wherein R₈ is selected from substituted and unsubstituted heterocyclic rings and amino substituted phenyl groups), $R_3$, $R_5$, $R_6$ and $R_7$ are H and $R_4$ is —Y—R₈. (or $R_3$, $R_4$, $R_5$ and $R_7$ are H and $R_6$ is —Y—R₈) (wherein R₈ is selected from substituted and unsubstituted heterocyclic rings and amino substituted phenyl groups), $R_4$, $R_5$, $R_6$ and $R_7$ are H and $R_3$ is —Y—R₈ (or $R_3$, $R_4$, $R_5$ and $R_6$ are H and $R_7$ is —Y—R₈) (wherein R₈ is selected from substituted and unsubstituted heterocyclic rings and amino substituted phenyl groups), A preferred compound of the present invention is a compound selected from compounds of the formulae

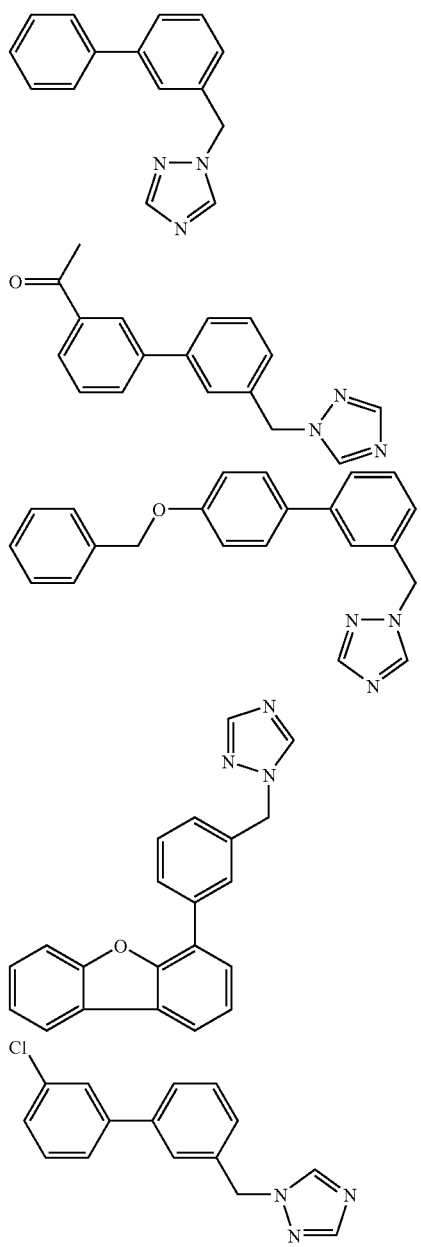

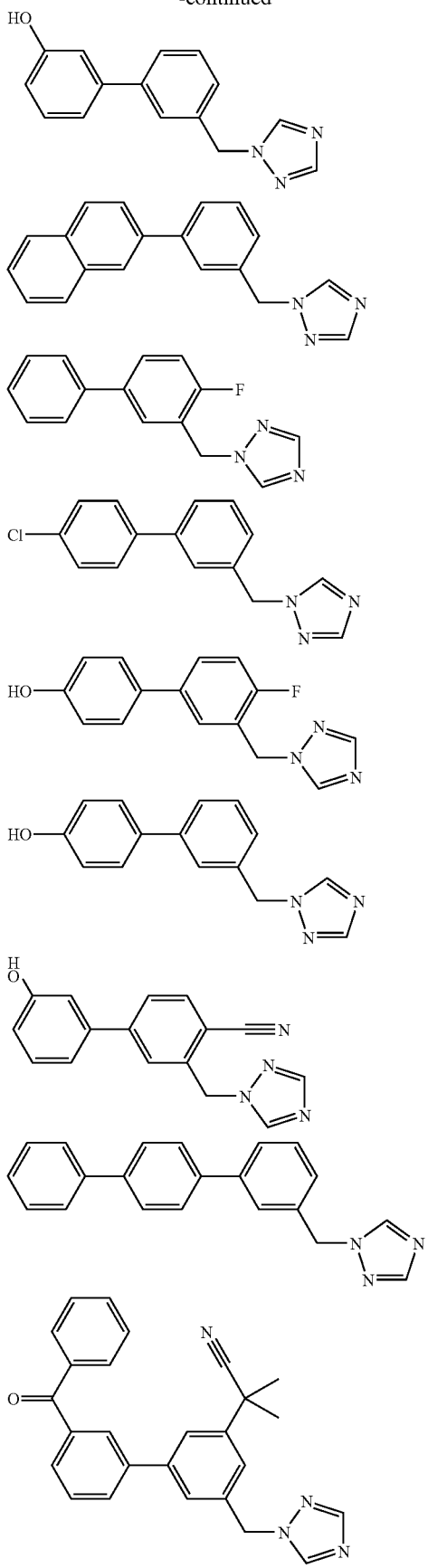
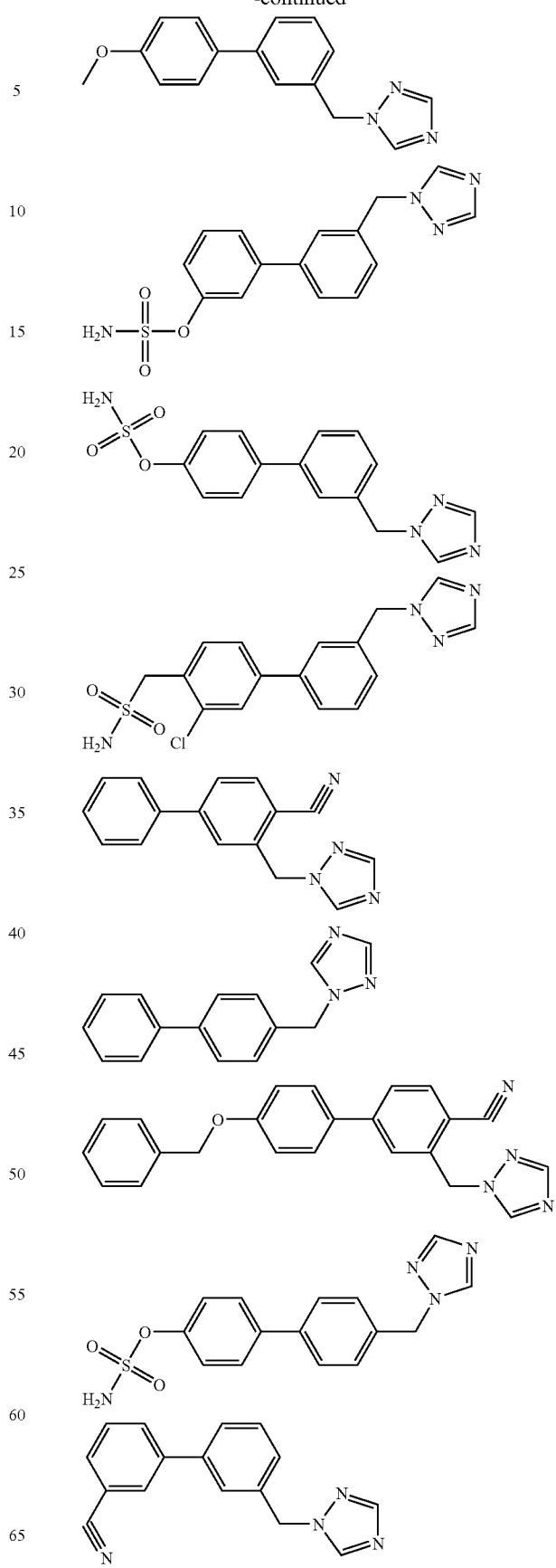

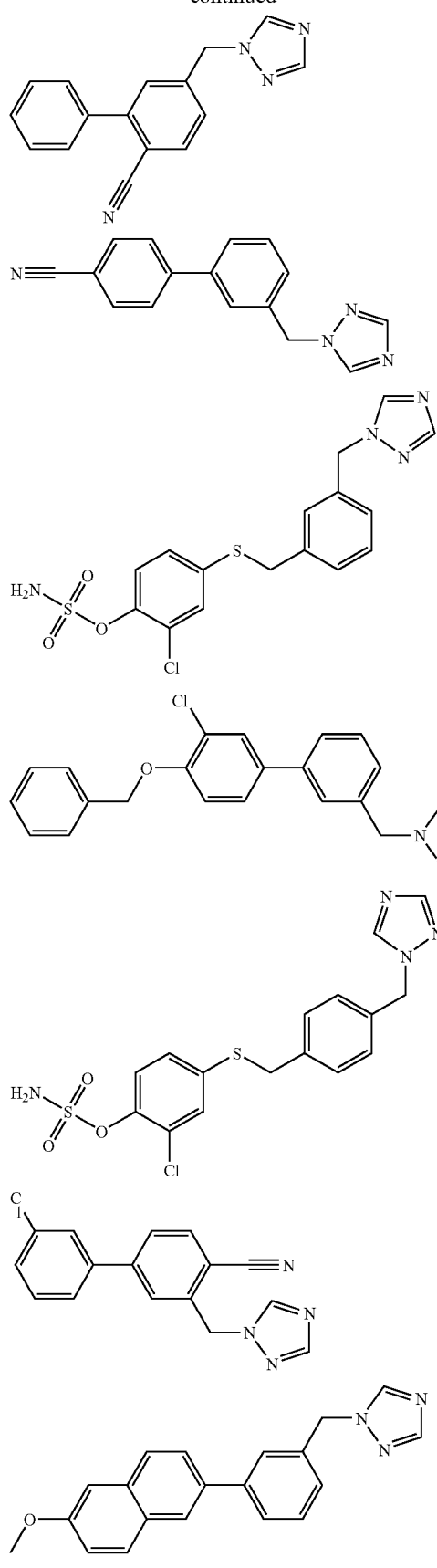
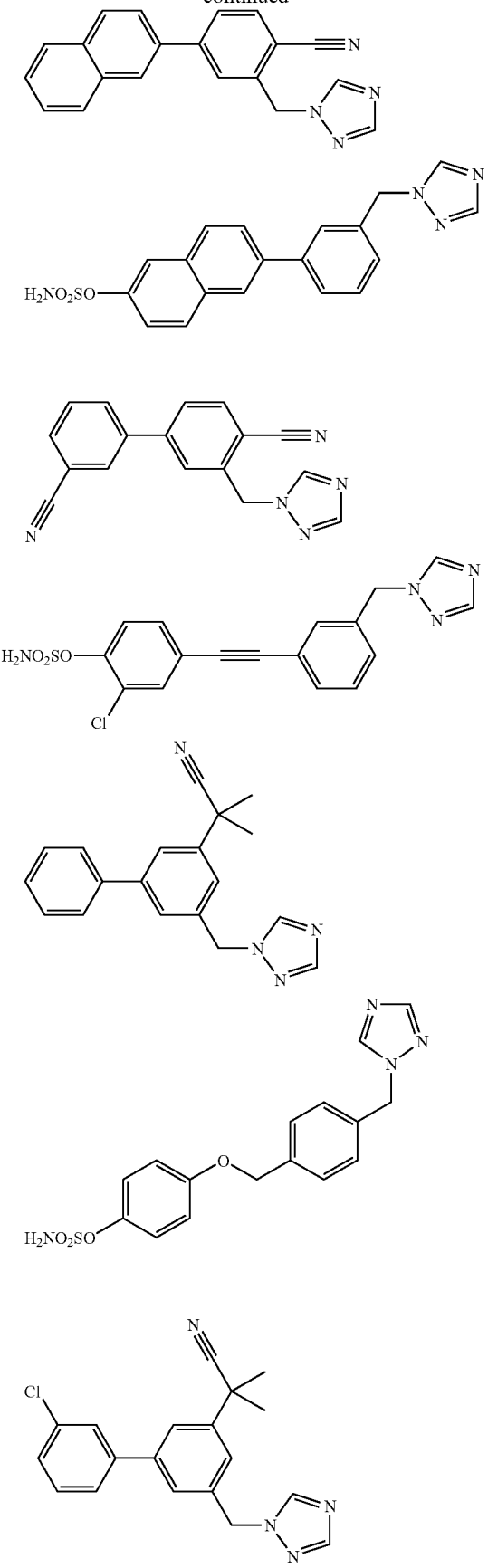

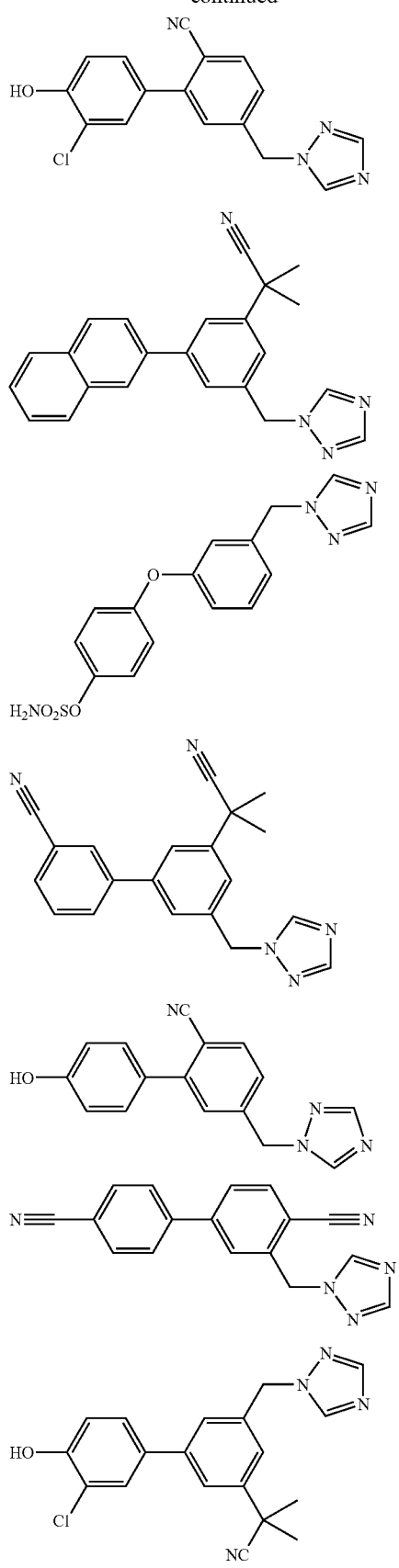
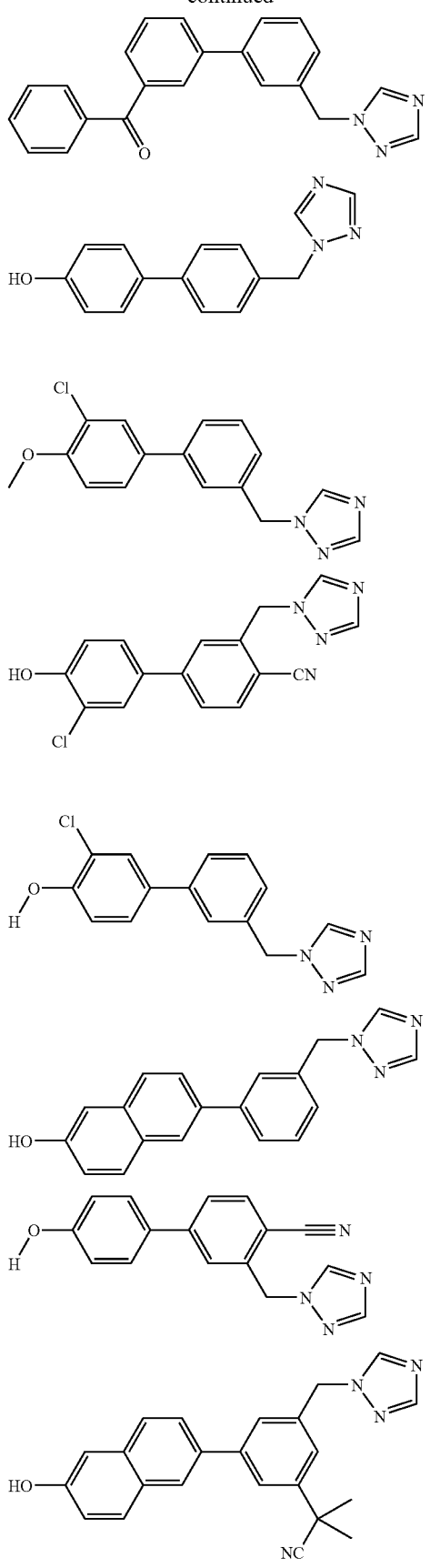

-continued
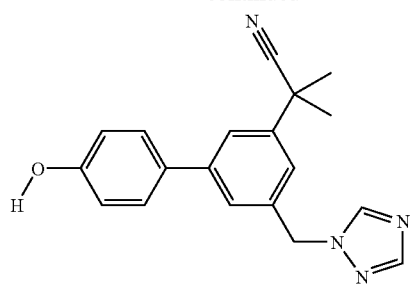
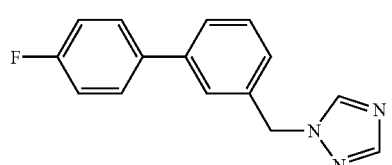
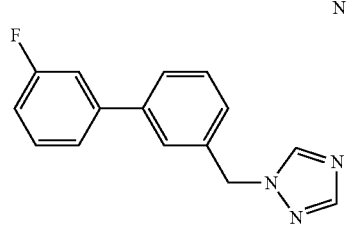
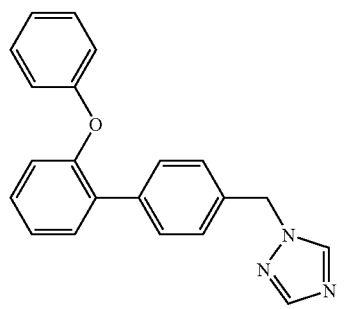
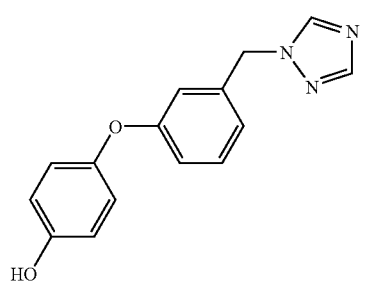
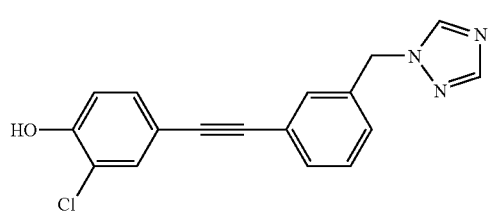
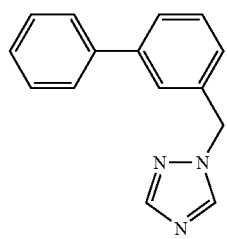
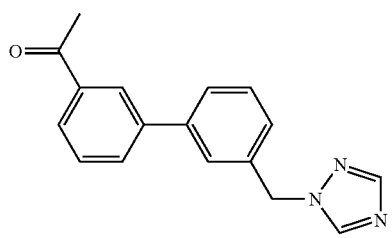
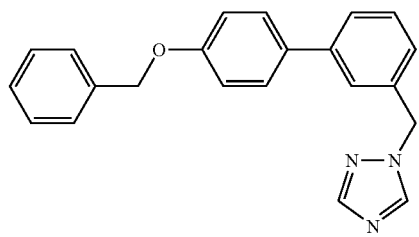
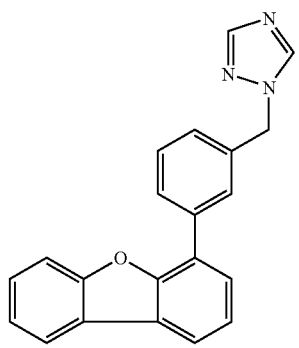
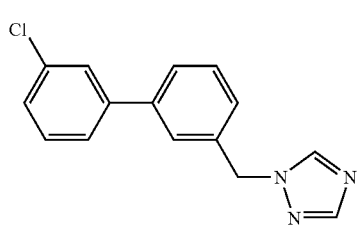
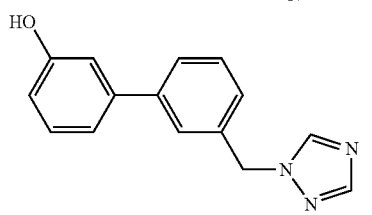
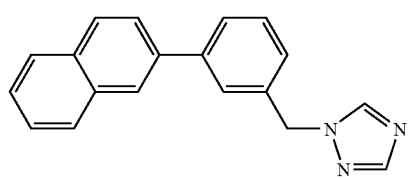
A preferred compound of the present invention is a compound selected from compounds of the formulae

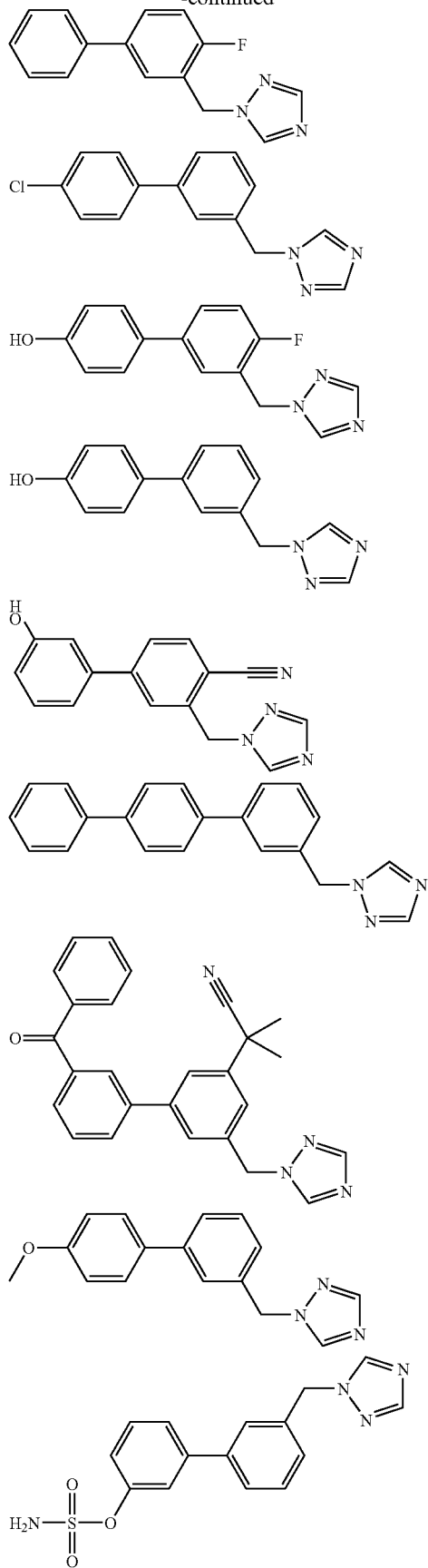
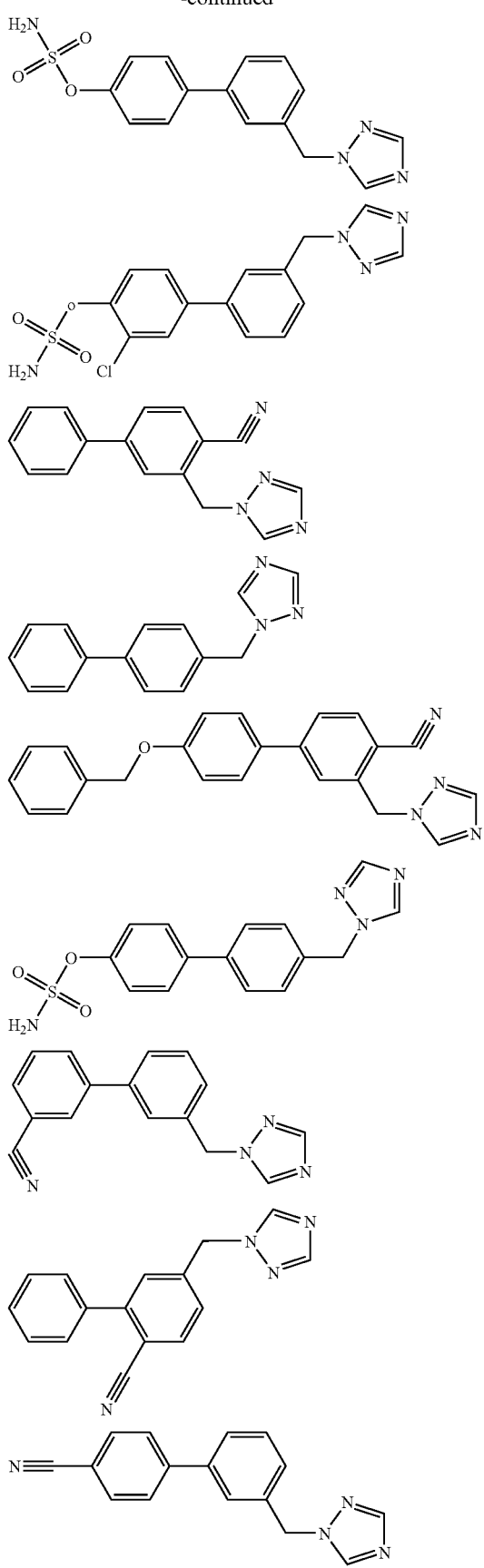

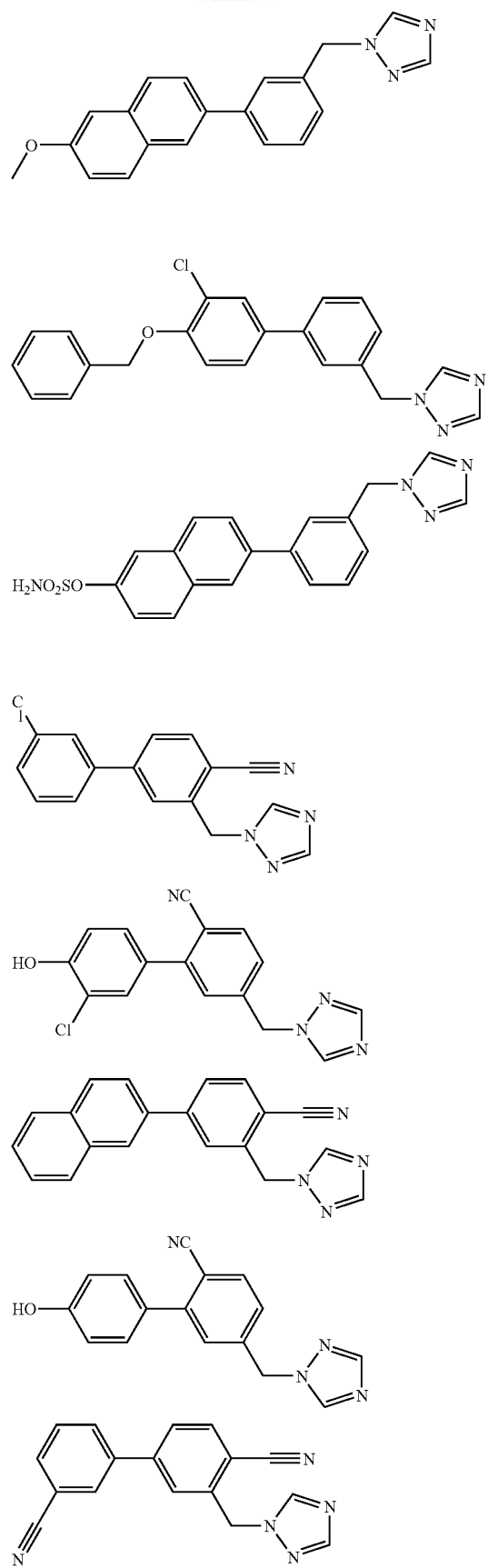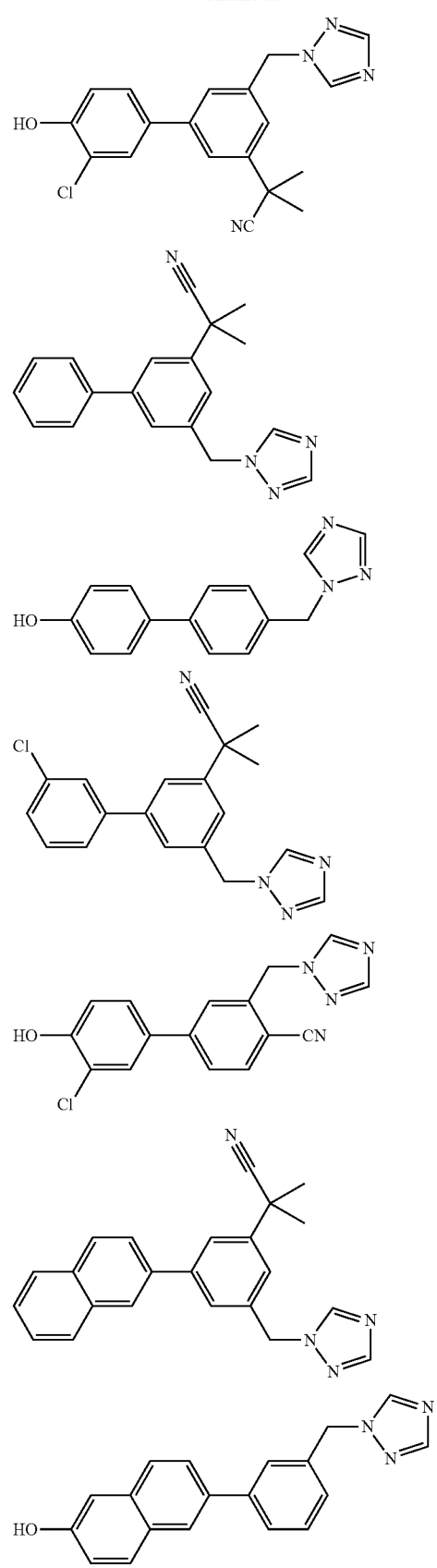

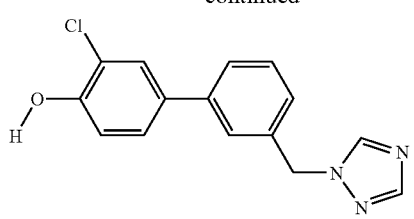
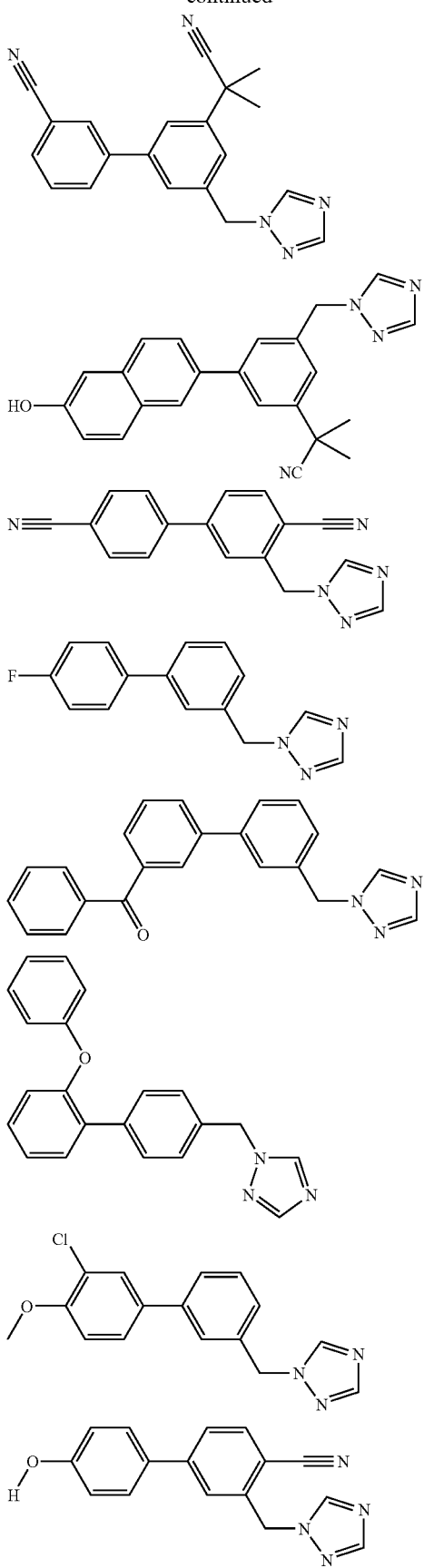
A preferred compound of the present invention is a compound selected from compounds of the formulae
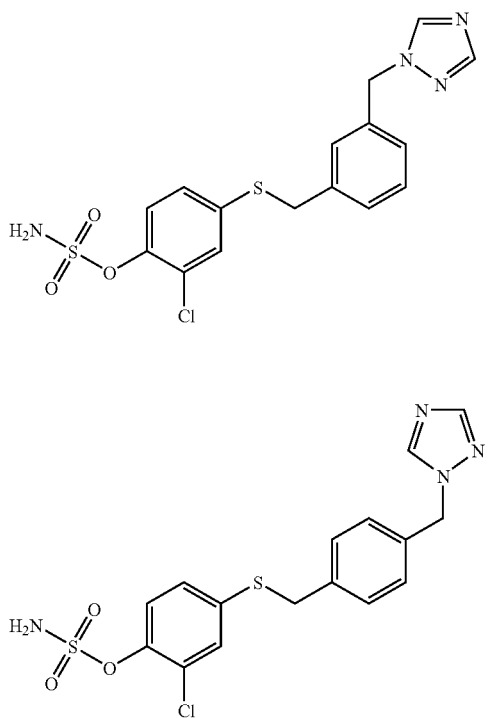

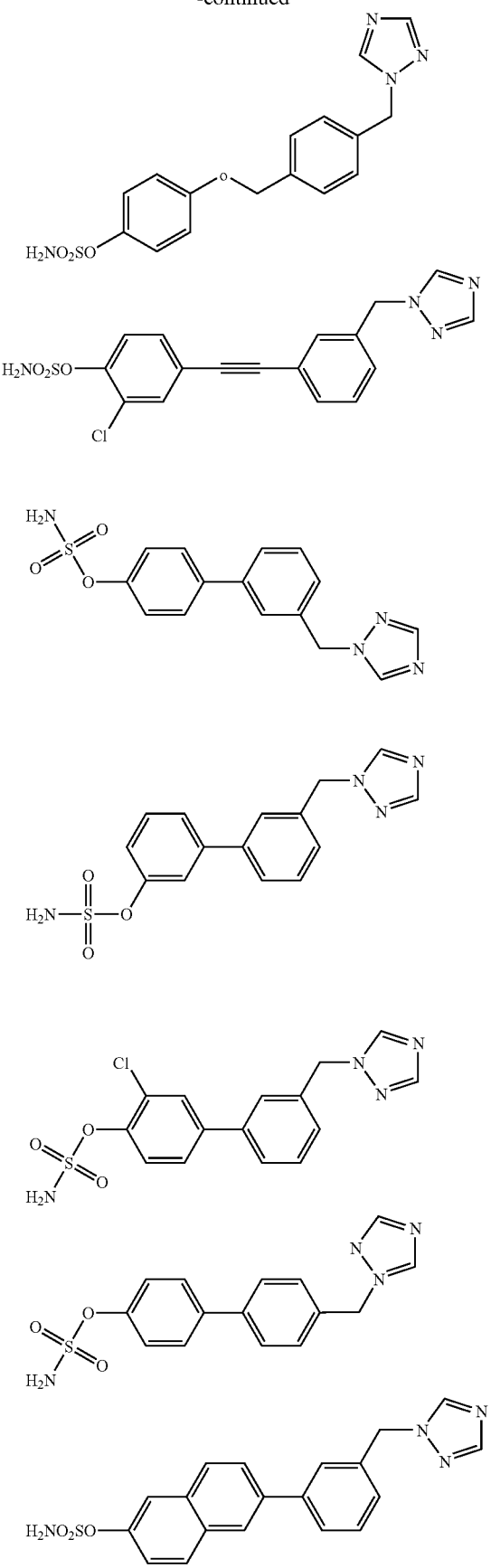

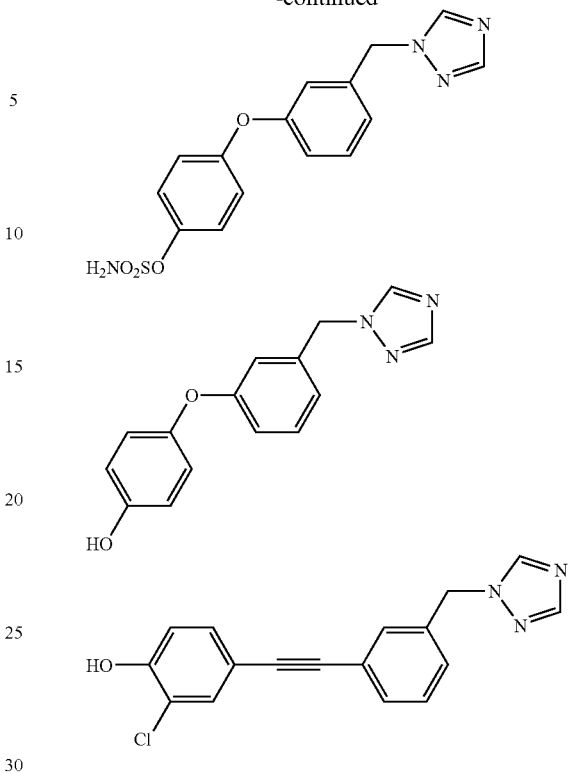

Other Aspects

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

In one embodiment, the compounds of the present invention are useful for the inhibition of a Cyp450 enzyme.

In one embodiment, the compounds of the present invention are useful for the inhibition of a Cyp17 enzyme.

In one embodiment, the compounds of the present invention are useful for the treatment of prostate cancer.

In one embodiment, the compounds of the present invention are useful for the inhibition of a Cyp11B2 enzyme.

In one embodiment, the compounds of the present invention are useful for the treatment of congestive heart failure.

In one embodiment, the compounds of the present invention are useful for the treatment of myocardial fybrosis.

The present invention also covers novel intermediates that are useful to prepare the compounds of the present invention and metabolites of the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

In one broad aspect, when $R_9$ is —$OSO_2NR_1R_2$ or —OH, each $R_8$ is independently selected from —OH, hydrocarbyl groups, oxyhydrocarbyl groups, cyano (—CN), nitro (—$NO_2$), H-bond acceptors, and halogens. Thus in this aspect the present invention provides a compound of Formula I

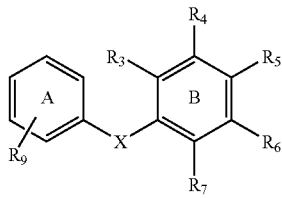

Formula I wherein $R_3$, $R_4$, $R_5$, $R_6$ and $R_7$ are independently selected from H and —Y—$R_8$
wherein each $R_8$ is independently selected from —OH, hydrocarbyl groups, oxyhydrocarbyl groups, cyano (—CN), nitro (—$NO_2$), H-bond acceptors, and halogens;
wherein X is a bond or a linker group
wherein Y is an optional linker group; and
wherein ring A is optionally further substituted
wherein $R_9$ is selected from H, —OH and —$OSO_2NR_1R_2$
wherein $R_1$ and $R_2$ are independently selected from H and hydrocarbyl
wherein
  (a) X is a bond and at least one of $R_3$, $R_4$, $R_5$, $R_6$ and $R_7$ is —Y—$R_8$ in which $R_8$ is selected from substituted and unsubstituted heterocyclic rings and amino substituted phenyl groups, or
  (b) $R_9$ is —$OSO_2NR_1R_2$ or —OH, and four of $R_3$, $R_4$, $R_5$, $R_6$ and $R_7$ are H and one of $R_3$, $R_4$, $R_5$, $R_6$ and $R_7$ is —Y—$R_8$.

Steroid Sulphatase

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454 (1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807-10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet. 1999 March; 29(2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact JEG3 choriocarcinoma cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

In one aspect, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

For some applications, preferably the compound of the present invention has at least about a 100 fold selectivity to a desired target (e.g. STS and/or aromatase), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS and/or aromatase activity.

Sulphamate Group

The term "sulphamate" as used herein includes an ester of sulphamic acid, or an ester of an N-substituted derivative of sulphamic acid, or a salt thereof.

If $R_9$ is a sulphamate group then the compound of the present invention is referred to as a sulphamate compound.

Typically, the sulphamate group has the formula:

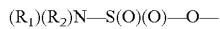

$(R_1)(R_2)N$—$S(O)(O)$—$O$— wherein preferably $R_1$ and $R_2$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms.

When $R_1$ and/or $R_2$ is hydrocarbyl, the preferred values are those where $R_1$ and $R_2$ are each independently selected $C_1$-$C_{10}$ hydrocarbyl, $C_1$-$C_5$ hydrocarbyl, $C_1$-$C_3$ hydrocarbyl, $C_1$-$C_{10}$ hydrocarbon, $C_1$-$C_5$ hydrocarbon, $C_1$-$C_3$ hydrocarbon, $C_1$-$C_{10}$ alkyl, $C_1$-$C_5$ alkyl and $C_1$-$C_3$ alkyl.

When $R_1$ and/or $R_2$ is alkyl, the preferred values are those where $R_1$ and $R_2$ are each independently selected from lower alkyl groups containing from 1 to 6 carbon atoms, that is to say methyl, ethyl, propyl etc. $R_1$ and $R_2$ may both be methyl.

When $R_1$ and/or $R_2$ is aryl, typical values are phenyl and tolyl ($PhCH_3$; o).

Where $R_1$ and/or $R_2$ represent cycloalkyl, typical values are cyclopropyl, cyclopentyl, cyclohexyl etc.

When joined together $R_1$ and $R_2$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on ring A.

In some embodiments, there may be more than one sulphamate group. By way of example, there may be two sulphamates (i.e. bis-sulphamate compounds).

In some preferred embodiments, at least one of $R_1$ and $R_2$ is H.

In some further preferred embodiments, each of $R_1$ and $R_2$ is H.

Other Substituents

The compound of the present invention may have substituents other than those of formula I. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more 0 groups, one or more hydroxy groups, one or more amino groups, one or more sulphur containing group(s), one or more hydrocarbyl group(s)—such as an oxyhydrocarbyl group.

Assay for Determining STS Activity Using Cancer Cells

Protocol 1

Inhibition of Steroid Sulphatase Activity in JEG3 Cells

Steroid sulphatase activity is measured in vitro using intact JEG3 choriocarcinoma cells. This cell line may be used to study the control of human breast cancer cell growth. It possesses significant steroid sulphatase activity (Boivin et al., J. Med. Chem., 2000, 43: 4465-4478) and is available in from the American Type Culture Collection (ATCC).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1 \times 10^5$ cells/flask using the above medium. Cells are grown to 80% confluency and the medium is changed every third day.

Intact monolayers of JEG3 cells in triplicate 25 $cm^2$ tissue culture flasks are washed with Earle's Balanced Salt Solution (EBSS from ICN Flow, High Wycombe, U.K.) and incubated for 3-4 hours at 37° C. with 5 μmol ($7 \times 10^5$ dpm) [6, 7-3H] oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone ($7 \times 103$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C]oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C]oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406-408; Academic Press, New York).

Results for steroid sulphatase activity are expressed as the mean±1 S.D. of the total product (oestrone+oestradiol) formed during the incubation period (3-4 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes

Protocol 2

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6, 7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 011mM; 0.2 mM; 0.4 mM; 0.6 mM; 0.8 mM; 1.0 mM. After incubation each sample is cooled and the medium (1 ml) was pipetted into separate tubes containing [14C]oestrone ($7 \times 10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C]oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity

Protocol 3

Inhibition of Oestrone Sulphatase Activity In Vivo

The compounds of the present invention may be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity

Protocol 4

The compounds of the present invention may be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight$\times$100.

Compounds having no significant effect on uterine growth are not oestrogenic.

Biotechnological Assays for Determining STS Activity

Protocol 5

The ability of compounds to inhibit oestrone sulphatase activity can also be assessed using amino acid sequences or nucleotide sequences encoding STS, or active fragments, derivatives, homologues or variants thereof in, for example, high-through put screens. Such assays and methods for their practice are taught in WO 03/045925 which is incorporated herein by reference.

In one preferred aspect, the present invention relates to a method of identifying agents that selectively modulate STS, which compounds have the formula (I).

Assay for Determining Aromatase Activity Using JEG3 Cells

Protocol 6

Aromatase activity is measured in JEG3 choriocarcinoma cells, obtained from the ATCC. This cell line possesses significant aromatase activity and is widely used to study the control of human aromatase activity (Bhatnager et al., J. Steroid Biochem. Molec. Biol. 2001, 76: 199-202). Cells are maintained in Minimal Essential Medium (MEM, Flow Laboratories, Irvine, Scotland) containing 20 mM HEPES, 10% foetal bovine serum, 2 mM glutamine, non-essential amino acids and 0.075% sodium bicarbonate. Intact monolayers of JEG3 cells ($2.5 \times 10^6$ cells) in triplicate 25 cm$^2$ tissue culture flasks are washed with Earle's Balanced salt solution (EBSS, from ICN Flow, High Wycombe, UK) and incubated with [β-3H]androstenedione (2-5 nM, 26 Ci/mmol, New England Nuclear, Boston, Mass., USA) for 30 min with inhibitors over the range of 10 pm-10 μM. During the aromatase reaction, $^3H_2O$ is liberated which can be quantified using a liquid scintillation spectrometer (Beckman-Coulter, High Wycombe, Bucks. UK). This $^3H_2O$-release method has been widely used to measure aromatase activity (Newton et al., J. Steroid Biochem. 1986, 24: 1033-1039). The number of cell nuclei per flask is determined using a Coulter Counter after treating the cell monolayers with Zaponin.

Results for aromatase activity are expressed as the mean±1 S.D. of the product formed during the incubation period (30 min) calculated for $10^6$ cells and, for values showing a statistical significance, as a percentage reduction (inhibition) over incubations containing no aromatase inhibitor. Unpaired Student's t test was used to test the statistical significance of results. IC$_{50}$ values were calculated as the concentration of inhibitor required to obtain a 50% inhibition of aromatase activity.

Animal Assays for Determining Aromatase Activity

Protocol 7

(i) Inhibition of PMSG-Induced Oestrogen Synthesis

The ability of compounds to inhibit aromatase activity in vivo was tested using a pregnant mare serum gonadotrophin (PMSG)-induced oestrogen synthesis assay. For this, female rats (250 g) were injected with PMSG (200 IU, s.c.). After 72 h rats were administered vehicle (propylene glycol) or various doses of test compounds orally. At 2 h after dosing blood samples were obtained by cardiac puncture (under anaesthesia). Plasma oestradiol levels were measured in control groups and groups receiving drugs. The efficacy of aromatase inhibition was determined by measurement of plasma oestradiol concentrations by radioimmunoassay. This method has been widely used to determine the effectiveness of aromatase inhibitors in vivo (Wouters et al., J. Steroid Biochem., 1989, 32: 781-788).

(ii) Inhibition of Androstenedione Stimulated Uterine Growth in Ovariectomised Rats Female rats (250 g) were ovariectomised and used to determine the effectiveness of aromatase inhibition on androstenedione stimulated uterine growth. Administration of androstenedione (30 mg/kg/d) for a 2-week period results in a significant increase in uterine growth in ovariectomised animals. This increase in uterine growth is stimulated by oestrogen which is derived from the administered androstenedione as a result of the action of the aromatase enzyme. By co-administration of compounds with androstenedione the extent of aromatase inhibition can be determined by measurements of uterine weights in treated and untreated animals.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4-hydroxyandrostenedione (4-OHA)) and/or steroids—such as the naturally occurring neurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds that are analogous to compound 5 presented herein.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)— such as TNF-α; Interferon alpha, beta and gamma; TGF-β. For some applications, preferably the cytokine is tumour necrosis factor (TNF). For some applications, the TNF may be any type of TNF—such as TNF-α, TNF-β, including derivatives or mixtures thereof. More preferably the cytokine is TNF-α. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2/M$ phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 7

Procedure
Stage 1

MCF-7 breast cancer cells are seeded into multi-well culture plates at a density of 105 cells/well. Cells were allowed to attach and grown until about 30% confluent when they are treated as follows:
Control—No Treatment
Compound of Interest (COI) 20CM Cells are grown for 6 days in growth medium containing the COI with changes of medium/COI every 3 days. At the end of this period cell numbers were counted using a Coulter cell counter.
Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.
Cancer As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2-OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in regulating TH1 cytokine response.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflamatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, hemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Compound Preparation

The compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R_3R_4NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059-2068).

The phosphonate compounds may be prepared by suitably combining the teachings of Page et al (1990 Tetrahedron 46; 2059-2068) and PCT/GB92/01586.

The sulphonate compounds may be prepared by suitably adapting the teachings of Page et al (1990 Tetrahedron 46; 2059-2068) and PCT/GB92/01586.

The thiophosphonate compounds may be prepared by suitably adapting the teachings of Page et al (1990 Tetrahedron 46; 2059-2068) and PCT/GB91/00270.

Preferred preparations are also presented in the following text.

SUMMARY

In summation, the present invention provides novel compounds for use as steroid sulphatase inhibitors and/or aromatase inhibitors and/or modulators of apoptosis and/or modulators of cell cycling and/or cell growth, and pharmaceutical compositions containing them.

EXAMPLES

The present invention will now be described in further detail by way of the following non-limiting example only with reference to the accompanying figure in which:—

FIG. 1 shows a summary scheme; and
FIG. 2 shows a summary scheme.

The present invention will now be described only by way of example. However, it is to be understood that the examples also present preferred compounds of the present invention, as well as preferred routes for making same and useful intermediates in the preparation of same.

EXPERIMENTAL

General Methods

NMR Spectra were recorded on Jeol 270 MHz or Bruker 400 MHz instruments. Low resolution mass spectra were obtained from a Micromass platform LCZ (APCI+). HPLC data was obtained from a Waters Alliance-HT-2790 machine with a Symmetry$^R$ C18 column. Unless otherwise stated HPLC grade solvents were used and commercial reagents and starting materials were used without further purification. Thin layer chromatography was undertaken using Kieselgel 60 $F_{254}$ plates (Merck). For automated chromatography the Arganaut parallel purification system Flashmaster II was used with Argonaut pre-packed silica columns of specified size. Elution methods employed:
method1: 0.00 min, 100% hexane; 5.00 min, 50% hexane, 50% EtOAc; 10.00 min, 50% hexane, 50% EtOAc; 12.00 min, 100% EtOAc; 20.00 min, 100% EtOAc; 20.01 min, 100% hexane; 25.00 min, 100% hexane.

method2: 0.00 min, 100% hexane; 5.00 min, 50% hexane, 50% EtOAc; 10.00 min, 50% hexane, 50% EtOAc; 12.50 min, 100% EtOAc; 25.00 min, 100% EtOAc; 25.01 min, 100% hexane; 30.00 min, 100% hexane.
method3: 0.00 min, 100% dichloromethane; 2.50 min, 100% hexane; 7.50 min, 50% hexane, 50% EtOAc; 12.50 min, 75% EtOAc, 25% dichloromethane; 15.00 min, 100% EtOAc; 25.00 min, 100% EtOAc; 25.01 min, 100% hexane; 30.00 min, 100% hexane.
method4: 0.00 min, 100% dichloromethane; 2.50 min, 100% hexane; 7.50 min, 50% hexane, 50% EtOAc; 12.50 min, 75% EtOAc, 25% dichloromethane; 20.00 min, 100% EtOAc; 30.00 min, 100% EtOAc; 30.01 min, 100% hexane; 35.00 min, 100% hexane.
method5: 0.00 min, 100% hexane; 10.00 min, 100% EtOAc; 20.00 min, 100% EtOAc; 20.01 min, 90% EtOAc, 10% MeOH; 25.00 min, 90% EtOAc, 10% MeOH; 25.01 min, 100% hexane; 30.00 min, 100% hexane.
method6: 0.00 min, 100% EtOAc; 20.00 min, 100% EtOAc; 20.01 min, 90% EtOAc, 10% MeOH; 30.00 min, 90% EtOAc, 10% MeOH; 30.01 min, 100% hexane; 35.00 min, 100% hexane.
method7: 0.00 min, 100% dcm; 7.50 min, 100% dcm; 7.51 min, 100% hexane; 20.00 min, 100% EtOAc; 30.00 min, 100% EtOAc; 30.01, 100% hexane; 35.00 min, 100% hexane.
method8: 0.00 min, 100% hexane; 5.00 min, 100% hexane; 15.00 min, 100% dcm; 25.00 min, 100% EtOAc; 35.00 min, 100% EtOAc; 35.01 min, 100% hexane; 40.00 min, 100% hexane.
method9: 0.00 min, 100% EtOAc; 25.00 min, 100% EtOAc; 25.01 min, 90% EtOAc, 10% MeOH; 35.00 min, 90% EtOAc, 10% MeOH; 35.01 min, 100% hexane; 38.00 min, 100% hexane.
method10: 0.00 min, 100% hexane; 10.00 min, 100% EtOAc; 20.00 min, 100% EtOAc; 20.01 min, 100% hexane; 25.00 min, 100% hexane.

Synthetic Routes

Compounds in accordance with the present invention were synthesised in accordance with the synthetic routes and schemes.

TJA02061

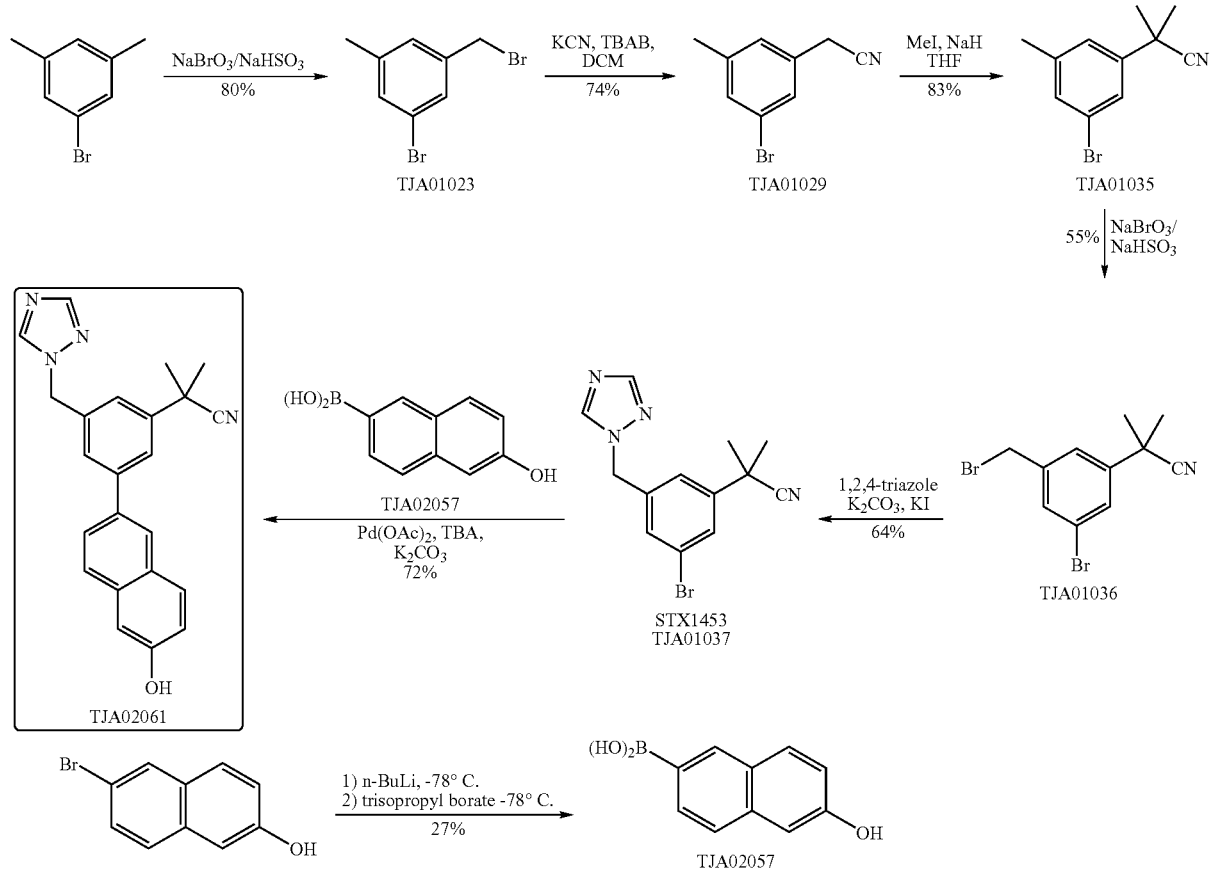

6-Hydroxynaphthalen-2-yl-2-boronic Acid (TJA02057)

$C_{10}H_9BO_3$ MW 187.99

A dry 250 ml r.b. flask was loaded with 6-bromo-2-naphthol (5.38 g, 24.1 mmol) and purged with $N_{2(g)}$. Anhydrous THF (80 mL) added with stirring and the vessel cooled to −78° C. (dry ice/acetone bath). After 30 mins n-BuLi, 2.3 M in hexanes, (12.9 mL, 28.9 mmol) was added dropwise over 20 min. The reaction was left to stir for 1 h. Triisopropyl borate (6.65 mL, 28.9 mmol) was added dropwise with the reaction still at −78° C. After 15 min of stirring at this temperature the dry ice/acetone bath was removed. At 0° C. 2 M $HCl_{(aq)}$ (5 mL) was added and the reaction left to stir for a further 15 min. THF removed under vacuum and residues taken up in distilled water (20 mL) and dichloromethane (50 mL) added. The resulting white precipitate was filtered and washed with dichloromethane and distilled water. Dried under vacuum at 70° C. to give the title compound as an off white solid (1.88 g, 43%).

$^1$H NMR (270 MHz, DMSO-d$_6$) δ 7.04-7.08 (2H, m, ArH), 7.58-7.61 (1H, d, J=8.4 Hz, ArH), 7.73-7.76 (2H, d, J=8.4 Hz, ArH), 7.72-7.73 (1H, d, J=1.5 Hz, ArH), 8.06 (2H, s, ArB(OH)$_2$), 8.23 (1H, s, ArH) and 9.83 (1H, s, ArOH);

HPLC (70% CH$_3$CN in H$_2$O) t$_r$=5.431 (97.67%);

LCMS (APCI), m/z 187.04 (M$^-$–H, 100%), 142.92 ((M$^-$–H)—B(OH)$_2$, 55).

1-Bromo-3-bromomethyl-5-methylbenzene (TJA01023)

C$_8$H$_8$Br$_2$ MW 263.96

To a solution of sodium bromate (24.4 g, 162 mmol) in distilled H$_2$O (40 mL) was added 5-bromo-m-xylene (10.0 g, 54.0 mmol) in cyclohexane (108 mL). To this clear mixture a solution of sodium hydrogen sulphate (30.8 g, 162 mmol) in distilled H$_2$O (81 mL) was added drop wise with vigorous stirring over 60 min. The reaction mixture was stirred for a further 3 h at room temperature. The ethyl acetate was separated and diethyl ether (100 mL) added. This was then washed with saturated Na$_2$SO$_{3(aq)}$ (100 mL), distilled water (100 ml×2) and brine (100 mL). Dried over Na$_2$SO$_4$ and solvent removed in vacuo to leave a clear syrup. Column chromatography (hexane) eluted the title compound as a clear oil that crystallised on standing to give a white crystalline solid that was used without further purification (8.45 g, 60%);

R$_f$ 0.52 (hexane), c.f 0.52 (dibromobenzylbromide), 0.45 (1,5-dibenzylbromide), 0.6 (5-bromo-m-xylene).

$^1$H NMR (270 MHz, CDCl$_3$) δ 2.31 (3H, s, ArCH$_3$), 4.38 (2H, s, ArCH$_2$Br), 7.11 (1H, s, ArH), 7.25 (1H, s, ArH) and 7.32 (1H, s, ArH);

HPLC (60% CH$_3$CN in H$_2$O) t$_r$=3.877 (67%), 4.644 (31%, dibromobenzylbromide).

(3-Bromo-5-methyl-phenyl)acetonitrile (TJA01029)

C$_9$H$_8$BrN MW 210.07

TJA01023 (11.3 g, 42.7 mmol), potassium cyanide (3.34 g, 51.2 mmol) and tetrabutylammonium bromide (0.700 g, 2.10 mmol) were loaded to an r.b. flask together with dichloromethane (60 mL) and distilled water (15 mL). With vigorous stirring the reaction mixture was set to reflux (45° C.) for 24 h. On cooling the organic fraction was separated and washed with distilled water (50 mL×2) and brine (50 mL) then dried over Na$_2$SO$_4$ and solvent removed in vacuo to leave a red/orange oil. Column chromatography initially eluting with hexane separated the dibromobenzylbromide impurity. Further elution with hexane/dichloromethane (50:50) gave the title compound as a clear yellow oil (6.63 g, 74%), R$_f$ 0.54 (hexane/dichloromethane 50:50)

$^1$H NMR (270 MHz, CDCl$_3$) δ 2.31 (3H, s, ArCH$_3$), 3.66 (2H, s, ArCH$_2$CN), 7.06 (1H, s, ArH), 7.25 (1H, s, ArH) and 7.27 (1H, s, ArH);

$^{13}$C NMR (100.5 MHz, CDCl$_3$) δ 21.1, 23.2, 117.4, 122.8, 127.4, 128.1, 131.7, 131.9 and 141.1;

HPLC (80% CH$_3$CN in H$_2$O) t$_r$=2.278 (72.5%);

LCMS (APCI), m/z 211.78 ($^{81}$BrM$^+$+H, 53%), 209.78 ($^{79}$BrM$^+$+H, 55), 184.83 (($^{81}$BrM$^+$+H)—CN, 80), 182.83 (($^{79}$BrM$^+$+H)—CN, 76).

2-(3-Bromo-5-methylphenyl)-2-methyl-propionitrile (TJA01035)

C$_{11}$H$_{12}$BrN MW 238.13

To a dry r.b. flask purged with N$_{2(g)}$ was added TJA01029 (6.00 g, 28.6 mmol) and dry THF (20 mL). With stirring this was cooled via an ice-water bath and NaH (1.71 g, 71.4 mmol) was added gradually and then left to stir at 0° C. under N$_{2(g)}$ for 15 min. Iodomethane (3.91 mL, 62.8 mmol) was then added dropwise. The resulting suspension was left to stir at room temperature for 16 h. Propan-2-ol (5 mL) was carefully added to the reaction mixture followed by dichloromethane (50 mL) and washed with distilled H$_2$O (50 mL×2) and brine (50 mL). Dried over Na$_2$SO$_4$ and solvent removed in vacuo to leave a red/orange oil. Column chromatography (hexane/dichloromethane 50:50) eluted the title compound as a light yellow oil (5.65 g, 83%);

R$_f$ 0.38 (hexane/dichloromethane 50:50), c.f 0.26 (3-Bromo-5-methyl-phenyl)acetonitrile;

$^1$H NMR (270 MHz, CDCl$_3$) δ 1.68 (6H, s, ArC(CH$_3$)$_2$CN), 2.33 (3H, s, ArCH$_3$), 7.20 (1H, s, ArH), 7.26 (1H, s, ArH) and 7.34 (1H, s, ArH);

$^{13}$C NMR (100.5 MHz, CDCl$_3$) δ 21.3 (CH$_3$), 29.0 (CH$_3$), 36.9 (C), 122.8, 124.1, 124.9, 125.2, 131.6, 140.9 and 143.4;

HPLC (80% CH$_3$CN in H$_2$O) t$_r$=2.600 (89.65%);

LCMS (APCI), m/z 239.93 ($^{81}$BrM$^+$+H, 3%), 237.93 ($^{79}$BrM$^+$+H, 4), 212.92 (($^{81}$BrM$^+$+H)—CN, 100), 210.92 (($^{79}$BrM$^+$+H)—CN, 96).

2-(3-Bromo-5-bromomethyl-phenyl)-2-methylpropionitrile (TJA01036)

C$_{11}$H$_{11}$Br$_2$N MW 317.03

To a solution of sodium bromate (9.51 g, 63.0 mmol) in distilled H$_2$O (32 mL) was added TJA01035 (5.00 g, 21.0 mmol) in cylcohexane (42 mL). To this clear mixture a solution of sodium hydrogen sulphate (7.56 g, 63.0 mmol) in distilled H$_2$O (63 mL) was added drop wise with vigorous stirring over 1 h. The reaction mixture was stirred for a further 4 h at room temperature. The cyclohexane was separated and diethyl ether (100 mL) added. This was then washed with saturated Na$_2$SO$_{3(aq)}$ (50 mL), distilled water (50 ml×2) and brine (50 mL). Dried over Na$_2$SO$_4$ and solvent removed in vacuo to leave viscous orange oil. Column chromatography (hexane/dichloromethane 50:50) eluted starting material and the title compound as a clear viscous oil (3.64 g, 54%), R$_f$ 0.55 (hexane/dichloromethane 50:50), c.f. 0.38 (2-(3-bromo-5-methylphenyl)-2-methyl-propionitrile);

$^1$H NMR (270 MHz, CDCl$_3$) δ 1.71 (6H, s, ArC(CH$_3$)$_2$CN), 4.41 (2H, s, ArCH$_2$Br), 7.40-7.41 (1H, t, J=1.7, ArH) and 7.48-7.51 (2H, m, ArH);

HPLC (80% CH$_3$CN in H$_2$O) t$_r$=2.508 (83.05%);

LRMS (FAB), m/z 319.1 ($^{81}$BrM$^+$+H, 100%), 317.1 ($^{79}$BrM$^+$+H, 100).

2-(3-Bromo-5-[1,2,4-triazole-1-yl-methylphenyl)-2-methylpropionitrile (TJA01037, STX1453)

C$_{13}$H$_{13}$BrN$_4$ MW 305.18

TJA01036 (3.20 g, 10.1 mmol), 1,2,4-triazole (1.05 g, 15.2 mmol), potassium carbonate (1.40 g, 10.1 mmol), potassium iodide (0.10 g, 0.600 mmol) and acetone (150 mL) were loaded to an r.b. flask. With vigorous stirring this mixture was set to reflux (60° C.) for 24 h. The reaction mixture was allowed to cool and acetone was removed in vacuo. The residues were taken up in ethyl acetate (50 mL) and washed with distilled water (50 mL×2), 1M NaOH (50 mL×1) and brine (50 mL). Dried over Na₂SO₄ and solvent removed in vacuo to leave a yellow oil. Column chromatography (ethyl acetate) eluted the title compound as a clear viscous oil that crystallised on standing to give a colourless crystalline solid (1.97 g, 64%), mp 70.9-71.8° C.;

$R_f$ 0.24 (ethyl acetate).

$^1$H NMR (270 MHz, CDCl₃) δ 1.68 (6H, s, ArC(CH₃)₂CN), 5.33 (2H, s, ArCH₂N), 7.40-7.41 (2H, t, J=1.7, ArH), 7.54-7.55 (1H, t, J=1.7, ArH), 7.99 (1H, s, C₂H₂N₃) and 8.12 (1H, s, C₂H₂N₃);

$^{13}$C NMR (100.5 MHz, CDCl₃) δ 29.0 (CH₃), 37.0 (C), 52.6 (CH₂), 123.5, 123.7, 128.6, 130.4, 137.7, 143.4, 144.5 and 152.6 (one overlapping peak);

HPLC (60% CH₃CN in H₂O increasing to 95% over 10 min) $t_r$=2.293 (98.87%); MS (EI), m/z 307.09 ($^{81}$BrM⁺+H, 100%), 305.09 ($^{79}$BrM⁺+H, 99), 238.01 (($^{81}$BrM⁺+H)—C₂H₂N₃, 22), 236.01 (($^{79}$BrM⁺+H)—C₂H₂N₃, 24).

2-(3-((1H-1,2,4-Triazol-1-yl)methyl)-5-(2-hydroxynaphthalen-6-yl)phenyl)-2-methylpropanenitrile (TJA02061)

C₂₃H₂₀N₄O MW 368.43

A 10 mL microwave vial was loaded with TJA02004 (0.150 g, 0.492 mmol), TJA02057 (0.138 g, 0.737 mmol), potassium carbonate (0.170 g, 1.23 mmol), tetrabutylammonium bromide (0.164 g, 0.492 mmol), Pd(OAc)₂ (0.003-0.004 g, 2-3 mol %), ethanol (1.5 mL) and distilled water (3.5 mL). The vial was sealed and loaded (with no prior degassing) into a CEM Explorer Microwave. After a run time of 10 min at 150° C. the reaction mixture was allowed to cool and ethyl acetate (50 mL) added. This was then washed with distilled water (30 mL×3) and brine (30 mL). The organic layer was dried over MgSO₄, filtered and solvent removed in vacuo to leave a yellow/brown residue. The crude product was purified via flash chromatography (20 g column, method4) which eluted the title compound as a light yellow solid (0.130 g, 72%), mp 193.7-198.4° C.;

$R_f$: 0.42 (ethyl acetate);

$^1$H NMR (270 MHz, DMSO-d₆) δ 1.76 (6H, s, ArC(CH₃)₂CN), 5.55 (2H, s, ArCH₂N), 7.11-7.21 (2H, m, ArH), 7.47 (1H, s, ArH), 7.66 (1H, s, ArH), 7.68-7.72 (1H, dd, J=1.8 & 8.7 Hz, ArH), 7.79-7.81 (2H, m, ArH), 7.85-7.88 (1H, d, J=8.7 Hz, ArH), 8.02 (1H, s, C₂H₂N₃), 8.09 (1H, s, ArH), 8.76 (1H, s, C₂H₂N₃) and 9.88 (1H, s, ArOH);

$^{13}$C NMR (67.9 MHz, DMSO-d₆) δ 28.9 (CH₃), 37.4 (C), 52.6 (CH₂), 109.0 (CH), 119.8 (CH), 123.6 (CH), 124.1 (CH), 125.1 (C), 125.8 (CH), 126.1 (CH), 126.4 (CH), 127.4 (CH), 128.4 (C), 130.5 (CH), 134.0 (C), 134.7 (C), 138.2 (C), 142.0 (C), 143.3 (C), 145.0 (CH), 152.4 (CH) and 156.3 (C);

HPLC (90% CH₃CN in H₂O) $t_r$=3.697 (100%);

LCMS (APCI), m/z 369.65 (M⁺+H, 100%).

STX1361

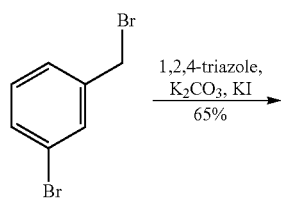

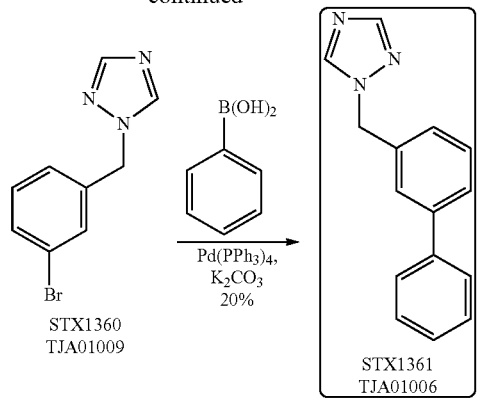

1-(3-BROMOBENZYL)-1H-(1,2,4)-TRIAZOLE (TJA01009, STX1360)

C₉H₈BrN₃ MW 238.08

To a solution of 3-bromobenzylbromide (20.0 g, 80.0 mmol) in acetone (300 mL) was added 1,2,4-triazole (10.8 g, 120 mmol), potassium carbonate (11.0 g, 80.0 mmol) and potassium iodide (0.790 g, 4.72 mmol). The resulting white suspension was heated to 55° C. with vigorous stirring for 16 h. The yellow reaction mixture was cooled and ethyl acetate (100 mL) added. This was then washed with distilled water (100 mL×2), 1M NaOH$_{(aq)}$ (100 mL×2) and brine (100 mL). The organic layer was dried over Na₂SO₄, filtered and solvent removed in vacuo to leave clear yellow oil. The crude product was purified by column chromatography (ethyl acetate) to give the title compound as a yellow crystalline solid (12.4 g, 65%), $R_f$: 0.4 (ethyl acetate), c.f. 0.95 (3-bromobenzylbromide);

$^1$H NMR (270 MHz, CDCl₃) δ 5.27 (2H, s, ArCH₂N), 7.15-7.42 (5H, m, ArH), 7.95 (1H, s, C₂H₂N₃) and 8.07 (1H, s, C₂H₂N₃);

$^{13}$C NMR (100.5 MHz, CDCl₃) δ 52.7 (CH₂), 123.1, 126.5, 130.6, 130.9, 131.8, 136.9, 143.2 and 152.4;

HPLC (90% CH₃CN in H₂O) $t_r$=2.273 (100%);

LRMS (FAB⁺), m/z 240.0 ($^{81}$BrM⁺+H, 100%), 238.0 ($^{79}$BrM⁺+H, 100);

Anal. Calcd. for C₉H₈BrN₃: C, 45.40; H, 3.39; N, 17.65. Found: C, 45.60, H, 3.55, N, 17.50%.

1-Biphenyl-3-Methyl-1H-(1,2,4)-Triazole (TJA01006, STX1361)

C₁₅H₁₃N₃ MW 235.28

A 3 necked round bottomed flask was loaded with TJA01009 (0.149 g 0.625 mmol), phenylboronic acid (0.738 g, 0.0900 mmol), toluene (9 mL), ethanol (1 mL) and 2M Na₂CO₃ $_{(aq)}$ (1 mL). This mixture was degassed by bubbling N₂ $_{(g)}$ through it for 1 h. A catalytic quantity of Pd(Ph₃)₄ was added and the reaction mixture heated with vigorous stirring to 115° C. for 20 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na₂SO₄, filtered and solvent removed in vacuo to leave a yellow/brown residue. The crude product was purified by column chromatography (ethyl acetate) to give a yellow oil that crystallised on standing to a waxy yellow solid ($R_f$ 0.4). Recrystallisation (cyclohexane) gave the title compound as a white crystalline solid (0.0300 g, 20%), m.p. 81.3-81.5° C.;

$R_f$: 0.4 (ethyl acetate), c.f. 0.4 (1-biphenyl-3-methyl-1H-(1,2,4)-triazole) and 0.8 (phenylboronic acid);

$^1$H NMR (270 MHz, CDCl$_3$) δ 5.40 (2H, s, ArCH$_2$N), 7.24-7.55 (9H, m, ArH), 7.98 (1H, s, C$_2$H$_2$N$_3$) and 8.09 (1H, s, C$_2$H$_2$N$_3$);

$^{13}$C NMR (100.5 MHz, CDCl$_3$) δ 53.7 (CH$_2$), 126.8, 127.2, 127.5, 127.7, 128.9, 129.6, 135.1, 140.4, 142.2, 143.2 and 152.3;

HPLC (90% CH$_3$CN in H$_2$O) t$_r$=2.216 (100%);

LCMS (APCI), m/z 236.87 (M$^+$+H, 12%), 235.74 (M$^+$, 100).

STX1362

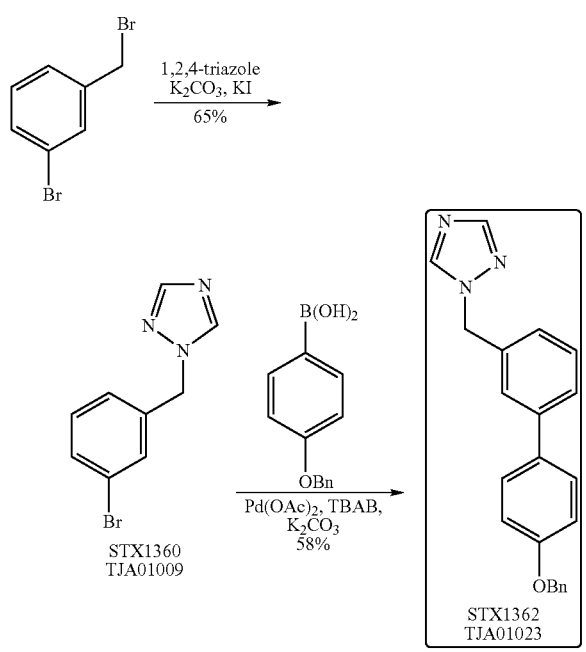

1-(4'-Benzyloxy-Biphenyl-3-Methyl)-1H-(1,2,4)-Triazole (TJA01023, STX1362)

C$_{22}$H$_{19}$N$_3$O MW 341.42

A 3 necked r.b. flask was loaded with TJA01009, (0.119 g 0.500 mmol), 4-benzyloxybenzeneboronic acid (0.137 g, 0.600 mmol), potassium carbonate (0.173 g, 1.25 mmol), tetrabutylammonium bromide (0.166 g, 0.500 mmol) and distilled H$_2$O (3.5 mL). This mixture was degassed by bubbling N$_{2\ (g)}$ through it for 1 h at 70° C. A catalytic quantity of Pd(OAc)$_2$ (0.006-0.007 g, 2-3 mol %) was added and the reaction mixture heated with vigorous stirring at 70° C. for 1 h. The reaction mixture was allowed to cool and ethyl acetate (100 mL) added. This was then washed with distilled water (50 mL×3) and brine (50 mL). The organic layer was dried over Na$_2$SO$_4$, filtered and solvent removed in vacuo to leave a yellow solids. The crude product was purified by flash chromatography (20 g column, method10) to give the title compound as yellow solid (0.099 g, 58%), $R_f$: 0.45 (ethyl acetate), c.f 0.40 (1-biphenyl-3-methyl-1H-(1,2,4)-triazole) and 0.8 (3-chlorophenylboronic acid);

$^1$H NMR (270 MHz, CDCl$_3$) δ 5.09 (2H, s, ArCH$_2$O), 5.38 (2H, s, ArCH$_2$N), 7.01-7.04 (2H, d, J=8 Hz, AA'BB'), 7.16-7.19 (1H, m, ArH), 7.31-7.53 (10H, m, ArH), 7.97 (1H, s, C$_2$H$_2$N$_3$) and 8.07 (1H, s, C$_2$H$_2$N$_3$);

$^{13}$C NMR (100.5 MHz, CDCl$_3$) δ 53.7 (CH$_2$), 70.1 (CH$_2$), 115.3 (C), 126.3, 126.4, 127.1, 127.5, 128.1, 128.3, 128.7, 129.5, 133.1, 135.1, 136.8, 141.8, 143.1, 152.3 and 158.7;

HPLC (80% CH$_3$CN in H$_2$O) t$_r$=2.400 (99.69%);

LCMS (APCI), m/z 341.86 (M$^+$+H, 100%), 272.77 ((M$^+$+H)—C$_2$H$_2$N$_3$, 40);

HRMS (FAB$^+$) calcd. for C$_{22}$H$_{19}$N$_3$O (M)$^+$341.1528, found 341.1526.

STX1384

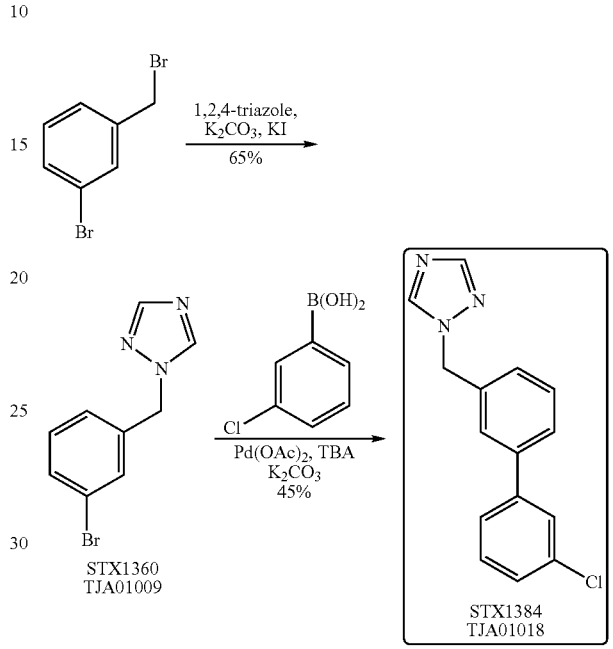

1-(3'-Chloro-Biphenyl-3-Yl-Methyl)-1H-(1,2,4)-Triazole (TJA01018, STX1384)

C$_{15}$H$_{12}$ClN$_3$ MW 269.74

A 3 necked r.b. flask was loaded with TJA01009 (0.238 g 1.00 mmol), 3-chlorophenylboronic acid (0.253 g, 2.00 mmol), potassium carbonate (0.346 g, 2.50 mmol), tetrabutylammonium bromide (0.332 g, 1.00 mmol), distilled H$_2$O (7 mL) and ethanol (3 mL). This mixture was degassed with N$_{2\ (g)}$ for 1 h at 70° C. A catalytic quantity of Pd(OAc)$_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method1) to give the title compound as a clear oil that crystallised on standing to a waxy white solid (0.219 g, 81%). Recrystallisation (cyclohexane) yielded a white crystalline solid (0.121 g, 45%), m.p. 71.8-72.4° C.;

$R_f$: 0.45 (ethyl acetate), c.f 0.40 (1-biphenyl-3-methyl-1H-(1,2,4)-triazole) and 0.8 (3-chlorophenylboronic acid)

$^1$H NMR (270 MHz, CDCl$_3$) δ 5.39 (2H, s, ArCH$_2$N), 7.24-7.51 (8H, m, ArH), 7.97 (1H, s, C$_2$H$_2$N$_3$) and 8.09 (1H, s, C$_2$H$_2$N$_3$);

$^{13}$C NMR (100.5 MHz, CDCl$_3$) δ 53.5 (CH$_2$), 125.4, 126.8, 127.3, 127.4, 127.5, 127.7, 129.7, 130.1, 134.8, 135.4, 140.8, 142.2, 143.1 and 152.3;

HPLC (60% CH$_3$CN in H$_2$O) t$_r$=2.521 (99.04%);

LCMS (APCI), m/z 271.58 ($^{37}$ClM$^+$+H, 35%), 269.2 ($^{35}$ClM$^+$+H, 100), 202.49 (($^{37}$ClM$^+$+H)—C$_2$H$_2$N$_3$, 22%), 200.49 (($^{35}$ClM$^+$+H)—C$_2$H$_2$N$_3$), 60);

HRMS (FAB$^+$) calcd. for C$_{15}$H$_{12}$N$_3$Cl (M)$^+$269.0720, found 269.0725.

STX1385

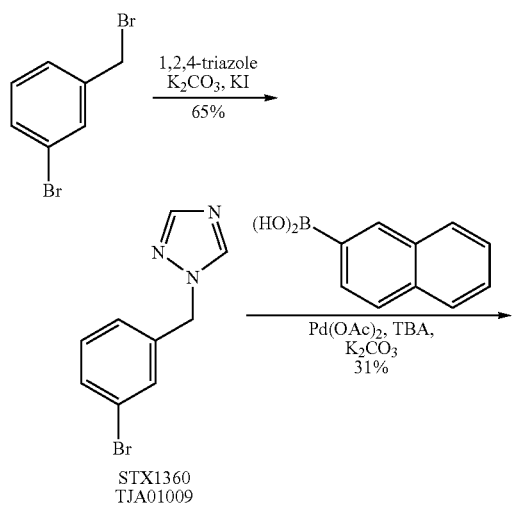

1-(3-Napthalen-biphenyl-2-yl-benzyl)-1H-(1,2,4)-triazole (TJA01019, STX1385)

C$_{19}$H$_{15}$N$_3$ MW 285.35

A 3 necked r.b. flask was loaded with TJA01009 (0.238 g 1.00 mmol), 2-naphthaleneboronic acid (0.344 g, 2.00 mmol), potassium carbonate (0.346 g, 2.50 mmol), tetrabutylammonium bromide (0.332 g, 1.00 mmol), distilled H$_2$O (7 mL) and ethanol (3 mL). This mixture was degassed with N$_{2\ (g)}$ for 1 h at 70° C. A catalytic quantity of Pd(OAc)$_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method2) to give the title compound as a clear yellow oil that crystallised on standing to a cream waxy solid (0.165 g, 58%). Recrystallisation (cyclohexane) yielded a white crystalline solid (0.087 g, 31%), mp 73.1-75.2° C.;

R$_f$: 0.42 (ethyl acetate), c.f. 0.40 (1-biphenyl-3-methyl-1H-(1,2,4)-triazole) and 0.75 (2-naphthaleneboronic acid).

$^1$H NMR (270 MHz, CDCl$_3$) δ 5.43 (2H, s, ArCH$_2$N), 7.26 (1H, s, ArH), 7.45-7.70 (5H, m, ArH), 7.83-7.91 (3H, m, ArH), 7.99 (1H, s, C$_2$H$_2$N$_3$) and 8.11 (1H, s, C$_2$H$_2$N$_3$);

$^{13}$C NMR (100.5 MHz, CDCl$_3$) δ53.7 (CH$_2$), 125.4, 126.0, 126.2, 126.5, 126.9, 127.1, 127.7, 127.8, 128.2, 128.6, 129.7, 132.8, 133.6, 135.2, 137.7, 142.2, 143.2 and 152.3;

HPLC (80% CH$_3$CN in H$_2$O) t$_r$=2.466 (99.15%);

LCMS (APCI), m/z 286.19 (M$^+$+H, 100%), 217.10 ((M$^+$+H)—C$_2$H$_2$N$_3$, 90);

HRMS (FAB$^+$) calcd. for C$_{19}$H$_{15}$N$_3$ (M)$^+$285.1266, found 285.1253.

STX1386

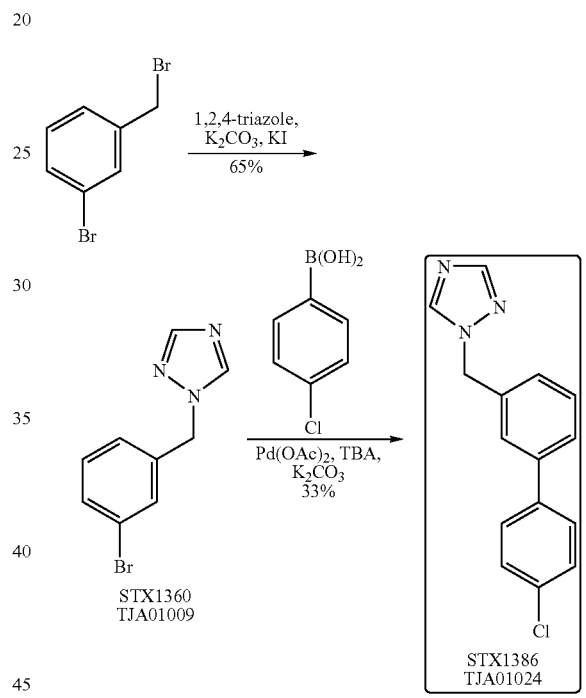

1-(4'-Chloro-Biphenyl-3-Yl-Methyl)-1H-(1,2,4)-Triazole (TJA01024, STX1386)

C$_{15}$H$_{12}$ClN$_3$ MW 269.74

A 3 necked r.b. flask was loaded with TJA01009 (0.238 g 1.00 mmol), 4-chlorophenylboronic acid (0.253 g, 2.00 mmol), potassium carbonate (0.346 g, 2.50 mmol), tetrabutylammonium bromide (0.332 g, 1.00 mmol), distilled H$_2$O (7 mL) and ethanol (3 mL). This mixture was degassed with N$_{2\ (g)}$ for 1 h at 70° C. A catalytic quantity of Pd(OAc)$_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method2) to give the title compound as a clear yellow oil that crystallised on standing to a yellow waxy solid (0.123 g, 46%). Recrystallisation (cyclohexane) yielded a white crystalline solid (0.087 g, 33%), mp 56.9-59.2° C.;

$R_f$: 0.45 (ethyl acetate), c.f. 0.40 (1-biphenyl-3-methyl-1H-(1,2,4)-triazole) and 0.80 (2-naphthaleneboronic acid).

$^1$H NMR (270 MHz, CDCl$_3$) δ 5.39 (2H, s, ArCH$_2$N), 7.37-7.50 (8H, m, ArH), 7.97 (1H, S, C$_2$H$_2$N$_3$) and 8.09 (1H, S, C$_2$H$_2$N$_3$);

$^{13}$C NMR (100.5 MHz, CDCl$_3$) δ 53.6 (CH$_2$), 126.6, 127.1, 127.3, 128.4, 129.1, 129.7, 135.3, 138.8, 141.0, 143.2 and 152.3 (one overlapping signal);

HPLC (80% CH$_3$CN in H$_2$O) t$_r$=2.401 (98.36%);

LCMS (APCI), m/z 272.02 ($^{37}$ClM$^+$+H, 35%), 270.0 ($^{35}$ClM$^+$+H, 100), 202.91 (($^{37}$ClM$^+$+H)—C$_2$H$_2$N$_3$, 21%), 200.491 (($^{35}$ClM$^+$+H)—C$_2$H$_2$N$_3$, 68);

HRMS (FAB$^+$) calcd. for C$_{15}$H$_{12}$N$_3$Cl (M)$^+$269.0720, found 269.0733.

STX1387

10% Pd/C (0.015 g) to form a black suspension on vigorous stirring. The flask was evacuated and back filled with H$_{2\,(g)}$ via a balloon (×3) and then left to stir for 24 h. The reaction mixture was filtered through celite which was subsequently washed with THF (30 mL×2). Solvent was removed in vacuo to leave a brown residue. Flash chromatography (20 g column, method2) eluted the title compound as a white solid (0.128 g, 88%). Recrystallisation from ethyl acetate/hexane (7:3) gave a white crystalline solid (0.0810 g, 56%), mp 164.4-166.2° C.;

$R_f$ 0.44 (ethyl acetate), c.f 0.50 (TJA01022).

$^1$H NMR (270 MHz, DMSO-d$_6$) δ 5.45 (2H, s, ArCH$_2$N), 6.82-6.85 (2H, d, J=8 Hz, AA'BB'), 7.14-7.16 (2H, d, J=7.5 Hz, ArH), 7.35-7.51 (5H, m, ArH), 7.98 (1H, s, C$_2$H$_2$N$_3$), 8.69 (1H, s, C$_2$H$_2$N$_3$) and 9.57 (1H, s, ArOH);

$^{13}$C NMR (100 MHz, DMSO-d$_6$) δ 52.6 (CH$_2$), 116.2, 126.0, 126.0, 126.3, 128.2, 129.6, 130.9, 137.3, 141.0, 144.8, 152.2, 157.8;

HPLC (80% CH$_3$CN in H$_2$O) t$_r$=1.820 (100%);

LCMS (APCI), m/z 251.74 (M$^+$, 72%), 182.71 (M$^+$—C$_2$H$_2$N$_3$, 100).

STX1388

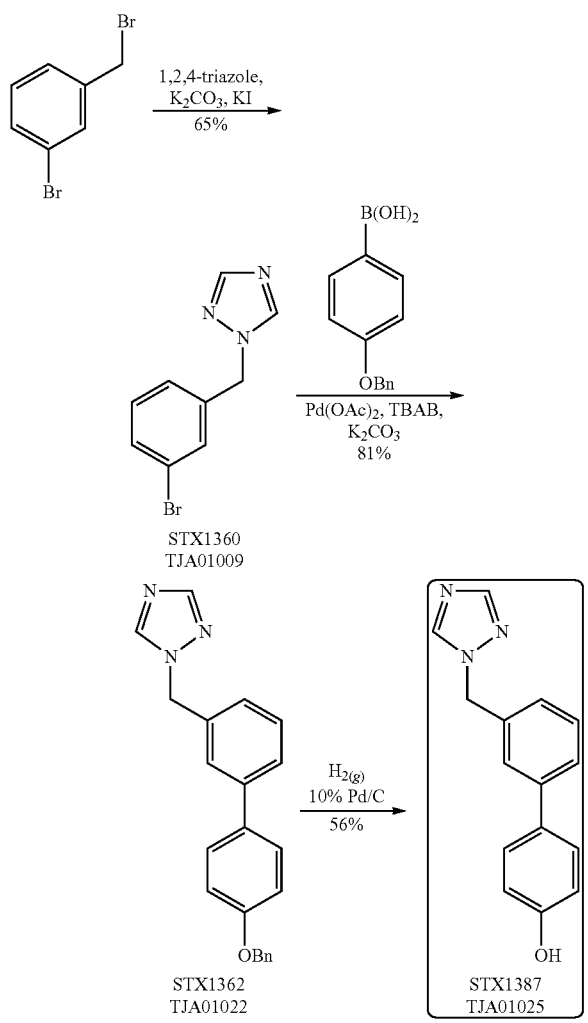

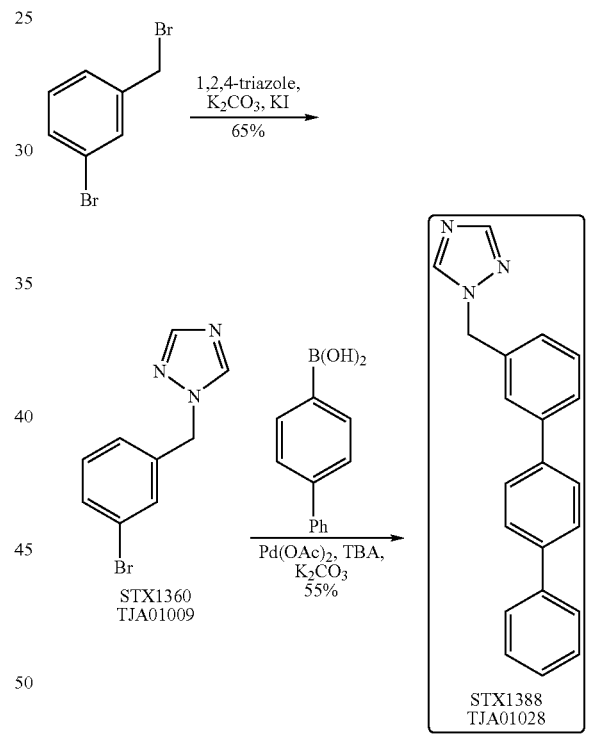

1-(1,1',4',1'')Terphenyl-3-yl-methyl-1H-(1,2,4)triazole (TJA01028, STX1388)

C$_{21}$H$_{17}$N$_3$ MW311.39

A 3 necked r.b. flask was loaded with TJA01009 (0.238 g 1.00 mmol), 4'-biphenylboronic acid (0.297 g, 1.50 mmol), potassium carbonate (0.346 g, 2.50 mmol), tetrabutylammonium bromide (0.332 g, 1.00 mmol), distilled H$_2$O (7 mL) and ethanol (3 mL). This mixture was degassed with N$_{2\,(g)}$ for 1 h at 70° C. A catalytic quantity of Pd(OAc)$_2$ (0.006-0.007 g, 2-3 mol %) was added and the reaction mixture heated with vigorous stirring to 70° C. for 1 h. The reaction mixture was 3'-(1,2,4)Triazole-1-yl-methyl-biphenyl-4-ol (TJA01025, STX1387)

C$_{15}$H$_{13}$N$_3$O MW 251.29

TJA01022 (0.198 g, 580 mmol) was dissolved in THF (5 mL) and MeOH (5 mL) in an r.b. flask to which was added allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method2) to give the title compound as a yellow solid (0.170 g, 55%), mp 144.6-147.3° C.;

$R_f$: 0.45 (ethyl acetate), c.f 0.40 (1-(3-bromobenzyl)-1H-(1,2,4)-triazole) and 0.80 (4'-biphenylboronic acid).

$^1$H NMR (270 MHz, CDCl$_3$) δ 5.41 (2H, s, ArCH$_2$N), 7.24-7.67 (13H, m, ArH), 7.98 (1H, s, C$_2$H$_2$N$_3$) and 8.10 (1H, s, C$_2$H$_2$N$_3$);

$^{13}$C NMR (100.5 MHz, CDCl$_3$) δ 53.7 (CH$_2$), 126.7, 126.9, 127.1, 127.4, 127.5, 127.5, 127.6, 128.9, 129.6, 135.2, 139.2, 140.5, 140.6, 141.7, 143.2 and 152.3;

HPLC (80% CH$_3$CN in H$_2$O) t$_r$=2.746 (99.28%);

LCMS (APCI), m/z 311.57 (M$^+$, 100%), 242.42 (M$^+$—C$_2$H$_2$N$_3$, 50).

HRMS (FAB$^+$) calcd. for C$_{21}$H$_{17}$N$_3$ (M)$^+$311.1422, found 311.1477.
STX1452 removed in vacuo to leave a yellow/brown residue. The crude product was purified by flash chromatography (20 g column, method2) to give the title compound as a clear yellow oil that crystallised on standing to a yellow waxy solid (0.129 g, 49%). Recrystallisation (cyclohexane) yielded a white crystalline solid (0.105 g, 39%), mp 101.5-102.0° C.;

$R_f$: 0.5 (ethyl acetate), c.f. 0.40 (1-(3-bromobenzyl)-1H-(1,2,4)-triazole) and 0.80 (4'-biphenylboronic acid).

$^1$H NMR (270 MHz, CDCl$_3$) δ 3.83 (3H, s, ArOCH$_3$), 5.38 (2H, s, ArCH$_2$N), 6.94-6.97 (2H, d, J=8.5 Hz, AA'BB'), 7.19 (1H, d, J=7.5 Hz, ArH), 7.40-7.50 (5H, m, ArH), 7.97 (1H, s, C$_2$H$_2$N$_3$) and 8.07 (1H, s, C$_2$H$_2$N$_3$);

$^{13}$C NMR (100.5 MHz, CDCl$_3$) δ 53.7 (CH$_3$), 55.4 (CH$_2$), 114.3, 126.2, 126.4, 127.1, 128.2, 129.5, 132.8, 135.0, 141.8, 143.1, 152.2 and 159.5;

HPLC (80% CH$_3$CN in H$_2$O) t$_r$=2.157 (99.21%);

LCMS (APCI), m/z 266.08 (M$^+$+H, 100%).
STX1455

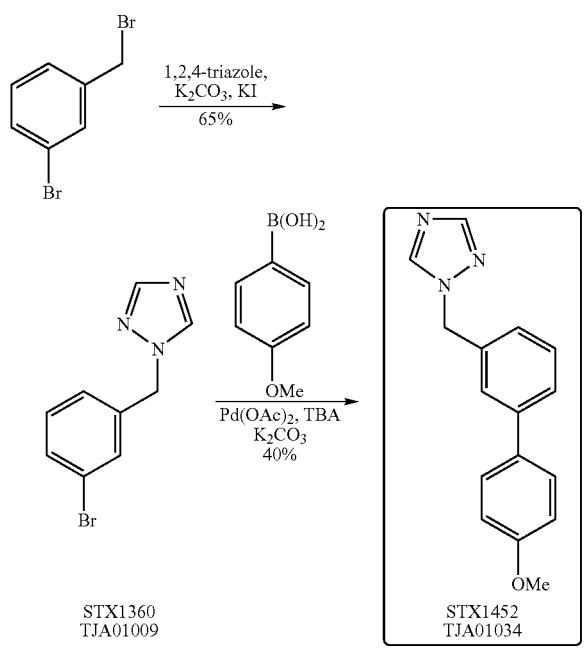

1-(4'-Methoxy-biphenyl-3-yl-methyl)-1H-(1,2,4) triazole (TJA01034, STX1452)

C$_{16}$H$_{15}$N$_3$O MW 265.32

A 3 necked r.b. flask was loaded with TJA01009 (0.238 g 1.00 mmol), 4-chlorophenylboronic acid (0.253 g, 2.00 mmol), potassium carbonate (0.346 g, 2.50 mmol), tetrabutylammonium bromide (0.332 g, 1.00 mmol), distilled H$_2$O (7 mL) and ethanol (3 mL). This mixture was degassed with N$_{2\,(g)}$ for 1 h at 70° C. A catalytic quantity of Pd(OAc)$_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent

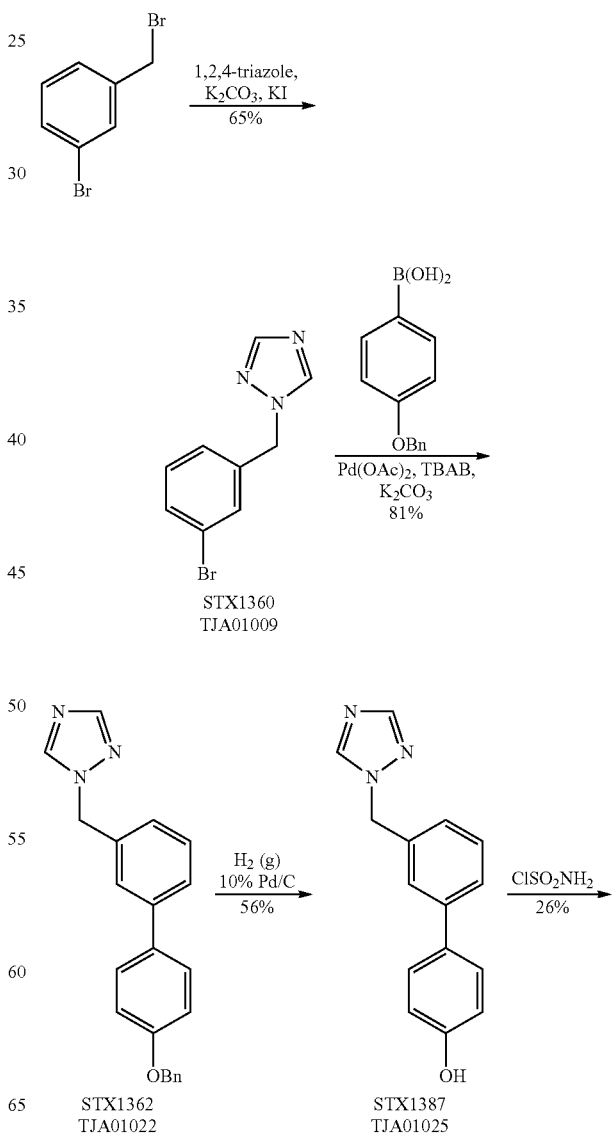

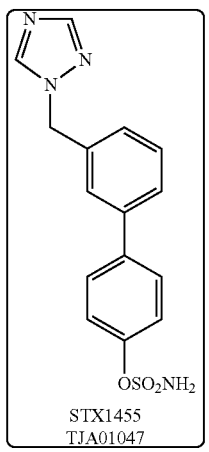

STX1455
TJA01047

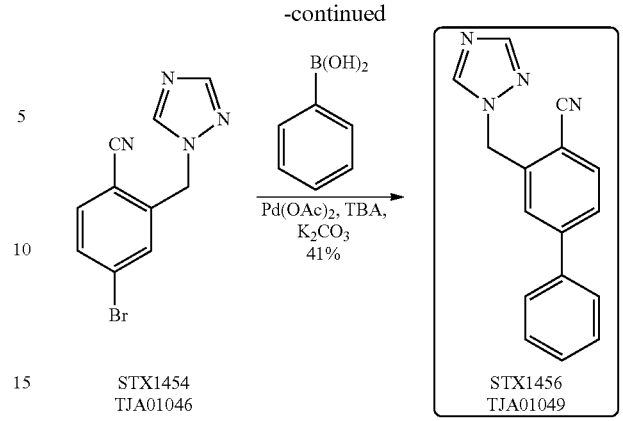

STX1454
TJA01046

STX1456
TJA01049

Sulfamic Acid 3'-(1,2,4)triazol-1-ylmethyl-biphenyl-4-yl Ester (TJA01047, STX1455)

$C_{15}H_{14}N_4O_3S$ MW 330.37

Sulfamoyl chloride in toluene (0.35 M, 2.86 mL) was transferred to a 10 mL r.b. flask and the solvent removed under vacuum at 30° C. On cooling a white solid formed to which was added N,N-dimethylacetamide (1.5 mL) to form a colourless solution. TJA01025 (0.050 g, 0.199 mmol) was added and the solution left to stir at room temperature under $N_{2\ (g)}$ for 20 h. The reaction mixture was then poured into distilled $H_2O$ (30 mL) and extracted with ethyl acetate (25 mL×2). The organic layers were combined and washed with distilled $H_2O$ (25 mL×4) and brine (25 mL). Dried over $Na_2SO_4$ and solvent removed in vacuo to leave off white residues. Column chromatography (dichloromethane/acetone 80:20) eluted the title compound as an off white waxy solid (0.017 g, 26%);

$R_f$ 0.42 (dichloromethane/acetone 80:20), c.f 0.38 3'-(1,2,4)triazole-1-yl-methyl-biphenyl-4-ol.

$^1$H NMR (400 MHz, DMSO-$d_6$) δ 5.51 (2H, s, ArCH$_2$N), 7.28-7.30 (1H, d, J=6.5 Hz, ArH), 7.38-7.40 (2H, d, J=9 Hz, AA'BB'), 7.46-7.50 (1H, t, J=7.5 Hz, ArH), 7.60-7.64 (2H, m, ArH), 7.98 (1H, s, $C_2H_2N_3$), 8.69 (1H, s, $C_2H_2N_3$) and 9.57 (1H, s, ArOH);

HPLC (80% CH$_3$CN in H$_2$O) $t_r$=1.772 min (99.13%);

LCMS (APCI), m/z 330.59 (M$^+$, 72%), 261.50 (M$^+$—$C_2H_2N_3$, 100), 182.40 ((M$^+$—$C_2H_2N_3$) —SO$_2$NH$_2$, 48);

HRMS (FAB$^+$) calcd. for $C_{15}H_{14}N_4O_3S$ (M)$^+$330.0787 found 330.0782.

STX1456

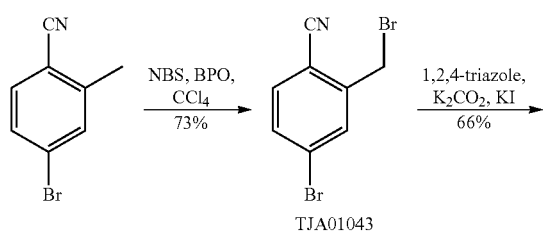

TJA01043

4-Bromo-2-bromomethylbenzonitrile (TJA01043)

$C_8H_5Br_2N$ MW 274.94

4-Bromo-2-methylbenzonitrile (5.00 g, 25.5 mmol), N-bromosuccinimide (4.99 g, 28.1 mmol), benzyl peroxide (0.198 g, 0.816 mmol) and carbon tetrachloride (100 mL) were loaded to a r.b. flask and set to reflux (79° C.) for 6 h. Once cooled the succinimide was filtered off and carbon tetrachloride removed via a dry ice-acetone cooled rotary evaporator. The residues were dissolved in dichloromethane (100 mL) and washed with distilled H$_2$O (50 mL×3) and brine (50 mL×2). Dried over Na$_2$SO$_4$ and solvent removed in vacuo to leave yellow residues. Column chromatography (hexane/dichloromethane 60:40) eluted the title compound as a yellow solid. Recrystallisation (cyclohexane) gave a white crystalline solid (5.07 g, 73%), mp 61.7-77.2° C.;

$R_f$ 0.30 (hexane/dichloromethane 60:40), c.f. 0.36 (dibromobenzylbromide), 0.36 (4-bromo-2-methylbenzonitrile);

HPLC (60% CH$_3$CN in H$_2$O) R$_t$ 3.130 (50.62%), 2.701 (42.38%, dibromobenzylbromide);

MS (EI), m/z 274.0 (M$^-$–H, 34%).

4-Bromo-2-(1,2,4)triazol-1-ylmethyl-benzonitrile (TJA01046, STX1454)

$C_{10}H_7BrN_4$ MW 263.10

TJA01043 (5.00 g, 18.2 mmol), 1,2,4-triazole (1.89 g, 27.3 mmol), potassium carbonate (2.52 g, 18.2 mmol), potassium iodide (0.178 g, 1.07 mmol) and acetone (150 mL) were loaded to an r.b. flask. With vigorous stirring this mixture was set to reflux (60° C.) for 4 h. The reaction mixture was allowed to cool and acetone was removed in vacuo. The residues were taken up in ethyl acetate (50 mL) and washed with distilled water (50 mL×2), 1M NaOH (50 mL×1) and brine (50 mL×2). Dried over Na$_2$SO$_4$ and solvent removed in vacuo to leave orange/yellow residues. Flash chromatography (50 g column, method8) eluted dibromobenzylbromide and the title compound as a yellow solid. Recrystallisation (ethyl acetate/hexane 1:6) gave a yellow crystalline solid (1.58 g, 66 mp 106.8-107.6° C.;

$R_f$ 0.55 (ethyl acetate).

$^1$H NMR (270 MHz, CDCl$_3$) δ 5.51 (2H, s, ArCH$_2$N), 7.50 (1H, s, ArH), 7.53-7.56 (1H, d, J=8.8 Hz, ArH), 7.59-7.62 (1H, dd, J=1.7 & 8.5 Hz, ArH), 7.99 (1H, s, $C_2H_2N_3$) and 8.27 (1H, s, $C_2H_2N_3$);

$^{13}$C NMR (100.5 MHz, CDCl$_3$) δ 50.7 (CH$_2$), 110.6, 116.3, 128.8, 132.8, 132.9, 134.2, 139.8, 143.9 and 153.0;

HPLC (80% CH$_3$CN in H$_2$O) t$_r$=1.947 min (100%);

MS (EI), m/z 264.71 ($^{81}$BrM$^+$+H, 100%), 262.71. ($^{79}$BrM$^+$+H, 99), 195.56 (($^{81}$BrM$^+$+H)—C$_2$H$_2$N$_3$, 81), 193.56 (($^{79}$BrM$^+$+H)—C$_2$H$_2$N$_3$, 80);

Anal. Calc. for C$_{10}$H$_7$BrN$_4$: C, 45.65; H, 2.68; N, 21.30. Found: C, 45.60; H, 2.70; N, 20.9%.

3-[1,2,4]Triazol-1-ylmethyl-biphenyl-4-carbonitrile (TJA01049, STX1456)

C$_{16}$H$_{12}$N$_4$ MW 260.30

A 3 necked r.b. flask was loaded with TJA01046 (0.100 g 0.380 mmol), phenylboronic acid (0.070 g, 0.570 mmol), potassium carbonate (0.131 g, 0.950 mmol), tetrabutylammonium bromide (0.126 g, 0.380 mmol), distilled H$_2$O (7 mL) and ethanol (3 mL). This mixture was degassed with N$_{2\ (g)}$ for 1 h at 70° C. A catalytic quantity of Pd(OAc)$_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method3) to give the title compound as a colourless oil (0.076 g, 49%). Recrystallisation (cyclohexane) yielded a white crystalline solid (0.105 g, 39%), mp 107.8-108.1° C.; R$_f$: 0.52 (ethyl acetate).

$^1$H NMR (270 MHz, CDCl$_3$) δ 5.59 (2H, s, ArCH$_2$N), 7.42-7.56 (6H, m, ArH), 7.63-7.67 (1H, dd, J=1.8 & 8.1 Hz, ArH), 7.74-7.77 (1H, d, J=8.2 Hz, ArH), 7.98 (1H, s, C$_2$H$_2$N$_3$) and 8.30 (1H, s, C$_2$H$_2$N$_3$);

$^{13}$C NMR (100.5 MHz, CDCl$_3$) δ 51.4 (CH$_2$), 110.3, 117.1, 127.3, 127.8, 128.2, 129.1, 129.2, 133.6, 138.4, 138.6, 143.9, 146.7 and 152.8;

HPLC (90% CH$_3$CN in H$_2$O) t$_r$=2.034 (100%);

LCMS (APCI), m/z 261.18 (M$^+$+H, 100%), 191.99 ((M$^+$+H)—C$_2$H$_2$N$_3$, 15).

STX1457

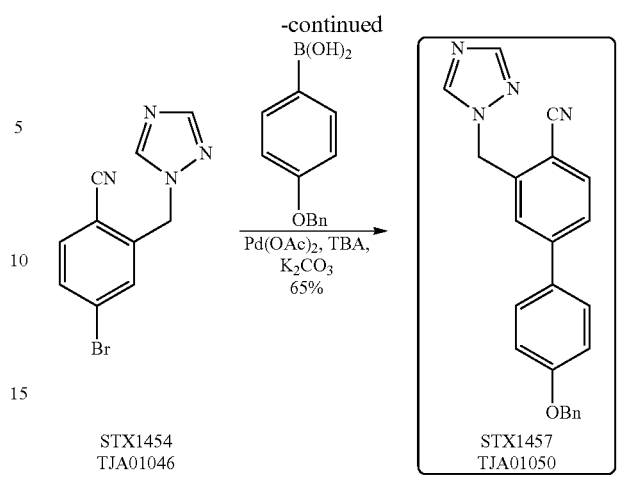

STX1454
TJA01046

STX1457
TJA01050

4'-Benzyloxy-3-[1,2,4]triazol-1-ylmethyl-biphenyl-4-carbonitrile (TJA01050, STX1457)

C$_{23}$H$_{18}$N$_4$O MW 366.43

A 3 necked r.b. flask was loaded with TJA01046 (0.300 g 1.14 mmol), 4-benzyloxybenzene boronic acid (0.390 g, 1.71 mmol), potassium carbonate (0.390 g, 2.85 mmol), tetrabutylammonium bromide (0.379 g, 1.14 mmol), distilled H$_2$O (7 mL) and ethanol (3 mL). This mixture was degassed with N$_{2\ (g)}$ for 1 h at 70° C. A catalytic quantity of Pd(OAc)$_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method3) to give the title compound as a pale yellow solid (0.315 g, 75%). Precipitation (EtOAc/hexane) yielded a white solid (0.270 g, 65%), mp 127.7-128.1° C.;

R$_f$: 0.52 (ethyl acetate).

$^1$H NMR (270 MHz, CDCl$_3$) δ 5.10 (2H, s, ArOCH$_2$), 5.58 (2H, s, ArCH$_2$N), 7.02-7.05 (2H, d, J=11.5 Hz, AA'BB'), 7.32-7.51 (8H, m, ArH), 7.58-7.61 (1H, d, J=8.0 Hz, ArH), 7.70-7.73 (1H, d, J=8.0 Hz, ArH), 7.98 (1H, s, C$_2$H$_2$N$_3$) and 8.28 (1H, s, C$_2$H$_2$N$_3$);

$^{13}$C NMR (100.5 MHz, CDCl$_3$) δ 51.4 (CH$_2$), 70.1 (CH$_2$), 109.5, 115.6, 117.3, 127.2, 127.5, 127.6, 128.2, 128.5, 128.7, 131.0, 133.6, 136.5, 138.5, 143.8, 146.1, 152.7 and 159.7;

HPLC (80% CH$_3$CN in H$_2$O) t$_r$=2.276 (99.82%);

LCMS (APCI), m/z 367.29 (M$^+$+H, 100%).

STX1458

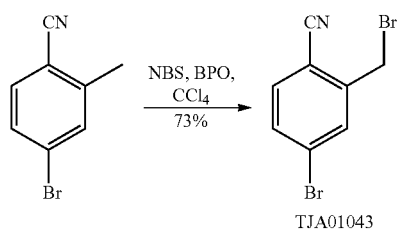

TJA01043

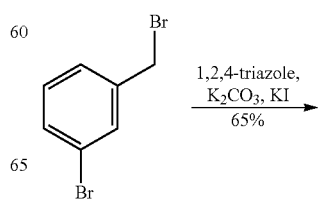

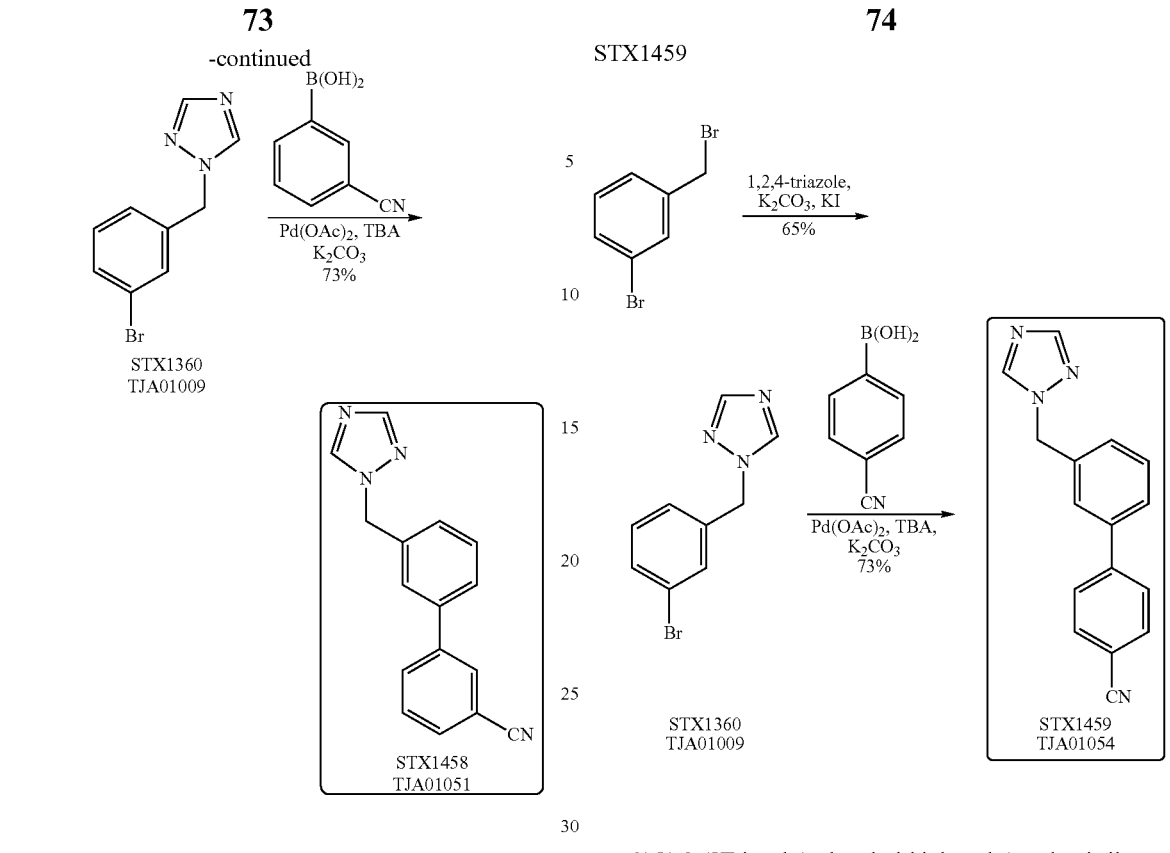

3'-[1,2,4]Triazol-1-ylmethyl-biphenyl-3-carbonitrile (TJA01051, STX1458)

$C_{16}H_{12}N_4$ MW 260.30

A 3 necked r.b. flask was loaded with TJA01009 (0.238 g 1.00 mmol), 3-cyanophenyl boronic acid (0.220 g, 1.50 mmol), potassium carbonate (0.346 g, 2.50 mmol), tetrabutylammonium bromide (0.332 g, 1.00 mmol), distilled $H_2O$ (7 mL) and ethanol (3 mL). This mixture was degassed with $N_{2\ (g)}$ for 1 h at 70° C. A catalytic quantity of $Pd(OAc)_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method3) to give the title compound as a viscous colourless oil (0.190 g, 73%), $R_f$: 0.30 (ethyl acetate);

$^1$H NMR (270 MHz, $CDCl_3$) δ 5.36 (2H, s, $ArCH_2N$), 7.22-7.26 (1H, dt, J=1.5 & 9.0 Hz, ArH), 7.38-7.51 (4H, m, ArH), 7.56-7.60 (1H, dt, J=1.5 & 7.5 Hz, ArH), 7.67-7.71 (1H, dt, J=1.5 & 7.7 Hz, ArH), 7.75-7.76 (1H, m, ArH), 7.93 (1H, s, $C_2H_2N_3$) and 8.07 (1H, s, $C_2H_2N_3$);

$^{13}$C NMR (100.5 MHz, $CDCl_3$) δ 53.4 ($CH_2$), 113.1, 118.7, 126.7, 127.5, 127.9, 129.8, 130.0, 130.8, 131.2, 131.6, 135.7, 139.9, 141.6, 143.2 and 152.4;

HPLC (80% $CH_3CN$ in $H_2O$) $t_r$=2.013 (100%);

LCMS (APCI), m/z 261.18 ($M^+$+H, 82%), 191.99 (($M^+$+H)—$C_2H_2N_3$, 100).

3'-[1,2,4]Triazol-1-ylmethyl-biphenyl-4-carbonitrile (TJA01054, STX1459)

$C_{16}H_{12}N_4$ MW 260.30

A 3 necked r.b. flask was loaded with TJA01009 (0.238 g 1.00 mmol), 4-cyanophenyl boronic acid (0.220 g, 1.50 mmol), potassium carbonate (0.346 g, 2.50 mmol), tetrabutylammonium bromide (0.332 g, 1.00 mmol), distilled $H_2O$ (7 mL) and ethanol (3 mL). This mixture was degassed with $N_{2\ (g)}$ for 1 h at 70° C. A catalytic quantity of $Pd(OAc)_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method4) to give the title compound as a viscous colourless oil that crystallised on standing to give a white crystalline solid (0.190 g, 73%), mp 117.4-117.9° C.;

$R_f$: 0.38 (ethyl acetate).

$^1$H NMR (270 MHz, $CDCl_3$) δ 5.38 (2H, s, $ArCH_2N$), 7.28-7.31 (1H, m, ArH), 7.44-7.57 (3H, m, ArH), 7.62-7.74 (4H, dd, J=2.0 & 8.5 Hz, AA'BB'), 7.97 (1H, s, $C_2H_2N_3$) and 8.07 (1H, s, $C_2H_2N_3$);

$^{13}$C NMR (100.5 MHz, $CDCl_3$) δ 53.4 ($CH_2$), 111.4, 118.8, 126.8, 127.6, 127.8, 128.1, 129.9, 132.7, 135.8, 140.2, 143.2, 144.8 and 152.4;

HPLC (80% $CH_3CN$ in $H_2O$) $t_r$=1.990 (98.29%);

LCMS (APCI), m/z 261.18 ($M^+$+H, 100%), 191.99 (($M^+$+H)—$C_2H_2N_3$, 88).

STX1502

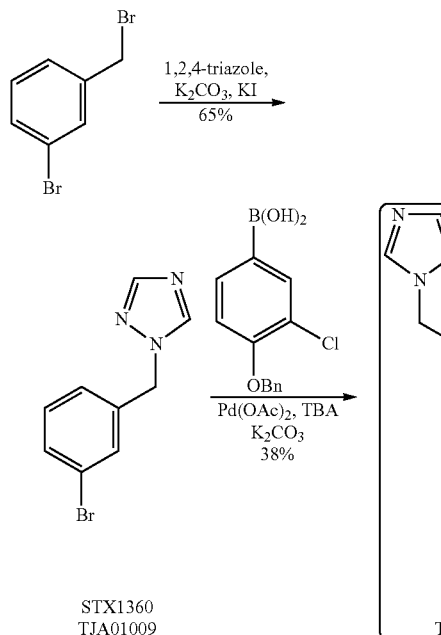

STX1503

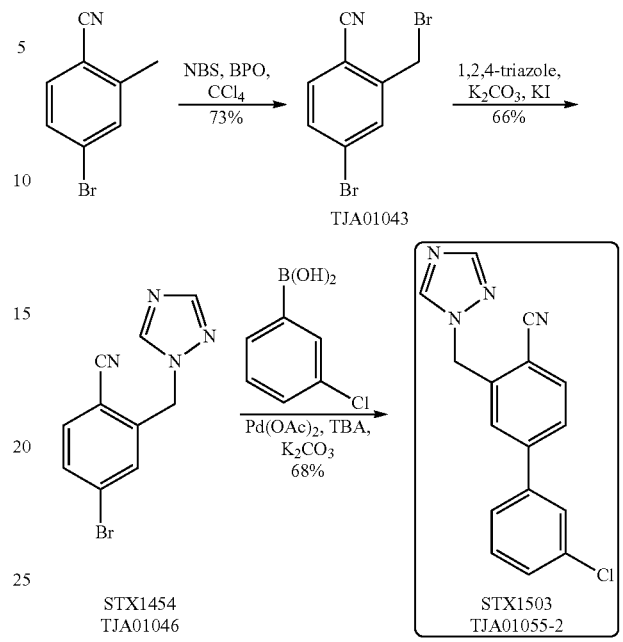

1-(4'-Benzyloxy-3'-chloro-biphenyl-3-ylmethyl)-1H-(1,2,4)triazole (TJA01055-1, STX1502)

$C_{22}H_{18}ClN_3O$ MW 375.11

A 3 necked r.b. flask was loaded with TJA01009 (0.250 g 1.05 mmol), 4-benzyloxy-3-chlorophenylboronic acid (0.413 g, 1.58 mmol), potassium carbonate (0.363 g, 2.63 mmol), tetrabutylammonium bromide (0.349 g, 1.05 mmol), distilled $H_2O$ (7 mL) and ethanol (3 mL). This mixture was degassed with $N_{2\ (g)}$ for 1 h at 70° C. A catalytic quantity of $Pd(OAc)_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method4) to give the title compound as a white crystalline solid (0.150 g, 38%), mp 91.2-91.8° C.;

$R_f$: 0.40 (ethyl acetate);

$^1$H NMR (270 MHz, $CDCl_3$) δ 5.19 (2H, s, $ArOCH_2$), 5.38 (2H, s, $ArCH_2N$), 6.98-7.01 (1H, d, J=8.6 Hz, ArH), 7.18-7.50 (9H, m, ArH), 7.57-7.58 (1H, d, J=2.2 Hz, ArH)), 7.97 (1H, s, $C_2H_2N_3$) and 8.08 (1H, s, $C_2H_2N_3$);

$^{13}$C NMR (100.5 MHz, $CDCl_3$) δ 53.6 ($CH_2$), 70.9 ($CH_2$), 114.2, 123.7, 126.3, 126.4, 126.8, 127.1, 128.1, 128.7, 129.0, 129.7, 134.1, 135.3, 136.4, 140.5, 143.2, 152.3 and 153.9 (one overlapping signal);

HPLC (80% $CH_3CN$ in $H_2O$) $t_r$=2.573 (99.33%);

LCMS (APCI), m/z 378.19 ($^{37}ClM^+$+H, 30%), 379.24 ($^{35}ClM^+$+H, 100).

3'Chloro-3-(1,2,4)triazol-1-ylmethyl-biphenyl-4-carbonitrile (TJA01055-2, STX1503)

$C_{16}H_{11}ClN_4$ MW 294.07

A 3 necked r.b. flask was loaded with TJA01046 (0.100 g, 0.380 mmol), 3-chlorophenylboronic acid (0.089 g, 0.570 mmol), potassium carbonate (0.131 g, 0.950 mmol), tetrabutylammonium bromide (0.126 g, 0.380 mmol), distilled $H_2O$ (7 mL) and ethanol (3 mL). This mixture was degassed with $N_{2\ (g)}$ for 1 h at 70° C. A catalytic quantity of $Pd(OAc)_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method4) to give the title compound as a yellow waxy solid (0.076 g, 68%), mp 107.8-108.2° C.;

$R_f$: 0.46 (ethyl acetate);

$^1$H NMR (270 MHz, $CDCl_3$) δ 5.59 (2H, s, $ArCH_2N$), 7.38 (3H, d, J=1.5 Hz, ArH), 7.49-7.64 (3H, m, ArH), 7.75-7.77 (1H, d, J=7.9 Hz, ArH)), 7.98 (1H, s, $C_2H_2N_3$) and 8.31 (1H, s, $C_2H_2N_3$);

$^{13}$C NMR (100.5 MHz, $CDCl_3$) δ 51.3 ($CH_2$), 111.0, 116.9, 125.5, 127.4, 127.9, 128.3, 129.1, 130.5, 133.7, 135.2, 138.8, 140.2, 143.9, 145.2 and 152.8;

HPLC (80% $CH_3CN$ in $H_2O$) $t_r$=2.136 (95.08%);

LCMS (APCI), m/z 297.26 ($^{37}ClM^+$+H, 30%), 295.25 ($^{35}ClM^+$+H, 100).

STX1504

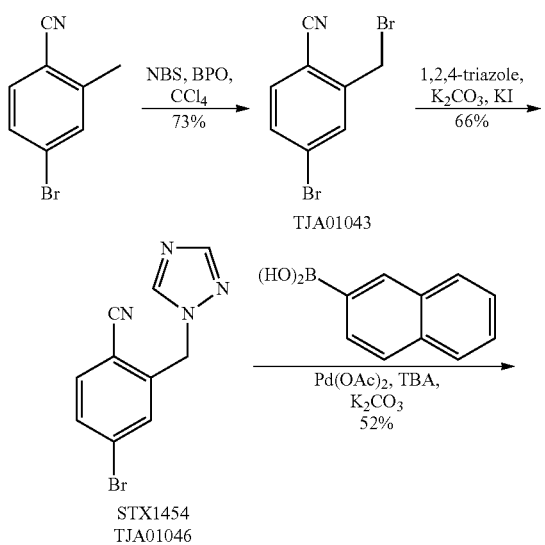

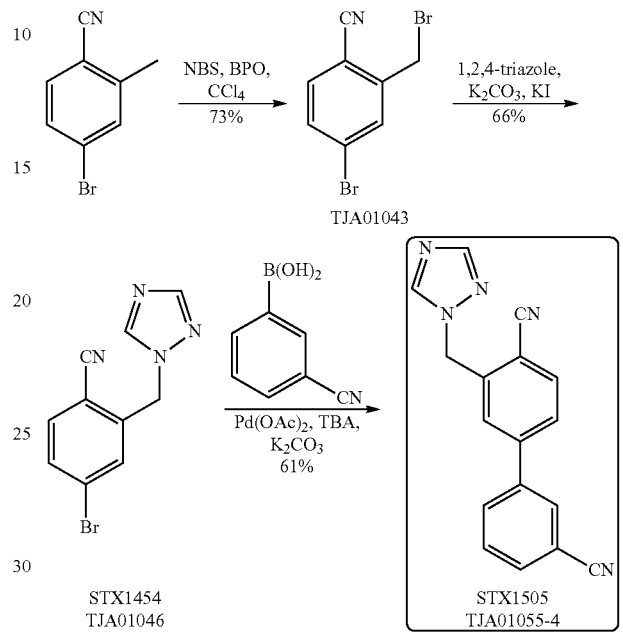

4-Naphthalene-2-yl-2-(1,2,4)triazol-1-ylmethyl-benzonitrile (TJA01055-3, STX1504)

$C_{20}H_{14}N_4$ MW 310.35

A 3 necked r.b. flask was loaded with TJA01046 (0.100 g, 0.380 mmol), 2-naphthaleneboronic acid (0.098 g, 0.570 mmol), potassium carbonate (0.131 g, 0.950 mmol), tetrabutylammonium bromide (0.126 g, 0.380 mmol), distilled $H_2O$ (7 mL) and ethanol (3 mL). This mixture was degassed with $N_{2\,(g)}$ for 1 h at 70° C. A catalytic quantity of $Pd(OAc)_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method4) to give the title compound as a yellow solid (0.061 g, 52%), mp 119.1-120.8° C.;

$R_f$: 0.47 (ethyl acetate);

$^1$H NMR (270 MHz, $CDCl_3$) δ 5.61 (2H, s, $ArCH_2N$), 7.49-7.98 (10H, m, ArH), 7.99 (1H, s, $C_2H_2N_3$) and 8.32 (1H, s, $C_2H_2N_3$);

$^{13}$C NMR (100.5 MHz, $CDCl_3$) δ 51.4 ($CH_2$), 110.3, 117.2, 124.7, 126.8, 126.9, 127.1, 127.8, 128.4, 128.5, 129.1, 133.3, 133.4, 133.7, 135.7, 138.6, 143.9, 146.6, and 152.8;

HPLC (80% $CH_3CN$ in $H_2O$) $t_r$=2.224 (99.00%);

LCMS (APCI), m/z 311.24 ($M^+$+H, 100%).

STX1505

3'-(1,2,4)Triazol-1-ylmethyl-biphenyl-3,4'-dicarbonitrile (TJA01055-4, STX1505)

$C_{17}H_{11}N_5$ MW 285.10

A 3 necked r.b. flask was loaded with TJA01046 (0.100 g, 0.380 mmol), 3-cyanophenylboronic acid (0.084 g, 0.570 mmol), potassium carbonate (0.131 g, 0.950 mmol), tetrabutylammonium bromide (0.126 g, 0.380 mmol), distilled $H_2O$ (7 mL) and ethanol (3 mL). This mixture was degassed with $N_{2\,(g)}$ for 1 h at 70° C. A catalytic quantity of $Pd(OAc)_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method4) to give the title compound as a white solid (0.066 g, 61%), mp 160.4-160.8° C.;

$R_f$: 0.35 (ethyl acetate);

$^1$H NMR (270 MHz, $CDCl_3$) δ 5.60 (2H, s, $ArCH_2N$), 7.36-7.81 (7H, m, ArH), 7.97 (1H, s, $C_2H_2N_3$) and 8.32 (1H, s, $C_2H_2N_3$);

$^{13}$C NMR (100.5 MHz, $CDCl_3$) δ 51.2 ($CH_2$), 111.6, 113.6, 116.7, 118.2, 127.9, 128.4, 130.2, 130.8, 131.6, 132.4, 133.9, 139.1, 139.8, 143.9, 144.2 and 152.9;

HPLC (80% $CH_3CN$ in $H_2O$) $t_r$=1.907 (100%);

LCMS (APCI), m/z 286.30 ($M^+$+H, 100%).

STX1506

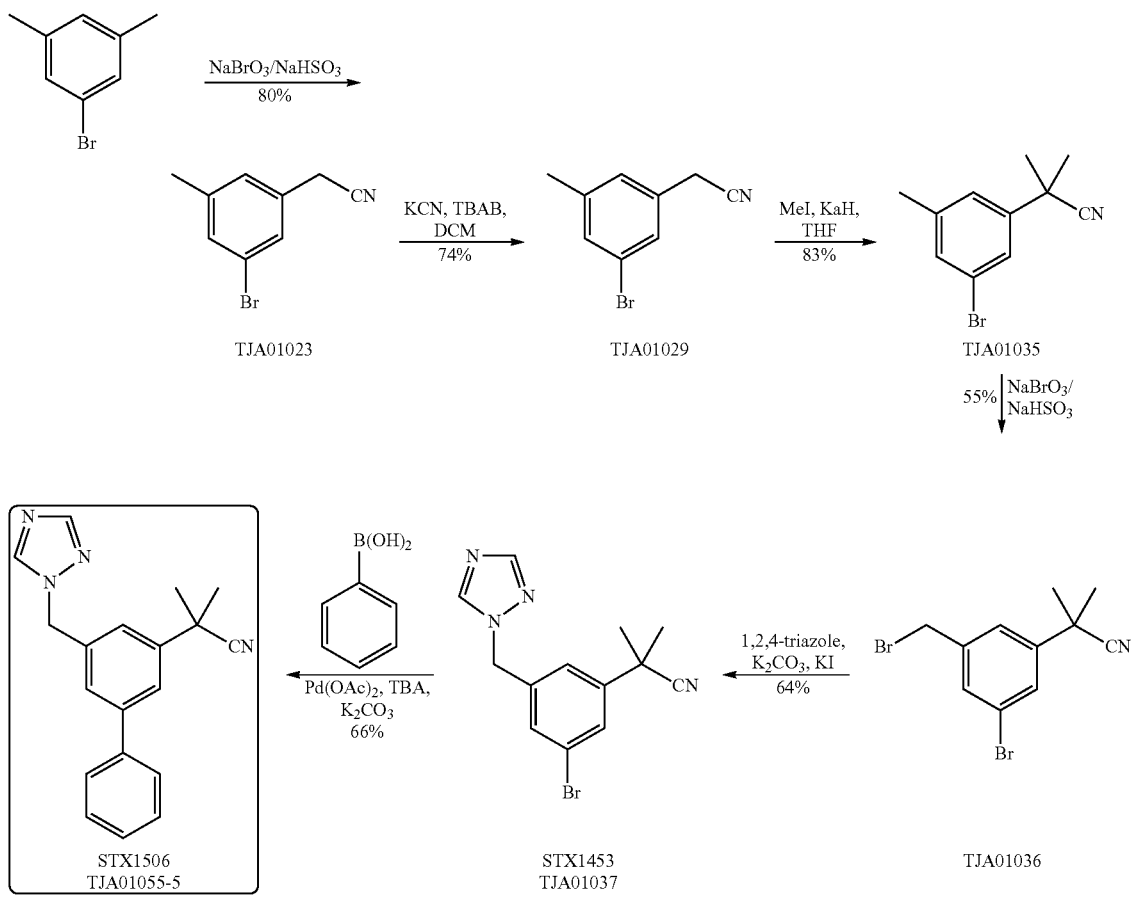

2-Methyl-2-(5-(1,2,4)triazol-1-ylmethyl-biphenyl-3-yl)-propionitrile (TJA01055-5, STX1506)

$C_{19}H_{18}N_4$ MW 302.15

A 3 necked r.b. flask was loaded with TJA01037 (0.100 g, 0.328 mmol), phenylboronic acid (0.060 g, 0.492 mmol), potassium carbonate (0.113 g, 0.820 mmol), tetrabutylammonium bromide (0.109 g, 0.328 mmol), distilled $H_2O$ (3.5 mL) and ethanol (1.5 mL). This mixture was degassed with $N_{2\,(g)}$ for 1 h at 70° C. A catalytic quantity of $Pd(OAc)_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method4) to give the title compound as a yellow viscous oil (0.065 g, 66%), $R_f$: 0.27 (ethyl acetate).

$^1$H NMR (270 MHz, $CDCl_3$) δ 1.67 (6H, s, $ArC(CH_3)_2$CN), 5.35 (2H, s, $ArCH_2N$), 7.23-7.47 (7H, m, ArH), 7.56-7.57 (1H, t, J=1.8 Hz, ArH), 7.92 (1H, s, $C_2H_2N_3$) and 8.08 (1H, s, $C_2H_2N_3$);

$^{13}$C NMR (100.5 MHz, $CDCl_3$) δ 29.2 ($CH_3$), 37.3 (C), 53.4 ($CH_2$), 123.4, 124.2, 124.4, 126.6, 127.3, 128.1, 129.0, 136.1, 139.8, 143.0, 143.2, 143.3 and 152.5;

HPLC (80% $CH_3CN$ in $H_2O$) $t_r$=2.062 (97.56%);

LCMS (APCI), m/z 303.31 ($M^+$+H, 100%), 234.17 (($M^+$+H)—$C_2H_2N_3$, 30%).

STX1507

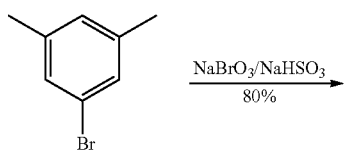

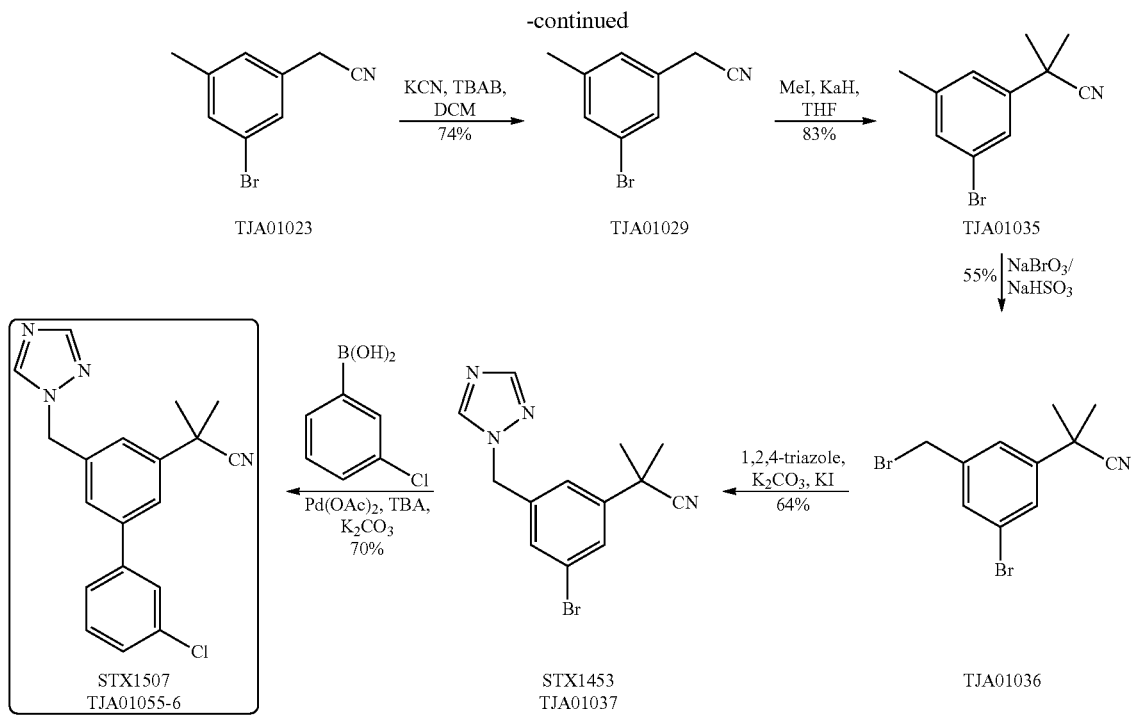

2-(3'-Chloro-5-(1,2,4)triazol-1-ylmethyl-biphenyl-3-yl)-2-methyl-propionitrile (TJA01055-6, STX1507)

$C_{19}H_{17}ClN_4$ MW336.11

A 3 necked r.b. flask was loaded with TJA01037 (0.100 g, 0.328 mmol), 3-chlorophenylboronic acid (0.077 g, 0.492 mmol), potassium carbonate (0.113 g, 0.820 mmol), tetrabutylammonium bromide (0.109 g, 0.328 mmol), distilled $H_2O$ (3.5 mL) and ethanol (1.5 mL). This mixture was degassed with $N_{2\,(g)}$ for 1 h at 70° C. A catalytic quantity of Pd(OAc)$_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method4) to give the title compound as a colourless viscous oil (0.077 g, 70%), R$_f$: 0.31 (ethyl acetate).

$^1$H NMR (270 MHz, CDCl$_3$) δ 1.73 (6H, s, ArC(CH$_3$)$_2$CN), 5.40 (2H, s, ArCH$_2$N), 7.29-7.38 (5H, m, ArH), 7.46-7.48 (1H, dd, J=1.4 & 1.5 Hz, ArH), 7.57-7.58 (1H, t, J=1.7 Hz, ArH), 7.98 (1H, s, C$_2$H$_2$N$_3$) and 8.14 (1H, S, C$_2$H$_2$N$_3$);

$^{13}$C NMR (100.5 MHz, CDCl$_3$) δ 29.2 (CH$_3$), 37.3 (C), 53.3 (CH$_2$), 124.0, 124.4, 125.5, 126.3, 127.4, 128.2, 130.3, 134.9, 136.4, 141.7, 141.8, 143.2, 143.3 and 152.5 (one overlapping signal);

HPLC (80% CH$_3$CN in H$_2$O) t$_r$=2.190 (95.03%);

LCMS (APCI), m/z 339.27 ($^{37}$ClM$^+$+H, 42%), 337.25 ($^{35}$ClM$^+$+H, 100), 270.25 (($^{37}$ClM$^+$+H)—C$_2$H$_2$N$_3$, 10) 268.17 (($^{35}$ClM$^+$+H)—C$_2$H$_2$N$_3$, 30).

STX1508

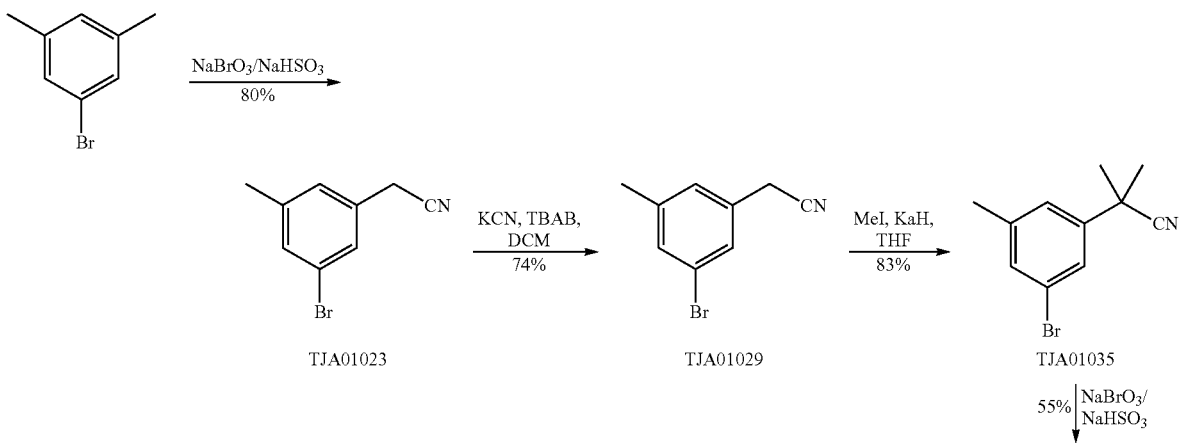

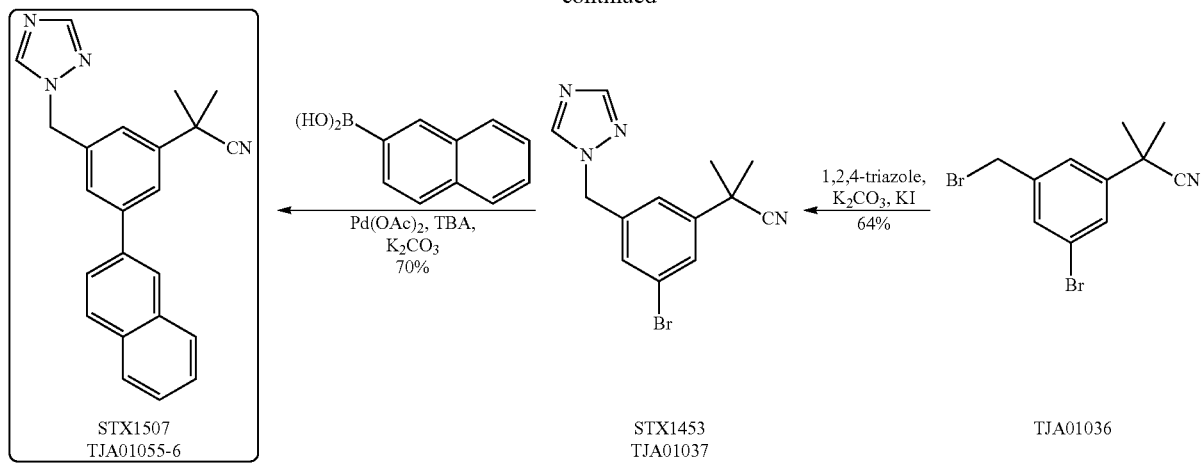

2-Methyl-2(3-naphthalene-2-yl-5-(1,2,4)triazol-1-ylmethyl-phenyl)-propionitrile TJA01055-7, STX1508)

$C_{23}H_{20}N_4$ MW 352.17

A 3 necked r.b. flask was loaded with TJA01037 (0.100 g, 0.328 mmol), 2-naphthaleneboronic acid (0.085 g, 0.492 mmol), potassium carbonate (0.113 g, 0.820 mmol), tetrabutylammonium bromide (0.109 g, 0.328 mmol), distilled $H_2O$ (3.5 mL) and ethanol (1.5 mL). This mixture was degassed with $N_{2\ (g)}$ for 1 h at 70° C. A catalytic quantity of Pd(OAc)$_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method4) to give the title compound as a pale yellow waxy solid (0.061 g, 53%), $R_f$: 0.31 (ethyl acetate).

$^1$H NMR (270 MHz, CDCl$_3$) δ 1.72 (6H, s, ArC(CH$_3$)$_2$CN), 5.40 (2H, s, ArCH$_2$N), 7.32-7.49 (4H, m, ArH), 7.57-7.60 (1H, dd, J=2.0 & 6.7 Hz, ArH), 7.70-7.71 (1H, t, J=1.7 Hz, ArH), 7.78-7.91 (4H, m, ArH), 7.95 (1H, s, C$_2$H$_2$N$_3$) and 8.11 (1H, s, C$_2$H$_2$N$_3$);

$^{13}$C NMR (100.5 MHz, CDCl$_3$) δ 29.2 (CH$_3$), 37.3 (C), 53.4 (CH$_2$), 109.9, 123.5, 124.2, 124.7, 125.3, 126.2, 126.5, 126.6, 126.7, 127.7, 128.3, 128.8, 132.9, 133.5, 136.2, 137.1, 143.1, 143.3 and 152.5;

HPLC (80% CH$_3$CN in H$_2$O) t$_r$=2.251 (98.56%);

LCMS (APCI), m/z 353.37 (M$^+$+H, 100%), 284.29 ((M$^+$+H)—C$_2$H$_2$N$_3$, 35).

STX1509

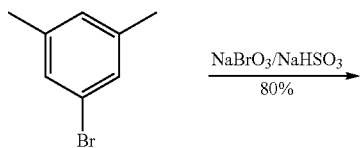

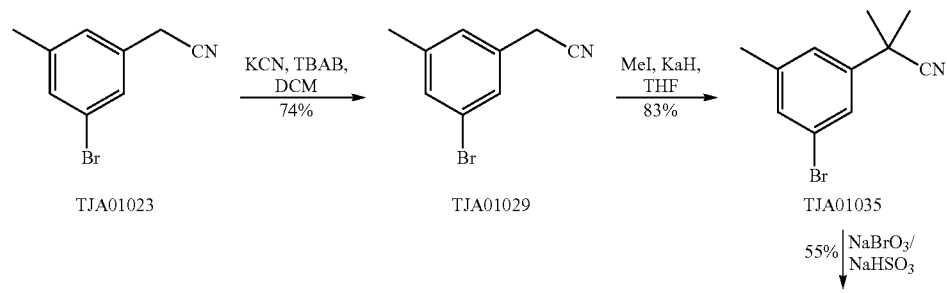

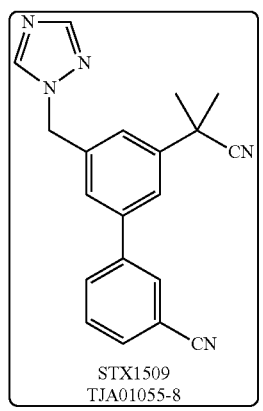
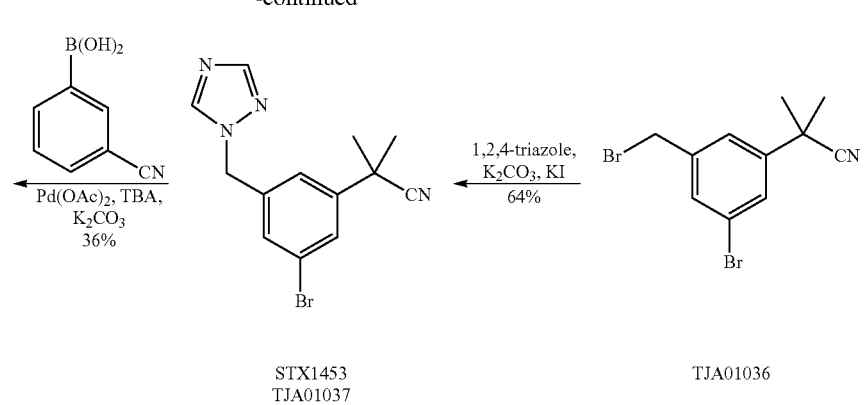

3'-(Cyano-dimethyl-methyl)-5'-(1,2,4)triazol-1-ylmethyl-biphenyl-3-carbonitrile (TJA01055-8, STX1509)

$C_{20}H_{17}N_5$ MW 327.15

A 3 necked r.b. flask was loaded with TJA01037 (0.100 g, 0.328 mmol), 3-cyanophenylboronic acid (0.072 g, 0.492 mmol), potassium carbonate (0.113 g, 0.820 mmol), tetrabutylammonium bromide (0.109 g, 0.328 mmol), distilled $H_2O$ (3.5 mL) and ethanol (1.5 mL). This mixture was degassed with $N_{2\ (g)}$ for 1 h at 70° C. A catalytic quantity of $Pd(OAc)_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method4) to give the title compound as a yellow viscous oil (0.038 g, 36%), $R_f$: 0.23 (ethyl acetate).

$^1$H NMR (270 MHz, $CDCl_3$) δ 1.70 (6H, s, $ArC(CH_3)_2$ CN), 5.38 (2H, s, $ArCH_2N$), 7.30-7.74 (7H, m, ArH), 7.93 (1H, S, $C_2H_2N_3$) and 8.12 (1H, S, $C_2H_2N_3$);

$^{13}$C NMR (100.5 MHz, $CDCl_3$) δ 29.1 ($CH_3$), 37.3 (C), 53.1 ($CH_2$), 113.3, 118.5, 123.9, 124.4, 124.5, 126.2, 129.9, 130.8, 131.5, 131.7, 136.8, 140.9, 141.1, 143.4, 143.6 and 152.5;

HPLC (80% $CH_3CN$ in $H_2O$) $t_r$=1.910 (100%);

LCMS (APCI), m/z 328.31 ($M^+$+H, 100%), 259.17 (($M^+$+H)—$C_2H_2N_3$, 22).

STX1510

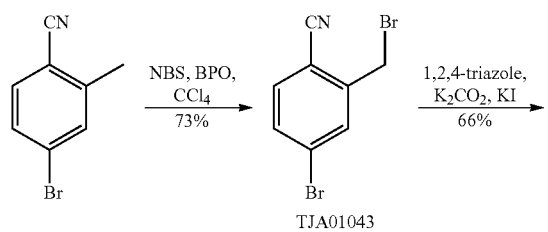

TJA01043

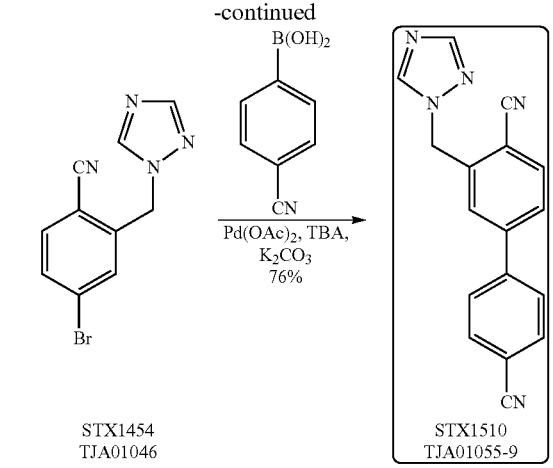

3-(1,2,4)Triazol-1-ylmethyl-biphenyl-4,4'-dicarbonitrile (TJA01055-9, STX1510)

$C_{17}H_{11}N_5$ MW 285.10

A 3 necked r.b. flask was loaded with TJA01046 (0.100 g, 0.380 mmol), 4-cyanophenylboronic acid (0.084 g, 0.570 mmol), potassium carbonate (0.131 g, 0.950 mmol), tetrabutylammonium bromide (0.126 g, 0.380 mmol), distilled $H_2O$ (7 mL) and ethanol (3 mL). This mixture was degassed with $N_{2\ (g)}$ for 1 h at 70° C. A catalytic quantity of $Pd(OAc)_2$ (0.002-0.003 g, 2-3 mol %) was added and the reaction mixture heated with vigorous stirring to 70° C. for 1 h. The reaction mixture was allowed to cool and ethyl acetate (100 mL) added. This was then washed with 1M $NaOH_{(aq)}$ (50 mL×2), distilled water (50 mL×2) and brine (50 mL). The organic layer was dried over $Na_2SO_4$, filtered and solvent removed in vacuo to leave a yellow/brown residue. The crude product was purified by flash chromatography (20 g column, method4) to give the title compound as a white solid (0.082 g, 76%), mp 222.1-222.6° C.

$R_f$: 0.36 (ethyl acetate).

$^1$H NMR (270 MHz, $CDCl_3$) δ 5.56 (2H, s, $ArCH_2N$), 7.52-7.77 (7H, m, ArH), 7.94 (1H, s, $C_2H_2N_3$) and 8.27 (1H, s, $C_2H_2N_3$);

$^{13}$C NMR (100.5 MHz, $CDCl_3$) δ 53.1 ($CH_2$), 111.8, 112.8, 116.6, 118.3, 128.0, 128.4, 133.0, 133.9, 139.1, 142.8, 144.0, 144.6 and 152.9;

HPLC (80% CH$_3$CN in H$_2$O) t$_r$=1.908 (100%);
LCMS (APCI), m/z 286.24 (M$^+$+H, 100%).
STX1511

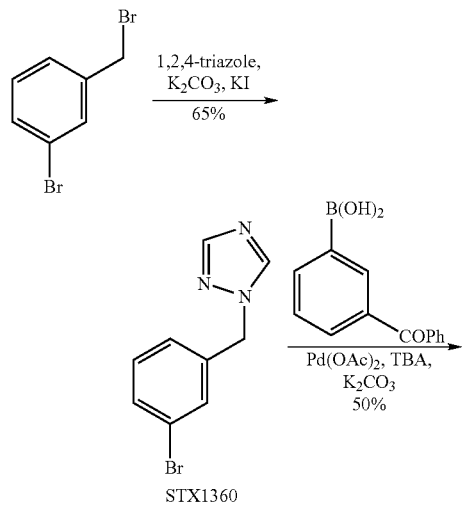

STX1360
TJA01009

STX1511
TJA01055-10

Phenyl-(3'-(1,2,4)triazol-1-ylmethyl-biphenyl-3-yl)-methanone (TJA01055-10, STX1511)

C$_{22}$H$_{17}$N$_3$O MW 339.14

A 3 necked r.b. flask was loaded with TJA01009 (0.100 g, 0.420 mmol), 4-benzoylphenylboronic acid (0.142 g, 0.630 mmol), potassium carbonate (0.145 g, 1.05 mmol), tetrabutylammonium bromide (0.139 g, 0.420 mmol), distilled H$_2$O (7 mL) and ethanol (3 mL). This mixture was degassed with N$_2$ $_{(g)}$ for 1 h at 70° C. A catalytic quantity of Pd(OAc)$_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method4) to give the title compound as a white solid (0.071 g, 50%), mp 120.7-120.9° C.;
R$_f$: 0.24 (ethyl acetate);
$^1$H NMR (270 MHz, CDCl$_3$) δ 5.41 (2H, s, ArCH$_2$N), 7.25-7.28 (1H, m, ArH), 7.43-7.64 (8H, m, ArH), 7.77-7.86 (4H, m, ArH), 7.97 (1H, s, C$_2$H$_2$N$_3$) and 8.12 (1H, s, C$_2$H$_2$N$_3$);
$^{13}$C NMR (100.5 MHz, CDCl$_3$) δ 52.0 (CH$_2$), 126.9, 127.1, 127.7, 128.4, 129.8, 130.1, 132.5, 135.5, 136.7, 137.6, 141.0, 143.2, 144.3, 152.4 and 196.3 (three overlapping signals);
HPLC (80% CH$_3$CN in H$_2$O) t$_r$=2.297 (96.90%);
LCMS (APCI), m/z 340.34 (M$^+$+H, 100%), 271.19 ((M$^+$+H)—C$_2$H$_2$N$_2$, 41).
STX1512

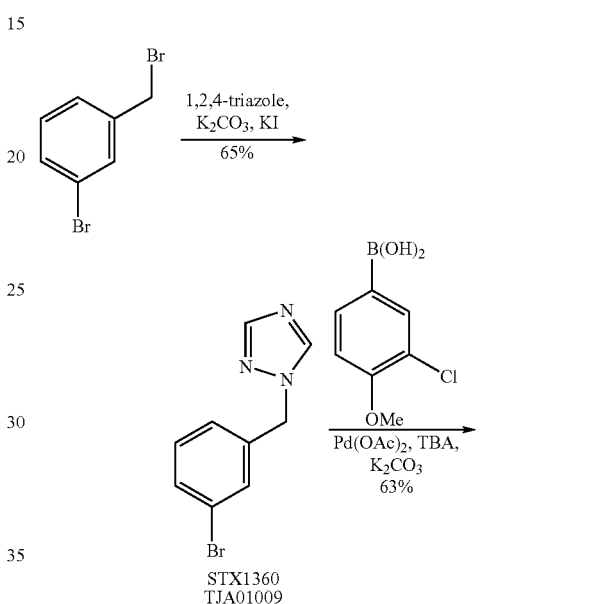

STX1360
TJA01009

STX1512
TJA01061

1-(3'-Chloro-4'-methoxy-biphenyl-3-ylmethyl)-1H-[1,2,4]triazole (TJA01061, STX1512)

C$_{16}$H$_{14}$ClN$_3$O MW 299.75

A 3 necked r.b. flask was loaded with TJA01009 (0.238 g, 1.00 mmol), 3-chloro-4-methoxyphenylboronic acid (0.280 g, 1.50 mmol), potassium carbonate (0.346 g, 2.50 mmol), tetrabutylammonium bromide (0.332 g, 1.00 mmol), distilled H$_2$O (7 mL) and ethanol (3 mL). This mixture was degassed with N$_2$ $_{(g)}$ for 1 h at 70° C. A catalytic quantity of Pd(OAc)$_2$ (0.006-0.007 g, 2-3 mol %) was added and the reaction mixture heated with vigorous stirring to 70° C. for 1 h. The reaction mixture was allowed to cool and ethyl acetate (100 mL) added. This was then washed with 1M NaOH$_{(aq)}$ (50 mL×2), distilled water (50 mL×2) and brine (50 mL). The organic layer was dried over Na$_2$SO$_4$, filtered and solvent removed in vacuo to leave a yellow/brown residue. The crude product was purified by flash chromatography (20 g column, method4) to give the title compound as a pale yellow solid (0.187 g, 63%), mp 78.2-78.4° C.;

R$_f$: 0.21 (ethyl acetate);

$^1$H NMR (270 MHz, CDCl$_3$) δ 3.87 (3H, s, ArOCH$_3$), 5.32 (2H, s, ArCH$_2$N), 6.90-6.93 (1H, d, J=8.4 Hz, ArH), 7.13-7.51 (6H, m, ArH), 7.92 (1H, s, C$_2$H$_2$N$_3$) and 8.04 (1H, s, C$_2$H$_2$N$_3$);

$^{13}$C NMR (100.5 MHz, CDCl$_3$) δ 53.6, 56.3, 112.3, 122.9, 126.4, 126.8, 127.1, 128.9, 129.7, 133.7, 135.3, 140.5, 143.2, 152.3 and 154.7;

HPLC (80% CH$_3$CN in H$_2$O) t$_r$=2.188 (99.43%);

LCMS (APCI), m/z 302.24 ($^{37}$ClM$^+$+H, 52%), 300.22 ($^{35}$ClM$^+$+H, 82), 233.10 (($^{37}$ClM$^+$+H)—C$_2$H$_2$N$_3$, 78), 231.09 (($^{35}$ClM$^+$+H)—C$_2$H$_2$N$_3$, 100).

STX1519

3-Chloro-3'-[1,2,4]triazol-1-ylmethyl-biphenyl-4-ol (TJA01064, STX1519)

C$_{15}$H$_{12}$ClN$_3$O MW 285.73

TJA01055-1 (0.100 g, 0.267 mmol) was dissolved in THF (5 mL) and MeOH (5 mL) in an r.b. flask to which was added 10% Pd/C (0.010 g) to form a black suspension on vigorous stirring. The flask was evacuated and back filled with H$_{2\ (g)}$ via a balloon (×3) and then left to stir for 16 h. The reaction mixture was filtered through celite which was subsequently washed with THF (30 mL×2). Solvent was removed in vacuo to leave a brown residue. Flash chromatography (20 g column, method5) eluted the title compound as a white solid (0.051 g, 67%), mp 153.2-153.3° C.

R$_f$: 0.28 (ethyl acetate).

$^1$H NMR (270 MHz, DMSO-d$_6$) δ 5.54 (2H, s, ArCH$_2$N), 7.03-7.06 (1H, d, J=8.4 Hz, ArH), 7.17-7.20 (1H, d, J=7.4 Hz, ArH), 7.36-7.45 (2H, m, ArH), 7.54-7.56 (2H, d, J=7.2 Hz, ArH), 7.60-7.61 (1H, d, J=2.5 Hz, ArH), 7.99 (1H, s, C$_2$H$_2$N$_3$), 8.70 (1H, s, C$_2$H$_2$N$_3$) and 10.36 (1H, s, ArOH);

HPLC (80% CH$_3$CN in H$_2$O) t$_r$=1.982 (95.50%);

LCMS (APCI), m/z 286.18 ($^{37}$ClM$^-$–H, 30%), 284.16 ($^{35}$ClM—H, 100).

STX1520

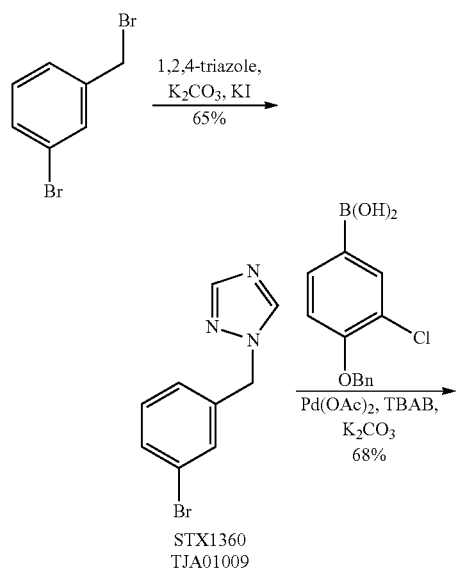

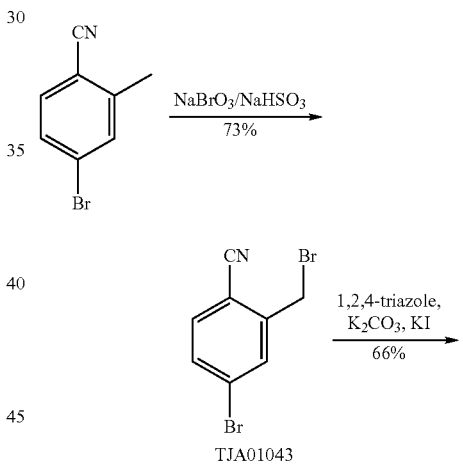

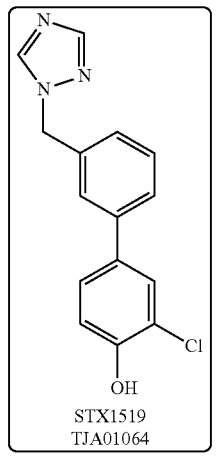

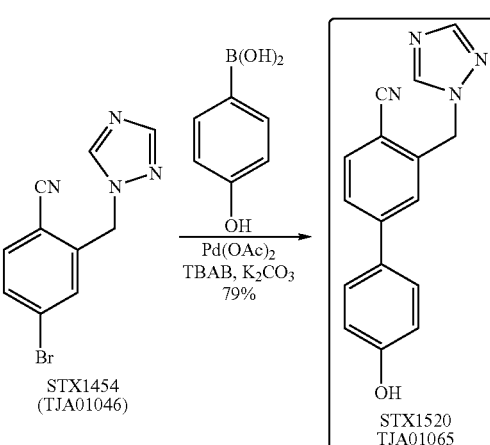

4'-Hydroxy-3-[1,2,4]triazol-1-ylmethyl-biphenyl-4-carbonitrile (TJA01065, STX1520)

$C_{16}H_{12}N_4O$ MW 276.30

A 10 mL microwave vial was loaded with TJA01046 (0.100 g, 0.380 mmol), 4-hydroxyphenylboronic acid (0.079 g, 0.570 mmol), potassium carbonate (0.131 g, 0.950 mmol), tetrabutylammonium bromide (0.126 g, 0.380 mmol), Pd(OAc)$_2$ (0.001-0.002 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30 mL×3) and brine (30 mL). The organic layer was dried over Na$_2$SO$_4$, filtered and solvent removed in vacuo to leave a yellow/brown residue. The crude product was purified by flash chromatography (20 g column, method4) eluting the title compound as a white solid (0.082 g, 79%), mp 203.4-203.6° C.

$R_f$: 0.43 (ethyl acetate).

$^1$H NMR (270 MHz, DMSO-d$_6$) δ 5.62 (2H, s, ArCH$_2$N), 6.85-6.88 (2H, d, J=8.7 Hz, ArH), 7.51-7.55 (2H, d, J=8.7 Hz, ArH), 7.67-7.89 (3H, m, ArH), 7.99 (1H, s, C$_2$H$_2$N$_3$), 8.71 (1H, s, C$_2$H$_2$N$_3$) and 9.83 (1H, s, ArOH);

$^{13}$C NMR (100.5 MHz, DMSO-d$_6$) δ 51.0, 109.2, 116.5, 117.8, 126.5, 127.5, 128.8, 134.3, 139.9, 145.4, 152.6 and 159.0;

HPLC (80% CH$_3$CN in H$_2$O) t$_r$=1.783 (97.91%);

LCMS (APCI), m/z 275.22 (M$^+$+H, 100%).
STX1521

2-(4'-Hydroxy-5-[1,2,4]triazol-1-ylmethyl-biphenyl-3-yl)-2-methyl-propionitrile (TJA01067, STX1521)

$C_{19}H_{18}N_4O$ MW 318.37

A 10 mL microwave vial was loaded with TJA01037 (0.200 g, 0.656 mmol), 4-hydroxyphenylboronic acid (0.136 g, 0.984 mmol), potassium carbonate (0.227 g, 1.64 mmol), tetrabutylammonium bromide (0.218 g, 0.656 mmol), Pd(OAc)$_2$ (0.004-0.005 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30×3 mL) and brine (30 mL). The organic layer was dried over Na$_2$SO$_4$, filtered and solvent removed in vacuo to leave a yellow/brown residue. The crude product was purified by flash chromatography (20 g column, method4) eluting the title compound as a pale yellow (0.216 g, 89%), mp 65.8-68.1° C.

$R_f$: 0.28 (ethyl acetate).

$^1$H NMR (270 MHz, DMSO-d$_6$) δ 1.71 (6H, s, ArC(CH$_3$)$_2$CN), 5.49 (2H, s, ArCH$_2$N), 6.84-6.87 (2H, d, J=8.7 Hz, ArH), 7.38 (1H, s, ArH), 7.42 (1H, s, ArH), 7.44-7.48 (2H, d, J=8.7 Hz, ArH), 7.59 (1H, s, ArH), 8.00 (1H, s, C$_2$H$_2$N$_3$), 8.72 (1H, s, C$_2$H$_2$N$_3$) and 9.64 (1H, s, ArOH);

$^{13}$C NMR (100.5 MHz, DMSO-d$_6$) δ 28.8 (CH$_3$), 37.3 (C), 52.5 (CH$_2$), 116.3, 122.9, 123.3, 125.0, 125.5, 128.5, 130.5, 138.0, 141.8, 143.0, 144.9, 152.3 and 158.0;

HPLC (80% CH$_3$CN in H$_2$O) t$_r$=1.787 (99.55%);

LCMS (APCI), m/z 317.29 (M—H, 100%).

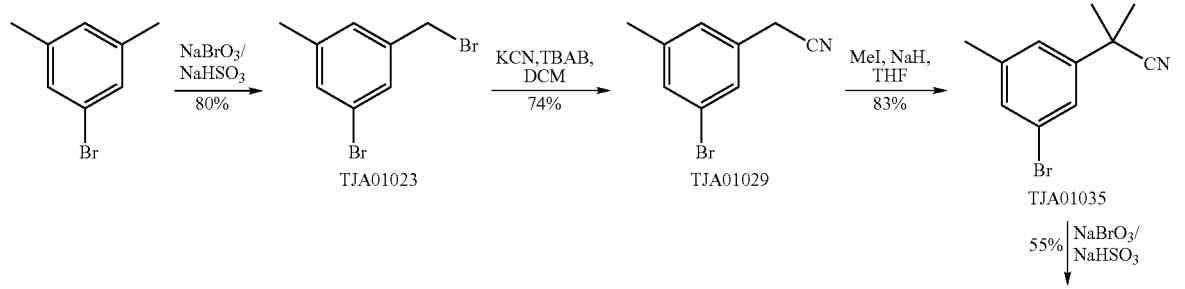

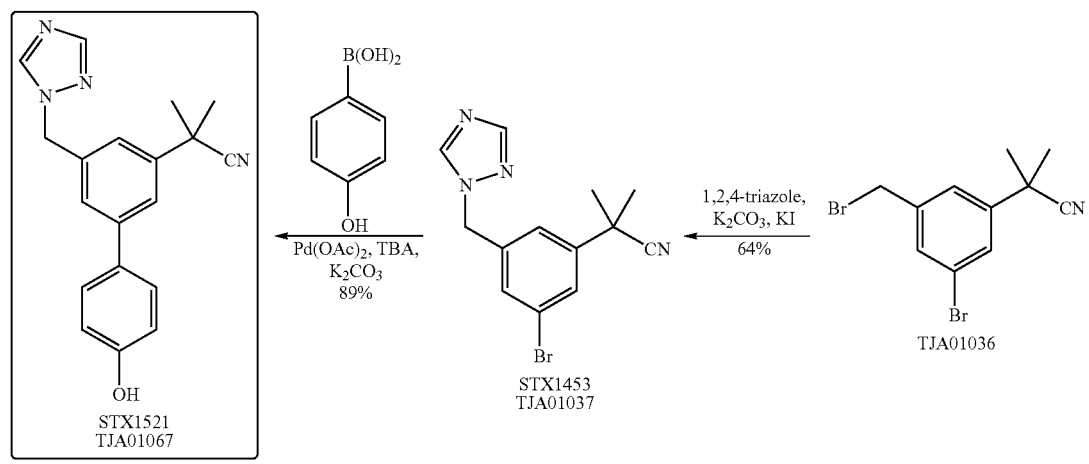

STX1524

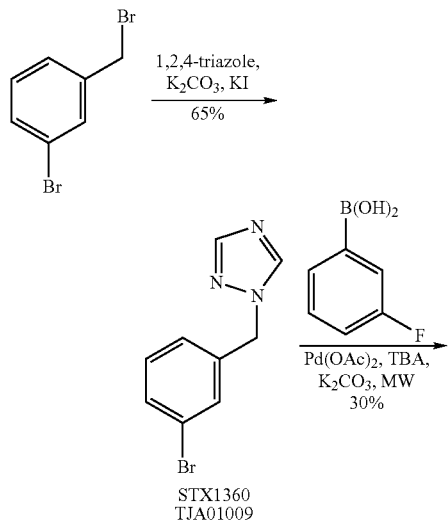

1-(3'-Fluoro-biphenyl-3-ylmethyl)-1H-[1,2,4]triazole (TJA01070, STX1524)

$C_{15}H_{12}FN_3$ MW 253.27

A 10 mL microwave vial was loaded with TJA01009 (0.100 g, 0.420 mmol), 3-fluorophenylboronic acid (0.088 g, 0.630 mmol), potassium carbonate (0.145 g, 1.05 mmol), tetrabutylammonium bromide (0.139 g, 0.420 mmol), Pd(OAc)$_2$ (0.002-0.003 g, 2-3 mol %), ethanol (1.5 mL) and distilled water (3.5 mL). The vial was sealed and loaded (with no prior degassing) into a CEM Discover Microwave. After a run time of 3 min at 120° C. complete conversion was evident by tlc (ethyl acetate). The reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified by flash chromatography (20 g column, method4) eluting the title compound as a colourless oil (0.035 g, 30%), R$_f$: 0.29 (ethyl acetate);

$^1$H NMR (270 MHz, CDCl$_3$) δ 5.39 (2H, s, ArCH$_2$N), 7.02-7.06 (1H, s, ArH), 7.20-7.54 (7H, m, ArH), 7.97 (1H, S, C$_2$H$_2$N$_3$) and 8.09 (1H, S, C$_2$H$_2$N$_3$);

HPLC (80% CH$_3$CN in H$_2$O) t$_r$=2.151 (96.90%);

LCMS (APCI), m/z 254.13 (M$^+$+H, 62%), 184.94 ((M$^+$+H)—C$_2$H$_2$N$_3$, 100).

STX1525

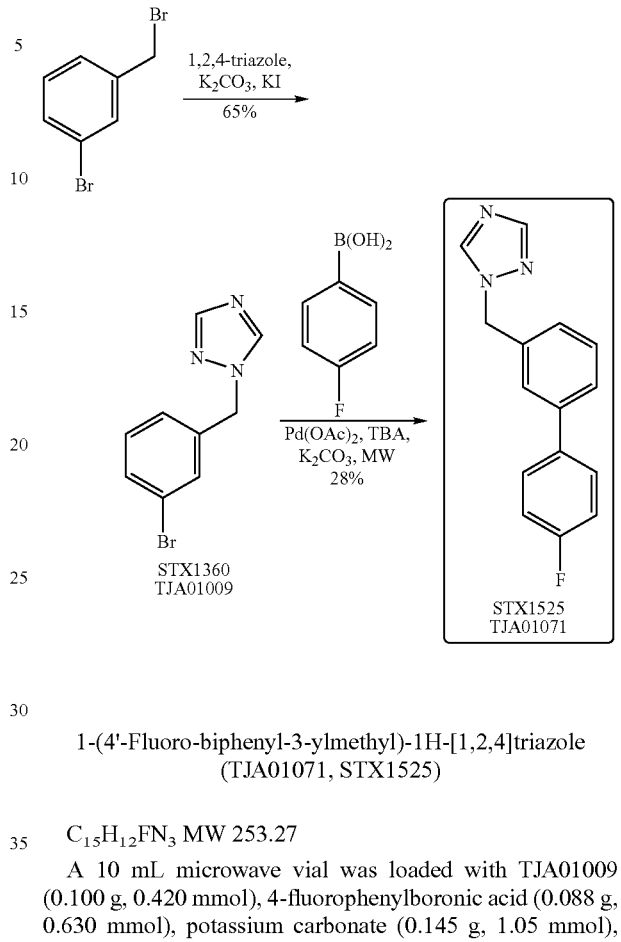

1-(4'-Fluoro-biphenyl-3-ylmethyl)-1H-[1,2,4]triazole (TJA01071, STX1525)

$C_{15}H_{12}FN_3$ MW 253.27

A 10 mL microwave vial was loaded with TJA01009 (0.100 g, 0.420 mmol), 4-fluorophenylboronic acid (0.088 g, 0.630 mmol), potassium carbonate (0.145 g, 1.05 mmol), tetrabutylammonium bromide (0.139 g, 0.420 mmol), Pd(OAc)$_2$ (0.002-0.003 g, 2-3 mol %), ethanol (1.5 mL) and distilled water (3.5 mL). The vial was sealed and loaded (with no prior degassing) into a CEM Discover Microwave. After a run time of 3 min at 120° C. complete conversion was evident by tlc (ethyl acetate). The reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified by flash chromatography (20 g column, method4) eluting the title compound as an off white solid (0.030 g, 28%), mp 82.9-83.8° C.;

R$_f$: 0.32 (ethyl acetate);

$^1$H NMR (270 MHz, CDCl$_3$) δ 5.34 (2H, s, ArCH$_2$N), 7.02-7.08 (2H, m, ArH), 7.15-7.19 (1H, d, J=7.6 Hz, ArH), 7.35-7.46 (5H, m, ArH), 7.92 (1H, s, C$_2$H$_2$N$_3$) and 8.04 (1H, s, C$_2$H$_2$N$_3$);

$^{13}$C NMR (100.5 MHz, CDCl$_3$) δ 53.6 (CH$_3$), 115.7-115.9 (J$_{C-F}$ 21.5 Hz), 126.7, 126.8, 127.4, 128.7-128.8 (J$_{C-F}$ 8.5 Hz), 129.6, 135.3, 136.5, 141.2, 143.2, 152.3 and 161.5-163.9 (J$_{C-F}$ 246.9 Hz);

HPLC (80% CH$_3$CN in H$_2$O) t$_r$=2.168 (98.68%);

LCMS (APCI), m/z 254.19 (M$^+$+H, 48%), 185.07 ((M$^+$+H)—C$_2$H$_2$N$_3$, 100).

STX1835

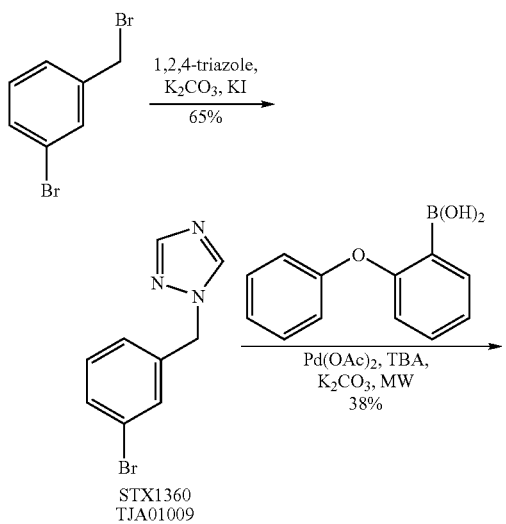

STX1360
TJA01009

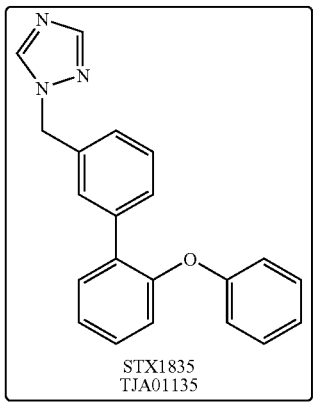

STX1835
TJA01135

1-(2'-Phenoxy-biphenyl-3-ylmethyl)-1H-[1,2,4]triazole (TJA01135, STX1835)

$C_{21}H_{17}N_3O$ MW 327.38

A 10 mL microwave vial was loaded with TJA01009 (0.100 g, 0.420 mmol), 4-phenoxyphenylboronic acid (0.135 g, 0.630 mmol), potassium carbonate (0.145 g, 1.05 mmol), tetrabutylammonium bromide (0.139 g, 0.420 mmol), Pd(OAc)$_2$ (0.002-0.003 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified by flash chromatography (20 g column, method4) eluting the title compound as a light yellow viscous oil (0.120 g, 88%), R$_f$: 0.44 (ethyl acetate);

$^1$H NMR (270 MHz, DMSO-d$_6$) δ 5.41 (2H, s, ArCH$_2$N), 6.83-6.86 (2H, d, J=7.7 Hz, ArH), 6.98-7.05 (2H, m, ArH), 7.19-7.51 (1H, m, ArH), 7.97 (1H, S, C$_2$H$_2$N$_3$) and 8.63 (1H, S, C$_2$H$_2$N$_3$);

$^{13}$C NMR (67.9 MHz, CDCl$_3$) δ 53.7, 117.9, 120.1, 120.4, 122.8, 124.3, 126.9, 129.0, 129.2, 129.6, 129.7, 131.2, 132.9, 134.4, 138.7, 143.1, 152.2, 153.5 and 157.7;

HPLC (90% CH$_3$CN in H$_2$O) t$_r$=2.278 (98.66%);
LCMS (APCI), m/z 328.46 (M$^+$+H, 100%);

STX1838

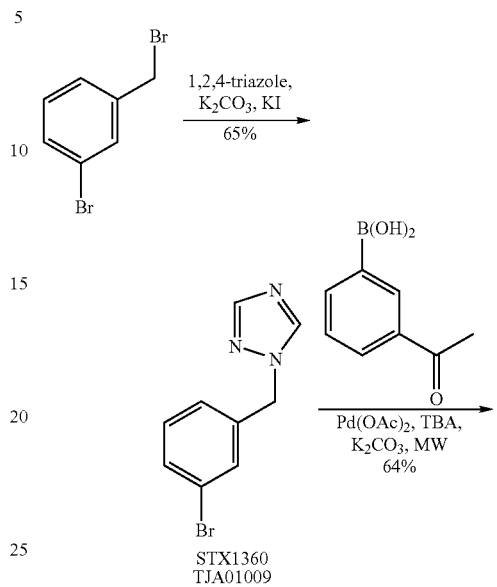

STX1360
TJA01009

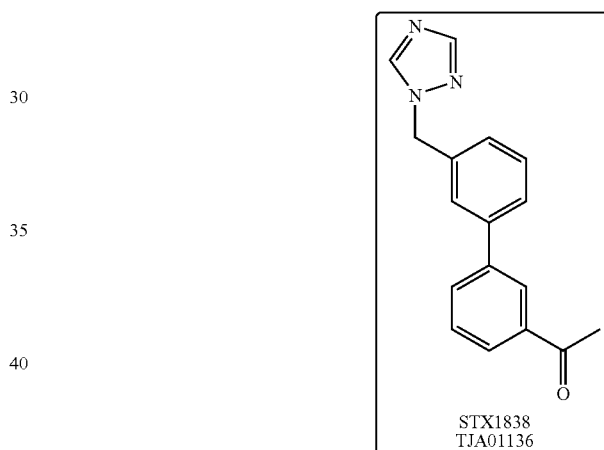

STX1838
TJA01136

1-(3'-[1,2,4]Triazol-1-ylmethyl-biphenyl-3-yl)-ethanone (TJA01136, STX1838)

$C_{17}H_{15}N_3O$ MW 277.32

A 10 mL microwave vial was loaded TJA01009 (0.100 g, 0.420 mmol), 3-acetylphenylboronic acid (0.103 g, 0.630 mmol), potassium carbonate (0.145 g, 1.05 mmol), tetrabutylammonium bromide (0.139 g, 0.420 mmol), Pd(OAc)$_2$ (0.002-0.003 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified by flash chromatography (20 g column, method4) eluting the title compound as a colourless viscous oil (0.074 g, 64%), R$_f$: 0.38 (ethyl acetate);

$^1$H NMR (270 MHz, CDCl$_3$) δ 2.62 (3H, s, ArCOCH$_3$), 5.42 (2H, s, ArCH$_2$N), 7.28 (1H, s, ArH), 7.41-7.62 (4H, m,

ArH), 7.71-7.76 (1H, ddd, J=0.7 & 2.0 & 11.0 Hz, ArH), 7.92-7.94 (1H, dt, J=0.5 & 7.7 Hz, ArH), 7.98 (1H, s, $C_2H_2N_3$), 8.11 (1H, S, $C_2H_2N_3$) and 8.13-8.15 (1H, t, J=1.8 Hz, ArH);

$^{13}$C NMR (100.5 MHz, CDCl$_3$) δ 26.9 (CH$_3$), 53.6 (CH$_2$), 126.9 (CH), 127.4 (CH), 127.7 (CH), 127.8 (CH), 129.3 (CH), 129.8 (CH), 131.9 (CH), 135.5 (C), 137.7 (C), 140.9 (C), 141.2 (C), 143.3 (CH), 152.4 (CH) and 198.1 (C=O) (one overlapping signal);

HPLC (90% CH$_3$CN in H$_2$O) t$_r$=2.300 (100%);
LCMS (APCI), m/z 278.39 (M$^+$+H, 100%).
STX1839

1-(3-Dibenzofuran-4-yl-benzyl)-1H-[1,2,4]triazole (TJA01137, STX1839)

$C_{21}H_{15}N_3O$ MW 325.36

A 10 mL microwave vial was loaded with TJA01009 (0.100 g, 0.420 mmol), 4-dibenzofuranboronic acid (0.134 g, 0.630 mmol), potassium carbonate (0.145 g, 1.05 mmol), tetrabutylammonium bromide (0.139 g, 0.420 mmol), Pd(OAc)$_2$ (0.002-0.003 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified by flash chromatography (20 g column, method4) eluting the title compound as a colourless viscous oil (0.097 g, 71%), R$_f$: 0.39 (ethyl acetate);
$^1$H NMR (270 MHz, CDCl$_3$) δ 5.47 (2H, s, ArCH$_2$N), 7.28-7.60 (7H, m, ArH), 7.81 (1H, m, ArH), 7.87-7.99 (3H, m, ArH), 8.04 (1H, s, $C_2H_2N_3$) and 8.16 (1H, s, $C_2H_2N_3$);
$^{13}$C NMR (67.9 MHz, CDCl$_3$) δ 53.8 (CH$_2$), 111.9 (CH), 120.2 (CH), 120.8 (CH), 123.0 (CH), 123.4 (CH), 124.1 (C), 125.0 (C), 125.1 (C), 126.8 (CH), 127.4 (CH), 127.5 (CH), 128.5 (CH), 129.2 (CH), 129.5 (CH), 135.1 (C), 137.4 (C), 143.3 (CH), 152.4 (CH), 153.3 (C) and 156.1 (C);
HPLC (90% CH$_3$CN in H$_2$O) t$_r$=3.018 (98.25%);
LCMS (APCI), m/z 326.45 (M$^+$+H, 100%).
STX1840

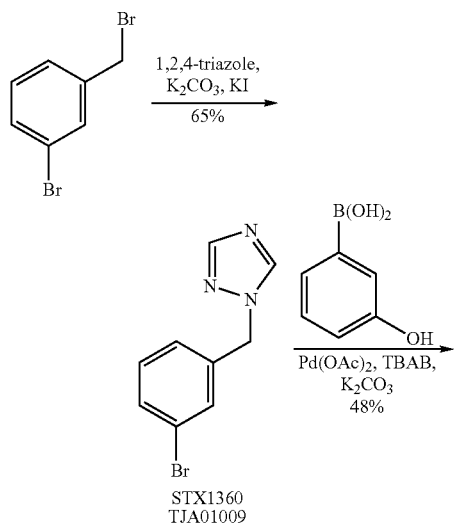

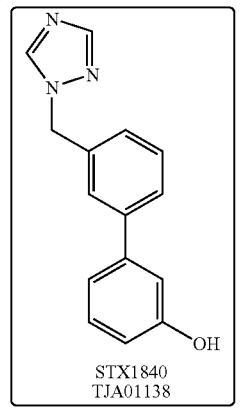

3'-[1,2,4]Triazol-1-ylmethyl-biphenyl-3-ol (TJA01138, STX1840)

$C_{15}H_{13}N_3O$ MW 251.29

A 10 mL microwave vial was loaded with TJA01009 (0.150 g, 0.630 mmol), 3-hydroxyphenylboronic acid (0.130 g, 0.945 mmol), potassium carbonate (0.218 g, 1.58 mmol), tetrabutylammonium bromide (0.209 g, 0.630 mmol), Pd(OAc)$_2$ (0.004-0.005 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (25×3 mL) and brine (25 mL). The organic layer was dried over MgSO$_4$, filtered and solvent removed in vacuo to leave a yellow/brown residue. The crude product was purified by flash chromatography (20 g column, method4) eluting the title compound as a pale yellow solid (0.130 g, 82%), R$_f$: 0.25 (ethyl acetate);
$^1$H NMR (270 MHz, DMSO-d$_6$) δ 5.48 (2H, s, ArCH$_2$N), 6.75-6.79 (1H, dd, J=0.8 & 8.9 Hz, ArH), 6.97-7.04 (2H, m, ArH), 7.23-7.29 (2H, m, ArH), 7.43-7.58 (3H, m, ArH), 8.01 (1H, s, $C_2H_2N_3$), 8.73 (1H, s, $C_2H_2N_3$) and 9.59 (1H, s, ArOH);
$^{13}$C NMR (67.9 MHz, DMSO-d$_6$) δ 52.6 (CH$_2$), 114.0 (CH), 115.2 (CH), 118.0 (CH), 126.7 (CH), 127.4 (CH), 129.8 (CH), 130.6 (CH), 137.5 (C), 141.2 (C), 141.7 (C), 144.9 (CH), 152.4 (CH) and 158.4 (C) (one overlapping signal);
HPLC (90% CH$_3$CN in H$_2$O) t$_r$=2.199 (99.70%);
LCMS (APCI), m/z 252.25 (M$^+$+H, 100%);
STX1841

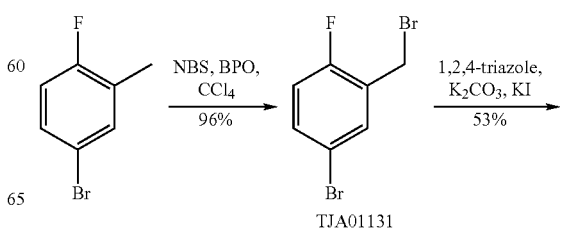

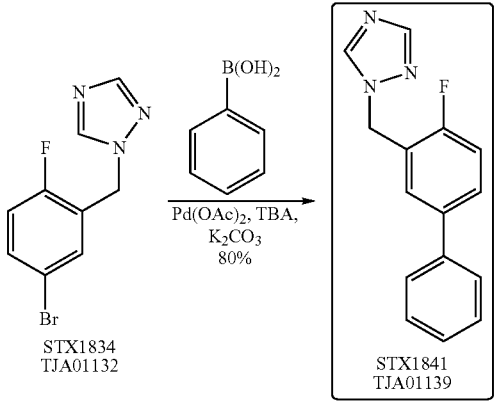

4-Bromo-2-bromomethyl-1-fluoro-benzene (TJA01131)

$C_7H_5Br_2F$ MW 267.92

5-bromo-2-fluorotoluene (5.00 g, 26.5 mmol), N-bromosuccinimide (5.18 g, 29.1 mmol), benzyl peroxide (0.205 g, 0.850 mmol) and carbon tetrachloride (50 mL) were loaded to a r.b. flask and set to reflux (79° C.) for 2 h. Once cooled the succinimide was filtered off and carbon tetrachloride removed via a dry ice-acetone cooled rotary evaporator. The residues were dissolved in dichloromethane (100 mL) and washed with distilled $H_2O$ (50 mL×3) and brine (50 mL). Dried over $MgSO_4$ and solvent removed in vacuo to yield the title compound as a colourless liquid yellow (6.80 g, 96%), $R_f$: 0.55 (dichloromethane/hexane 10:90), c.f. 0.79 (5-bromo-2-fluorotoluene);

HPLC (70% $CH_3CN$ in $H_2O$) $t_r$=4.786 (71.55%);

1-(5-Bromo-2-fluoro-benzyl)-1H-[1,2,4]triazole (TJA01132, STX1834)

$C_9H_7BrFN_3$ MW 256.07

To a solution of TJA01131 (5.00 g, 18.7 mmol) in acetone (50 mL) was added 1,2,4-triazole (1.94 g, 28.1 mmol), potassium carbonate (2.58 g, 18.7 mmol) and potassium iodide (0.182 g, 1.10 mmol). The resulting white suspension was heated to 55° C. with vigorous stirring for 16 h. The yellow reaction mixture was cooled and ethyl acetate (100 mL) added. This was then washed with distilled water (100 mL×2) and brine (100 mL). The organic layer was dried over $MgSO_4$, filtered and solvent removed in vacuo to leave clear yellow oil that crystallises on standing to give the title compound as a yellow crystalline solid (2.54 g, 53%), $R_f$: 0.57 (ethyl acetate);

$^1H$ NMR (270 MHz, $CDCl_3$) δ 5.33 (2H, s, $ArCH_2N$), 6.94-7.01 (1H, t, J=8.9 Hz, ArH), 7.34-7.44 (2H, m, ArH), 7.95 (1H, s, $C_2H_2N_3$) and 8.14 (1H, s, $C_2H_2N_3$);

$^{13}C$ NMR (67.9 MHz, $CDCl_3$) δ 46.8 ($CH_2$), 117.2-117.3 (C, $J_{C-F}$ 3.8 Hz), 117.5-117.9 (CH, $J_{C-F}$ 26.8 Hz), 124.1-124.3 (C, $J_{C-F}$ 15.3 Hz), 133.2-133.2 (CH, $J_{C-F}$ 4.5 Hz), 133.7-133.8 (CH, $J_{C-F}$ 8.3 Hz), 143.5 (CH), 152.5 (CH) and 157.8-161.5 (C, $J_{C-F}$ 254 Hz);

HPLC (70% $CH_3CN$ in $H_2O$) $t_r$=2.630 (99.30%);

LCMS (APCI), m/z 258.24 ($^{81}BrM^++H$, 100%), 258.24 ($^{79}BrM^++H$, 95);

1-(4-Fluoro-biphenyl-3-ylmethyl)-1H-[1,2,4]triazole (TJA01139, STX1841)

$C_{15}H_{12}FN_3$ MW 253.27

A 10 mL microwave vial was loaded with TJA01132 (0.100 g, 0.391 mmol), phenylboronic acid (0.071 g, 0.586 mmol), potassium carbonate (0.135 g, 0.978 mmol), tetrabutylammonium bromide (0.130 g, 0.391 mmol), $Pd(OAc)_2$ (0.002-0.003 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30 mL×3) and brine (30 mL). The organic layer was dried over $MgSO_4$, filtered and solvent removed in vacuo to leave a yellow/brown residue. The crude product was purified by flash chromatography (20 g column, method7) eluting the title compound as a colourless viscous oil (0.079 g, 80%), $R_f$: 0.45 (ethyl acetate);

$^1H$ NMR (270 MHz, $CDCl_3$) δ 5.44 (2H, s, $ArCH_2N$), 7.13-7.20 (2H, m, ArH), 7.31-7.57 (7H, m, ArH), 7.96 (1H, s, $C_2H_2N_3$) and 8.17 (1H, s, $C_2H_2N_3$);

$^{13}C$ NMR (67.9 MHz, $CDCl_3$) δ 47.4-47.5 ($CH_2$, $J_{C-F}$ 4.5 Hz), 116.1-116.4 (CH, $J_{C-F}$ 21.7 Hz), 122.1-122.4 (C, $J_{C-F}$ 20.4 Hz), 127.1 (CH), 127.8 (CH), 129.0 (CH), 129.3-129.3 (CH, $J_{C-F}$ 3.2 Hz), 129.6-129.5 (CH, $J_{C-F}$ 8.9 Hz), 138.2 (C), 139.5 (C), 143.3 (CH), 152.4 (CH) and 158.4-162.1 (C, $J_{C-F}$ 260 Hz);

HPLC (90% $CH_3CN$ in $H_2O$) $t_r$=2.197 (98.14%);

LCMS (APCI), m/z 254.33 ($M^++H$, 100%).

STX1842

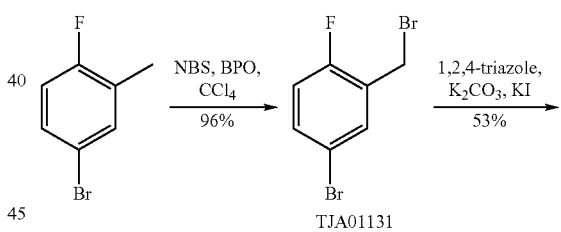

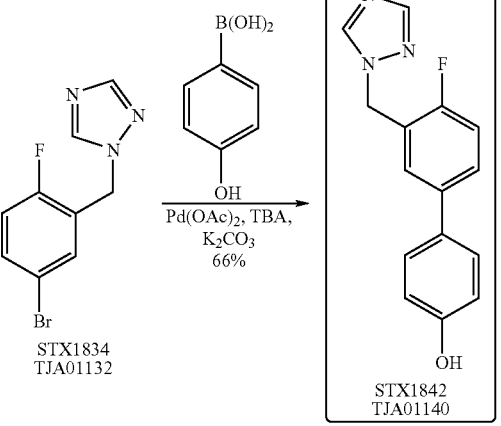

4'-Fluoro-3'-[1,2,4]triazol-1-ylmethyl-biphenyl-4-ol (TJA01140, STX1842)

$C_{15}H_{12}FN_3O$ MW 269.27

A 10 mL microwave vial was loaded with TJA01132 (0.200 g, 0.781 mmol), 4-hydroxyphenylboronic acid (0.164 g, 1.17 mmol), potassium carbonate (0.270 g, 1.95 mmol), tetrabutylammonium bromide (0.260 g, 0.781 mmol), Pd(OAc)$_2$ (0.005-0.006 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified by flash chromatography (20 g column, method7) eluting the title compound as a white solid (0.139 g, 66%), $R_f$: 0.40 (ethyl acetate);
$^1$H NMR (270 MHz, DMSO-d$_6$) δ 5.51 (2H, ArCH$_2$N), 6.82-6.86 (2H, d, J=8.4 Hz, AA'BB'), 7.22-7.30 (1H, t, J=8.6 Hz, ArH), 7.40-7.43 (2H, d, J=8.4 Hz, AA'BB'), 7.53-7.58 (2H, m, ArH), 7.99 (1H, s, C$_2$H$_2$N$_3$), 8.69 (1H, s, C$_2$H$_2$N$_3$) and 9.63 (1H, s, ArOH);
$^{13}$C NMR (67.9 MHz, DMSO-d$_6$) δ 46.8-46.9 (CH$_2$, J$_{C-F}$ 3.2 Hz), 116.3-116.6 (CH, J$_{C-F}$ 21.7 Hz), 123.7-123.9 (C, J$_{C-F}$ 15.9 Hz), 128.3 (CH), 128.4 (CH), 128.8-128.9 (CH, J$_{C-F}$ 3.8 Hz), 130.1 (C), 137.4 (C), 137.5 (C), 145.0 (CH), 152.3 (CH), 157.8 (C), 157.0-161.6 (C, J$_{C-F}$ 251.7 Hz);
HPLC (90% CH$_3$CN in H$_2$O) t$_r$=1.965 (100%);
LCMS (APCI), m/z 270.40 (M$^+$+H, 100%);
STX1843

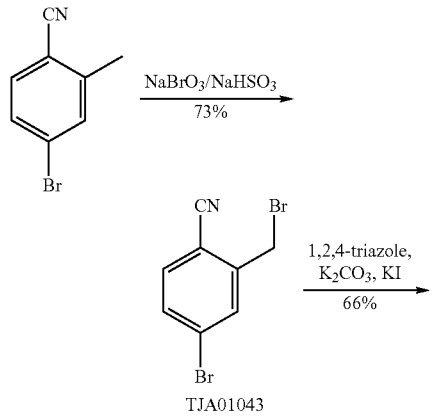

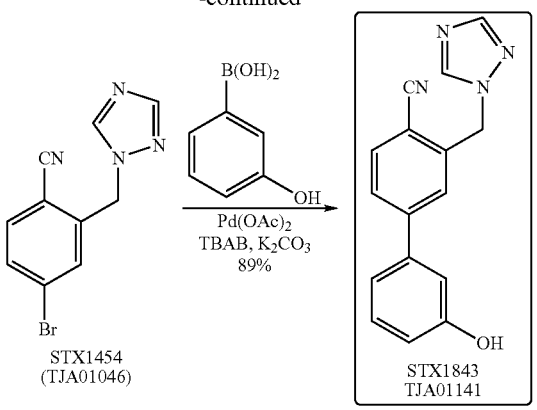

3'-Hydroxy-3-[1,2,4]triazol-1-ylmethyl-biphenyl-4-carbonitrile (TJA01141, STX1843)

$C_{16}H_{12}N_4O$ MW 276.29

A 10 mL microwave vial was loaded with TJA01046 (0.200 g, 0.760 mmol), 3-hydroxyphenylboronic acid (0.160 g, 1.14 mmol), potassium carbonate (0.263 g, 1.90 mmol), tetrabutylammonium bromide (0.253 g, 0.760 mmol), Pd(OAc)$_2$ (0.005-0.006 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified by flash chromatography (20 g column, method7) eluting the title compound as a white solid (0.184 g, 89%), mp 182.7-184.3° C.;
$R_f$: 0.33 (ethyl acetate);
$^1$H NMR (270 MHz, DMSO-d$_6$) δ 5.68 (2H, s, ArCH$_2$N), 6.83-6.87 (1H, dd, J=2.5 & 8.2 Hz, ArH), 7.01-7.10 (2H, m, ArH), 7.28-7.34 (1H, t, J=7.9 Hz, ArH), 7.68 (1H, s, ArH), 7.76-7.79 (1H, dd, J=1.8 & 8.1 Hz, ArH), 7.93-7.96 (1H, d, J=8.2 Hz, ArH), 8.06 (1H, s, C$_2$H$_2$N$_3$), 8.75 (1H, s, C$_2$H$_2$N$_3$) and 9.73 (1H, s, ArOH);
$^{13}$C NMR (67.9 MHz, DMSO-d$_6$) δ 51.0 (CH$_2$), 110.5 (C), 114.2 (CH), 116.5 (CH), 117.7 (C), 118.3 (CH), 127.6 (CH), 128.4 (CH), 130.9 (CH), 134.5 (CH), 139.8 (C), 140.2 (C), 145.5 (CH), 145.6 (C), 152.7 (CH) and 158.6 (C);
HPLC (90% CH$_3$CN in H$_2$O) t$_r$=1.963 (100%);
LCMS (APCI), m/z 277.39 (M$^+$+H, 100%).
STX1844

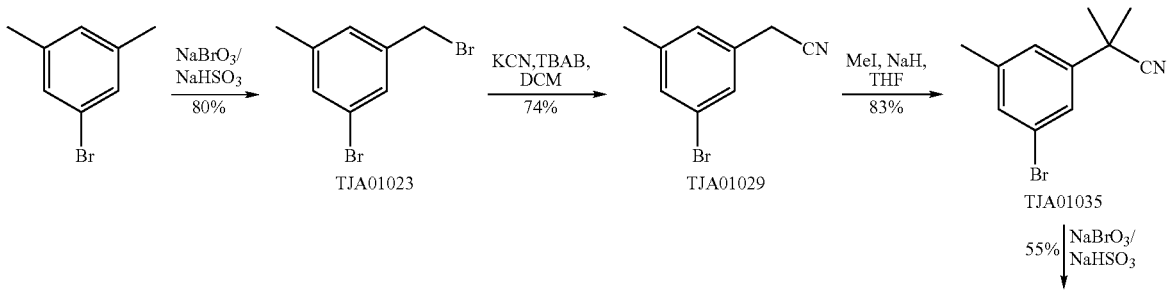

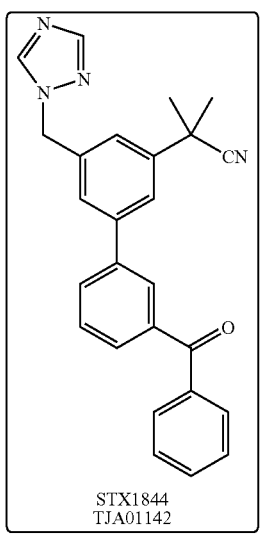
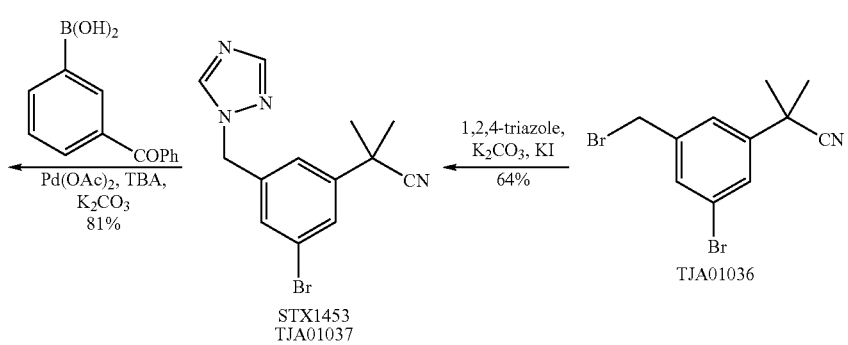

2-(3'-Benzoyl-5-[1,2,4]triazol-1-ylmethyl-biphenyl-3-yl)-2-methyl-propionitrile (TJA01142, STX1844)

$C_{26}H_{22}N_4O$ MW 406.48

A 10 mL microwave vial was loaded with TJA01037 (0.100 g, 0.328 mmol), 4-benzoylphenylboronic acid (0.111 g, 0.492 mmol), potassium carbonate (0.113 g, 0.820 mmol), tetrabutylammonium bromide (0.109 g, 0.328 mmol), Pd(OAc)$_2$ (0.002-0.003 g, 2-3 mol %), ethanol (1.5 mL) and distilled water (3.5 mL). The vial was sealed and loaded (with no prior degassing) into a CEM Discover Microwave. After a run time of 3 min at 120° C. the reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified by flash chromatography (20 g column, method 7) eluting the title compound as a colourless viscous oil (0.108 g, 81%).

$R_f$: 0.19 (ethyl acetate);

$^1$H NMR (270 MHz, CDCl$_3$) δ 1.74 (6H, s, ArC(CH$_3$)$_2$CN), 5.45 (2H, s, ArCH$_2$N), 7.38-7.52 (4H, m, ArH), 7.57-7.70 (4H, m, ArH), 7.79-7.89 (4H, m, ArH), 8.00 (1H, s, C$_2$H$_2$N$_3$) and 8.17 (1H, S, C$_2$H$_2$N$_3$);

$^{13}$C NMR (67.9 MHz, CDCl$_3$) δ 29.2 (CH$_3$), 37.4 (C), 53.3 (CH$_2$), 124.1 (C), 124.3 (CH), 124.6 (CH), 126.4 (CH), 127.4 (CH), 128.5 (CH), 130.1 (CH), 130.9 (CH), 132.7 (CH), 136.6 (C), 137.1 (C), 137.5 (c), 142.0 (C), 143.4 (C), 143.4 (CH), 143.7 (C), 152.6 (CH) and 196.2 (C=O) (two overlapping signals);

HPLC (90% CH$_3$CN in H$_2$O) t$_r$=2.072 (96.88%);

LCMS (APCI), m/z 407.42 (M$^+$+H, 100%).

STX1848

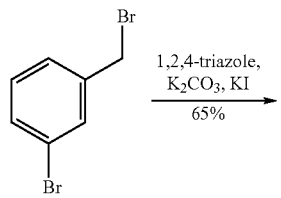

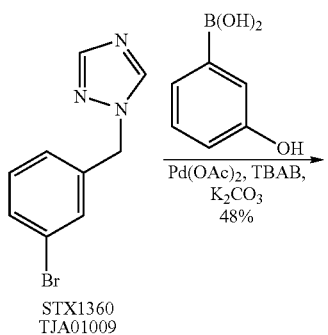

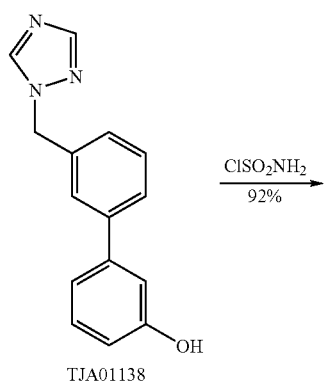

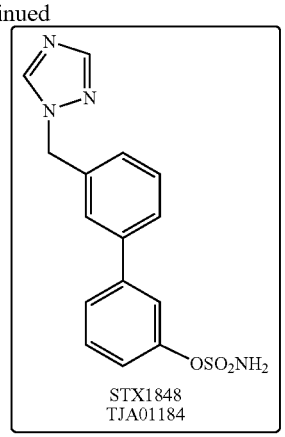

Sulfamic Acid 3'-(1,2,4)triazol-1-ylmethyl-biphenyl-3-yl Ester (TJA01184, STX1848)

$C_{15}H_{14}N_4O_3S$ MW 330.37

Sulfamoyl chloride in toluene (1.24 mL, 0.743 mmol) was transferred to a 10 mL r.b. flask and the solvent removed under vacuum at 30° C. On cooling a white solid formed to which was added N,N-dimethylacetamide (1.5 mL) to form a colourless solution. TJA01138 (0.040 g, 0.149 mmol) was added and the solution left to stir at room temperature under $N_{2\ (g)}$ for 20 h. The reaction mixture was then poured into distilled $H_2O$ (30 mL) and extracted with ethyl acetate (25 mL×2). The organic layers were combined and washed with distilled $H_2O$ (25 mL×4) and brine (25 mL). Dried over $MgSO_4$ and solvent removed in vacuo to leave off white residues. Column chromatography (dichloromethane/acetone 80:20) eluted the title compound as a white solid (0.045 g, 92%).

$R_f$: 0.20 (dichloromethane/acetone 80:20).

$^1$H NMR (270 MHz, DMSO-$d_6$) δ 5.50 (2H, s, ArCH$_2$N), 7.28-7.31 (2H, d, J=5.2 Hz, ArH), 7.48-7.63 (6H, m, ArH), 8.00 (3H, bs, ArOSO$_2$NH$_2$ & C$_2$H$_2$N$_3$), and 8.79 (1H, s, C$_2$H$_2$N$_3$);

$^{13}$C NMR (67.9 MHz, DMSO-$d_6$) δ 52.6 (CH$_2$), 121.1 (CH), 122.0 (CH), 125.5 (CH), 127.0 (CH), 128.1 (CH), 130.0 (CH), 131.0 (CH), 137.4 (C), 140.0 (C), 142.1 (C), 144.9 (CH), 151.2 (C) and 152.4 (CH) (one overlapping signal);

HPLC (90% CH$_3$CN in H$_2$O) $t_r$=1.869 (100%);

LCMS (APCI), m/z 331.42 (M$^+$+H, 100%), 252.38 ((M$^+$+H)—SO$_2$NH$_2$, 20).

HRMS (ES$^+$) calcd. for $C_{15}H_{14}N_4O_3S$ (M+H)$^+$ 331.0859, found 331.0857.

STX1854

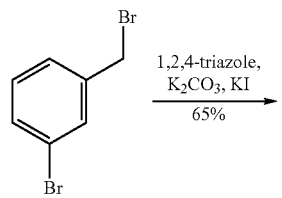

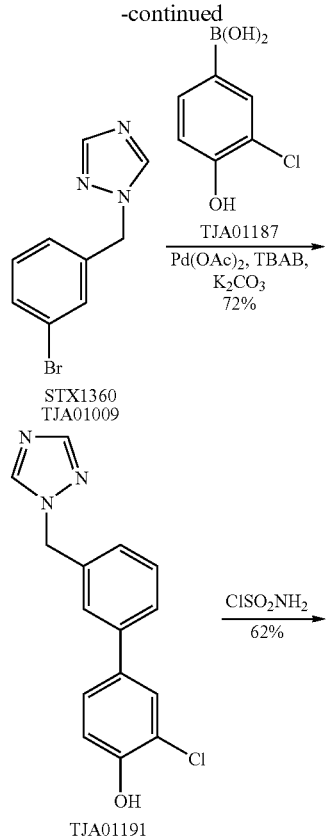

3-Chloro-4-hydroxyphenylboronic acid (TJA01187)

$C_6H_6ClO_3$ MW 172.37

A dry 250 ml r.b. flask was loaded with 4-bromo-2-chlorophenol (5.00 g, 24.1 mmol) and purged with $N_{2(g)}$. Anhydrous THF (100 mL) added with stirring and the vessel cooled to −78° C. (dry ice/acetone bath). After 30 mins n-BuLi, 2.3 M in hexanes, (12.9 mL, 28.9 mmol) was added dropwise over 20 min. The reaction was left to stir for 1 h. Triisopropyl borate (6.65 mL, 28.9 mmol) was added dropwise with the reaction still at −78° C. After 15 min of stirring at this temperature the dry ice/acetone bath was removed. At about 0° C. 2 M HCl$_{(aq)}$ (5 mL) was added and the reaction left to stir for a further 15 min. THF removed under vacuum and residues taken up in ethyl acetate (50 mL). Distilled H$_2$O (50 mL) was

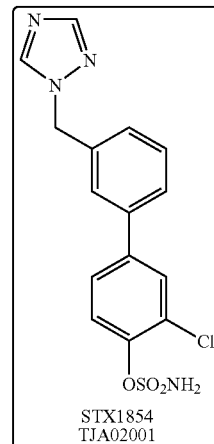

added and the organic layer separated. The aqueous layer was extracted with ethyl acetate (50 mL×2). The organic portions were combined and washed with sat. $Na_2CO_{3\ (aq)}$. The aqueous layer was separated and treated with 2M HCl (aq) until the pH was about 4. This was then extracted with ethyl acetate (50 mL×2). The organic portions were then dried over $MgSO_4$ and solvent removed. The resultant off white residues were taken up in a minimum of ethyl acetate (2-3 mL) and added to dropwise to hexane (50 mL) with stirring. The white ppt was filtered to give the title compound as an off white solid (0.490 g, 12%).

$^1$H NMR (600 MHz, DMSO-$d_6$) δ 6.89-6.92 (1H, d, J=8.2 Hz, ArH), 7.52-7.56 (1H, dd, J=1.8 & 7.9 Hz, ArH), 7.72-7.73 (1H, d, J=1.5 Hz, ArH), 7.98 (2H, s, ArB(OH)$_2$) and 10.33 (1H, s, ArOH);

HPLC (70% $CH_3CN$ in $H_2O$) $t_r$=3.654 (97.92%);

LCMS (APCI), m/z 173.11 ($^{37}$ClM—H, 15%), 171.10 ($^{35}$ClM—H, 55), 129.05 (($^{37}$ClM—H)—B(OH)$_2$, 30), 127.04 (($^{35}$ClM$^-$–H)—B(OH)$_2$, 100).

3'-(1,2,4)Triazole-1-yl-methyl-biphenyl-3-chloro-4-ol (TJA01191)

$C_{15}H_{12}ClN_3O$ MW 285.73

A 10 mL microwave vial was loaded with TJA01009 (0.150 g, 0.630 mmol), TJA01187 (0.130 g, 0.756 mmol), potassium carbonate (0.218 g, 1.58 mmol), tetrabutylammonium bromide (0.209 g, 0.630 mmol), Pd(OAc)$_2$ (0.004-0.005 g, 2-3 mol %), ethanol (1.5 mL) and distilled water (3.5 mL). The vial was sealed and loaded (with no prior degassing) into a CEM Explorer Microwave. After a run time of 3 min at 120° C. the reaction mixture was allowed to cool and ethyl acetate (50 mL) added. This was then washed with distilled water (25 mL×3) and brine (25 mL). The organic layer was dried over $MgSO_4$, filtered and solvent removed in vacuo to leave a yellow/brown residue. The crude product was purified via flash chromatography (20 g column, method4) eluted the title compound as an off white solid (0.129 g, 72%), $R_f$: 0.35 (ethyl acetate).

$^1$H NMR (270 MHz, DMSO-$d_6$) δ 5.46 (2H, s, ArCH$_2$N), 7.04-7.07 (1H, d, J=8.4 Hz, ArH), 7.18-7.20 (1H, d, J=7.4 Hz, ArH), 7.28-7.62 (5H, m, ArH), 8.01 (1H, s, $C_2H_2N_3$), 8.71 (1H, s, $C_2H_2N_3$) and 10.40 (1H, bs, ArOH);

HPLC (70% $CH_3CN$ in $H_2O$) $t_r$=4.274 (96.66%);

LCMS (APCI), m/z 286.33 ($^{37}$ClM—H, 30%), 284.32 ($^{35}$ClM$^-$–H, 100).

Sulfamic acid 3'-(1,2,4)triazol-1-ylmethyl-biphenyl-3-chloro-4-yl ester (TJA02001, STX1854)

$C_{15}H_{13}ClN_4O_3S$ MW 364.81

Sulfamoyl chloride in toluene (2.03 mL, 1.22 mL) was transferred to a 10 mL r.b. flask and the solvent removed under vacuum at 30° C. On cooling a white solid formed to which was added N,N-dimethylacetamide (1.5 mL) to form a colourless solution. TJA01191 (0.070 g, 0.244 mmol) was added and the solution left to stir at room temperature under $N_{2\ (g)}$ for 72 h. The reaction mixture was then poured into distilled $H_2O$ (30 mL) and extracted with ethyl acetate (25 mL×2). The organic layers were combined and washed with distilled $H_2O$ (25 mL×4) and brine (25 mL). Dried over $MgSO_4$ and solvent removed in vacuo to leave off white residues. Column chromatography (dichloromethane/acetone 80:20) eluted the title compound as a white solid (0.055 g, 62%), Following the same procedure used for TJA01047, TJA02001 was prepared from TJA01191 (0.070 g, 0.244 mmol) and sulfamoyl chloride (2.03 mL, 1.22 mmol) after 72 h. Purification via column chromatography (dichloromethane/acetone 80:20) eluted the title compound as a white solid (0.055 g, 62%), mp 148.3-153.3° C.;

$R_f$: 0.18 (dichloromethane/acetone 80:20).

$^1$H NMR (270 MHz, DMSO-$d_6$) δ 5.49 (2H, s, ArCH$_2$N), 7.27-7.31 (1H, d, J=7.4 Hz, ArH), 7.44-7.50 (1H, t, J=5.9 Hz, ArH), 7.57-7.72 (4H, m, ArH), 7.86-7.87 (1H, d, J=2.0 Hz), 8.00 (1H, s, $C_2H_2N_3$), 8.34 (2H, bs, ArOSO$_2$NH$_2$) and 8.72 (1H, s, $C_2H_2N_3$);

$^{13}$C NMR (67.9 MHz, DMSO-$d_6$) δ 52.5 (CH$_2$), 124.8 (CH), 127.0 (CH), 127.1 (CH), 127.6 (C), 128.2 (CH), 129.0 (CH), 130.0 (CH), 137.7 (C), 138.7 (C), 139.9 (C), 144.9 (CH), 146.1 (C) and 152.4 (CH) (one overlapping signal);

HPLC (70% $CH_3CN$ in $H_2O$) $t_r$=2.694 (100%);

LCMS (APCI), m/z 367.25 ($^{37}$ClM$^+$+H, 20%), 365.24 ($^{35}$ClM$^+$+H, 55%), 288.22 (($^{37}$ClM$^+$+H)—SO$_2$NH$_2$, 30%), 286.20 (($^{35}$ClM$^+$+H)—SO$_2$NH$_2$, 100);

HRMS (ES$^+$) calcd. for $C_{15}H_{13}ClN_4O_3S$ (M+H)$^+$ 365.0470, found 365.0471.

STX1975

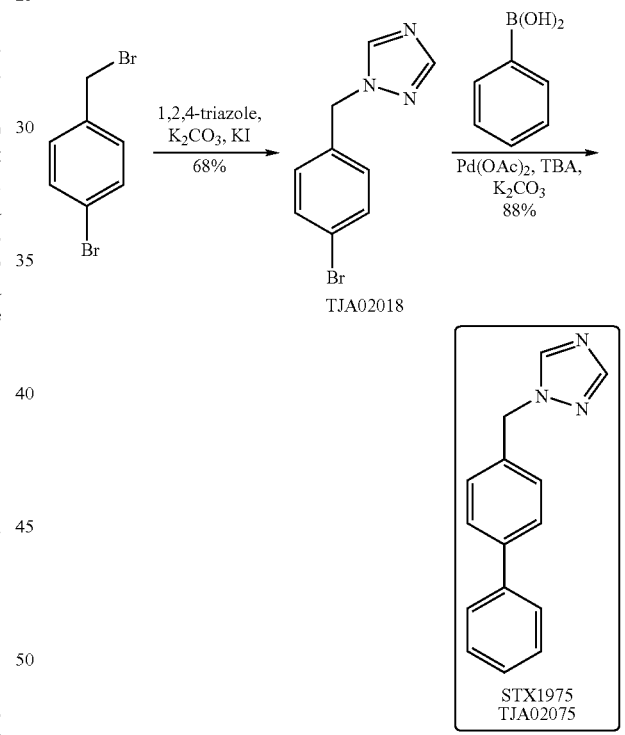

1-(4-Bromobenzyl)-1H-1,2,4-triazole (TJA02018)

$C_9H_8BrN_3$ MW 238.08

4-Bromobenzylbromide (5.00 g, 20.0 mmol), 1,2,4-triazole (2.07 g, 30.0 mmol), potassium carbonate (2.76 g, 20.0 mmol), potassium iodide (0.190 g, 1.18 mmol) and acetone (100 mL) were loaded to an r.b. flask. With vigorous stirring this mixture was set to reflux (60° C.) for 24 h. The reaction mixture was allowed to cool and acetone was removed in vacuo. The residues were taken up in ethyl acetate (50 mL) and washed with distilled water (50 mL×2) and brine (50 mL). Dried over $MgSO_4$ and solvent removed in vacuo to leave a yellow solid. Column chromatography (ethyl acetate) eluted the title compound as a white solid (3.24 g, 68%), $R_f$ 0.50 (ethyl acetate).

$^1$H NMR (270 MHz, CDCl$_3$) δ 5.29 (2H, s, ArCH$_2$N), 7.10-7.13 (2H, d, J=8.7 Hz, AA'BB'), 7.47-7.50 (2H, d, J=8.6 Hz, AA'BB'), 7.96 (1H, s, C$_2$H$_2$N$_3$) and 8.06 (1H, s, C$_2$H$_2$N$_3$);

$^{13}$C NMR (67.9 MHz, CDCl$_3$) δ 52.9 (CH$_2$), 122.9 (C), 129.7 (CH), 132.3 (CH), 133.7 (C), 143.2 (CH) and 152.5 (CH);

HPLC (90% CH$_3$CN in H$_2$O) $t_r$=2.693 (100%);

LCMS (APCI), m/z 239.95 ($^{81}$BrM$^+$+H, 95%), 237.95 ($^{79}$BrM$^+$+H, 100).

1-Biphenyl-4-methyl-1H-(1,2,4)-triazole (TJA02025, STX1975)

C$_{15}$H$_{13}$N$_3$ MW 235.28

A 10 mL microwave vial was loaded with TJA02018 (0.150 g, 0.630 mmol), phenylboronic acid (0.115 g, 0.945 mmol), potassium carbonate (0.218 g, 1.58 mmol), tetrabutylammonium bromide (0.209 g, 0.630 mmol), Pd(OAc)$_2$ (0.003-0.004 g, 2-3 mol %), ethanol (1.5 mL) and distilled water (3.5 mL). The vial was sealed and loaded (with no prior degassing) into a CEM Explorer Microwave (150 W, 3 min, 120° C.). The reaction mixture was allowed to cool and ethyl acetate (50 mL) added. This was then washed with distilled water (25 mL×3) and brine (25 mL). The organic layer was dried over MgSO$_4$, filtered and solvent removed in vacuo to leave a yellow/brown residue. Flash chromatography (20 g column, method4) eluted the title compound as a white solid (0.130 g, 88%), mp 160.4-164.2° C.;

$R_f$: 0.44 (ethyl acetate);

$^1$H NMR (270 MHz, CDCl$_3$) δ 5.37 (2H, s, ArCH$_2$N), 7.31-7.47 (5H, m, ArH), 7.54-7.61 (4H, m, ArH), 7.99 (1H, s, C$_2$H$_2$N$_3$) and 8.10 (1H, s, C$_2$H$_2$N$_3$);

$^{13}$C NMR (67.9 MHz, CDCl$_3$) δ 53.4 (CH$_2$), 127.2 (CH), 127.8 (CH), 127.9 (CH), 128.6 (CH), 129.0 (CH), 133.5 (C), 140.4 (C), 141.8 (C), 143.2 (CH) and 152.4 (CH);

HPLC (90% CH$_3$CN in H$_2$O) $t_r$=2.414 (99.30%);

LCMS (APCI), m/z 236.06 (M$^+$+H, 100%);

STX1976

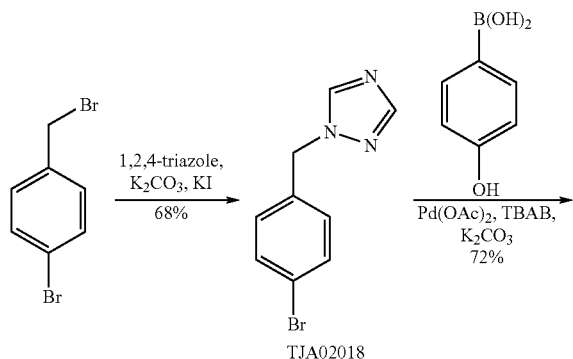

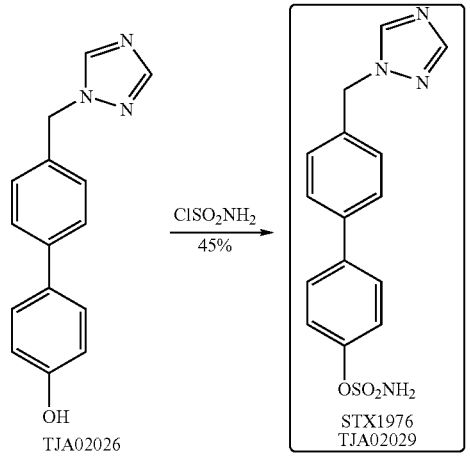

4'-(1,2,4)Triazole-1-yl-methyl-biphenyl-4-ol (TJA02026)

C$_{15}$H$_{13}$N$_3$O MW 251.28

A 10 mL microwave vial was loaded with TJA02018 (0.200 g, 0.840 mmol), 4-hydroxyphenylboronic acid (0.174 g, 1.26 mmol), potassium carbonate (0.290 g, 2.10 mmol), tetrabutylammonium bromide (0.279 g, 0.840 mmol), Pd(OAc)$_2$ (0.005-0.006 g, 2-3 mol %), ethanol (1.5 mL) and distilled water (3.5 mL). The vial was sealed and loaded (with no prior degassing) into a CEM Explorer Microwave. After a run time of 3 min at 120° C. the reaction mixture was allowed to cool and ethyl acetate (50 mL) added. This was then washed with distilled water (25 mL×3) and brine (25 mL). The organic layer was dried over MgSO$_4$, filtered and solvent removed in vacuo to leave a yellow/brown residue. The crude product was purified via flash chromatography (20 g column, method4) eluted the title compound as an off white solid (0.151 g, 72%), $R_f$: 0.37 (ethyl acetate);

$^1$H NMR (270 MHz, DMSO-d$_6$) δ 5.42 (2H, s, ArCH$_2$N), 6.82-6.85 (2H, d, J=8.6 Hz, AA'BB'), 7.32-7.29 (2H, d, J=8.2 Hz, AA'BB'), 7.45-7.48 (2H, d, J=8.6 Hz, AA'BB'), 7.54-7.57 (2H, d, J=8.2 Hz, AA'BB'), 7.99 (1H, S, C$_2$H$_2$N$_3$), 8.68 (1H, s, C$_2$H$_2$N$_3$) and 9.58 (1H, bs, ArOH);

HPLC (90% CH$_3$CN in H$_2$O) $t_r$=2.163 (92.21%);

LCMS (APCI), m/z 252.25 (M$^+$+H, 100%).

Sulfamic Acid 4'-(1,2,4)triazol-1-ylmethyl-biphenyl-4-yl Ester (TJA02029, STX1976)

C$_{15}$H$_{14}$N$_4$O$_3$S MW 330.37

Sulfamoyl chloride in toluene (0.30 M, 9.50 mL) was transferred to a 10 mL r.b. flask and the solvent removed under vacuum at 30° C. On cooling a white solid formed to which was added N,N-dimethylacetamide (1.5 mL) to form a colourless solution. TJA02026 (0.143 g, 0.570 mmol) was added and the solution left to stir at room temperature under N$_2$ $_{(g)}$ for 72 h. The reaction mixture was then poured into distilled H$_2$O (30 mL) and extracted with ethyl acetate (25 mL×2). The organic layers were combined and washed with distilled H$_2$O (25 mL×4) and brine (25 mL). Dried over MgSO$_4$ and solvent removed in vacuo to leave off white residues. Column chromatography (dichloromethane/acetone 80:20) eluted the title compound as a white solid (0.085 g, 45 mp 169.6-175.0° C.;

R$_f$: 0.28 (dichloromethane/acetone 80:20).

$^1$H NMR (270 MHz, DMSO-d$_6$) δ 5.47 (2H, s, ArCH$_2$N), 7.35-7.39 (4H, dd, J=7.4 & 8.2 Hz, AA'BB'), 7.65-7.76 (4H, dd, J=7.9 & 8.4 Hz, AA'BB'), 8.01 (1H, s, C$_2$H$_2$N$_3$), 8.07 (2H, bs, ArOSO$_2$NH$_2$) and 8.77 (1H, s, C$_2$H$_2$N$_3$);

$^{13}$C NMR (67.9 MHz, DMSO-d$_6$) δ 52.3 (CH$_2$), 123.3 (CH), 127.6 (CH), 128.6 (CH), 129.1 (CH), 136.3 (C), 138.6 (C), 139.3 (C), 144.9 (CH), 150.3 (C) and 152.4 (CH);

HPLC (70% CH$_3$CN in H$_2$O) t$_r$=3.000 (99.36%);

LCMS (APCI), m/z 331.05 (M$^+$+H, 100%);

HRMS (FAB$^+$) calcd. for C$_{15}$H$_{14}$N$_4$O$_3$S (M+H)$^+$ 331.0859, found 331.0858.

STX1978

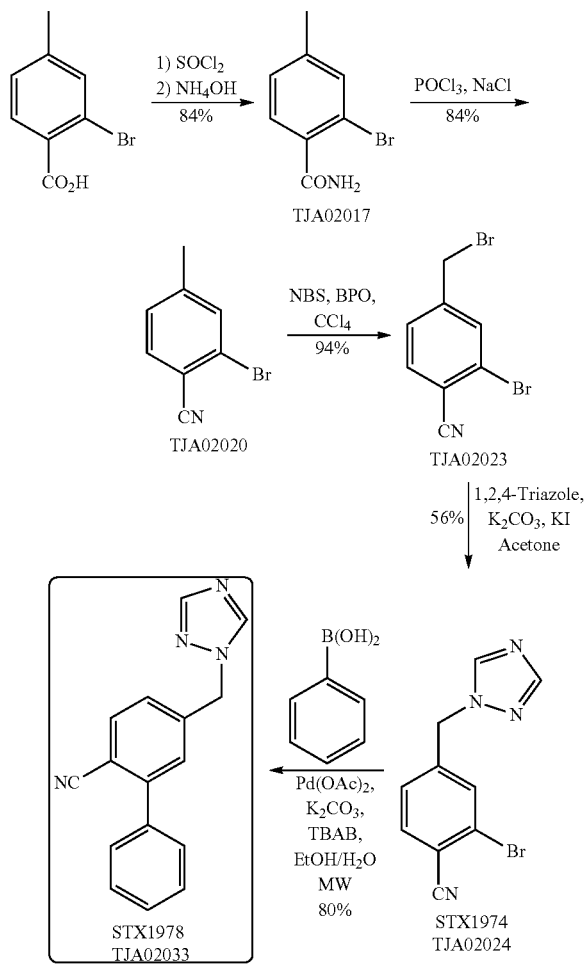

2-Bromo-4-methylbenzamide (TJA02017)

C$_8$H$_8$BrNO MW 214.06

2-bromo-4-methylbenzoic acid (5.00 g, 23.3 mmol) and thionyl chloride (30 mL) were loaded to a 100 mL r.b. flask and the mixture set to reflux for 20 h. The reaction was then allowed to cool and excess thionyl chloride was removed via a rotary evaporator. Resultant dark brown residues were taken up in THF (40 mL) and added, with stirring, to ammonia water (35%, 50 mL) which had been cooled to 0° C. Left to stir for 1 h. Conc. HCl$_{(aq)}$ was carefully added dropwise until the mixture had reached pH 3-5. THF was removed via a rotary evaporator and the solids were filtered and washed thoroughly with distilled H$_2$O. After drying under vacuum at 70° C. the title compound was obtained as a white solid (4.24 g, 84%), mp 173.2-175.8° C.;

$^1$H NMR (270 MHz, DMSO-d$_6$) δ 2.35 (3H, s, ArCH$_3$), 7.20-7.23 (1H, d, J=8.2 Hz, ArH), 7.28-7.31 (1H, d, J=7.7 Hz, ArH), 7.47 (1H, s, ArH), 7.51 (1H, bs, ArCONH$_2$) and 7.79 (1H, bs, ArCONH$_2$);

$^{13}$C NMR (67.9 MHz, DMSO-d$_6$) δ 20.9 (CH$_3$), 119.1 (C), 128.6 (CH), 129.0 (CH), 133.5 (CH), 136.9 (C), 141.3 (C) and 169.6 (C=O);

HPLC (70% CH$_3$CN in H$_2$O) t$_r$=4.446 (100%);

LCMS (APCI), m/z 215.95 ($^{81}$BrM$^+$+H, 95%), 213.95 ($^{79}$BrM$^+$+H, 100).

2-Bromo-4-methylbenzonitrile (TJA02020)

C$_8$H$_6$BrN MW 196.04

Phosphorus oxychloride (22.6 mL, 243 mmol), TJA02017 (4.00 g, 18.7 mmol) and sodium chloride (2.40 g, 41.1 mmol) were loaded to a 100 mL r.b. flask and set to reflux with stirring for 4 h. The mixture was allowed to cool and excess phosphorus oxychloride was removed via a rotary evaporator. The resultant brown residues were poured into iced water with stirring and left for 10 min. A brown ppt. had formed and was collected via filtration, washed thoroughly with distilled H$_2$O and dried under vacuum at 70° C. Recrystallisation (hexane) yielded the title compound as a white crystalline solid (3.07 g, 84%), mp 49.9-51.9° C.;

$^1$H NMR (270 MHz, CDCl$_3$) δ 2.40 (3H, s, ArH), 7.18-7.22 (1H, d, J=8.6 Hz, ArH) and 7.49-7.54 (2H, m, ArH);

$^{13}$C NMR (67.9 MHz, CDCl$_3$) δ 21.7 (CH$_3$), 112.8 (C), 117.5 (C), 125.2 (C), 128.6 (CH), 133.8 (CH), 134.1 (CH) and 145.5 (C);

HPLC (70% CH$_3$CN in H$_2$O) t$_r$=4.917 (99.75%);

LCMS (APCI), m/z 198.07 ($^{81}$BrM$^+$+H, 100%), 196.07 ($^{79}$BrM$^+$+H, 98%).

2-Bromo-4-(bromomethyl)benzonitrile (TJA02023)

C$_8$H$_5$Br$_2$N MW 274.94

TJA02020 (2.50 g, 12.8 mmol), N-bromosuccinimde (2.73 g, 14.4 mmol), benzyl peroxide (0.100 g, 0.410 mmol) and carbon tetrachloride (50 mL) were loaded to a 100 mL r.b. flask and set to reflux with stirring for 4 h. Allowed to cool. The succinimide was filtered off and carbon tetrachloride removed via a dry ice-acetone cooled rotary evaporator. The residues were dissolved in dichloromethane (50 mL) and washed with distilled H$_2$O (50 mL×3) and brine (50 mL×2). Dried over MgSO$_4$ and solvent removed in vacuo to leave yellow residues. Column chromatography (hexane/dichloromethane 60:40) eluted the title compound as a white crystalline solid (3.31 g, 94%) of which (by HPLC) 23.39% is TJA02020 and 1.32% is 2-bromo-4-(dibromomethyl)benzonitrile.

HPLC (70% CH$_3$CN in H$_2$O) t$_r$=4.150 (75.29%);

LCMS (APCI), m/z 276.06 (M$^+$+H, 40%).

4-((1H-1,2,4-triazol-1-yl)methyl)-2-bromobenzonitrile (TJA02024, STX1974)

C$_{10}$H$_7$BrN$_4$ MW 263.09

TJA02023 (3.31 g, 12.0 mmol), 1,2,4-triazole (1.24 g, 18.0 mmol), potassium carbonate (1.66 g, 12.0 mmol), potassium iodide (0.117 g, 0.706 mmol) and acetone (50 mL) were loaded to an r.b. flask. With vigorous stirring this mixture was set to reflux (60° C.) for 24 h. The reaction mixture was allowed to cool and acetone was removed in vacuo. The residues were taken up in ethyl acetate (50 mL) and washed with distilled water (50 mL×2) and brine (50 mL). Dried over MgSO$_4$ and solvent removed in vacuo to leave yellow residues. Column chromatography (ethyl acetate) eluted the title compound as a light yellow solid (1.44 g, 56%), mp 95.7-97.6° C.;

R$_f$ 0.30 (ethyl acetate).

$^1$H NMR (270 MHz, CDCl$_3$) δ 5.38 (2H, s, ArCH$_2$N), 7.23-7.27 (1H, dd, J=1.7 & 8.2 Hz, ArH), 7.53-7.54 (1H, d, J=1.2 Hz, ArH), 7.63-7.66 (1H, d, J=7.9 Hz, ArH), 8.01 (1H, s, C$_2$H$_2$N$_3$) and 8.17 (1H, s, C$_2$H$_2$N$_3$);

$^{13}$C NMR (67.9 MHz, CDCl$_3$) δ 52.1 (CH$_2$), 115.9 (C), 116.8 (C), 126.1 (C), 126.9 (CH), 132.2 (CH), 134.8 (CH), 141.5 (C), 143.7 (CH) and 153.0 (CH);

HPLC (70%) R$_t$ 2.425 (100%);

LCMS (APCI), m/z 265.15 ($^{81}$BrM$^+$+H, 95%), 263.15 ($^{79}$BrM$^+$+H, 100).

3-[1,2,4]Triazol-1-ylmethyl-biphenyl-6-carbonitrile (TJA02033, STX1978)

C$_{16}$H$_{12}$N$_4$ MW 260.30

A 10 mL microwave vial was loaded with TJA02024 (0.150 g, 0.570 mmol), phenylboronic acid (0.104 g, 0.855 mmol), potassium carbonate (0.198 g, 1.43 mmol), tetrabutylammonium bromide (0.189 g, 0.570 mmol), Pd(OAc)$_2$ (0.003-0.004 g, 2-3 mol %), ethanol (1.5 mL) and distilled water (3.5 mL). The vial was sealed and loaded (with no prior degassing) into a CEM Explorer Microwave (150 W, 3 min, 120° C.). The reaction mixture was allowed to cool and ethyl acetate (50 mL) added. This was then washed with distilled water (25 mL×3) and brine (25 mL). The organic layer was dried over MgSO$_4$, filtered and solvent removed in vacuo to leave a yellow/brown residue. Flash chromatography (20 g column, method4) eluted the title compound as a white solid (0.118 g, 80%), mp 119.3-126.8° C.;

R$_f$ 0.49 (ethyl acetate);

$^1$H NMR (270 MHz, CDCl$_3$) 5.40 (2H, s, ArCH$_2$N), 7.24-7.34 (2H, m, ArH), 7.45-7.48 (5H, m, ArH), 7.74-7.77 (1H, d, J=7.9 Hz, ArH), 8.00 (1H, s, C$_2$H$_2$N$_3$) and 8.17 (1H, s, C$_2$H$_2$N$_3$);

$^{13}$C NMR (67.9 MHz, CDCl$_3$) δ 52.8 (CH$_2$), 111.6 (C), 118.2 (C), 126.7 (CH), 128.8 (CH), 128.9 (CH), 129.2 (CH), 129.3 (CH), 134.5 (CH), 137.4 (C), 140.0 (C), 143.6 (CH), 146.7 (C) and 152.8 (CH);

HPLC (70% CH$_3$CN in H$_2$O) t$_r$=3.900 (100%);

LCMS (APCI), m/z 261.20 (M$^+$+H, 100%);

HRMS (FAB$^+$) calcd. for C$_{16}$H$_{12}$N$_4$ (M+H)$^+$ 261.1135, found 261.1134.

STX1979

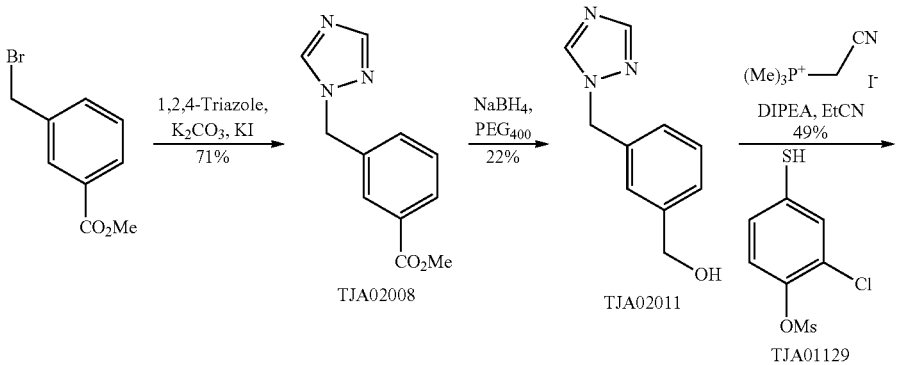

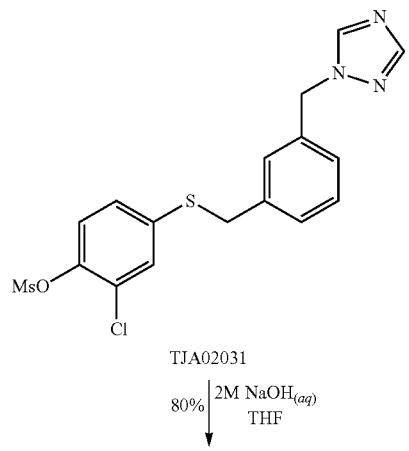

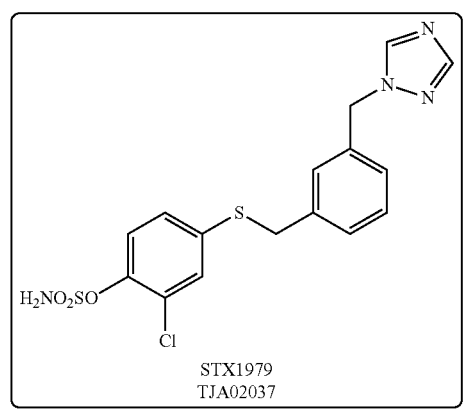

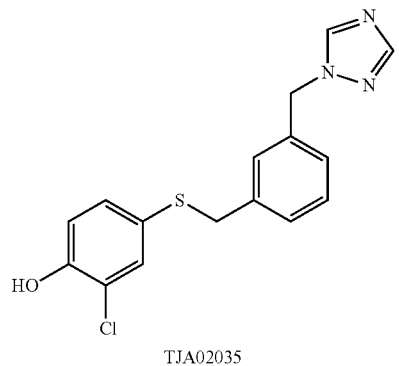

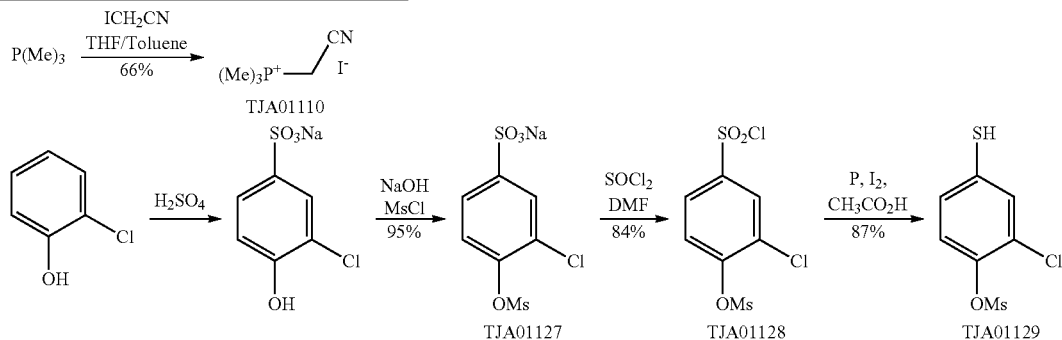

Cyanomethyl-trimethyl-phosphonium iodide (TJA01110)

$C_5H_{11}INP$ MW 243.03

Trimethylphosphine in THF (1M, 20.0 mL, 20.0 mmol) at 0° C. under $N_{2\,(g)}$ was diluted with anhydrous toluene (40 mL). Iodoacetonitrile (1.40 mL, 19.4 mmol) was added dropwise with vigorous stirring forming a white ppt. The mixture was allowed to warm to r.t. and left to stir for 40 h. The mixture was filtered and washed with toluene to give a white solid which was dried under vacuum. Recrystallisation (acetonitrile) provided the title compound as a white crystalline solid (3.23 g, 66%), $^1$H NMR (300 MHz, DMSO-$d_6$) δ 2.01-2.06 (9H, d, J=15.3 Hz, P(CH$_3$)$_3$), 4.01-4.07 (2H, d, J=16.4 Hz, PCH$_2$CN);
$^{31}$P NMR (121.5 MHz, DMSO-$d_6$) δ 32.9.

3-Chloro-4-methanesulfonyloxy-benzenesulfonic acid sodium salt (TJA01127)

$C_7H_6ClNaO_6S_2$ MW 308.69

4-hydroxy-3-chlorobenzenesulfonic acid sodium salt (11.53 g, 50.0 mmol) and sodium hydroxide (2.00 g, 50.0 mmol) were dissolved in distilled water (50 mL) and the solution cooled to 0° C. Methane sulfonyl chloride (4.25 mL, 55.0 mmol) was added dropwise with stirring and the mixture then allowed to warm to room temp. and left for 2 h. Brine (20 mL) was added and the solution left to stand for 1 h with the formation of white crystalline solid. The solids were filtered, recrystallised (brine), and dried under vacuum to give the title compound as a white crystalline solid (9.40 g, 61%), mp>250° C.;

$^1$H NMR (300 MHz, DMSO-$d_6$) δ 3.31 (3H, s, ArOSO$_2$CH$_3$), 7.48-7.51 (1H, d, J=8.4 Hz, ArH), 7.59-7.62 (1H, dd, J=2.2 & 8.4 Hz, ArH) and 7.69-7.72 (1H, d, J=2.2 Hz, ArH);

$^{13}$C NMR (67.9 MHz, DMSO-$d_6$) δ 39.1 (CH$_3$), 124.4 (CH), 126.3 (C), 126.5 (CH), 128.3 (CH), 145.3 (C) and 148.8 (C).

Methanesulfonic Acid 2-chloro-4-chlorosulfonyl-phenyl Ester (TJA01128)

$C_7H_6Cl_2O_5S_2$ MW 305.16

Thionyl chloride (30 mL) was cooled to 0° C. Cautiously, with stirring, TJA01127 (8.60 g, 28.0 mmol) was added followed by DMF (0.5 mL). The reaction mixture was subsequently heated to reflux (79° C.) for 1 h (or until evolution of gas has ceased) and then cooled. Thionyl chloride was removed in vacuo and the resulting yellow residues were taken up in dichloromethane (50 mL) and distilled water (50 mL) carefully added.

The organic layer was separated and washed with distilled water (50 mL×2) and brine (50 mL), dried over MgSO$_4$ and solvent removed in vacuo to leave yellow residues. Recystallisation (dichloromethane/hexane) gave the title compound as a white crystalline solid (7.10 g, 84%), $^1$H NMR (300 MHz, CDCl$_3$) δ 3.37 (3H, s, ArOSO$_2$CH$_3$), 7.70-7.73 (1H, d, J=8.8 Hz, ArH), 7.99-8.03 (1H, dd, J=2.4 & 8.8 Hz, ArH) and 8.19-8.20 (1H, d, J=2.4 Hz, ArH);
$^{13}$C NMR (67.9 MHz, CDCl$_3$) δ 39.6 (CH$_3$), 125.6 (CH), 127.2 (CH), 128.8 (C), 129.9 (CH), 143.1 (C) and 149.9 (C);
HPLC (90% CH$_3$CN in H$_2$O) t$_r$=2.489 (99.62%);

Methanesulfonic Acid 2-chloro-4-mercapto-phenyl Ester (TJA01129)

$C_7H_7ClO_3S_2$ MW 238.71

A 50 mL r.b. flask was loaded with red phosphorus powder (0.630 g, 20.5 mmol), iodine (0.035 g, 0.137 mmol) and acetic acid (7 mL). Cautiously TJA01128 (2.50 g, 8.19 mmol)

was added and the reaction mixture then set to reflux (118° C.) for 2 h. Distilled water (1.5 mL) was added and the mixture left to reflux for a further 1 h. Reaction allowed to cool. Chloroform (30 mL) and distilled water (30 mL) were added. The organic layer was separated and washed with distilled water (30 mL×3) and brine (30 mL). Dried over $MgSO_4$, filtered and solvent removed in vacuo. Column chromatography (ethyl acetate/hexane 50:50) eluted the title compound as a colourless viscous oil (1.68 g, 87%), $R_f$: 0.71 (ethyl acetate);

$^1$H NMR (300 MHz, $CDCl_3$) δ 3.24 (3H, s, $ArOSO_2CH_3$), 3.56 (1H, s, ArSH), 7.18-7.22 (1H, dd, J=2.3 & 8.5 Hz, ArH), 7.30-7.33 (1H, d, J=8.1 Hz, ArH) and 7.39-7.40 (1H, d, J=2.2 Hz, ArH);

$^{13}$C NMR (67.9 MHz, $CDCl_3$) δ 38.7 ($CH_3$), 125.1 (CH), 127.4 (C), 128.9 (CH), 130.9 (CH), 132.1 (C) and 143.2 (C);

HPLC (90% $CH_3CN$ in $H_2O$) $t_r$=1.811 (92.46%);

LCMS (APCI), m/z 239.01 ($^{37}ClM^--H$, 10%), 237.01 ($^{35}ClM^--H$, 30).

Methyl 3-((1H-1,2,4-triazol-1-yl)methyl)benzoate (TJA02008)

$C_{11}H_{11}N_3O_2$ MW 217.22

Methyl 3-(bromobenzyl)benzoate (5.00 g, 21.8 mmol), 1,2,4-triazole (2.26 g, 32.7 mmol), potassium carbonate (3.01 g, 21.8 mmol), potassium iodide (0.213 g, 1.28 mmol) and acetone (100 mL) were loaded to an r.b. flask. With vigorous stirring this mixture was set to reflux (60° C.) for 24 h. The reaction mixture was allowed to cool and acetone was removed in vacuo. The residues were taken up in ethyl acetate (50 mL) and washed with distilled water (50 mL×2) and brine (50 mL). Dried over $MgSO_4$ and solvent removed in vacuo to leave a yellow oil. Column chromatography (ethyl acetate) eluted the title compound as a yellow viscous oil to give a yellow crystalline solid (3.35 g, 71%), $R_f$ 0.42 (ethyl acetate).

$^1$H NMR (270 MHz, $CDCl_3$) δ 3.86 (3H, s, $ArCO_2CH_3$), 5.37 (2H, s, $ArCH_2N$), 7.39-7.44 (2H, m, ArH), 7.93-7.94 (1H, m, ArH), 7.96 (1H, s, $C_2H_2N_3$), 7.97-8.01 (1H, m, ArH), and 8.09 (1H, s, $C_2H_2N_3$);

$^{13}$C NMR (67.9 MHz, $CDCl_3$) δ 52.4 ($CH_3$), 53.2 ($CH_2$), 129.1 (CH), 129.3 (CH), 129.9 (CH), 131.1 (C), 132.5 (CH), 135.1 (C), 143.2 (CH), 152.5 (CH) and 166.5 (C=O);

HPLC (90% $CH_3CN$ in $H_2O$) $t_r$=2.080 (100%);

LCMS (APCI), m/z 218.42 ($M^++H$, 100%).

(3-((1H-1,2,4-Triazol-1-yl)methyl)phenyl)methanol (TJA02011)

$C_{10}H_{11}N_3O$ MW 189.21

A 25 mL r.b. flask was loaded with TJA02008 (0.500 g, 2.36 mmol) and polyethylene glycol 400 (6.0 g). The mixture was heated to 80° C. with stirring until a solution had formed. Sodium borahydride (0.261 g, 6.91 mmol) was added carefully resulting in evolution of gas. The reaction mixture was stirred vigorously at 80° C. for 16 h. Extremely viscous glue formed that gradually dissolved in dichloromethane (50 mL) with heating (40° C.). This solution was washed with 1M $HCl_{(aq)}$ (10 mL) and then carefully neutralised with sodium bicarbonate. Washed with distilled water (50 mL×4) and brine (50 mL), separated and dried over $MgSO_4$. Solvent removed in vacuo to leave a viscous yellow oil. Flash chromatography (20 g column, method6) eluted the title compound as a colourless viscous oil (0.101 g, 22%), $R_f$: 0.24 (ethyl acetate);

$^1$H NMR (270 MHz, $CDCl_3$) δ 2.53 (1H, bs, $ArCH_2OH$), 4.66 (2H, s, $ArCH_2OH$), 5.30 (2H, s, $ArCH_2N$), 7.14-7.17 (1H, m, ArH), 7.29-7.37 (2H, m, ArH), 7.89 (1H, s, $C_2H_2N_3$) and 8.00 (1H, s, $C_2H_2N_3$);

$^{13}$C NMR (67.9 MHz, $CDCl_3$) δ 53.6 ($CH_2$), 64.7 ($CH_2$), 126.5 (CH), 127.2 (CH), 129.3 (CH), 134.8 (C), 142.2 (C), 143.1 (CH) and 152.2 (CH);

HPLC (70% $CH_3CN$ in $H_2O$) $t_r$=3.647 (100%);

LCMS (APCI), m/z 189.75 ($M^++H$, 100%).

4-(3-((1H-1,2,4-triazol-1-yl)methyl)benzylthio)-2-chlorophenyl methanesulfonate (TJA02031)

$C_{17}H_{16}ClN_3O_3S_2$ MW 409.91

A dry 5 mL r.b. flask purged with $N_{2\ (g)}$ was loaded with TJA02011 (0.100 g, 0.529 mmol), TJA01129 (0.189 g, 0.794 mmol), TJA01110 (0.154, 0.635 mmol), diisopropylethylamine (119 μL, 0.687 mmol) and propionitrile (1.0 mL). The mixture was then set to stir at 93° C. After 18 h the reaction was allowed to cool. Dichloromethane (20 mL) and distilled water (20 mL) were added and the aqueous layer separated and extracted with dichloromethane (20 mL×2). The organic fractions were combined and washed with brine (20 mL), dried over $MgSO_4$ and solvent removed in vacuo to leave yellow residues. Column chromatography (ethyl acetate) eluted the title compound as a yellow viscous oil (0.105 g, 49%), $R_f$: 0.55 (ethyl acetate);

$^1$H NMR (270 MHz, $CDCl_3$) δ 3.23 (3H, s, $ArOSO_2CH_3$), 4.07 (2H, s, $ArCH_2SAr$), 5.30 (2H, s, $ArCH_2N$), 7.09-7.16 (3H, m, ArH), 7.26-7.34 (4H, m, ArH), 7.98 (1H, s, $C_2H_2N_3$) and 8.06 (1H, s, $C_2H_2N_3$);

$^{13}$C NMR (67.9 MHz, $CDCl_3$) δ 38.7 ($CH_2$), 38.9 ($CH_3$), 53.3 ($CH_2$), 124.8 (CH), 127.2 (CH), 128.3 (CH), 129.2 (CH), 129.3 (CH), 129.6 (CH), 131.4 (CH), 135.2 (C), 136.9 (C), 137.6 (C), 143.2 (CH), 143.6 (C) and 152.3 (CH) (one overlapping signal);

HPLC (90% $CH_3CN$ in $H_2O$) $t_r$=2.006 (99.32%);

LCMS (APCI), m/z 412.08 ($^{37}ClM^++H$, 43%), 410.07 ($^{35}ClM^++H$, 100).

4-(3-((1H-1,2,4-Triazol-1-yl)methyl)benzylthio)-2-chlorophenol (TJA02035)

$C_{16}H_{14}ClN_3OS$ MW 331.82

TJA02031 (0.100 g, 0.244 mmol) was dissolved in THF (2.0 mL) and methanol (2.0 mL) to which 2M $NaOH_{(aq)}$ (0.61 mL) was added. The mixture was set to stir at room temp. for 3 h. THF was removed under reduced pressure and the residues taken up in ethyl acetate (20 mL) and washed with 2M $KHSO_{4(aq)}$ (20 mL), distilled water (20 mL×2) and brine (20 mL). The organic layer was then dried over $MgSO_4$ and solvent removed under reduced pressure to leave a colourless viscous oil. Column chromatography (dichloromethane/acetone 80:20) eluted the title compound as a colourless viscous oil (0.065 g, 80%) that crystallised on standing to a white crystalline solid, mp 131.5-134.9° C.;

$R_f$: 0.38 (dichloromethane/acetone 80:20);

$^1$H NMR (270 MHz, DMSO-$d_6$) δ 4.08 (2H, s, $ArCH_2SAr$), 5.38 (2H, s, $ArCH_2N$), 6.84-6.88 (1H, d, J=8.4 Hz, ArH), 7.07-7.29 (6H, m, ArH), 7.20 (1H, s, ArH), 7.98 (1H, s, $C_2H_2N_3$), 8.63 (1H, s, $C_2H_2N_3$) and 10.36 (1H, s, ArOH);

$^{13}$C NMR (67.9 MHz, DMSO-$d_6$) δ 39.1 ($CH_2$), 52.5 ($CH_2$), 117.6 (CH), 120.5 (C), 125.4 (C), 127.1 (CH), 128.7 (CH), 129.0 (CH), 129.2 (CH), 131.7 (CH), 132.8 (CH), 136.9 (C), 138.8 (C), 144.8 (CH), 152.3 (CH) and 153.0 (C);

HPLC (100% $CH_3CN$ in $H_2O$) $t_r$=3.561 (94.57%);

LCMS (APCI), m/z 334.26 ($^{37}$ClM$^+$+H, 35%), 332.24 ($^{35}$ClM$^+$+H, 100).

4-(3-((1H-1,2,4-Triazol-1-yl)methyl)benzylthio)-2-chlorophenyl sulfamate (TJA02037, STX1979)

$C_{16}H_{15}ClN_4O_3S_2$ MW 410.03

Sulfamoyl chloride in toluene (2.76 mL, 0.829 mmol) was transferred to a 10 mL r.b. flask and the solvent removed under vacuum at 30° C. On cooling a white solid formed to which was added N,N-dimethylacetamide (1.5 mL) to form a colourless solution. TJA02035 (0.055 g, 0.166 mmol) was added and the solution left to stir at room temperature under $N_{2\,(g)}$ for 20 h. The reaction mixture was then poured into distilled $H_2O$ (30 mL) and extracted with ethyl acetate (25 mL×2). The organic layers were combined and washed with distilled $H_2O$ (25 mL×4) and brine (25 mL). Dried over $Na_2SO_4$ and solvent removed in vacuo to leave off white residues. Column chromatography (dichloromethane/acetone 80:20) eluted the title compound as an off white waxy solid (0.061 g, 90%);

$R_f$: 0.45 (dichloromethane/acetone 80:20).

$^1$H NMR (270 MHz, DMSO-$d_6$) δ 4.22 (2H, s, ArSCH$_2$Ar), 5.39 (2H, s, ArCH$_2$N), 7.14-7.17 (1H, m, ArH), 7.28-7.40 (5H, m, ArH), 7.52-7.53 (1H, d, J=2.0 Hz, ArH), 7.98 (1H, s, $C_2H_2N_3$), 8.29 (2H, bs, ArOSO$_2$NH$_2$) and 8.64 (1H, s, $C_2H_2N_3$);

$^{13}$C NMR (67.9 MHz, DMSO-$d_6$) δ 36.7 (CH$_2$), 52.4 (CH$_2$), 124.7 (CH), 127.4 (CH), 127.6 (C), 128.2 (CH), 128.7 (CH), 129.0 (CH), 129.4 (CH), 129.6 (CH), 136.6 (C), 137.2 (C), 138.0 (C), 144.5 (C), 144.8 (CH) and 152.3 (CH);

HPLC (100% CH$_3$CN in H$_2$O) $t_r$=7.961 (98.96%);

LCMS (APCI), m/z 413.40 ($^{37}$ClM$^+$+H, 35%), 411.39 ($^{35}$ClM$^+$+H, 100).

STX1980

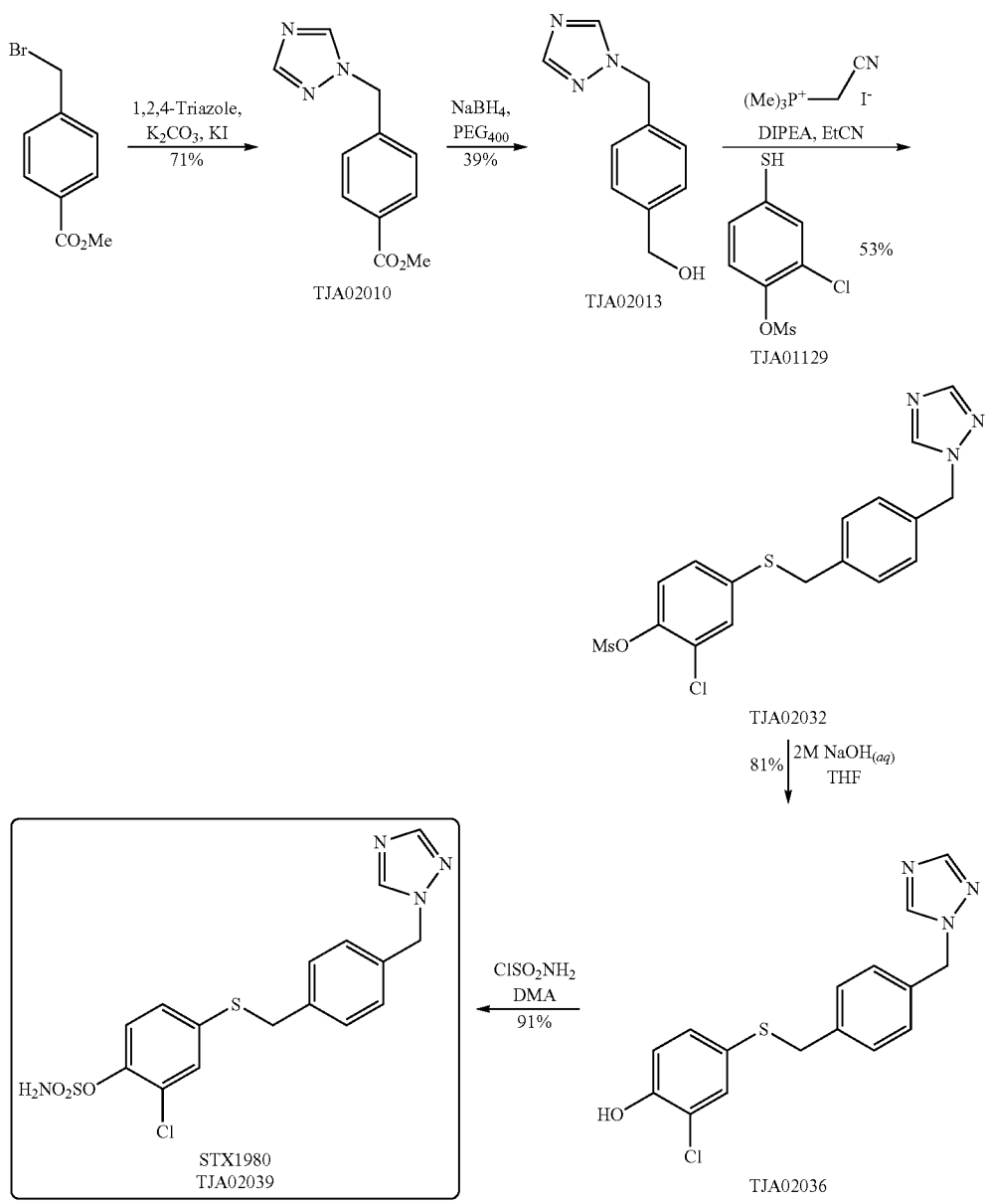

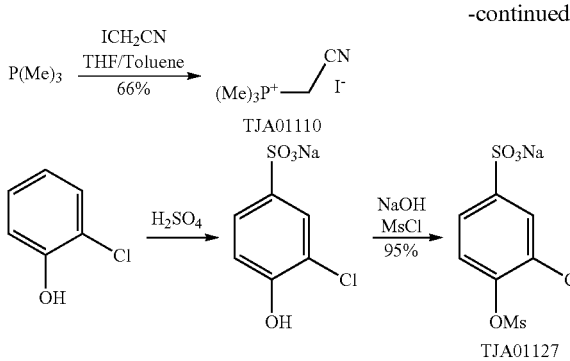

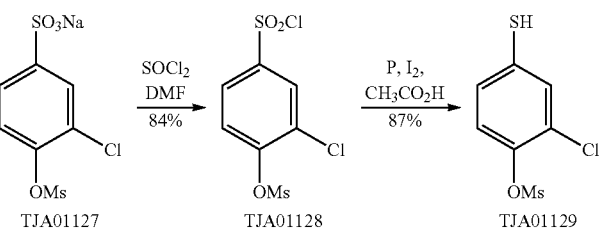

Methyl 4-((1H-1,2,4-triazol-1-yl)methyl)benzoate (TJA02010)

$C_{11}H_{11}N_3O_2$ MW 217.22

Methyl 4-(bromobenzyl)benzoate (5.00 g, 21.8 mmol), 1,2,4-triazole (2.26 g, 32.7 mmol), potassium carbonate (3.01 g, 21.8 mmol), potassium iodide (0.213 g, 1.28 mmol) and acetone (100 mL) were loaded to an r.b. flask. With vigorous stirring this mixture was set to reflux (60° C.) for 24 h. The reaction mixture was allowed to cool and acetone was removed in vacuo. The residues were taken up in ethyl acetate (50 mL) and washed with distilled water (50 mL×2) and brine (50 mL). Dried over MgSO₄ and solvent removed in vacuo to leave a yellow solid. Column chromatography (ethyl acetate) eluted the title compound as a light yellow crystalline solid (2.77 g, 71%), mp 119.2-120° C.;

$R_f$ 0.38 (ethyl acetate).

$^1$H NMR (270 MHz, CDCl₃) δ 3.85 (3H, s, ArCO₂CH₃), 5.39 (2H, s, ArCH₂N), 7.26-7.29 (2H, d, J=8.7 Hz, AA'BB'), 7.97 (1H, s, C₂H₂N₃), 8.00-8.03 (2H, d, J=8.4 Hz, AA'BB') and 8.10 (1H, s, C₂H₂N₃);

$^{13}$C NMR (67.9 MHz, CDCl₃) δ 52.4 (CH₃), 53.1 (CH₂), 127.8 (CH), 130.4 (CH), 130.5 (C), 139.6 (C), 143.4 (CH), 152.3 (CH) and 166.3 (C=O);

HPLC (90% CH₃CN in H₂O) $t_r$=2.181 (100%);

LCMS (APCI), m/z 218.23 (M⁺+H, 100%).

(4-((1H-1,2,4-Triazol-1-yl)methyl)phenyl)methanol (TJA02013)

$C_{10}H_{11}N_3O$ MW 189.21

A 25 mL r.b. flask was loaded with TJA02010 (0.500 g, 2.36 mmol) and polyethylene glycol 400 (6.0 g). The mixture was heated to 80° C. with stirring until a solution had formed. Sodium borahydride (0.261 g, 6.91 mmol) was added carefully resulting in evolution of gas. The reaction mixture was stirred vigorously at 80° C. for 16 h. An extremely viscous glue formed that gradually dissolved in dichloromethane (50 mL) with heating (40° C.). This solution was washed with 1M HCl$_{(aq)}$ (10 mL) and then carefully neutralised with sodium bicarbonate. Washed with distilled water (50 mL×4) and brine (50 mL), separated and dried over MgSO₄. Solvent removed in vacuo to leave a viscous yellow oil. Flash chromatography (20 g column, method6) eluted the title compound as a colourless viscous oil (0.175 g, 39%), mp 72.9-74.2° C.;

$^1$H NMR (270 MHz, CDCl₃) δ 2.26-2.31 (1H, t, J=5.7 Hz, ArCH₂OH), 4.67-4.69 (2H, d, J=5.7 Hz, ArCH₂OH), 5.31 (2H, s, ArCH₂N), 7.22-7.25 (2H, d, J=7.8 Hz, AA'BB'), 7.35-7.38 (2H, d, J=8.2 Hz, AA'BB'), 7.93 (1H, s, C₂H₂N₃) and 8.01 (1H, S, C₂H₂N₃);

$^{13}$C NMR (67.9 MHz, CDCl₃) δ 53.4 (CH₂), 64.7 (CH₂), 127.6 (CH), 128.4 (CH), 133.8 (C), 141.8 (C), 143.1 (CH) and 152.2 (CH);

HPLC (90% CH₃CN in H₂O) $t_r$=2.971 (100%);

LCMS (APCI), m/z 190.19 (M⁺+H, 100%).

4-(4-((1H-1,2,4-triazol-1-yl)methyl)benzylthio)-2-chlorophenyl methanesulfonate (TJA02032)

$C_{17}H_{16}ClN_3O_3S_2$ MW 409.91

A dry 5 mL r.b. flask purged with $N_{2\,(g)}$ was loaded with TJA02013 (0.100 g, 0.529 mmol), TJA01129 (0.189 g, 0.794 mmol), TJA01175 (0.154, 0.635 mmol), diisopropylethylamine (119 μL, 0.687 mmol) and propionitrile (1.0 mL). The mixture was then set to stir at 93° C. After 20 h the reaction was allowed to cool. Dichloromethane (20 mL) and distilled water (20 mL) were added and the aqueous layer separated and extracted with dichloromethane (20 mL×2). The organic fractions were combined and washed with brine (20 mL), dried over MgSO₄ and solvent removed in vacuo to leave yellow residues. Column chromatography (ethyl acetate) eluted the title compound as a yellow viscous oil (0.115 g, 53%), $R_f$: 0.58 (ethyl acetate);

$^1$H NMR (270 MHz, CDCl₃) δ 3.21 (3H, s, ArOSO₂CH₃), 4.12 (2H, s, ArCH₂SAr), 5.30 (2H, s, ArCH₂N), 7.14-7.32 (7H, m, ArH), 7.96 (1H, s, C₂H₂N₃) and 8.06 (1H, s, C₂H₂N₃);

$^{13}$C NMR (67.9 MHz, CDCl₃) δ 38.4 (CH₂), 38.8 (CH₃), 53.3 (CH₂), 124.9 (CH), 126.3 (C), 128.4 (CH), 128.9 (CH), 129.6 (CH), 131.0 (CH), 134.1 (C), 137.0 (C), 137.1 (C), 143.2 (CH), 143.5 (C) and 152.3 (CH);

HPLC (90% CH₃CN in H₂O) $t_r$=1.986 (97.35%);

LCMS (APCI), m/z 412.27 ($^{37}$ClM⁺+H, 35%), 410.26 ($^{35}$ClM⁺+H, 100).

4-(4-((1H-1,2,4-Triazol-1-yl)methyl)benzylthio)-2-chlorophenol (TJA02036)

$C_{16}H_{14}ClN_3OS$ MW 331.82

TJA02032 (0.100 g, 0.244 mmol) was dissolved in THF (2.0 mL) and methanol (2.0 mL) to which 2M NaOH$_{(aq)}$ (0.61 mL) was added. The mixture was set to stir at room temp. for 2 h. THF was removed under reduced pressure and the residues taken up in ethyl acetate (20 mL) and washed with 2M KHSO$_{4(aq)}$ (20 mL), distilled water (20 mL×2) and brine (20 mL). The organic layer was then dried over MgSO₄ and solvent removed under reduced pressure to leave a colourless viscous oil. Column chromatography (dichloromethane/acetone 80:20) eluted the title compound as a white solid (0.066 g, 81 mp 133.4-135.7° C.;

$R_f$: 0.35 (dichloromethane/acetone 80:20);

$^1$H NMR (270 MHz, DMSO-$d_6$) δ 4.09 (2H, s, ArCH$_2$SAr), 5.37 (2H, s, ArCH$_2$N), 6.85-6.88 (1H, d, J=8.4 Hz, ArH), 7.09-7.13 (1H, dd, J=2.2 & 8.4 Hz, ArH), 7.15-7.25 (4H, dd, J=8.2 & 16.8 Hz, AA'BB'), 7.28-7.29 (1H, d, J=2.2 Hz, ArH), 7.97 (1H, s, C$_2$H$_2$N$_3$), 8.63 (1H, s, C$_2$H$_2$N$_3$) and 10.34 (1H, s, ArOH);

$^{13}$C NMR (67.9 MHz, DMSO-$d_6$) δ 39.0 (CH$_2$), 52.3 (CH$_2$), 117.6 (CH), 120.5 (C), 125.5 (C), 128.4 (CH), 129.6 (CH), 131.6 (CH), 132.7 (CH), 135.6 (C), 138.1 (C), 144.8 (CH), 152.3 (CH) and 152.9 (C);

HPLC (100% CH$_3$CN in H$_2$O) $t_r$=3.527 (93.93%);

LCMS (APCI), m/z 334.26 ($^{37}$ClM$^+$+H, 35%), 332.31 ($^{35}$ClM$^+$+H, 100).

4-(4-((1H-1,2,4-Triazol-1-yl)methyl)benzylthio)-2-chlorophenyl sulfamate (TJA02039, STX1980)

C$_{16}$H$_{15}$ClN$_4$O$_3$S$_2$ MW 410.03

Sulfamoyl chloride in toluene (3.01 mL, 0.904 mmol) was transferred to a 10 mL r.b. flask and the solvent removed under vacuum at 30° C. On cooling a white solid formed to which was added N,N-dimethylacetamide (1.5 mL) to form a colourless solution. TJA02036 (0.060 g, 0.181 mmol) was added and the solution left to stir at room temperature under N$_2$ $_{(g)}$ for 20 h. The reaction mixture was then poured into distilled H$_2$O (30 mL) and extracted with ethyl acetate (25 mL×2). The organic layers were combined and washed with distilled H$_2$O (25 mL×4) and brine (25 mL). Dried over Na$_2$SO$_4$ and solvent removed in vacuo to leave off white residues. Column chromatography (dichloromethane/acetone 80:20) eluted the title compound as an off white waxy solid (0.067 g, 91%);

mp 128.1-132.5° C.;

$R_f$: 0.31 (dichloromethane/acetone 80:20).

$^1$H NMR (270 MHz, DMSO-$d_6$) δ 4.30 (2H, s, ArSCH$_2$Ar), 5.38 (2H, s, ArCH$_2$N), 7.20-7.22 (2H, d, J=8.2 Hz, ArH), 7.37 (3H, m, ArH), 7.40 (1H, s, ArH), 7.54 (1H, s, ArH) 7.97 (1H, s, C$_2$H$_2$N$_3$), 8.27 (2H, bs, ArOSO$_2$NH$_2$) and 8.65 (1H, s, C$_2$H$_2$N$_3$);

$^{13}$C NMR (67.9 MHz, DMSO-$d_6$) δ 36.3 (CH$_2$), 52.9 (CH$_2$), 124.7 (CH), 127.6 (C), 128.0 (CH), 128.5 (CH), 129.4 (CH), 129.7 (CH), 135.9 (C), 136.6 (C), 137.3 (C), 144.4 (C), 144.8 (CH) and 152.3 (CH);

HPLC (90% CH$_3$CN in H$_2$O) $t_r$=3.246 (100%);

LCMS (APCI), m/z 413.15 ($^{37}$ClM$^+$+H, 42%), 411.14 ($^{35}$ClM$^+$+H, 100).

STX1981

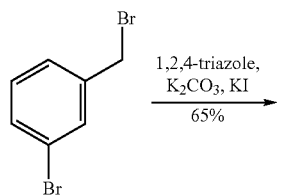

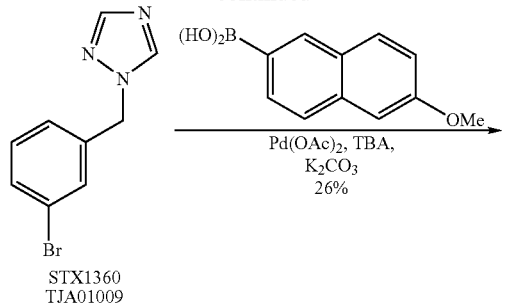

STX1360
TJA01009

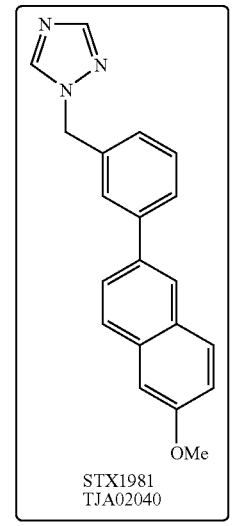

STX1981
TJA02040

1-(3-(2-Methoxynaphthalen-6-yl)benzyl)-1H-1,2,4-triazole (TJA02040, STX1981)

C$_{20}$H$_{17}$N$_3$O MW 315.37

A 10 mL microwave vial was loaded with TJA01009 (0.150 g, 0.630 mmol), 6-methoxy-2-naphthalene (0.153 g, 0.756 mmol), potassium carbonate (0.218 g, 1.58 mmol), tetrabutylammonium bromide (0.209 g, 0.630 mmol), Pd(OAc)$_2$ (0.004-0.005 g, 2-3 mol %), ethanol (1.5 mL) and distilled water (3.5 mL). The vial was sealed and loaded (with no prior degassing) into a CEM Explorer Microwave. After a run time of 5 min at 150° C. the reaction mixture was allowed to cool and ethyl acetate (50 mL) added. This was then washed with distilled water (25 mL×3) and brine (25 mL). The organic layer was dried over MgSO$_4$, filtered and solvent removed in vacuo to leave a yellow/brown residue. Flash chromatography (20 g column, method4) eluted the title compound as a white solid (0.051 g, 26%), mp 133.5-134.1° C.;

$R_f$: 0.52 (ethyl acetate);

$^1$H NMR (270 MHz, CDCl$_3$) δ 3.93 (3H, s, ArOCH$_3$), 5.42 (2H, s, ArCH$_2$N), 7.15-7.24 (3H, m, ArH), 7.44-7.50 (1H, t, J=7.7 Hz, ArH), 7.58-7.69 (3H, m, ArH), 7.76-7.81 (2H, dd, J=5.0 & 8.4 Hz, ArH), 7.92-7.93 (1H, d, J=1.2 Hz, ArH), 8.00 (1H, s, C$_2$H$_2$N$_3$) and 8.12 (1H, s, C$_2$H$_2$N$_3$);

$^{13}$C NMR (67.9 MHz, CDCl$_3$) δ 53.8 (CH$_2$), 55.4 (CH$_3$), 105.6 (CH), 119.4 (CH), 125.9 (CH), 126.7 (CH) 127.0 (CH), 127.5 (CH), 127.7 (CH), 129.1 (C), 129.7 (CH), 129.8 (CH), 134.0 (C), 135.2 (C), 135.5 (C), 142.3 (C), 143.2 (CH), 152.4 (CH) and 158.0 (C) (one overlapping signal);

HPLC (90% CH$_3$CN in H$_2$O) $t_r$=3.674 (98.77%);

LCMS (APCI), m/z 316.25 (M$^+$+H, 100%);

HRMS (FAB⁺) calcd. for $C_{20}H_{17}N_3O$ (M+H)⁺ 316.1444, found 316.1447.

STX2052

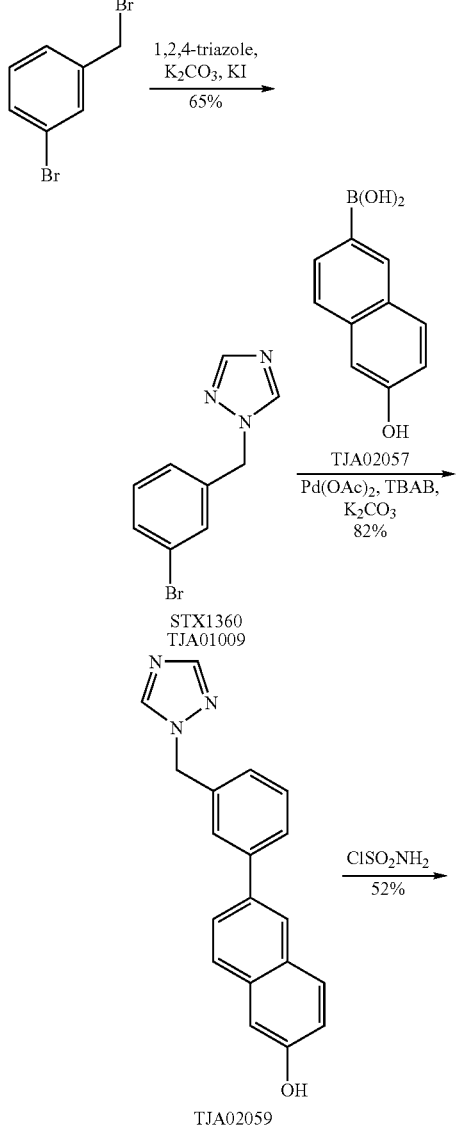

6-(3-((1H-1,2,4-Triazol-1-yl)methyl)phenyl)naphthalen-2-ol (TJA02059)

$C_{19}H_{15}N_3O$ MW 301.34

A 10 mL microwave vial was loaded with TJA01009 (0.150 g, 0.630 mmol), TJA02057 (0.178 g, 0.945 mmol), potassium carbonate (0.218 g, 1.58 mmol), tetrabutylammonium bromide (0.209 g, 0.630 mmol), Pd(OAc)$_2$ (0.004-0.005 g, 2-3 mol %), ethanol (1.5 mL) and distilled water (3.5 mL). The vial was sealed and loaded (with no prior degassing) into a CEM Explorer Microwave. After a run time of 10 min at 150° C. the reaction mixture was allowed to cool and ethyl acetate (50 mL) added. This was then washed with distilled water (25 mL×3) and brine (25 mL). The organic layer was dried over MgSO$_4$, filtered and solvent removed in vacuo to leave a yellow/brown residue. The crude product was purified via flash chromatography (20 g column, method4) which eluted the title compound as a white solid (0.155 g, 82%).

$R_f$: 0.51 (ethyl acetate);

¹H NMR (270 MHz, DMSO-d$_6$) δ 5.50 (2H, s, ArCH$_2$N), 7.10-7.14 (2H, m, ArH), 7.23-7.26 (1H, d, J=7.7 Hz, ArH), 7.44-7.50 (1H, t, J=7.7 Hz, ArH), 7.66-7.86 (5H, m, ArH), 8.00 (1H, s, C$_2$H$_2$N$_3$), 8.05 (1H, s, ArH), 8.72 (1H, s, C$_2$H$_2$N$_3$) and 9.85 (1H, bs, ArOH);

¹³C NMR (67.9 MHz, DMSO-d$_6$) δ 52.7 (CH$_2$), 109.0 (CH), 119.7 (CH), 125.7 (CH), 125.8 (CH), 126.8 (CH), 126.9 (CH), 127.1 (CH), 127.3 (CH), 128.5 (C), 129.9 (CH), 130.4 (CH), 134.4 (C), 134.5 (C), 137.5 (C), 141.2 (C), 144.9 (CH), 152.3 (CH) and 156.2 (C);

HPLC (90% CH$_3$CN in H$_2$O) t$_r$=3.136 (97.81%);

LCMS (APCI), m/z 300.38 (M⁻–H, 100%).

2-(3-((1H-1,2,4-Triazol-1-yl)methyl)phenyl)naphthalen-6-yl sulfamate (TJA02060, STX2052)

$C_{19}H_{16}N_4O_3S$ MW 380.42

Sulfamoyl chloride in toluene (5.53 mL, 1.66 mmol) was transferred to a 10 mL r.b. flask and the solvent removed under vacuum at 30° C. On cooling a white solid formed to which was added N,N-dimethylacetamide (1.5 mL) to form a colourless solution. TJA02059 (0.100 g, 0.332 mmol) was added and the solution left to stir at room temperature under N$_2$ (g) for 18 h. The reaction mixture was then poured into distilled H$_2$O (30 mL) and extracted with ethyl acetate (25 mL×2). The organic layers were combined and washed with distilled H$_2$O (25 mL×4) and brine (25 mL). Dried over MgSO$_4$ and solvent removed in vacuo to leave off white residues. Column chromatography (dichloromethane/acetone 80:20) eluted the title compound as a white solid (0.066 g, 52 mp 172.5-177.6° C.;

$R_f$: 0.26 (dichloromethane/acetone 80:20).

¹H NMR (270 MHz, DMSO-d$_6$) δ 5.53 (2H, s, ArCH$_2$N), 7.29-7.31 (1H, d, J=7.4 Hz, ArH), 7.46-7.51 (2H, m, ArH), 7.78-7.91 (4H, dd, J=9.2 & 25.4 Hz, ArH), 8.01 (1H, s, C$_2$H$_2$N$_3$), 8.07-8.11 (4H, m, ArH & ArOSO$_2$NH$_2$), 8.28 (1H, s, ArH) and 8.75 (1H, s, C$_2$H$_2$N$_3$);

¹³C NMR (67.9 MHz, DMSO-d$_6$) δ 52.7 (CH$_2$), 119.6 (CH), 122.7 (CH), 125.7 (CH), 126.4 (CH), 127.2 (CH), 127.2 (CH), 127.8 (CH), 129.1 (CH), 130.0 (CH), 130.7 (CH), 132.2 (C), 133.1 (C), 137.7 (C), 137.8 (C), 140.5 (C), 144.9 (CH), 148.5 (C) and 152.4 (CH);

HPLC (90% CH$_3$CN in H$_2$O) t$_r$=8.729 (100%);

LCMS (APCI), m/z 379.47 (M⁻–H, 100%).

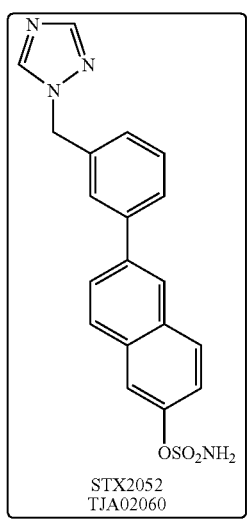

STX2052
TJA02060

STX2054

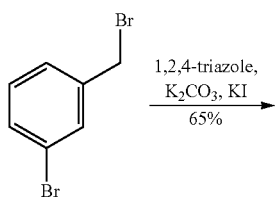

1,2,4-triazole,
K₂CO₃, KI
65%

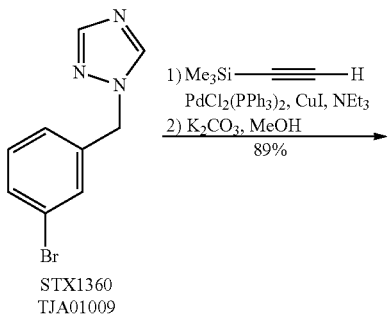

STX1360
TJA01009

1) Me₃Si—≡—H
PdCl₂(PPh₃)₂, CuI, NEt₃
2) K₂CO₃, MeOH
89%

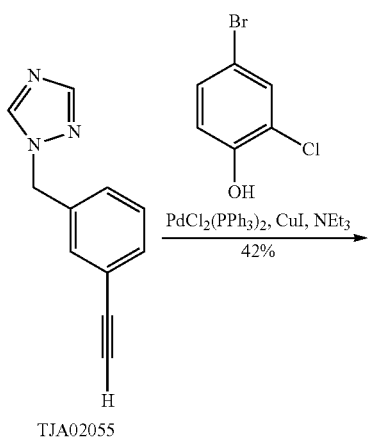

TJA02055

PdCl₂(PPh₃)₂, CuI, NEt₃
42%

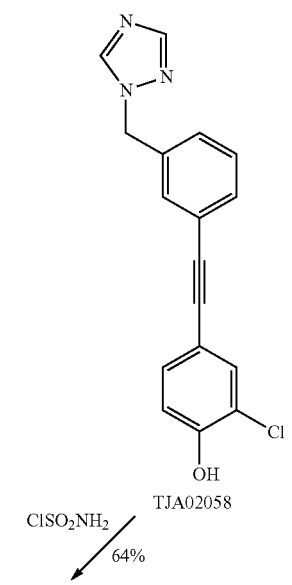

TJA02058

ClSO₂NH₂
64%

1-(3-Ethynylbenzyl)-1H-1,2,4-triazole (TJA02055)

$C_{11}H_9N_3$ MW 183.21

A dry 25 mL r.b. flask fitted with a condenser was purged with $N_{2\,(g)}$ and loaded with TJA01009 (0.250 g, 1.05 mmol), trimethylsilylacetylene (174 μL, 1.26 mmol), copper iodide (0.006 g, 3 mol %), PdCl₂(PPh₃)₂ (0.022 g, 3 mol %), NEt₃ (3 mL) and anhydrous THF (10 mL). The reaction vessel was then evacuated and backfilled with $N_{2\,(g)}$ three times. The reaction was heated to reflux for 20 h then allowed to cool and the THF was removed under reduced pressure. Residues were dissolved in EtOAc and filtered through a pad of silica. Solvent was removed under reduced pressure and the yellow residues (HPLC (100% CH₃CN in H₂O) $t_r$=7.161 (90.61%); LCMS (APCI), m/z 256.35 (M⁺+H, 100%))
were dissolved in MeOH (5 mL) and potassium carbonate (0.174 g, 1.26 mmol) was added and the mixture turned brown. Stirred at room temperature for 20 h. Solvent removed under reduced pressure. Dark brown residues dissolved in EtOAc (30 mL) and washed with distilled water (30 mL×2) and brine (30 mL). Dried over MgSO₄ and solvent removed under reduced pressure to give brown residues. Column chromatography (ethyl acetate) eluted the title compound as an orange/red oil (0.171 g, 89%), $R_f$: 0.60 (ethyl acetate).
¹H NMR (270 MHz, CDCl₃) δ 3.08 (1H, s, ArCCH), 5.30 (2H, s, ArCH₂N), 7.17-7.38 (3H, m, ArH), 7.43-7.46 (1H, d, J=7.7 Hz, ArH), 7.96 (1H, S, C₂H₂N₃) and 8.07 (1H, s, C₂H₂N₃);
HPLC (90% CH₃CN in H₂O) $t_r$=3.796 (87.54%);
LCMS (APCI), m/z 184.02 (M⁺+H, 100%).

4-(2-(3-((1H-1,2,4-Triazol-1-yl)methyl)phenyl)ethynyl)-2-chlorophenol (TJA02058)

$C_{17}H_{12}ClN_3O$ MW 309.75
A dry 10 mL r.b. flask fitted with a condenser was purged with $N_{2\,(g)}$ and loaded with TJA02055 (0.100 g, 0.546 mmol), 4-bromo-2-chlorophenol (0.136 g, 0.655 mmol), copper iodide (0.003 g, 3 mol %), PdCl₂(PPh₃)₂ (0.011 g, 3 mol %), NEt₃ (1 mL) and anhydrous THF (5 mL). The reaction vessel was then evacuated and backfilled with $N_{2\,(g)}$ three times. The reaction was heated to reflux for 22 h then allowed to cool and the THF was removed under reduced pressure. Residues were dissolved in EtOAc (30 mL) and washed with distilled water (30 mL×2) and brine (30 mL). Dried over MgSO$_4$ and solvent removed under reduced pressure to give brown residues. Column chromatography (ethyl acetate) eluted the title compound as a yellow solid (0.071 g, 42%), $R_f$: 0.55 (ethyl acetate).

$^1$H NMR (270 MHz, CDCl$_3$) δ 5.31 (2H, s, ArCH$_2$N), 6.47 (1H, bs, ArOH), 6.96-6.99 (1H, d, J=8.4 Hz, ArH), 7.19-7.69 (6H, m, ArH), 7.99 (1H, s, C$_2$H$_2$N$_3$) and 8.09 (1H, s, C$_2$H$_2$N$_3$);

HPLC (90% CH$_3$CN in H$_2$O) t$_r$=2.814 (95.24%);

LCMS (APCI), m/z 310.33 ($^{37}$ClM$^-$–H, 30%), 308.31 ($^{35}$ClM$^-$–H, 100).

4-(2-(3-((1H-1,2,4-Triazol-1-yl)methyl)phenyl)ethynyl)-2-chlorophenyl sulfamate (TJA02065, STX2054)

C$_{17}$H$_{13}$ClN$_4$O$_3$S MW 388.83

Sulfamoyl chloride in toluene (1.75 mL, 1.05 mmol) was transferred to a 10 mL r.b. flask and the solvent removed under vacuum at 30° C. On cooling a white solid formed to which was added N,N-dimethylacetamide (1.5 mL) to form a colourless solution. TJA02058 (0.065 g, 0.210 mmol) was added and the solution left to stir at room temperature under N$_2$ $_{(g)}$ for 18 h. The reaction mixture was then poured into distilled H$_2$O (30 mL) and extracted with ethyl acetate (25 mL×2). The organic layers were combined and washed with distilled H$_2$O (25 mL×4) and brine (25 mL). Dried over MgSO$_4$ and solvent removed in vacuo to leave off white residues. Column chromatography (dichloromethane/acetone 80:20) eluted the title compound as a white solid (0.053 g, 64 mp 172.5-177.6° C.;

$R_f$: 0.36 (dichloromethane/acetone 80:20).

$^1$H NMR (270 MHz, DMSO-d$_6$) δ 5.46 (2H, s, ArCH$_2$N), 7.35-7.61 (6H, m, ArH), 7.84 (1H, s, ArH), 8.02 (1H, s, C$_2$H$_2$N$_3$), 8.41 (2H, bs, ArOSO$_2$NH$_2$) and 8.71 (1H, s, C$_2$H$_2$N$_3$);

$^{13}$C NMR (67.9 MHz, DMSO-d$_6$) δ 52.1 (CH$_2$), 88.0 (C), 90.8 (C), 122.0 (C), 122.5 (C), 124.6 (CH), 127.4 (C), 129.4 (CH), 129.8 (CH), 131.4 (CH), 131.6 (CH), 132.1 (CH), 133.7 (CH), 137.6 (C), 145.0 (CH), 146.9 (C) and 152.5 (CH);

HPLC (90% CH$_3$CN in H$_2$O) t$_r$=2.802 (97.73%);

LCMS (APCI), m/z 391.18 ($^{37}$ClM$^+$+H, 35%), 389.16 ($^{35}$ClM$^+$+H, 100).

STX2112

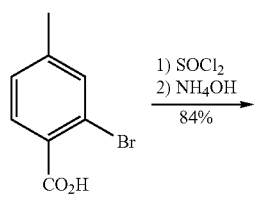

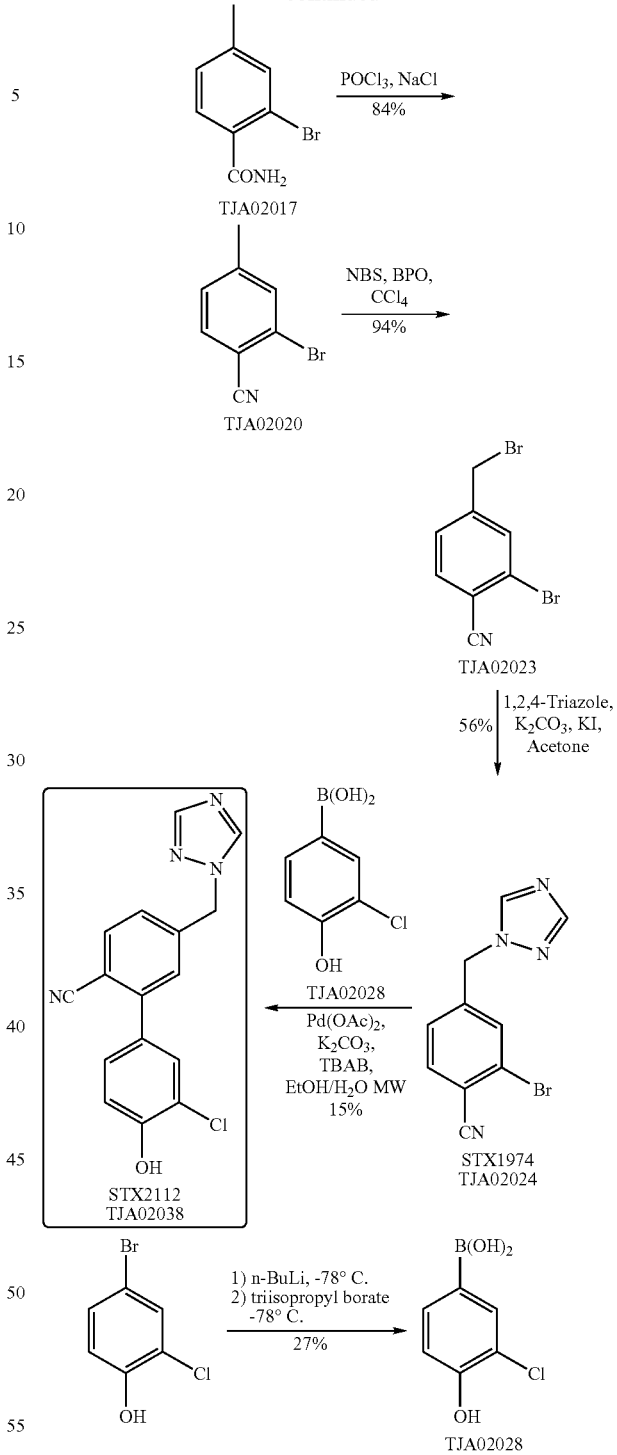

3-Chloro-4-hydroxyphenylboronic acid (TJA02028)

C$_6$H$_6$ClO$_3$ MW 172.37

A dry 250 ml r.b. flask was loaded with 4-bromo-2-chlorophenol (5.00 g, 24.1 mmol) and purged with N$_{2(g)}$. Anhydrous THF (100 mL) added with stirring and the vessel cooled to −78° C. (dry ice/acetone bath). After 30 mins n-BuLi, 2.3 M in hexanes, (12.9 mL, 28.9 mmol) was added dropwise over 20 min. The reaction was left to stir for 1 h. Triisopropyl borate (6.65 mL, 28.9 mmol) was added dropwise with the reaction still at −78° C. After 15 min of stirring at this temperature the dry ice/acetone bath was removed. At about 0° C. 2 M HCl$_{(aq)}$ (5 mL) was added and the reaction left to stir for a further 15 min. THF removed under vacuum and residues taken up in ethyl acetate (50 mL). Distilled H$_2$O (50 mL) was added and the organic layer separated. The aqueous layer was extracted with ethyl acetate (50 mL×2). The organic portions were combined and washed with sat. Na$_2$CO$_{3\ (aq)}$. The aqueous layer was separated and treated with 2M HCl (aq) until the pH was about 4. This was then extracted with ethyl acetate (50 mL×2). The organic portions were then dried over MgSO$_4$ and solvent removed. The resultant brown residues were taken up in a minimum of ethyl acetate (2-3 mL) and added to dropwise to hexane (50 mL) with stirring. The brown ppt was filtered to give the title compound as a brown solid (1.11 g, 27%).

$^1$H NMR (270 MHz, DMSO-d$_6$) δ 6.89-6.92 (1H, d, J=8.2 Hz, ArH), 7.52-7.56 (1H, dd, J=1.8 & 7.9 Hz, ArH), 7.72-7.73 (1H, d, J=1.5 Hz, ArH), 7.98 (2H, s, ArB(OH)$_2$) and 10.33 (1H, s, ArOH);

HPLC (70% CH$_3$CN in H$_2$O) t$_r$=3.447 (96.77%);

LCMS (APCI), m/z 172.86 ($^{37}$ClM$^-$–H, 28%), 171.10 ($^{35}$ClM—H, 55), 126.78 (($^{35}$ClM$^-$–H)—B(OH)$_2$, 100).

4'-Hydroxy-3'-chloro-3-[1,2,4]triazol-1-ylmethyl-biphenyl-6-carbonitrile (TJA02038, STX2112)

C$_{16}$H$_{11}$ClN$_4$O MW 310.74

A 10 mL microwave vial was loaded with TJA01024 (0.150 g, 0.570 mmol), TJA02028 (0.147 g, 0.855 mmol), potassium carbonate (0.198 g, 1.43 mmol), tetrabutylammonium bromide (0.189 g, 0.570 mmol), Pd(OAc)$_2$ (0.003-0.004 g, 2-3 mol %), ethanol (1.5 mL) and distilled water (3.5 mL). The vial was sealed and loaded (with no prior degassing) into a CEM Explorer Microwave. After a run time of 5 min at 150° C. the reaction mixture was allowed to cool and ethyl acetate (50 mL) added. This was then washed with distilled water (25 mL×3) and brine (25 mL). The organic layer was dried over MgSO$_4$, filtered and solvent removed in vacuo to leave a yellow/brown residue. The crude product was purified via flash chromatography (20 g column, method4) to give a white solid (0.074 g). Recrystallisation (dichloromethane) gave the title compound as a white solid (0.026 g, 13%), mp 186.2-188.9° C.;

R$_f$: 0.44 (ethyl acetate);

$^1$H NMR (270 MHz, DMSO-d$_6$) δ 5.56 (2H, s, ArCH$_2$N), 7.09-7.12 (1H, d, J=8.4 Hz, ArH), 7.33-7.37 (2H, m, ArH), 7.52 (1H, s, ArH), 7.55-7.56 (1H, d, J=2.2 Hz, ArH), 7.90-7.92 (1H, d, J=7.9 Hz, ArH), 8.03 (1H, S, C$_2$H$_2$N$_3$), 8.72 (1H, S, C$_2$H$_2$N$_3$) and 10.67 (1H, bs, ArOH);

HPLC (70% CH$_3$CN in H$_2$O) t$_r$=3.774 (97.17%);

LCMS (APCI), m/z 311.08 ($^{37}$ClM$^-$–H, 30%), 309.13 ($^{35}$ClM$^-$–H, 100).

STX2114

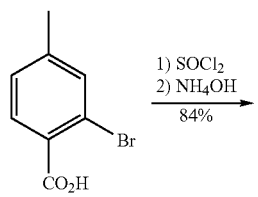

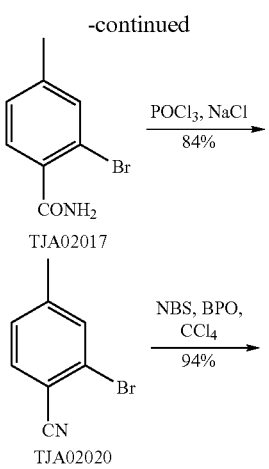

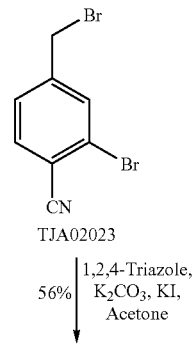

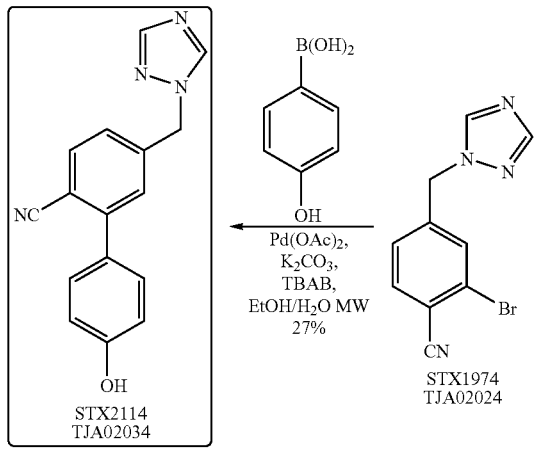

4'-Hydroxy-3-[1,2,4]triazol-1-ylmethyl-biphenyl-6-carbonitrile (TJA02034, STX2114)

C$_{16}$H$_{12}$N$_4$O MW 276.29

A 10 mL microwave vial was loaded with TJA02024 (0.150 g, 0.570 mmol), 4-hydroxyphenylboronic acid (0.118 g, 0.855 mmol), potassium carbonate (0.198 g, 1.43 mmol), tetrabutylammonium bromide (0.189 g, 0.570 mmol), Pd(OAc)$_2$ (0.003-0.004 g, 2-3 mol %), ethanol (1.5 mL) and distilled water (3.5 mL). The vial was sealed and loaded (with no prior degassing) into a CEM Explorer Microwave (150 W, 3 min, 120° C.). The reaction mixture was allowed to cool and ethyl acetate (50 mL) added. This was then washed with distilled water (25 mL×3) and brine (25 mL). The organic layer was dried over MgSO$_4$, filtered and solvent removed in vacuo to leave a yellow/brown residue. Flash chromatography (20 g column, method4) eluted a white solid (0.102 g, 65%). Precipitation from MeOH/CHCl$_3$ gave the title compound as a white solid (0.085 g, 54%).

mp 211.2-212.7° C.;

R$_f$: 0.42 (ethyl acetate);

$^1$H NMR (270 MHz, CDCl$_3$) 5.62 (2H, s, ArCH$_2$N), 6.88-6.92 (2H, d, J=8.6 Hz, AA'BB'), 7.31-7.33 (1h, d, J=8.2 Hz, ArH), 7.37-7.39 (2H, d, J=8.5 Hz, AA'BB'), 7.45 (1H, s, ArH), 7.87-7.90 (1H, d, J=7.9 Hz, ArH), 8.02 (1H, s, C$_2$H$_2$N$_3$), 8.17 (1H, s, C$_2$H$_2$N$_3$) and 9.87 (1H, s, ArOH);

$^{13}$C NMR (69.5.5 MHz, DMSO-d$_6$) δ 52.0 (CH$_2$), 109.8 (C), 116.1 (CH), 119.2 (C), 127.0 (CH), 128.6 (C), 129.6 (CH), 130.5 (CH), 134.8 (CH), 142.4 (C), 145.3 (C), 145.5 (C), 152.6 (CH) and 158.8 (C);

HPLC (90% CH$_3$CN in H$_2$O) t$_r$=1.683 (98.59%);

LCMS (APCI), m/z 277.32 (M$^+$+H, 100%);

TJA01189 a further 15 min. THF removed under vacuum and residues taken up in ethyl acetate (50 mL). Distilled H$_2$O (50 mL) was added and the organic layer separated. The aqueous layer was extracted with ethyl acetate (50 mL×2). The organic portions were combined and washed with sat. Na$_2$CO$_3$ $_{(aq)}$. The aqueous layer was separated and treated with 2M HCl (aq) until the pH was about 4. This was then extracted with ethyl acetate (50 mL×2). The organic portions were then dried over MgSO$_4$ and solvent removed. The resultant brown residues were taken up in a minimum of ethyl acetate (2-3 mL) and added to dropwise to hexane (50 mL) with stirring. The brown ppt was filtered to give the title compound as a brown solid (1.11 g, 27%).

$^1$H NMR (270 MHz, DMSO-d$_6$) δ 6.89-6.92 (1H, d, J=8.2 Hz, ArH), 7.52-7.56 (1H, dd, J=1.8 & 7.9 Hz, ArH), 7.72-7.73

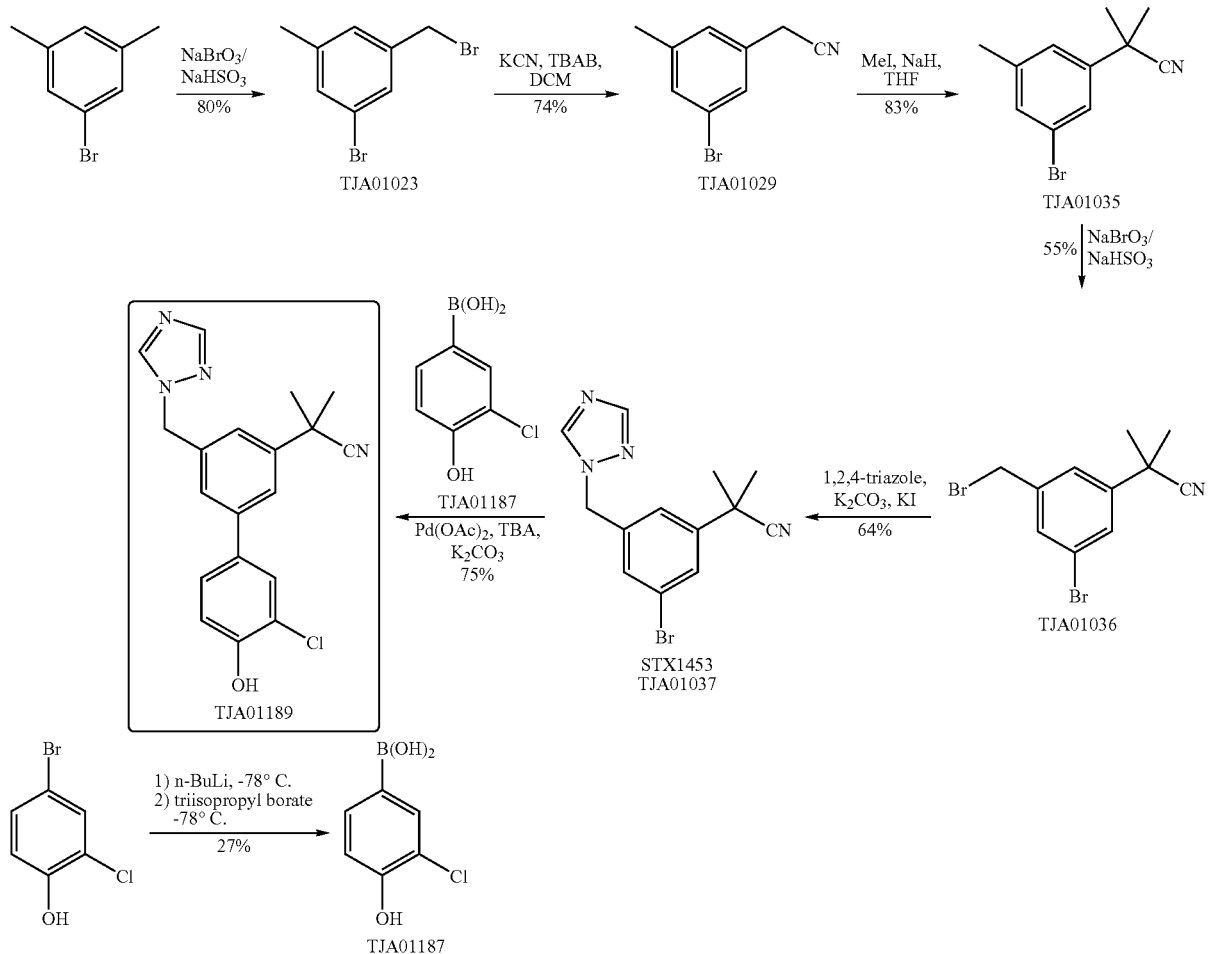

3-Chloro-4-hydroxyphenylboronic acid (TJA01187)

C$_6$H$_6$ClO$_3$ MW 172.37

A dry 250 ml r.b. flask was loaded with 4-bromo-2-chlorophenol (5.00 g, 24.1 mmol) and purged with N$_{2(g)}$. Anhydrous THF (100 mL) added with stirring and the vessel cooled to −78° C. (dry ice/acetone bath). After 30 mins n-BuLi, 2.3 M in hexanes, (12.9 mL, 28.9 mmol) was added dropwise over 20 min. The reaction was left to stir for 1 h. Triisopropyl borate (6.65 mL, 28.9 mmol) was added dropwise with the reaction still at −78° C. After 15 min of stirring at this temperature the dry ice/acetone bath was removed. At about 0° C. 2 M HCl$_{(aq)}$ (5 mL) was added and the reaction left to stir for (1H, d, J=1.5 Hz, ArH), 7.98 (2H, s, ArB(OH)$_2$) and 10.33 (1H, s, ArOH);

HPLC (70% CH$_3$CN in H$_2$O) t$_r$=3.447 (96.77%);

LCMS (APCI), m/z 172.86 ($^{37}$ClM$^-$−H, 28%), 171.10 ($^{35}$ClM—H, 55), 126.78 (($^{35}$ClM$^+$—H)—B(OH)$_2$, 100).

2-(4'-Hydroxy-3-chloro-5-[1,2,4]triazol-1-ylmethyl-biphenyl-3-yl)-2-methyl-propionitrile (TJA01189)

C$_{19}$H$_{17}$ClN$_4$O MW 352.82

A 10 mL microwave vial was loaded with TJA01037 (0.200 g, 0.656 mmol), TJA01187 (0.136 g, 0.787 mmol), potassium carbonate (0.227 g, 1.64 mmol), tetrabutylammonium bromide (0.218 g, 0.656 mmol), Pd(OAc)$_2$ (0.004-0.005 g, 2-3 mol %), ethanol (1.5 mL) and distilled water (3.5 mL). The vial was sealed and loaded (with no prior degassing) into a CEM Explorer Microwave. After a run time of 5 min at 150° C. the reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified via flash chromatography (20 g column, method4) to give a white solid (0.074 g). Recrystallisation (dichloromethane) gave the title compound as a white solid (0.175 g, 75%), R$_f$: 0.19 (ethyl acetate).

$^1$H NMR (270 MHz, DMSO-d$_6$) δ 1.72 (6H, s, ArC(CH$_3$)$_2$CN), 5.49 (2H, s, ArCH$_2$N), 7.05-7.08 (1H, d, J=8.4 Hz, ArH), 7.42-7.51 (3H, m, ArH), 7.64-7.68 (2H, m, ArH), 8.02 (1H, s, C$_2$H$_2$N$_3$), 8.73 (1H, s, C$_2$H$_2$N$_3$) and 10.44 (1H, s, ArOH);

$^{13}$C NMR (67.9 MHz, DMSO-d$_6$) δ 28.8 (CH$_3$), 37.4 (C), 52.5 (CH$_2$), 117.6 (CH), 120.9 (C), 123.1 (CH), 124.1 (CH), 125.1 (CH), 125.9 (CH), 127.1 (CH), 128.6 (CH), 131.9 (C), 138.2 (C), 140.5 (C), 143.2 (C), 144.9 (CH), 152.4 (CH) and 153.6 (C);

HPLC (90% CH$_3$CN in H$_2$O) t$_r$=1.921 (94.06%);

LCMS (APCI), m/z 353.40 ($^{37}$ClM—H, 35%), 351.39 ($^{35}$ClM$^-$–H, 100).

TJA02027

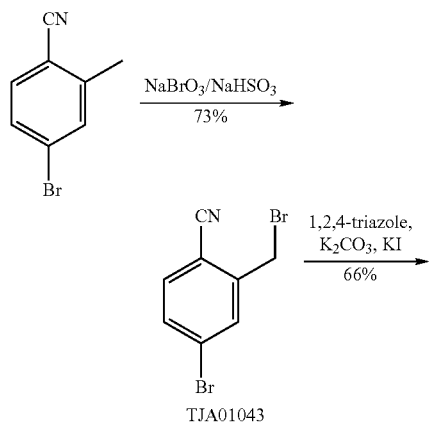

TJA01043

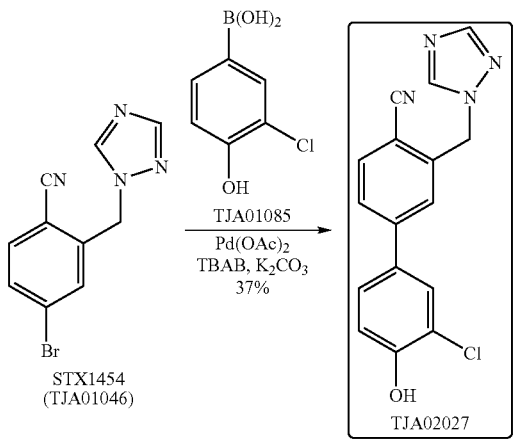

STX1454
(TJA01046)

TJA02027

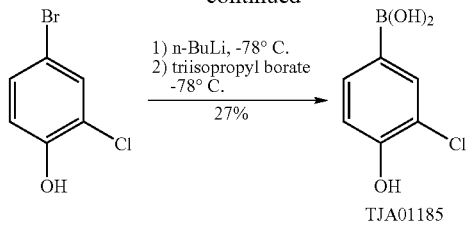

TJA01185

3-Chloro-4-hydroxyphenylboronic Acid (TJA01185)

C$_6$H$_6$ClO$_3$ MW 172.37

A dry 250 ml r.b. flask was loaded with 4-bromo-2-chlorophenol (5.00 g, 24.1 mmol) and purged with N$_{2(g)}$. Anhydrous THF (100 mL) added with stirring and the vessel cooled to −78° C. (dry ice/acetone bath). After 30 mins n-BuLi, 2.3 M in hexanes, (12.9 mL, 28.9 mmol) was added dropwise over 20 min. The reaction was left to stir for 1 h. Triisopropyl borate (6.65 mL, 28.9 mmol) was added dropwise with the reaction still at −78° C. After 15 min of stirring at this temperature the dry ice/acetone bath was removed. At about 0° C. 2 M HCl$_{(aq)}$ (5 mL) was added and the reaction left to stir for a further 15 min. THF removed under vacuum and residues taken up in ethyl acetate (50 mL). Distilled H$_2$O (50 mL) was added and the organic layer separated. The aqueous layer was extracted with ethyl acetate (50 mL×2). The organic portions were combined and washed with sat. Na$_2$CO$_3$ $_{(aq)}$. The aqueous layer was separated and treated with 2M HCl (aq) until the pH was about 4. This was then extracted with ethyl acetate (50 mL×2). The organic portions were then dried over MgSO$_4$ and solvent removed. The resultant brown residues were taken up in a minimum of ethyl acetate (2-3 mL) and added to dropwise to hexane (50 mL) with stirring. The brown ppt was filtered to give the title compound as a brown solid (1.11 g, 27%).

$^1$H NMR (270 MHz, DMSO-d$_6$) δ 6.89-6.92 (1H, d, J=8.2 Hz, ArH), 7.52-7.56 (1H, dd, J=1.8 & 7.9 Hz, ArH), 7.72-7.73 (1H, d, J=1.5 Hz, ArH), 7.98 (2H, s, ArB(OH)$_2$) and 10.33 (1H, s, ArOH);

HPLC (70% CH$_3$CN in H$_2$O) t$_r$=3.447 (96.77%);

LCMS (APCI), m/z 172.86 ($^{37}$ClM$^-$–H, 28%), 171.10 ($^{35}$ClM—H, 55), 126.78 (($^{35}$ClM$^+$—H)—B(OH)$_2$, 100).

4'-Hydroxy-3'-chloro-3-[1,2,4]triazol-1-ylmethyl-biphenyl-4-carbonitrile (TJA02027)

C$_{16}$H$_{11}$ClN$_4$O MW 310.74

A 10 mL microwave vial was loaded with TJA01046 (0.150 g, 0.570 mmol), TJA01085 (0.118 g, 0.684 mmol), potassium carbonate (0.197 g, 1.43 mmol), tetrabutylammonium bromide (0.189 g, 0.570 mmol), Pd(OAc)$_2$ (0.003-0.004 g, 2-3 mol %), ethanol (1.5 mL) and distilled water (3.5 mL). The vial was sealed and loaded (with no prior degassing) into a CEM Explorer Microwave. After a run time of 3 min at 120° C. the reaction mixture was allowed to cool and ethyl acetate (50 mL) added. This was then washed with distilled water (30 mL×3) and brine (30 mL). The organic layer was dried over MgSO$_4$, filtered and solvent removed in vacuo to leave a yellow/brown residue. The crude product was purified via flash chromatography (20 g column, method4) eluted the title compound as a white solid (0.065 g, 37%), R$_f$: 0.44 (ethyl acetate);

$^1$H NMR (270 MHz, DMSO-d$_6$) δ 5.67 (2H, s, ArCH$_2$N), 7.07-7.10 (1H, d, J=8.4 Hz, ArH), 7.52-7.56 (1H, dd, J=2.2 &

8.2 Hz, ArH), 7.74-7.75 (1H, d, J=2.2 Hz, ArH), 7.80-7.83 (2H, m, ArH), 7.89-7.93 (2H, m, ArH & $C_2H_2N_3$), 8.04 (1H, s, $C_2H_2N_3$) and 8.73 (1H, s, ArOH);

$^{13}$C NMR (69.5 MHz, DMSO-$d_6$) δ 51.1 ($CH_2$), 110.0 (C), 117.7 (CH), 121.2 (C), 126.9 (CH), 127.4 (CH), 128.1 (CH), 128.9 (CH), 130.1 (C), 134.5 (CH), 140.0 (C), 144.0 (C), 145.4 (CH), 152.6 (CH) and 154.6 (C) (one overlapping signal);

HPLC (90% $CH_3CN$ in $H_2O$) $t_r$=2.073 (98.19%);

LCMS (APCI), m/z 312.66 ($^{37}ClM^+$+H, 35%), 310.64 ($^{35}ClM^+$+H, 100).

STX2110

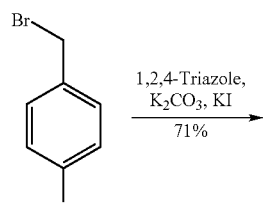

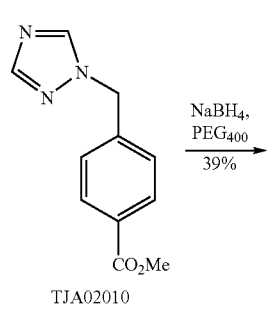

TJA02010

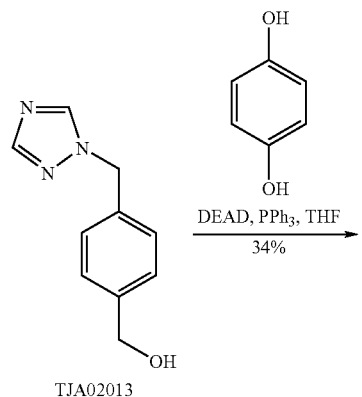

TJA02013

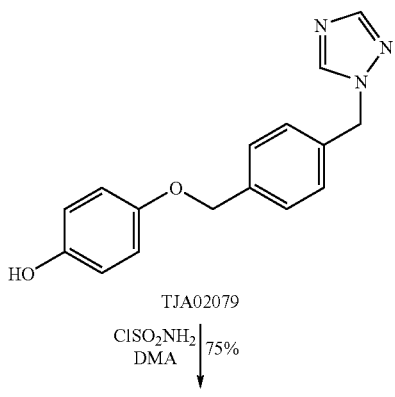

TJA02079

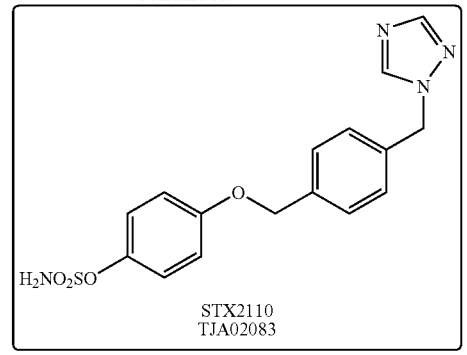

STX2110
TJA02083

4-(4-((1H-1,2,4-triazol-1-yl)methyl)benzyloxy)phenol (TJA02079)

$C_{16}H_{15}N_3O_2$ MW 281.31

A 10 mL r.b. flask, purged with $N_{2\,(g)}$ was loaded with TJA02078 (0.100 g, 0.528 mmol), triphenyl phosphine (0.168 g, 0.634 mmol), hydroquinone (0.581 g, 5.28 mmol) and anhydrous THF (3 mL) and cooled to 0° C. With stirring diethylazodicarboxylate (99.8 µL, 0.634 mmol) was added dropwise and the reaction mixture left to stir at room temperature for 20 h. THF was then removed in vacuo and the resulting residues dissolved in ethyl acetate (30 mL) and washed with distilled $H_2O$ (30 mL×3), brine (30 mL) and dried over $MgSO_4$. Solvents were removed in vacuo. Column chromatography (ethyl acetate) eluted a white solid that was recrystallised (ethyl acetate/hexane) to give the title compound as a white crystalline solid (0.051 g, 34%), mp 167.4-168.9° C.;

$R_f$: 0.41 (ethyl acetate);

$^1$H NMR (270 MHz, DMSO-$d_6$) δ 4.96 (2H, s, ArCH$_2$OAr), 5.41 (2H, s, ArCH$_2$N), 6.64-6.81 (4H, dd, J=8.9 & 30.1 Hz, AA'BB'), 7.25-7.41 (4H, dd, J=7.9 & 34.6 Hz, AA'BB'), 7.98 (1H, s, $C_2H_2N_3$), 8.66 (1H, s, $C_2H_2N_3$) and 8.93 (1H, bs, ArOH);

HPLC (90% $CH_3CN$ in $H_2O$) $t_r$=3.486 (98.68%);

LCMS (APCI), m/z 282.49 ($M^+$+H, 70%), 213.32 (($M^+$+H)—$C_2H_2N_3$, 100%).

4-(4-((1H-1,2,4-Triazol-1-yl)methyl)benzyloxy)phenyl sulfamate (STX2110, TJA02083)

$C_{16}H_{16}N_4O_4S$ MW 360.39

Sulfamoyl chloride in toluene (1.37 mL, 0.889 mmol) was transferred to a 10 mL r.b. flask and the solvent removed under vacuum at 30° C. On cooling a white solid formed to which was added N,N-dimethylacetamide (1.5 mL) to form a colourless solution. TJA02079 (0.050 g, 0.178 mmol) was added and the solution left to stir at room temperature under $N_{2\,(g)}$ for 60 h. The reaction mixture was then poured into distilled $H_2O$ (25 mL) and extracted with ethyl acetate (25 mL×2). The organic layers were combined and washed with distilled $H_2O$ (25 mL×4) and brine (25 mL). Dried over $MgSO_4$ and solvent removed in vacuo to leave off white residues. Column chromatography (dichloromethane/acetone 80:20) eluted the title compound as a white solid (0.048 g, 75 mp 164-166.7° C.

$R_f$: 0.32 (dichloromethane/acetone 75:25).

$^1$H NMR (270 MHz, DMSO-$d_6$) δ 5.09 (2H, s, ArCH$_2$OAr), 5.41 (2H, s, ArCH$_2$N), 7.02-7.19 (4H, dd, J=6.7

& 37.1 Hz, AA'BB'), 7.27-7.45 (4H, dd, J=8.2 & 38.8 Hz, ArH), 7.85 (2H, bs, ArOSO$_2$NH$_2$), 7.98 (1H, s, C$_2$H$_2$N$_3$) and 8.67 (1H, s, C$_2$H$_2$N$_3$);

HPLC (70% CH$_3$CN in H$_2$O) t$_r$=6.254 (100%);

LCMS (APCI), m/z 361.46 (M$^+$+H, 100%).
STX2113

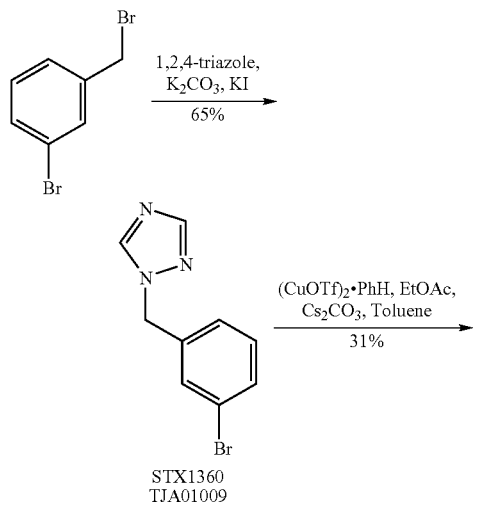

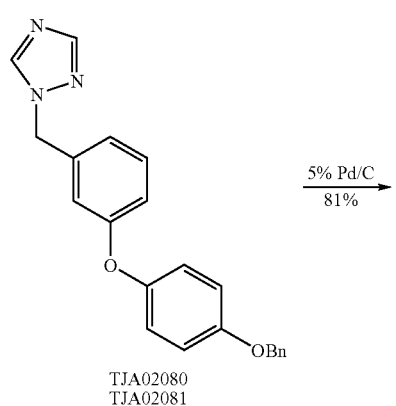

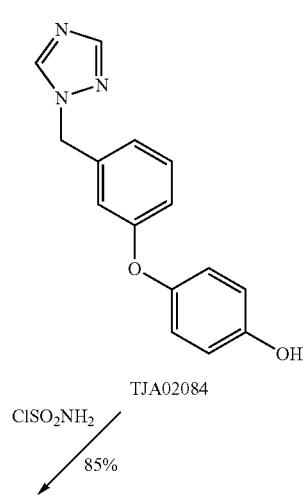

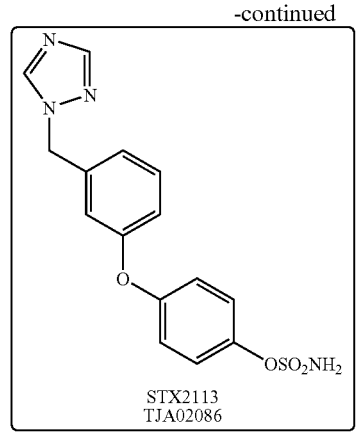

1-(3-(4-(Benzyloxy)phenoxy)benzyl)-1H-1,2,4-triazole (TJA02081)

C$_{22}$H$_{19}$N$_3$O$_2$ MW 357.41

A 10 mL r.b. flask was loaded with TJA01009 (0.400 g, 1.68 mmol), 4-(benzyloxy)phenol (0.504 g, 2.52 mmol), cesium carbonate (0.888 g, 2.52 mmol), (CuOTf)$_2$.PhH (0.020 g, 5 mol % Cu), ethyl acetate (8 μL, 5 mol %), 1-naphthoic acid (0.432 g, 2.52 mmol), 4 Å molecular sieves (0.350 g) and anhydrous toluene (3.0 mL). The flask was sealed and heated to 110° C. under N$_{2\,(g)}$ with stirring for 24 h. The reaction was then cooled, ethyl acetate (50 mL) added and then washed with distilled H$_2$O (30 mL×4), brine (30 mL), dried over MgSO$_4$ and solvent removed in vacuo to leave brown residues. Column chromatography (ethyl acetate) eluted the title compound as an off white solid (0.190 g, 32%), R$_f$: 0.56 (ethyl acetate);

$^1$H NMR (270 MHz, CDCl$_3$) δ 5.04 (2H, s, ArCH$_2$OAr), 5.30 (2H, s, ArCH$_2$N), 6.84-6.96 (7H, m, ArH), 7.24-7.45 (6H, m, ArH), 7.95 (1H, s, C$_2$H$_2$N$_3$) and 8.04 (1H, s, C$_2$H$_2$N$_3$);

HPLC (90% CH$_3$CN in H$_2$O) t$_r$=5.976 (97.22%);

LCMS (APCI), m/z 358.56 (M$^+$+H, 100%).

4-(3-((1H-1,2,4-Triazol-1-yl)methyl)phenoxy)phenol (STX2111, TJA02084)

C$_{15}$H$_{13}$N$_3$O$_2$ MW 267.28

TJA02081 (0.185 g, 0.518 mmol) was dissolved in THF (2.5 mL) and MeOH (2.5 mL) in an r.b. flask to which was added 5% Pd/C (0.015 g) to form a black suspension on vigorous stirring. The flask was evacuated and back filled with H$_{2\,(g)}$ via a balloon (×3) and then left to stir for 16 h. The reaction mixture was filtered through celite which was subsequently washed with THF (30 mL×2). Solvent was removed in vacuo to leave a brown residue. Flash chromatography (20 g column, method9) eluted the title compound as a white solid (0.112 g, 81%), mp 156.3-159.7° C.;

R$_f$: 0.46 (ethyl acetate), c.f TJA02081 (0.36);

$^1$H NMR (270 MHz, DMSO-d$_6$) δ 5.37 (2H, s, ArCH$_2$N), 6.74-6.92 (7H, m, ArH), 7.26-7.31 (1H, t, J=7.5 Hz, ArH), 7.98 (1H, s, C$_2$H$_2$N$_2$), 8.64 (1H, s, C$_2$H$_2$N$_2$) and 9.39 (1H, s, ArOH);

$^{13}$C NMR (67.9 MHz, DMSO-d$_6$) δ 52.3 (CH$_2$), 116.6 (CH), 116.7 (CH), 116.8 (CH), 121.7 (CH), 122.0 (CH), 130.6 (CH), 138.8 (C), 144.8 (CH), 147.9 (C), 152.3 (CH), 154.6 (C) and 159.2 (C);

HPLC (90% CH$_3$CN in H$_2$O) t$_r$=3.294 (97.07%);

LCMS (APCI), m/z 268.44 (M$^+$+H, 85%), 199.33 ((M$^+$+H)—C$_2$H$_2$N$_3$, 100%).

4-(3-((1H-1,2,4-Triazol-1-yl)methyl)phenoxy)phenyl sulfamate (STX2113, TJA02086)

C$_{15}$H$_{14}$N$_4$O$_4$S MW 346.36

Sulfamoyl chloride in toluene (2.17 mL, 1.41 mmol) was transferred to a 10 mL r.b. flask and the solvent removed under vacuum at 30° C. On cooling a white solid formed to which was added N,N-dimethylacetamide (1.5 mL) to form a colourless solution. TJA02084 (0.075 g, 0.281 mmol) was added and the solution left to stir at room temperature under N$_2$ $_{(g)}$ for 70 h. The reaction mixture was then poured into distilled H$_2$O (25 mL) and extracted with ethyl acetate (25 mL×2). The organic layers were combined and washed with distilled H$_2$O (25 mL×4) and brine (25 mL). Dried over MgSO$_4$ and solvent removed in vacuo to leave off white residues. Column chromatography (dichloromethane/acetone 75:25) eluted the title compound as a white solid (0.082 g, 85%);

mp 131.5-133.3° C.

R$_f$: 0.23 (dichloromethane/acetone 75:25).

$^1$H NMR (270 MHz, DMSO-d$_6$) δ 5.42 (2H, s, ArCH$_2$N), 6.89-7.05 (3H, m, ArH), 7.07-7.09 (2H, d, J=9.2 Hz, AA'BB'), 7.27-7.29 (2H, d, J=9.2 Hz, AA'BB'), 7.35-7.41 (1H, t, J=7.7 Hz, ArH), 7.99 (3H, s, ArOSO$_2$NH$_2$ & C$_2$H$_2$N$_3$) and 8.66 (1H, s, C$_2$H$_2$N$_3$);

HPLC (90% CH$_3$CN in H$_2$O) t$_r$=3.459 (100%);

LCMS (APCI), m/z 347.49 (M$^+$+H, 100%).

Biological Data

A number of compounds were tested for aromatase and steroid sulphatase inhibition in accordance with the above Protocols 1 and 6.

| STX | STRUCTURE | JEG3-cells Aromatase IC$_{50}$ A: <10 μM B: <1 μM | JEG3-cells STS IC$_{50}$ A: <10 μM B: <1 μM |
|---|---|---|---|
| 1361 | 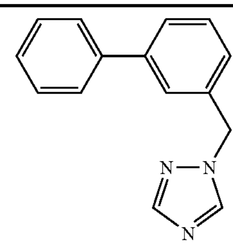 | B | NR |
| 1362 | 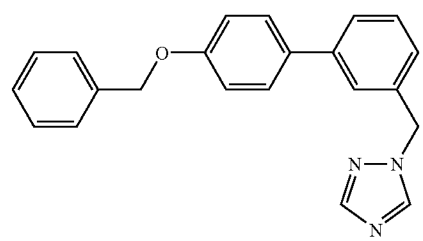 | A | NR |
| 1384 | 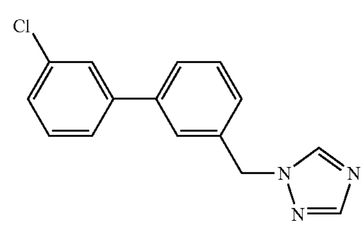 | B | NR |
| 1385 | 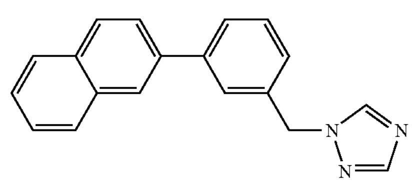 | B | NR |
| 1386 | 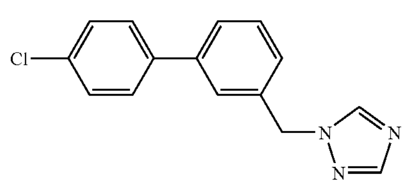 | B | NR |

-continued
| STX | STRUCTURE | JEG3-cells Aromatase IC$_{50}$ A: <10 μM B: <1 μM | JEG3-cells STS IC$_{50}$ A: <10 μM B: <1 μM |
|---|---|---|---|
| 1387 | 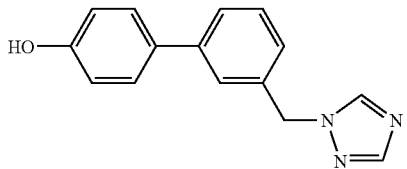 | B | NR |
| 1388 | 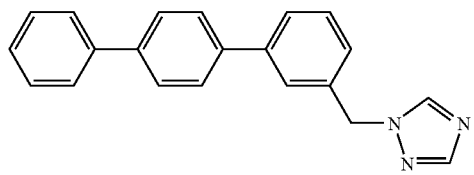 | A | NR |
| 1452 | 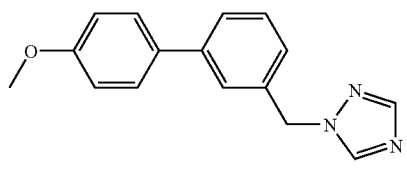 | B | NR |
| 1455 | 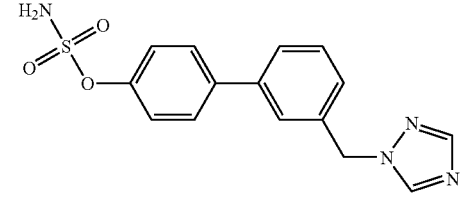 | B | A |
| 1456 | 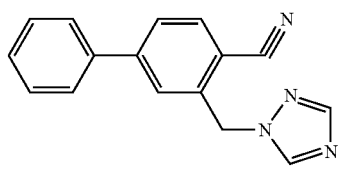 | B | NR |
| 1457 | 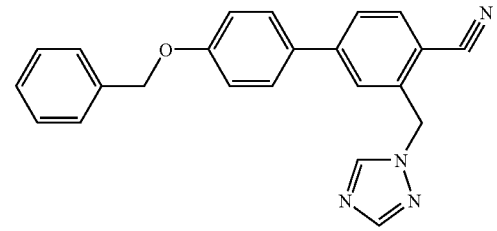 | A | NR |
| 1458 | 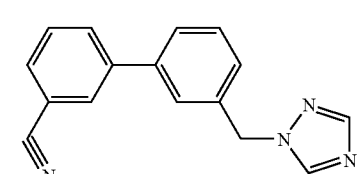 | B | NR |
| 1459 | 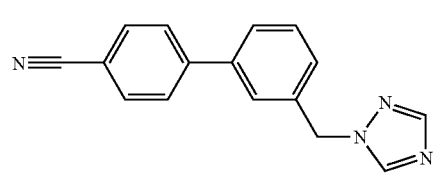 | B | NR |

-continued
| STX | STRUCTURE | JEG3-cells Aromatase IC$_{50}$ A: <10 μM B: <1 μM | JEG3-cells STS IC$_{50}$ A: <10 μM B: <1 μM |
|---|---|---|---|
| 1502 | 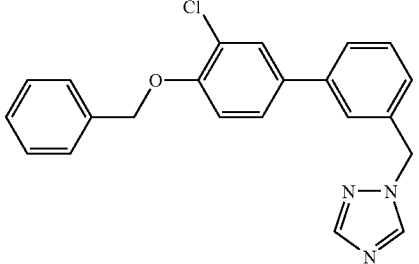 | A | NR |
| 1503 | 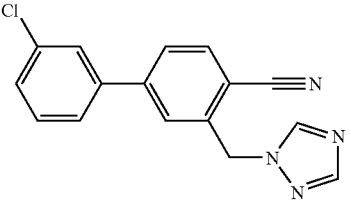 | B | NR |
| 1504 | 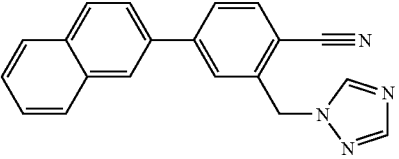 | B | NR |
| 1505 | 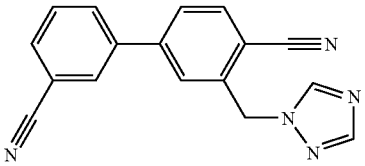 | A | NR |
| 1506 | 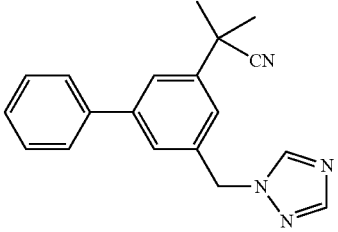 | B | NR |
| 1507 | 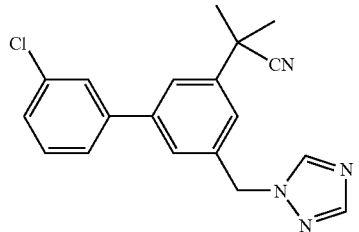 | B | NR |

| STX | STRUCTURE | JEG3-cells Aromatase IC$_{50}$ A: <10 μM B: <1 μM | JEG3-cells STS IC$_{50}$ A: <10 μM B: <1 μM |
|---|---|---|---|
| 1508 | 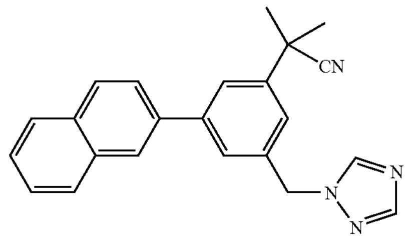 | B | NR |
| 1509 | 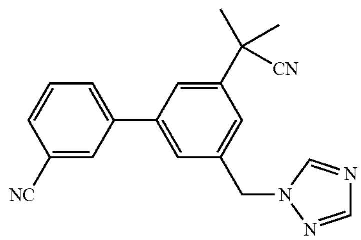 | B | NR |
| 1510 | 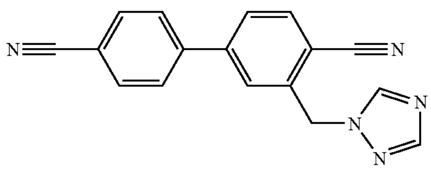 | B | NR |
| 1511 | 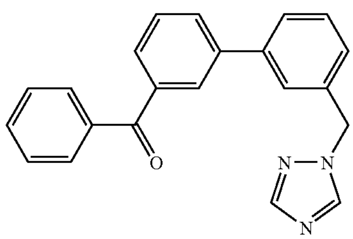 | B | NR |
| 1512 | 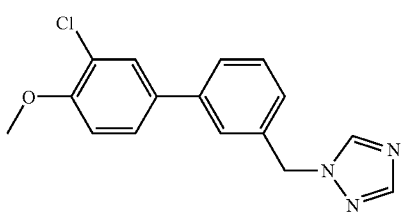 | B | NR |
| 1519 | 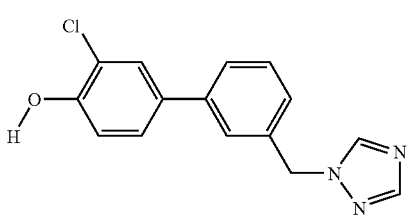 | B | NR |
| 1520 | 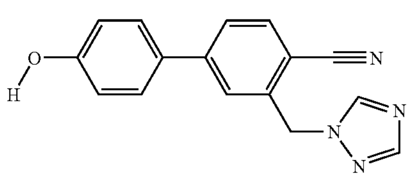 | B | NR |

-continued

| STX | STRUCTURE | JEG3-cells Aromatase IC$_{50}$ A: <10 μM B: <1 μM | JEG3-cells STS IC$_{50}$ A: <10 μM B: <1 μM |
|---|---|---|---|
| 1521 | 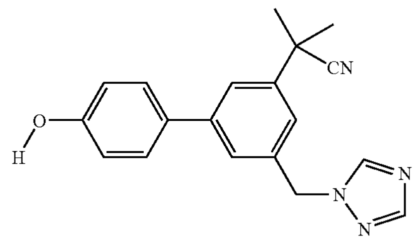 | B | NR |
| 1524 | 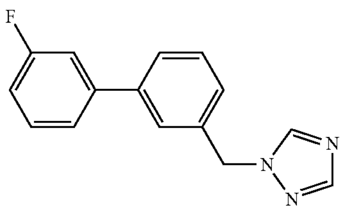 | B | NR |
| 1525 | 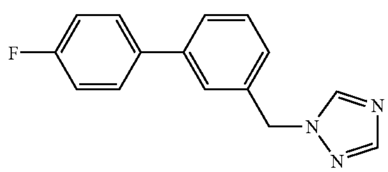 | B | NR |
| 1835 | 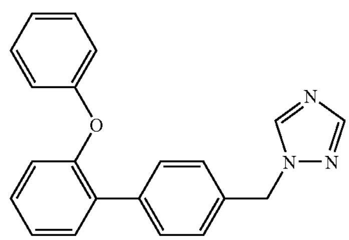 | B | NR |
| 1838 | 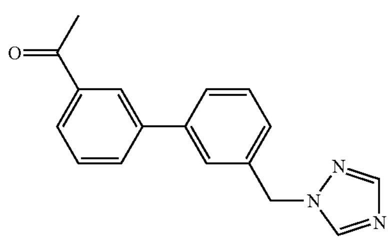 | B | NR |
| 1839 | 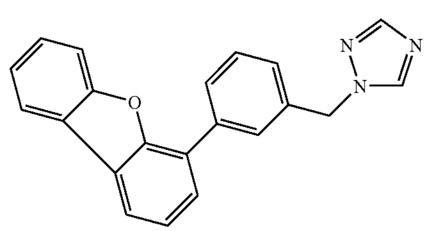 | B | NR |
| 1840 | 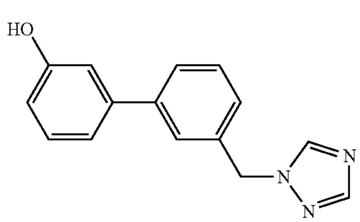 | B | NR |

-continued

| STX | STRUCTURE | JEG3-cells Aromatase IC$_{50}$ A: <10 μM B: <1 μM | JEG3-cells STS IC$_{50}$ A: <10 μM B: <1 μM |
|---|---|---|---|
| 1841 | 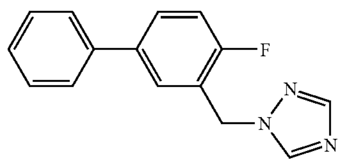 | B | NR |
| 1842 | 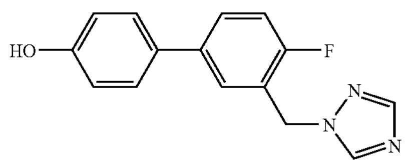 | B | NR |
| 1843 | 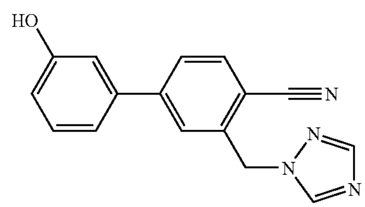 | B | NR |
| 1844 | 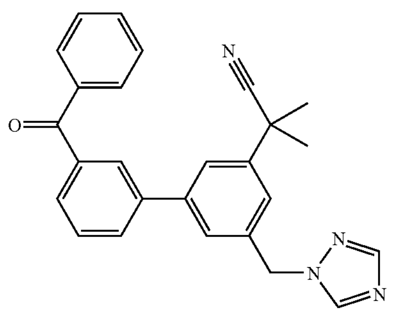 | B | NR |
| 1848 | 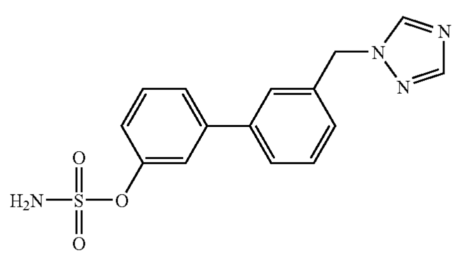 | B | A |
| 1854 | 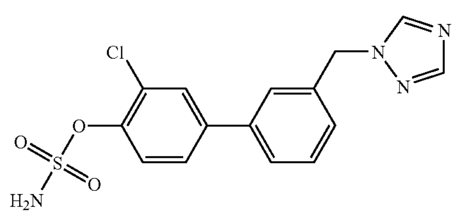 | B | B |
| 1975 | 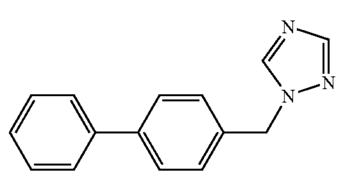 | A | NR |

-continued

| STX | STRUCTURE | JEG3-cells Aromatase IC$_{50}$ A: <10 µM B: <1 µM | JEG3-cells STS IC$_{50}$ A: <10 µM B: <1 µM |
|---|---|---|---|
| 1976 | 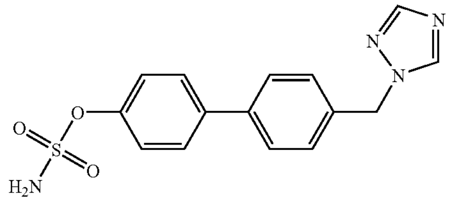 | A | A |
| 1978 | 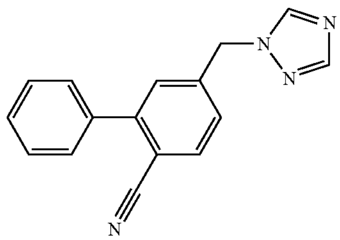 | B | NR |
| 1979 | 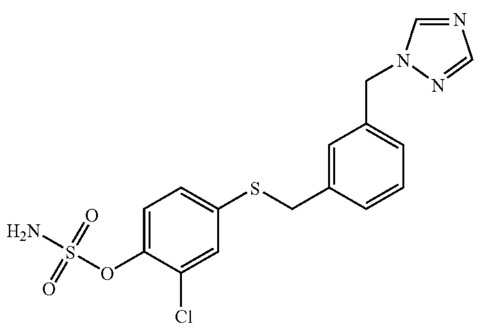 | B | B |
| 1980 | 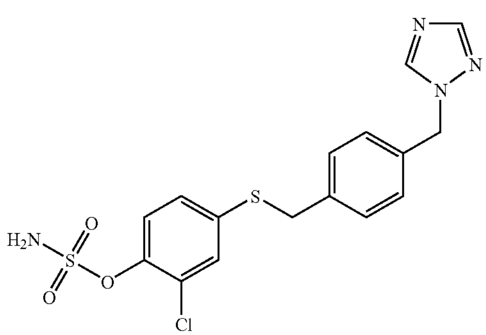 | B | B |
| 1981 | 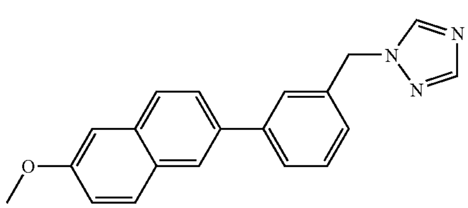 | B | NR |
| 2052 | 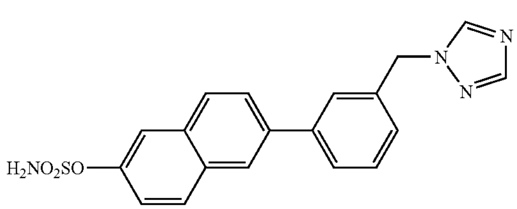 | A | NR |

| STX | STRUCTURE | JEG3-cells Aromatase IC$_{50}$ A: <10 μM B: <1 μM | JEG3-cells STS IC$_{50}$ A: <10 μM B: <1 μM |
|---|---|---|---|
| 2054 | 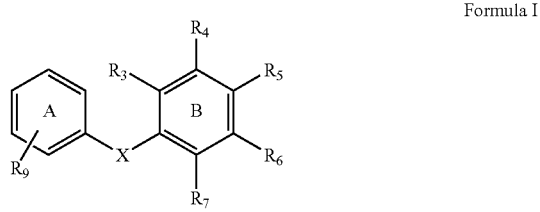 | NR | B |

NR—not recorded

All publications and patents and patent applications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims. The invention is further described by the following numbered paragraphs:

1. A compound of Formula I

Formula I wherein $R_3$, $R_4$, $R_5$, $R_6$ and $R_7$ are independently selected from H and —Y—$R_8$
wherein each $R_5$ is independently selected from —OH, hydrocarbyl groups, oxyhydrocarbyl groups, cyano (—CN), nitro (—NO$_2$), H-bond acceptors, and halogens;
wherein at least one of $R_3$, $R_4$, $R_5$, $R_6$ and $R_7$ is —Y—$R_8$ in which $R_8$ is selected from substituted and unsubstituted heterocyclic rings and amino substituted phenyl groups,
wherein X is a bond or a linker group
wherein Y is an optional linker group; and
wherein ring A is optionally further substituted
wherein $R_9$ is selected from H, —OH and —OSO$_2$NR$_1$R$_2$
wherein $R_1$ and $R_2$ are independently selected from H and hydrocarbyl
wherein
  (a) X is a bond and at least one of $R_3$, $R_4$, $R_5$, $R_6$ and $R_7$ is —Y—$R_8$; OR
  (b) $R_9$ is —OSO$_2$NR$_1$R$_2$ or —OH and four of $R_3$, $R_4$, $R_5$, $R_6$ and $R_7$ are H and one of $R_3$, $R_4$, $R_5$, $R_6$ and $R_7$ is —Y—$R_8$.

2. A compound according to paragraph 1 wherein X is a bond and at least $R_3$, $R_4$, $R_5$, $R_6$ and $R_7$ is —Y—$R_8$.

3. A compound according to paragraph 2 wherein $R_8$ is selected from cyano (—CN), halogens and substituted and unsubstituted heterocyclic rings.

4. A compound according to paragraph 2 or 3 wherein $R_8$ is selected from cyano (—CN), halogens and ring systems comprising carbon and one, two or three hetero atoms.

5. A compound according to paragraph 2, 3 or 4 wherein $R_8$ is selected from cyano (—CN), halogens and ring systems comprising carbon and one or more hetero atoms selected from Nitrogen, Sulphur and Oxygen.

6. A compound according to any one of paragraphs 2 to 5 wherein $R_8$ is selected from cyano (—CN), halogens and heterocyclic ring systems, wherein the ring comprises carbon and nitrogen.

7. A compound according to any one of paragraphs 2 to 6 wherein $R_8$ is selected from cyano (—CN), halogens and ring systems comprising from 3 to 10 members.

8. A compound according to any one of paragraphs 2 to 7 wherein $R_8$ is selected from cyano (—CN), halogens and ring systems comprising from 5, 6 or 7 members.

9. A compound according to any one of the preceding paragraphs wherein $R_8$ is selected from cyano (—CN), halogens and 4H-1,2,4-triazole, 1H-1,2,4-triazole and 1H-1,2,3-triazole.

10. A compound according to any one of the preceding paragraphs wherein $R_8$ is selected from 4H-1,2,4-triazole, 1H-1,2,4-triazole and 1H-1,2,3-triazole.

11. A compound according to any one of the preceding paragraphs wherein $R_8$ is 1H-1,2,4-triazole.

12. A compound according to any one of paragraphs 1 to 9 wherein when present Y is selected from —CH$_2$— and —C(CH$_3$)$_2$—

13. A compound according to any one of paragraphs 1 to 9 wherein —Y—$R_8$ is selected —CH$_2$-1H-1,2,4-triazole, —CN, —C(CH$_3$)$_2$—CN, and —F.

14. A compound according to any one of paragraphs 1 to 9 wherein one —Y—$R_8$ group is —CH$_2$-1H-1,2,4-triazole and optionally one further —Y—$R_8$ group selected from —CN, —C(CH$_3$)$_2$—CN, and —F.

15. A compound according to any one of the preceding paragraphs wherein at least one of $R_3$, $R_4$, $R_5$, $R_6$ and $R_7$ is —Y—$R_8$ wherein $R_8$ is selected from substituted and unsubstituted heterocyclic rings.

16. A compound according to any one of the preceding paragraphs wherein at least one of $R_3$, $R_4$, $R_5$, $R_6$ and $R_7$ is —Y—$R_8$ wherein $R_8$ is selected from substituted and unsubstituted ring systems comprising carbon and one, two or three hetero atoms.

17. A compound according to any one of the preceding paragraphs wherein at least one of $R_3$, $R_4$, $R_5$, $R_6$ and $R_7$ is —Y—$R_8$ wherein $R_8$ is selected from substituted and unsubstituted ring systems comprising carbon and one or more hetero atoms selected from Nitrogen, Sulphur and Oxygen.

18. A compound according to any one of the preceding paragraphs wherein at least one of $R_3$, $R_4$, $R_5$, $R_6$ and $R_7$ is —Y—$R_8$ wherein $R_8$ is selected from substituted and unsubstituted heterocyclic ring systems, wherein the ring comprises carbon and nitrogen.

19. A compound according to any one of the preceding paragraphs wherein at least one of $R_3$, $R_4$, $R_5$, $R_6$ and $R_7$ is —Y—$R_8$ wherein $R_8$ is selected from substituted and unsubstituted heterocyclic ring systems comprising from 3 to 10 members.

20. A compound according to any one of the preceding paragraphs wherein at least one of $R_3$, $R_4$, $R_5$, $R_6$ and $R_7$ is —Y—$R_8$ wherein $R_8$ is selected from substituted and unsubstituted heterocyclic ring systems comprising from 5, 6 or 7 members.

21. A compound according to any one of the preceding paragraphs wherein at least one of $R_3$, $R_4$, $R_5$, $R_6$ and $R_7$ is —Y—$R_8$ wherein $R_8$ is selected from 4H-1,2,4-triazole, 1H-1,2,4-triazole and 1H-1,2,3-triazole.

22. A compound according to any one of the preceding paragraphs wherein at least one of $R_3$, $R_4$, $R_5$, $R_6$ and $R_7$ is —Y—$R_8$ wherein $R_8$ is 1H-1,2,4-triazole.

23. A compound according to any one of the preceding paragraphs wherein at least one of $R_3$, $R_4$, $R_5$, $R_6$ and $R_7$ is —Y—$R_8$ wherein —Y—$R_8$ is —$CH_2$-1H-1,2,4-triazole.

24. A compound according to any one of paragraphs 1 to 23 of Formula II

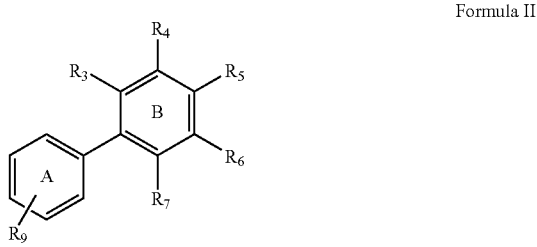

Formula II wherein at least one of $R_3$, $R_4$, $R_5$, $R_6$ and $R_7$ is —Y—$R_8$ wherein $R_8$ is selected from substituted and unsubstituted heterocyclic rings and amino substituted phenyl groups, and at least one of $R_3$, $R_4$, $R_5$, $R_6$ and $R_7$ is —Y—$R_8$ wherein $R_8$ is selected from cyano (—CN), nitro (—$NO_2$), H-bond acceptors, and halogens.

25. A compound according to paragraph 24 wherein at least one of $R_3$, $R_4$, $R_5$, $R_6$ and $R_7$ is —Y—$R_8$ wherein $R_8$ is selected from substituted and unsubstituted heterocyclic rings and amino substituted phenyl groups, and at least one of $R_3$, $R_4$, $R_5$, $R_6$ and $R_7$ is —Y—$R_8$ wherein $R_8$ is —CN.

26. A compound according to paragraph 1 wherein $R_9$ is —$OSO_2NR_1R_2$ or —OH and four of $R_3$, $R_4$, $R_5$, $R_6$ and $R_7$ are H and one of $R_3$, $R_4$, $R_5$, $R_6$ and $R_7$ is —Y—$R_8$.

27. A compound according to paragraph 26 wherein $R_9$ is —$OSO_2NR_1R_2$ or —OH; wherein $R_3$, $R_4$, $R_6$ and $R_7$ are H and $R_5$ is —Y—$R_8$.

28. A compound according to paragraph 26 wherein $R_9$ is —$OSO_2NR_1R_2$ or —OH, wherein $R_3$, $R_5$, $R_6$ and $R_7$ are H and $R_4$ is —Y—$R_8$.

29. A compound according to any one of paragraphs 26 to 28 wherein X is a bond or a linker group selected from —$CH_2$—S—, —C≡C—, —$CH_2$—O—, —O—, and —$CH_2CH_2$—.

30. A compound according to any one of paragraphs 26 to 29 wherein $R_8$ is selected from cyano (—CN), halogens and substituted and unsubstituted heterocyclic rings.

31. A compound according to any one of paragraphs 26 to 30 wherein $R_8$ is selected from cyano (—CN), halogens and substituted and unsubstituted ring systems comprising carbon and one, two or three hetero atoms.

32. A compound according to any one of paragraphs 26 to 31 wherein $R_8$ is selected from cyano (—CN), halogens and substituted and unsubstituted ring systems comprising carbon and one or more hetero atoms selected from Nitrogen, Sulphur and Oxygen.

33. A compound according to any one of paragraphs 26 to 32 wherein $R_8$ is selected from cyano (—CN), halogens and substituted and unsubstituted heterocyclic ring systems, wherein the ring comprises carbon and nitrogen.

34. A compound according to any one of paragraphs 26 to 33 wherein $R_8$ is selected from cyano (—CN), halogens and substituted and unsubstituted heterocyclic ring systems comprising from 3 to 10 members.

35. A compound according to any one of paragraphs 26 to 34 wherein $R_8$ is selected from cyano (—CN), halogens and substituted and unsubstituted heterocyclic ring systems comprising from 5, 6 or 7 members.

36. A compound according to any one of paragraphs 26 to 35 wherein $R_8$ is selected from cyano (—CN), halogens and 4H-1,2,4-triazole, 1H-1,2,4-triazole and 1H-1,2,3-triazole.

37. A compound according to any one of paragraphs 26 to 36 wherein $R_8$ is selected from 4H-1,2,4-triazole, 1H-1,2,4-triazole and 1H-1,2,3-triazole.

38. A compound according to any one of paragraphs 26 to 37 wherein —Y—$R_8$ is selected —$CH_2$-1H-1,2,4-triazole, —CN, —$C(CH_3)_2$—CN, and —F.

39. A compound according to any one of paragraphs 26 to 38 wherein at least one of $R_3$, $R_4$, $R_5$, $R_6$ and $R_7$ is —Y—$R_8$ wherein $R_8$ is selected from substituted and unsubstituted heterocyclic rings.

40. A compound according to any one of paragraphs 26 to 39 wherein at least one of $R_3$, $R_4$, $R_5$, $R_6$ and $R_7$ is —Y—$R_8$ wherein $R_8$ is selected from substituted and unsubstituted ring systems comprising carbon and one, two or three hetero atoms.

41. A compound according to any one of paragraphs 26 to 40 wherein at least one of $R_3$, $R_4$, $R_5$, $R_6$ and $R_7$ is —Y—$R_8$ wherein $R_8$ is selected from substituted and unsubstituted ring systems comprising carbon and one or more hetero atoms selected from Nitrogen, Sulphur and Oxygen.

42. A compound according to any one of paragraphs 26 to 41 wherein at least one of $R_3$, $R_4$, $R_5$, $R_6$ and $R_7$ is —Y—$R_8$ wherein $R_8$ is selected from substituted and unsubstituted heterocyclic ring systems, wherein the ring comprises carbon and nitrogen.

43. A compound according to any one of paragraphs 26 to 42 wherein at least one of $R_3$, $R_4$, $R_5$, $R_6$ and $R_7$ is —Y—$R_8$ wherein $R_8$ is selected from substituted and unsubstituted heterocyclic ring systems comprising from 3 to 10 members.

44. A compound according to any one of paragraphs 26 to 43 wherein at least one of $R_3$, $R_4$, $R_5$, $R_6$ and $R_7$ is —Y—$R_8$ wherein $R_8$ is selected from substituted and unsubstituted heterocyclic ring systems comprising from 5, 6 or 7 members.

45. A compound according to any one of paragraphs 26 to 44 wherein at least one of $R_3$, $R_4$, $R_5$, $R_6$ and $R_7$ is —Y—$R_8$ wherein $R_8$ is selected from 4H-1,2,4-triazole, 1H-1,2,4-triazole and 1H-1,2,3-triazole.

46. A compound according to any one paragraphs 26 to 45 wherein at least one of $R_3$, $R_4$, $R_5$, $R_6$ and $R_7$ is —Y—$R_9$ wherein $R_5$ is 1H-1,2,4-triazole.

47. A compound according to any one of paragraphs 26 to 46 wherein at least one of $R_3$, $R_4$, $R_5$, $R_6$ and $R_7$ is —Y—$R_8$ wherein —Y—$R_8$ is —$CH_2$-1H-1,2,4-triazole.

48. A compound according to any one of paragraphs 26 to 47 wherein $R_8$ is 1H-1,2,4-triazole.

49. A compound according to any one of paragraphs 26 to 48 wherein when present Y is selected from —$CH_2$— and —$C(CH_3)_2$—

50. A compound according to any one of paragraphs 26 to 49 wherein —Y—$R_8$ is —$CH_2$-1H-1,2,4-triazole.

51. A compound according to any one of the preceding paragraphs wherein A is optionally further substituted by groups selected from —OH, hydrocarbyl groups, oxyhydrocarbyl groups, cyano (—CN), nitro (—$NO_2$), H-bond acceptors, and halogens.

52. A compound according to any one of the preceding paragraphs wherein A is optionally further substituted by groups selected —Cl, —OH, fused phenyl, phenyl, —OMe, —$OCH_2Ph$, —CN, —C(O)-Ph, —F, —O-Ph, —C(O)-Me, fused phenyl optional substituted with one of —OMe or —OH, and a fused heterocyclic group such that ring A forms a bibezofuranyl.

53. A compound according to any one of the preceding paragraphs wherein A is optionally further substituted by only one or two groups.

54. A compound according to paragraph 1 selected from compounds of the formulae

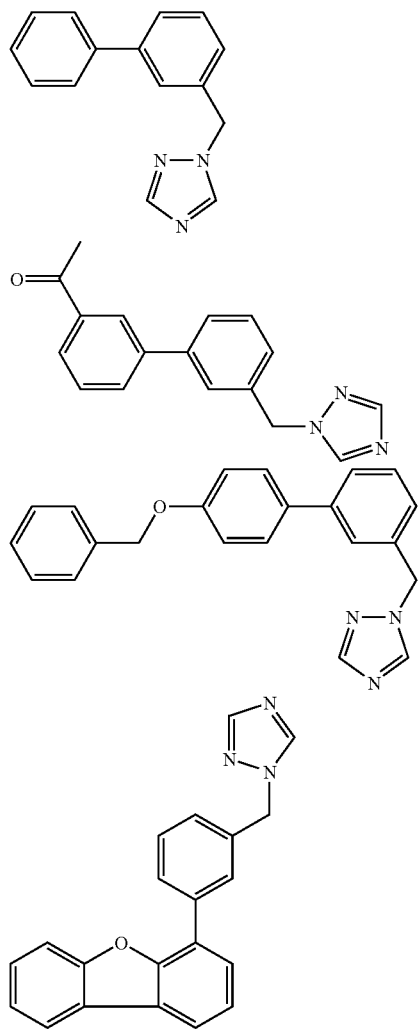

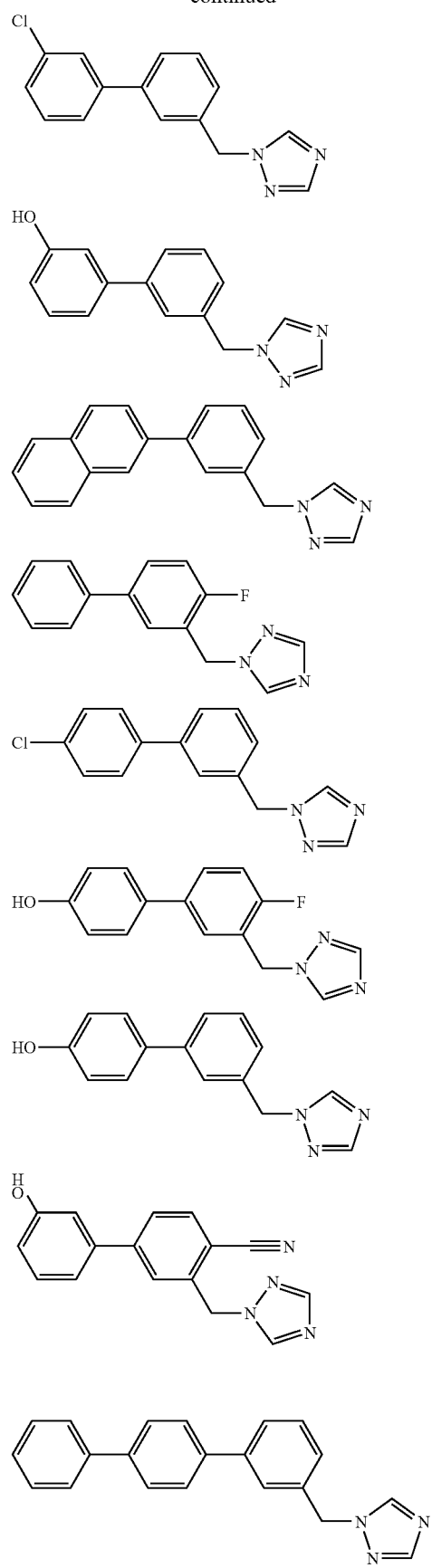

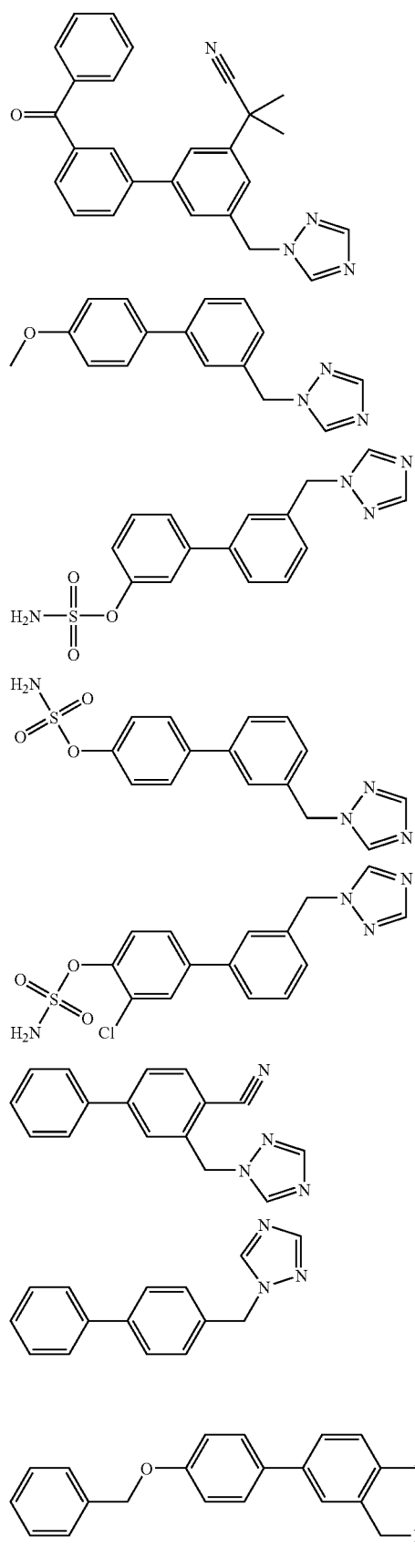
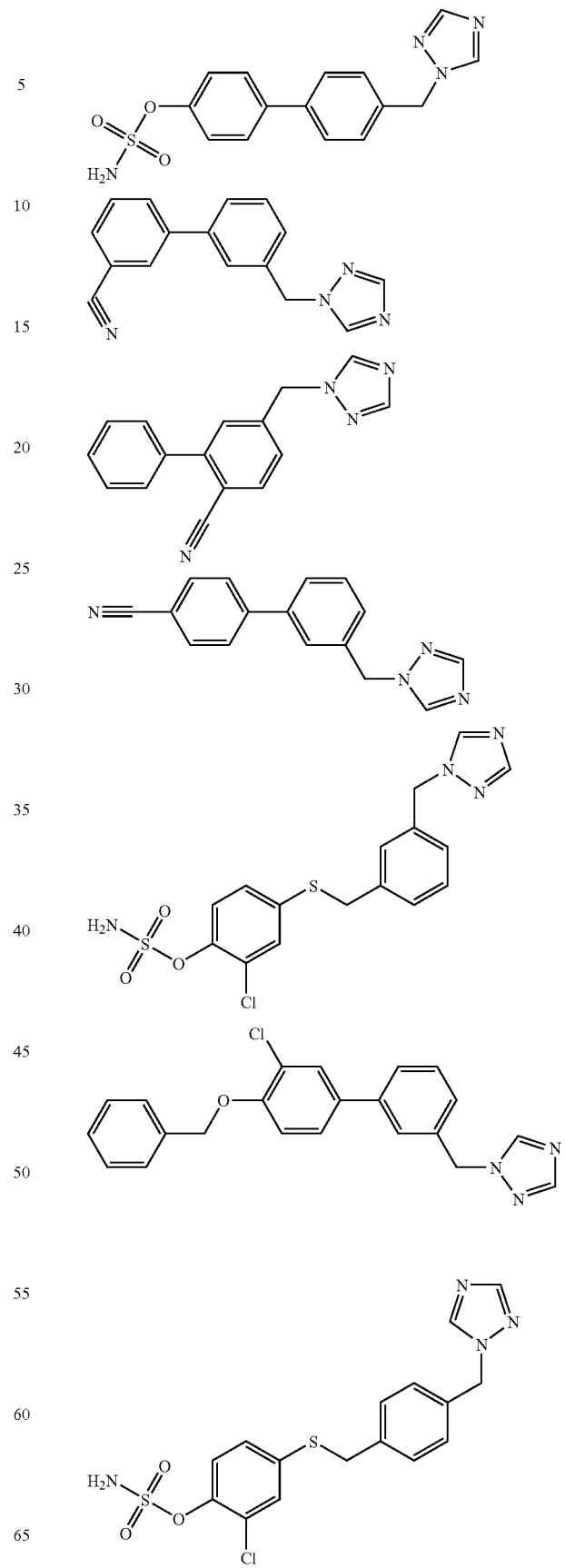

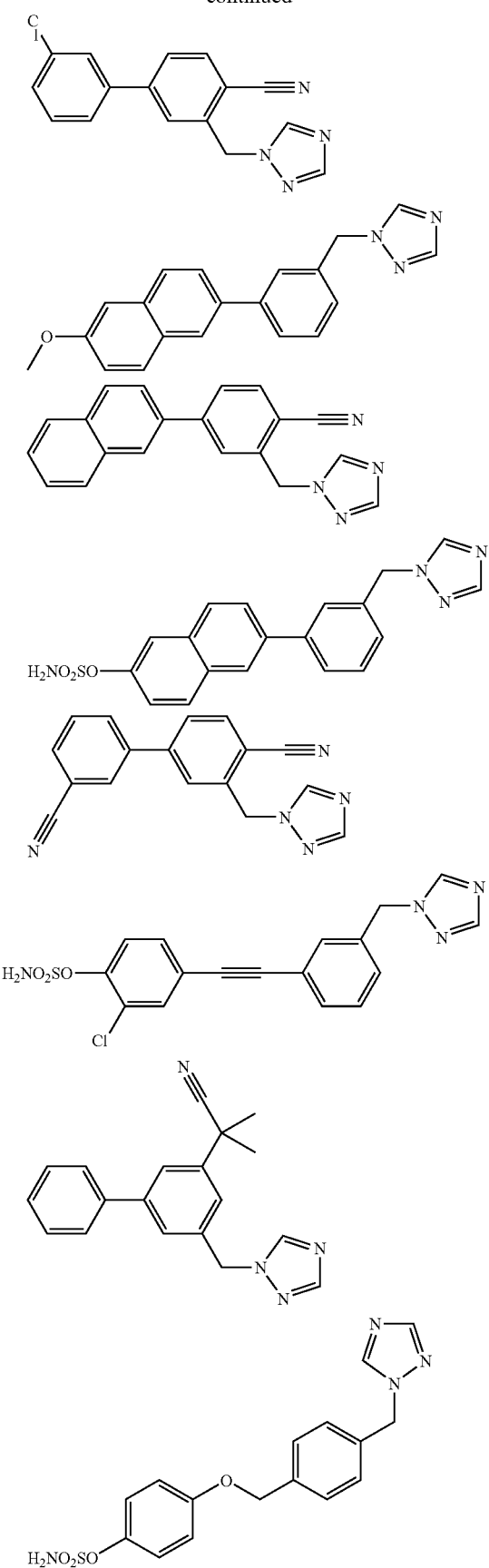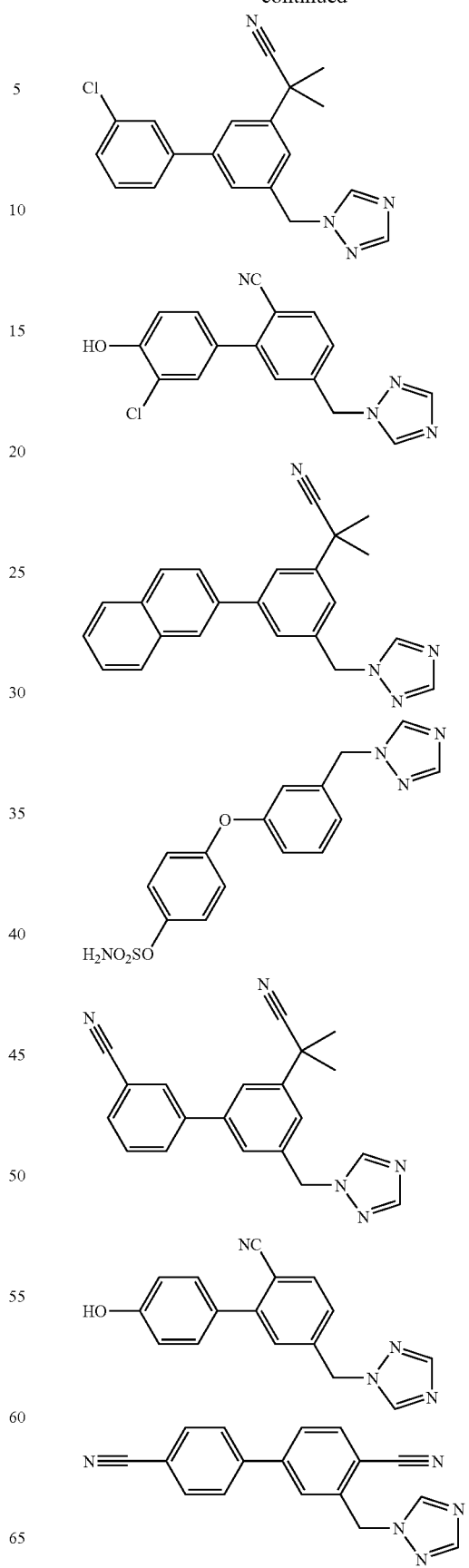

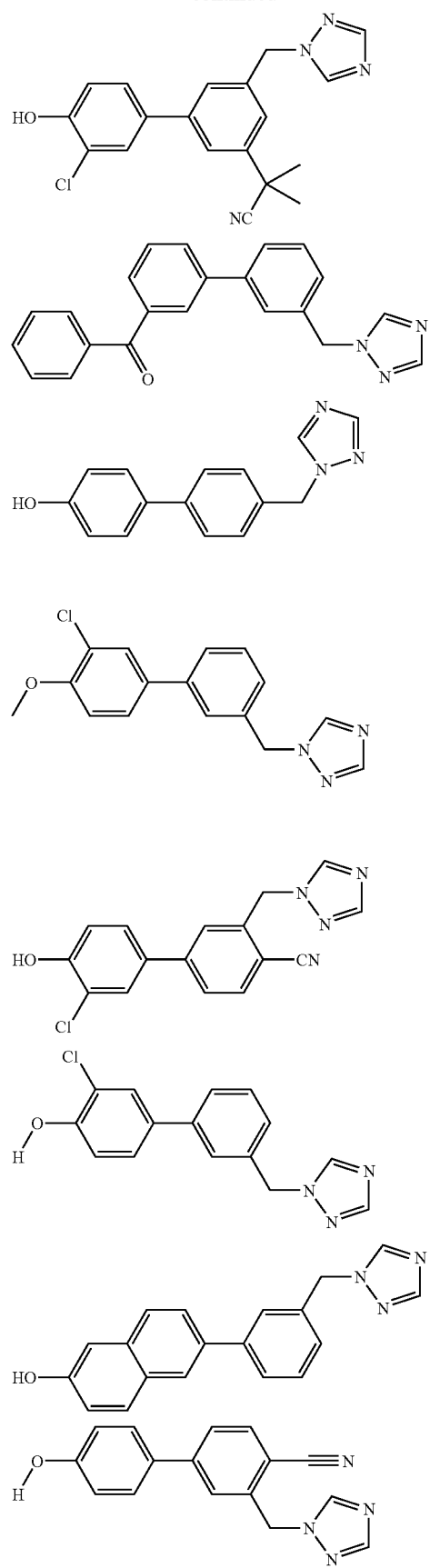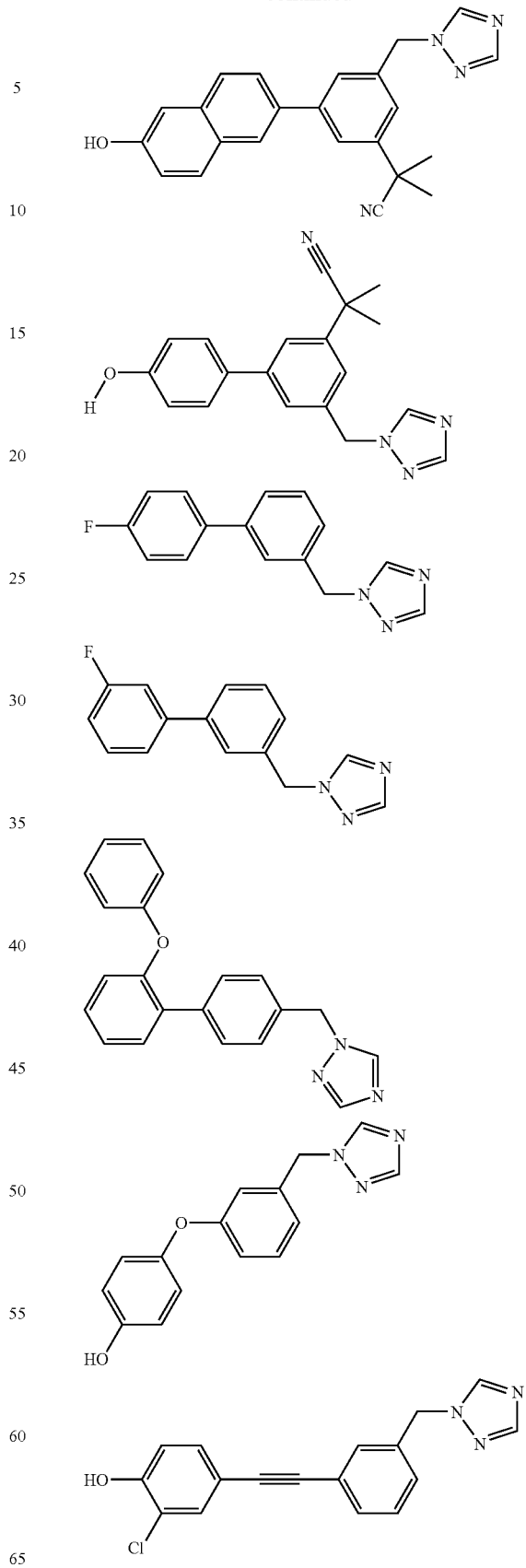

55. A compound according to any one of paragraphs 1 to 54 for use in medicine.
56. A pharmaceutical composition comprising the compound according to any one of paragraphs 1 to 54 optionally admixed with a pharmaceutically acceptable carrier, diluent, excipient or adjuvant.
57. Use of a compound according to any one of paragraphs 1 to 54 in the manufacture of a medicament for use in the therapy of a condition or disease associated with STS and/or aromatase and/or cell cycling and/or apoptosis and/or cell growth.
58. Use of a compound according to any one of paragraphs 1 to 54 in the manufacture of a medicament for use in the therapy of a condition or disease associated with STS and aromatase.
59. Use of a compound according to any one of paragraphs 1 to 54 in the manufacture of a medicament for use in the therapy of a condition or disease associated with adverse STS levels and/or adverse aromatase levels and/or cell cycling and/or apoptosis and/or cell growth.
60. Use of a compound according to any one of paragraphs 1 to 54 in the manufacture of a medicament for use in the therapy of a condition or disease associated with adverse STS levels and adverse aromatase levels.
61. Use of a compound according to any one of paragraphs 1 to 54 in the manufacture of a medicament for inhibiting STS activity and/or inhibiting aromatase activity.
62. Use of a compound according to any one of paragraphs 1 to 54 in the manufacture of a medicament for inhibiting STS activity and inhibiting aromatase activity.
63. A compound as substantially hereinbefore described with reference to the Examples.
64. A composition as substantially hereinbefore described with reference to the Examples.
65. A method or use as substantially hereinbefore described with reference to the Examples.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:
1. A compound of Formula II:

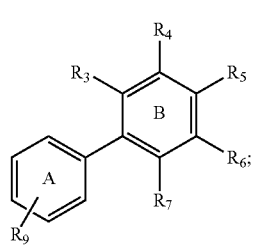

Formula II wherein $R_3$, $R_5$, $R_6$ and $R_7$ are each H;
wherein $R_4$ is —Y—$R_8$ in which $R_8$ is selected from substituted and unsubstituted heterocyclic rings and amino substituted phenyl groups,
wherein Y is a bond or —$CH_2$; and
wherein ring A is phenyl optionally substituted,
wherein $R_9$ is —$OSO_2NR_1R_2$,
wherein $R_1$ and $R_2$ are independently selected from H and hydrocarbyl.

2. The compound according to claim 1, wherein $R_8$ is selected from 4H-1,2,4-triazole, 1H-1,2,4-triazole, and 1H-1,2,3-triazole.
3. The compound according to claim 2, wherein $R_8$ is 1H-1,2,4-triazole.
4. The compound according to claim 1, wherein $R_4$ is —Y—$R_8$ wherein $R_8$ is selected from substituted and unsubstituted heterocyclic rings.
5. The compound according to claim 1, wherein $R_4$ is —Y—$R_8$ wherein $R_8$ is selected from substituted and unsubstituted heterocyclic rings comprising carbon and one, two, or three hetero atoms.
6. The compound according to claim 1, wherein $R_4$ is —Y—$R_8$ wherein $R_8$ is selected from substituted and unsubstituted heterocyclic rings comprising carbon and one or more hetero atoms selected from nitrogen, sulphur, and oxygen.
7. The compound according to claim 1, wherein $R_4$ is —Y—$R_8$ wherein $R_8$ is selected from substituted and unsubstituted heterocyclic rings, wherein the ring comprises carbon and nitrogen.
8. The compound according to claim 1, wherein $R_4$ is —Y—$R_8$ wherein $R_8$ is selected from substituted and unsubstituted heterocyclic rings comprising from 3 to 10 members.
9. The compound according to claim 8, wherein $R_4$ is —Y—$R_8$ wherein $R_8$ is selected from substituted and unsubstituted heterocyclic rings comprising 5, 6, or 7 members.
10. The compound according to claim 1, wherein $R_4$ is —Y—$R_8$ wherein —Y—$R_8$ is —$CH_2$-1H-1,2,4-triazole.
11. The compound according to claim 1, wherein A is optionally substituted by groups selected from —OH, hydrocarbyl groups, oxyhydrocarbyl groups, cyano (—CN), nitro (—$NO_2$), and halogens.
12. The compound according to claim 1, wherein A is optionally substituted by groups selected from —Cl, —OH, fused phenyl, phenyl, —OMe, —$OCR_2Ph$, —CN, —C(O)-Ph, —F, —O-Ph, —C(O)-Me, fused phenyl optional substituted with one of —OMe or —OH, and a fused heterocyclic group such that ring A forms a bibezofuranyl.
13. The compound according to claim 1, wherein A is optionally substituted by one or two groups.
14. The compound according to claim 1 selected from compounds of formulae

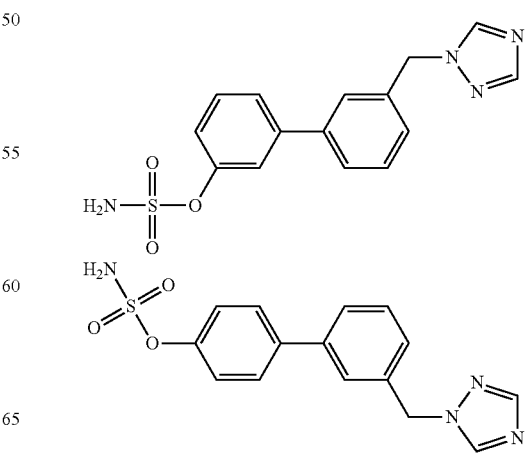

-continued
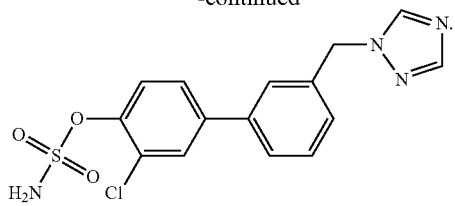
15. A pharmaceutical composition comprising the compound according to claim 1, and a pharmaceutically acceptable carrier, diluent, excipients, or adjuvant.
16. The compound according to claim 1, wherein A is optionally substituted by halogen.
\* \* \* \* \*